US006576238B1

(12) United States Patent
Weber et al.

(10) Patent No.: US 6,576,238 B1
(45) Date of Patent: Jun. 10, 2003

(54) ECTOPARASITE SALIVA PROTEINS AND APPARATUS TO COLLECT SUCH PROTEINS

(75) Inventors: Eric R. Weber, Ft. Collins, CO (US); Shirley Wu Hunter, Fort Collins, CO (US); Glenn Robert Frank, Wellington, CO (US); Lynda Wallenfels, St. George, UT (US)

(73) Assignee: Heska Corporation, Fort Collins, CO (US)

( * ) Notice: Subject to any disclaimer, the term of this patent is extended or adjusted under 35 U.S.C. 154(b) by 0 days.

(21) Appl. No.: 08/981,799

(22) PCT Filed: Oct. 15, 1997

(86) PCT No.: PCT/US97/18669

§ 371 (c)(1),
(2), (4) Date: Aug. 27, 1998

(87) PCT Pub. No.: WO98/45408

PCT Pub. Date: Oct. 15, 1998

Related U.S. Application Data

(63) Continuation-in-part of application No. PCT/US97/05959, filed on Apr. 10, 1997, which is a continuation-in-part of application No. 08/630,822, filed on Apr. 10, 1996, now Pat. No. 5,840,695, which is a continuation-in-part of application No. 08/487,001, filed on Jun. 7, 1995, now Pat. No. 5,795,862, which is a continuation-in-part of application No. 08/319,590, filed on Oct. 7, 1994, now Pat. No. 5,646,115.

(51) Int. Cl.$^7$ .............................................. A61K 39/00
(52) U.S. Cl. .................... 424/184.1; 530/350; 530/329; 514/12; 424/265.1; 424/275.1
(58) Field of Search .......................... 530/350; 514/12; 424/184.1, 185.1, 265.1, 275.1

(56) References Cited

U.S. PATENT DOCUMENTS

| 5,356,622 A |   | 10/1994 | Heath et al. |
| 5,646,115 A | * | 7/1997  | Frank et al. |
| 5,795,862 A | * | 8/1998  | Frank et al. |
| 5,840,695 A | * | 11/1998 | Frank et al. |

FOREIGN PATENT DOCUMENTS

| WO | WO 93/18788 | 9/1993 |
| WO | WO 96/11271 | 4/1996 |
| WO | WO 96/14089 | 5/1996 |
| WO | WO 96/28469 | 9/1996 |

OTHER PUBLICATIONS

Baker et al., 1975, *J. Small Anim. Pract.*, 16:317–327 (abstract).
Benjamin et al., "Allergy to Flea Bites. IV. In Vitro Collection and Antigenic Properties of the Oral Secretion of the Cat Flea, *Ctenocephalides felis felis* (Bouché)", pp. 143–154, 1963, *Exp. Parasitol.*, vol. 13.
Benjamin et al., "Allergy to Flea Bites. III. The Experimental Induction of Flea Bite Sensitivity in Guinea Pigs by Exposure to Flea Bites and by Antigen Prepared from Whole Flea Extracts of *Ctenocephalides felis felis*", pp. 214–222, 1960, *Exp. Parasitol.*, vol. 10.
Greene et al., 1963, *Vet. Immunol. Immunopathol.*, 37(1):15–23 (abstract).
Greene et al., "Characterization of Allergens of the Cat Flea, *Ctenocephalides felis*: Detection and Frequency of IgE Antibodies in Canine Sera", pp. 69–74, 1993, *Parasite Immunol.*, vol. 15.
Halliwell et al., "The Role of Basophils in the Immunopathogenesis of Hypersensitivity to Fleas (*Ctenocephalides felis*) in Dogs", pp. 203–213, 1987, *Vet. Immunol. Immunopathol.*, vol. 15.
Halliwell et al., 1985, Ivet. Immunol. and Immunopath., 8(3):215–23 (abstract).
Keep et al., "Whole Flea Extract as a Desensitising Agent in Canine Summer Dermatitis", pp. 425–426, 1967, *Austral. Vet. J.*, vol. 43.
Kristensen et al., "A Study of Skin Diseases in Dogs and Cats. V. The Intradermal Test in the Diagnosis of Flea Allergy in Dogs and Cats", pp. 414–423, 1978, *Nord. Vet.–Med.*, vol. 30.
Kunkle et al., 1985, *J. Amer. Vet. Med. Assn.*, 186(7):677–80 (abstract).
McKeon et al., 1994, *Int. J. Parasitol.*, 24(2):259–63 (abstract).
Michaeli et al., "In Vitro Studies on the Role of Collagen in the Induction of Hypersensitivity to Flea Bites", pp. 402–406, 1966, *J. Immunol.*, vol. 97, No. 3.
Michaeli et al., "The Role of Collagen in the Induction of Flea Bite Hypersensitivity", pp. 162–170, 1965, *J. Immunol.*, vol. 95, No. 1.
Van Winkle, "An Evaluation of Flea Antigens Used in Intradermal Skin Testing for Flea Allergy in the Canine", pp. 343–354, 1981, *J. Amer. Anim. Hosp. Assoc.*, vol. 17.
Wade et al., "Survival and Reproduction of Artificially Fed Cat Fleas, *Ctenocephalides felis* Bouché (Siphonaptera: Pulicidae)", pp. 186–189, 1988, *J. Med. Entomol.*, vol. 25, No. 3.
Young et al., Allergy to Flea Bites. V. Preliminary Results of Fractionation, Characterization, and Assay for Allergenic Activity of Material Derived from the Oral Secretion of the Cat Flea, *Ctenocephalides felis felis*, pp. 155–166, 1963, *Exp. Parasitol.*, vol. 13.

* cited by examiner

Primary Examiner—Marianne P. Allen
(74) Attorney, Agent, or Firm—Sheridan Ross P.C.

(57) ABSTRACT

The present invention is directed to a novel product and method for isolating ectoparasite saliva proteins, and a novel product and method for detecting and/or treating allergic dermatitis in an animal. The present invention also relates to ectoparasite saliva proteins, nucleic acid molecules having sequences that encode such proteins, and antibodies raised against such proteins. The present invention also includes methods to obtain such proteins and to use such proteins to identify animals susceptible to or having allergic dermatitis. The present invention also includes therapeutic compositions comprising such proteins and their use to treat animals susceptible to or having allergic dermatitis.

11 Claims, 13 Drawing Sheets

FRACTIONATED FLEA SALIVA ELISA WITH PURIFIED ALLERGIC DOG IGE

SEQUENCE LISTING

<160> NUMBER OF SEQ ID NOS: 150

<210> SEQ ID NO 1
<211> LENGTH: 26
<212> TYPE: PRT
<213> ORGANISM: Ctenocephalides felis

<400> SEQUENCE: 1

Met Arg Gly Asn His Val Phe Leu Glu Asp Gly Met Ala Asp Met Thr
1               5                   10                  15

Gly Gly Gln Gln Met Gly Arg Asp Leu Tyr
            20                  25

<210> SEQ ID NO 2
<211> LENGTH: 12
<212> TYPE: PRT
<213> ORGANISM: Ctenocephalides felis
<220> FEATURE:
<221> NAME/KEY: misc_feature
<222> LOCATION: (5)..()
<223> OTHER INFORMATION: Xaa = Tyr or Asp
<221> NAME/KEY: misc_feature
<222> LOCATION: (6)..()
<223> OTHER INFORMATION: Xaa = any amino acid

<400> SEQUENCE: 2

Lys Tyr Arg Asn Xaa Xaa Thr Asn Asp Pro Gln Tyr
1               5                   10

<210> SEQ ID NO 3
<211> LENGTH: 27
<212> TYPE: PRT
<213> ORGANISM: Ctenocephalides felis

<400> SEQUENCE: 3

Glu Ile Lys Arg Asn Asp Arg Glu Pro Gly Asn Leu Ser Lys Ile Arg
1               5                   10                  15

Thr Val Met Asp Lys Val Ile Lys Gln Thr Gln
            20                  25

<210> SEQ ID NO 4
<211> LENGTH: 23
<212> TYPE: PRT
<213> ORGANISM: Ctenocephalides felis
<220> FEATURE:
<221> NAME/KEY: misc_feature
<222> LOCATION: (8)..()
<223> OTHER INFORMATION: Xaa - Ala or His
<221> NAME/KEY: misc_feature
<222> LOCATION: (9)..()
<223> OTHER INFORMATION: Xaa - Ala or His

<400> SEQUENCE: 4

Leu Lys Asp Asn Asp Ile Tyr Xaa Xaa Arg Asp Ile Asn Glu Ile Leu
1               5                   10                  15

Arg Val Leu Asp Pro Ser Lys
            20

<210> SEQ ID NO 5
<211> LENGTH: 27
<212> TYPE: PRT
<213> ORGANISM: Ctenocephalides felis
<220> FEATURE:
<221> NAME/KEY: misc_feature
<222> LOCATION: (12)..()
<223> OTHER INFORMATION: Xaa = any amino acid
<221> NAME/KEY: misc_feature
<222> LOCATION: (18)..()
<223> OTHER INFORMATION: Xaa = any amino acid

<400> SEQUENCE: 5

Asn Tyr Gly Arg Val Gln Ile Glu Asp Tyr Thr Xaa Ser Asn His Lys
1               5                   10                  15

Asp Xaa Glu Glu Lys Asp Gln Ile Asn Gly Leu
            20                  25

<210> SEQ ID NO 6
<211> LENGTH: 18
<212> TYPE: PRT
<213> ORGANISM: Ctenocephalides felis
<220> FEATURE:
<221> NAME/KEY: misc_feature
<222> LOCATION: (5)..()
<223> OTHER INFORMATION: Xaa = any amino acid

<400> SEQUENCE: 6

Lys Tyr Arg Asn Xaa Tyr Thr Asn Asp Pro Gln Leu Lys Leu Leu Asp
1               5                   10                  15

Glu Gly

<210> SEQ ID NO 7
<211> LENGTH: 22
<212> TYPE: PRT
<213> ORGANISM: Ctenocephalides felis
<220> FEATURE:
<221> NAME/KEY: misc_feature
<222> LOCATION: (13)..()
<223> OTHER INFORMATION: Xaa = any amino acid
<221> NAME/KEY: misc_feature
<222> LOCATION: (19)..()
<223> OTHER INFORMATION: Xaa = any amino acid
<221> NAME/KEY: misc_feature
<222> LOCATION: (21)..()
<223> OTHER INFORMATION: Xaa = any amino acid

<400> SEQUENCE: 7

Tyr Phe Asn Asp Gln Ile Lys Ser Val Met Glu Pro Xaa Val Phe Lys
1               5                   10                  15

Tyr Pro Xaa Ala Xaa Leu
            20

<210> SEQ ID NO 8
<211> LENGTH: 20
<212> TYPE: DNA
<213> ORGANISM: Ctenocephalides felis
<220> FEATURE:
<221> NAME/KEY: misc_feature
<222> LOCATION: (1)..(20)
<223> OTHER INFORMATION: primer

<400> SEQUENCE: 8
tgrtttccwa traartcttc                                            20

<210> SEQ ID NO 9
<211> LENGTH: 225
<212> TYPE: DNA
<213> ORGANISM: Ctenocephalides felis

<400> SEQUENCE: 9
gaattcggca cgagtgaaat tcaatatttt gttttacatt aaattttca aattcgatat    60 gaaattttta ctgcaatttt gcgtgttgtg tgttttatta aatcaagtat ctatgtcaaa  120
aatggtcact gaaaagtgta agtcaggtgg aaataatcca agtacagaag aggtgtcaat  180
accatctggg aagcttacta ttgaagattt ttgtattgga aatca                  225

<210> SEQ ID NO 10
<211> LENGTH: 15
<212> TYPE: DNA
<213> ORGANISM: Ctenocephalides felis
<220> FEATURE:
<221> NAME/KEY: misc_feature

```
<222> LOCATION: (1)..(15)
<223> OTHER INFORMATION: primer

<400> SEQUENCE: 10
aattcggcac gagtg                                                      15

<210> SEQ ID NO 11
<211> LENGTH: 565
<212> TYPE: DNA
<213> ORGANISM: Ctenocephalides felis
<220> FEATURE:
<221> NAME/KEY: CDS
<222> LOCATION: (45)..(314)

<400> SEQUENCE: 11
tgaaattcaa tattttgttt tacattaaat ttttcaaatt cgat atg aaa ttt tta     56
                                                 Met Lys Phe Leu
                                                  1 ctg gca att tgc gtg ttg tgt gtt tta tta aat caa gta tct atg tca    104
Leu Ala Ile Cys Val Leu Cys Val Leu Leu Asn Gln Val Ser Met Ser
 5              10                  15                  20 aaa atg gtc act gaa aag tgt aag tca ggt gga aat aat cca agt aca    152
Lys Met Val Thr Glu Lys Cys Lys Ser Gly Gly Asn Asn Pro Ser Thr
             25                  30                  35 gaa gag gtg tca ata cca tct ggg aag ctt act att gaa gat ttt tgt    200
Glu Glu Val Ser Ile Pro Ser Gly Lys Leu Thr Ile Glu Asp Phe Cys
         40                  45                  50 att gga aat cat caa agt tgc aaa ata ttt tac aaa agt caa tgt gga    248
Ile Gly Asn His Gln Ser Cys Lys Ile Phe Tyr Lys Ser Gln Cys Gly
     55                  60                  65 ttt gga ggt ggt gct tgt gga aac ggt ggt tca aca cga cca aat caa    296
Phe Gly Gly Gly Ala Cys Gly Asn Gly Gly Ser Thr Arg Pro Asn Gln
 70                  75                  80 aaa cac tgt tat tgc gaa taaccatatt ccggatgaaa gaccaaattg            344
Lys His Cys Tyr Cys Glu
 85                  90 atataaatta ctaaaattat gctagatagc aatcataaaa ttttgaagtt ttcaatgatc   404
ctaacatgtt ttgcctccaa tttatttttaa cagcaaattg ctggaactta ccgtaccgta  464
actaaatgtt caagaaatac tgaatgttta caaatagatt attataaata ttgtaacatt   524
gtctaatatt tataagaatt atataaactg aattgcaaaa a                       565

<210> SEQ ID NO 12
<211> LENGTH: 90
<212> TYPE: PRT
<213> ORGANISM: Ctenocephalides felis

<400> SEQUENCE: 12

Met Lys Phe Leu Leu Ala Ile Cys Val Leu Cys Val Leu Leu Asn Gln
 1               5                  10                  15

Val Ser Met Ser Lys Met Val Thr Glu Lys Cys Lys Ser Gly Gly Asn
             20                  25                  30

Asn Pro Ser Thr Glu Glu Val Ser Ile Pro Ser Gly Lys Leu Thr Ile
         35                  40                  45

Glu Asp Phe Cys Ile Gly Asn His Gln Ser Cys Lys Ile Phe Tyr Lys
     50                  55                  60

Ser Gln Cys Gly Phe Gly Gly Gly Ala Cys Gly Asn Gly Gly Ser Thr
 65                  70                  75                  80

Arg Pro Asn Gln Lys His Cys Tyr Cys Glu
                 85                  90
```

```
<210> SEQ ID NO 13
<211> LENGTH: 270
<212> TYPE: DNA
<213> ORGANISM: Ctenocephalides felis
<220> FEATURE:
<221> NAME/KEY: CDS
<222> LOCATION: (1)..(270)

<400> SEQUENCE: 13 atg aaa ttt tta ctg gca att tgc gtg ttg tgt gtt tta tta aat caa      48
Met Lys Phe Leu Leu Ala Ile Cys Val Leu Cys Val Leu Leu Asn Gln
1               5                   10                  15 gta tct atg tca aaa atg gtc act gaa aag tgt aag tca ggt gga aat      96
Val Ser Met Ser Lys Met Val Thr Glu Lys Cys Lys Ser Gly Gly Asn
            20                  25                  30 aat cca agt aca gaa gag gtg tca ata cca tct ggg aag ctt act att     144
Asn Pro Ser Thr Glu Glu Val Ser Ile Pro Ser Gly Lys Leu Thr Ile
        35                  40                  45 gaa gat ttt tgt att gga aat cat caa agt tgc aaa ata ttt tac aaa     192
Glu Asp Phe Cys Ile Gly Asn His Gln Ser Cys Lys Ile Phe Tyr Lys
    50                  55                  60 agt caa tgt gga ttt gga ggt ggt gct tgt gga aac ggt ggt tca aca     240
Ser Gln Cys Gly Phe Gly Gly Gly Ala Cys Gly Asn Gly Gly Ser Thr
65                  70                  75                  80 cga cca aat caa aaa cac tgt tat tgc gaa                             270
Arg Pro Asn Gln Lys His Cys Tyr Cys Glu
                85                  90

<210> SEQ ID NO 14
<211> LENGTH: 90
<212> TYPE: PRT
<213> ORGANISM: Ctenocephalides felis

<400> SEQUENCE: 14

Met Lys Phe Leu Leu Ala Ile Cys Val Leu Cys Val Leu Leu Asn Gln
1               5                   10                  15

Val Ser Met Ser Lys Met Val Thr Glu Lys Cys Lys Ser Gly Gly Asn
            20                  25                  30

Asn Pro Ser Thr Glu Glu Val Ser Ile Pro Ser Gly Lys Leu Thr Ile
        35                  40                  45

Glu Asp Phe Cys Ile Gly Asn His Gln Ser Cys Lys Ile Phe Tyr Lys
    50                  55                  60

Ser Gln Cys Gly Phe Gly Gly Gly Ala Cys Gly Asn Gly Gly Ser Thr
65                  70                  75                  80

Arg Pro Asn Gln Lys His Cys Tyr Cys Glu
                85                  90

<210> SEQ ID NO 15
<211> LENGTH: 26
<212> TYPE: DNA
<213> ORGANISM: Ctenocephalides felis
<220> FEATURE:
<221> NAME/KEY: misc_feature
<222> LOCATION: (1)..(26)
<223> OTHER INFORMATION: primer

<400> SEQUENCE: 15
agtggatccg tcaaaaatgg tcactg                                         26

<210> SEQ ID NO 16
<211> LENGTH: 28
```

```
<212> TYPE: DNA
<213> ORGANISM: Ctenocephalides felis
<220> FEATURE:
<221> NAME/KEY: misc_feature
<222> LOCATION: (1)..(28)
<223> OTHER INFORMATION: primer

<400> SEQUENCE: 16
ccggaattcg gttattcgca ataacagt                                           28

<210> SEQ ID NO 17
<211> LENGTH: 897
<212> TYPE: DNA
<213> ORGANISM: Ctenocephalides felis
<220> FEATURE:
<221> NAME/KEY: CDS
<222> LOCATION: (97)..(567)

<400> SEQUENCE: 17
```

| | | |
|---|---|---|
| ccgaaatctc ctatcacagt gtacggagtg taaaatattg ttgaagtatt ttgaaattta | | 60 |
| ttaatttatt cgaaaggag atttcattaa ataaaa atg gtt tac gaa agt gac<br>                                                        Met Val Tyr Glu Ser Asp<br>                                                         1              5 | | 114 |
| ttt tac acg acc cgt cgg ccc tac agt cgt ccg gct ttg tct tca tac<br>Phe Tyr Thr Thr Arg Arg Pro Tyr Ser Arg Pro Ala Leu Ser Ser Tyr<br>          10                   15                   20 | | 162 |
| tcc gta acg gca cgt cca gag ccg gtt cct tgg gac aaa ttg ccg ttc<br>Ser Val Thr Ala Arg Pro Glu Pro Val Pro Trp Asp Lys Leu Pro Phe<br> 25                    30                   35 | | 210 |
| gtc ccc cgt cca agt ttg gta gca gat ccc ata aca gca ttt tgc aag<br>Val Pro Arg Pro Ser Leu Val Ala Asp Pro Ile Thr Ala Phe Cys Lys<br>    40                    45                   50 | | 258 |
| cga aaa cct cgc cga gaa gaa gtt gtt caa aaa gag tcc att gtt cga<br>Arg Lys Pro Arg Arg Glu Glu Val Val Gln Lys Glu Ser Ile Val Arg<br>55                 60                   65                   70 | | 306 |
| agg atc aat tct gca gga att aaa ccc agc cag aga gtt tta tcg gct<br>Arg Ile Asn Ser Ala Gly Ile Lys Pro Ser Gln Arg Val Leu Ser Ala<br>               75                   80                   85 | | 354 |
| cca ata aga gaa tac gaa tcc cca agg gac cag acc agg cgt aaa gtt<br>Pro Ile Arg Glu Tyr Glu Ser Pro Arg Asp Gln Thr Arg Arg Lys Val<br>          90                   95                   100 | | 402 |
| ttg gaa agc gtc aga aga caa gaa gct ttt ctg aac caa gga gga att<br>Leu Glu Ser Val Arg Arg Gln Glu Ala Phe Leu Asn Gln Gly Gly Ile<br>105                110                  115 | | 450 |
| tgt cca ttg acc acc aga aat gat gac atg gat aga ctt cta ccc cgt<br>Cys Pro Leu Thr Thr Arg Asn Asp Asp Met Asp Arg Leu Leu Pro Arg<br>    120                    125                  130 | | 498 |
| ctc cac agt tca cac aca aca cct tct gcg gat agg aaa gtt ttg ttg<br>Leu His Ser Ser His Thr Thr Pro Ser Ala Asp Arg Lys Val Leu Leu<br>135                140                  145                  150 | | 546 |
| acc act ttt cac aga aga tac tgattaaaaa tgaagttaa gaaatttgtt<br>Thr Thr Phe His Arg Arg Tyr<br>               155 | | 597 |
| gaagtcatgt ggtgttttt atacattctt tattaatcga tattcctaac gaacgatacg | | 657 |
| ataactttcg ataacttttt ctggttaatt ttgacaaaat atgcatttgc aagcataaca | | 717 |
| ttcattttca aggcaaacgc tttctgatga ttatcttgtt aaaagtgtgg aaacaagcgt | | 777 |
| agtgttaaca aatgcattgc ttgttttgat tatttattta tctattatat attccatatt | | 837 |
| gtattgtagg tggtgtactt ggtattacta atacacgtac tttgtgaaaa aaaaaaaaaa | | 897 |

<210> SEQ ID NO 18
<211> LENGTH: 157
<212> TYPE: PRT
<213> ORGANISM: Ctenocephalides felis

<400> SEQUENCE: 18

Met Val Tyr Glu Ser Asp Phe Tyr Thr Thr Arg Arg Pro Tyr Ser Arg
1               5                   10                  15

Pro Ala Leu Ser Ser Tyr Ser Val Thr Ala Arg Pro Glu Pro Val Pro
                20                  25                  30

Trp Asp Lys Leu Pro Phe Val Pro Arg Pro Ser Leu Val Ala Asp Pro
            35                  40                  45

Ile Thr Ala Phe Cys Lys Arg Lys Pro Arg Arg Glu Glu Val Val Gln
50                  55                  60

Lys Glu Ser Ile Val Arg Arg Ile Asn Ser Ala Gly Ile Lys Pro Ser
65                  70                  75                  80

Gln Arg Val Leu Ser Ala Pro Ile Arg Glu Tyr Glu Ser Pro Arg Asp
                85                  90                  95

Gln Thr Arg Arg Lys Val Leu Glu Ser Val Arg Gln Glu Ala Phe
                100                 105                 110

Leu Asn Gln Gly Gly Ile Cys Pro Leu Thr Thr Arg Asn Asp Asp Met
            115                 120                 125

Asp Arg Leu Leu Pro Arg Leu His Ser Ser His Thr Thr Pro Ser Ala
130                 135                 140

Asp Arg Lys Val Leu Leu Thr Thr Phe His Arg Arg Tyr
145                 150                 155

<210> SEQ ID NO 19
<211> LENGTH: 471
<212> TYPE: DNA
<213> ORGANISM: Ctenocephalides felis

<400> SEQUENCE: 19
atggtttacg aaagtgactt ttacacgacc cgtcggccct acagtcgtcc ggctttgtct       60
tcatactccg taacggcacg tccagagccg gttccttggg acaaattgcc gttcgtcccc      120
cgtccaagtt tggtagcaga tcccataaca gcattttgca agcgaaaacc tcgccgagaa      180
gaagttgttc aaaaagagtc cattgttcga aggatcaatt ctgcaggaat taaacccagc      240
cagagagttt tatcggctcc aataagagaa tacgaatccc caaggaccag accaggcgt       300 aaagttttgg aaagcgtcag aagacaagaa gcttttctga accaaggagg aatttgtcca      360
ttgaccacca gaaatgatga catggataga cttctacccc gtctccacag ttcacacaca      420
acaccttctg cggataggaa agtttttgttg accactttttc acagaagata c             471

<210> SEQ ID NO 20
<211> LENGTH: 2706
<212> TYPE: DNA
<213> ORGANISM: Ctenocephalides felis
<220> FEATURE:
<221> NAME/KEY: CDS
<222> LOCATION: (5)..(2704)

<400> SEQUENCE: 20 gcgg atg aag agc atc gag gct tat aca aac aga tat gaa atc ata gct      49
     Met Lys Ser Ile Glu Ala Tyr Thr Asn Arg Tyr Glu Ile Ile Ala
     1               5                   10                  15 tct gaa ata gtt aat ctt cga atg aaa cca gat gat ttt aat tta ata       97
Ser Glu Ile Val Asn Leu Arg Met Lys Pro Asp Asp Phe Asn Leu Ile
                20                  25                  30

```
aaa gtt att ggt cga gga gca ttt ggt gaa gta cag tta gtg cga cac      145
Lys Val Ile Gly Arg Gly Ala Phe Gly Glu Val Gln Leu Val Arg His
         35                  40                  45 aaa tca act gca caa gtt ttt gct atg aaa cgc cta tca aaa ttt gaa      193
Lys Ser Thr Ala Gln Val Phe Ala Met Lys Arg Leu Ser Lys Phe Glu
 50                  55                  60 atg att aag aga cca gac tct gca ttt ttt tgg gaa gaa cgt cat ata      241
Met Ile Lys Arg Pro Asp Ser Ala Phe Phe Trp Glu Glu Arg His Ile
 65                  70                  75 atg gct cat gca aaa tca gaa tgg att gta caa tta cat ttt gct ttt      289
Met Ala His Ala Lys Ser Glu Trp Ile Val Gln Leu His Phe Ala Phe
 80                  85                  90                  95 caa gat caa aaa tat ctt tat atg gtc atg gat tat atg ccg ggg ggt      337
Gln Asp Gln Lys Tyr Leu Tyr Met Val Met Asp Tyr Met Pro Gly Gly
                100                 105                 110 gac ttg gtg agt ctt atg tcc gat tat gaa att cca gaa aaa tgg gca      385
Asp Leu Val Ser Leu Met Ser Asp Tyr Glu Ile Pro Glu Lys Trp Ala
            115                 120                 125 atg ttc tat aca atg gaa gtg gtg cta gca ctt gat aca att cac tcc      433
Met Phe Tyr Thr Met Glu Val Val Leu Ala Leu Asp Thr Ile His Ser
        130                 135                 140 atg gga ttt gta cat cgt gat gtt aaa cct gat aat atg ctt cta gac      481
Met Gly Phe Val His Arg Asp Val Lys Pro Asp Asn Met Leu Leu Asp
    145                 150                 155 aaa tat ggt cat tta aag tta gct gac ttt gga acc tgt atg aaa atg      529
Lys Tyr Gly His Leu Lys Leu Ala Asp Phe Gly Thr Cys Met Lys Met
160                 165                 170                 175 gat aca gat ggt ttg gta cgt tct aat aat gct gtt gga acg cct gat      577
Asp Thr Asp Gly Leu Val Arg Ser Asn Asn Ala Val Gly Thr Pro Asp
                180                 185                 190 tac att tct ccc gaa gtt ttg cag tcc caa ggt ggt gaa gga gtt tac      625
Tyr Ile Ser Pro Glu Val Leu Gln Ser Gln Gly Gly Glu Gly Val Tyr
            195                 200                 205 ggt cgt gaa tgc gat tgg tgg tct gtg gga att ttt ttg tat gaa atg      673
Gly Arg Glu Cys Asp Trp Trp Ser Val Gly Ile Phe Leu Tyr Glu Met
        210                 215                 220 tta ttt gga gaa aca cct ttt tat gca gac agt ttg gtt gga act tac      721
Leu Phe Gly Glu Thr Pro Phe Tyr Ala Asp Ser Leu Val Gly Thr Tyr
225                 230                 235 agt aaa att atg gat cac aga aac tca tta act ttt cct cca gaa gtg      769
Ser Lys Ile Met Asp His Arg Asn Ser Leu Thr Phe Pro Pro Glu Val
240                 245                 250                 255 gaa ata agc caa tat gcc cga tct ttg ata caa gga ttt tta aca gac      817
Glu Ile Ser Gln Tyr Ala Arg Ser Leu Ile Gln Gly Phe Leu Thr Asp
                260                 265                 270 aga aca cag cgt tta ggc aga aat gaa gtg gaa gaa att aaa cga cat      865
Arg Thr Gln Arg Leu Gly Arg Asn Glu Val Glu Glu Ile Lys Arg His
            275                 280                 285 cca ttt ttc ata aat gat caa tgg act ttt gac aat tta aga gac tct      913
Pro Phe Phe Ile Asn Asp Gln Trp Thr Phe Asp Asn Leu Arg Asp Ser
        290                 295                 300 gcc cca cct gta gtg cca gag ctg agt ggt gat gat gat aca agg aac      961
Ala Pro Pro Val Val Pro Glu Leu Ser Gly Asp Asp Asp Thr Arg Asn
305                 310                 315 ttt gat gat att gaa cgt gat gaa aca cct gaa gag aat ttt cct ata     1009
Phe Asp Asp Ile Glu Arg Asp Glu Thr Pro Glu Glu Asn Phe Pro Ile
320                 325                 330                 335 cca aaa act ttt gct ggt aat cat ctg cca ttt gtt gga ttc aca tat     1057
Pro Lys Thr Phe Ala Gly Asn His Leu Pro Phe Val Gly Phe Thr Tyr
```

```
                    340                 345                 350
aat ggt gat tac caa tta tta aca aat gga ggt gtt aga aat agt gat      1105
Asn Gly Asp Tyr Gln Leu Leu Thr Asn Gly Gly Val Arg Asn Ser Asp
            355                 360                 365 atg gtt gat aca aaa tta aac aac att tgt gtt tca agt aag gat gat      1153
Met Val Asp Thr Lys Leu Asn Asn Ile Cys Val Ser Ser Lys Asp Asp
            370                 375                 380 gtg tta aat tta caa aat tta tta gaa caa gag aaa ggt aac agt gaa      1201
Val Leu Asn Leu Gln Asn Leu Leu Glu Gln Glu Lys Gly Asn Ser Glu
385                 390                 395 aat ttg aaa aca aac acc caa tta tta agt aat aaa tta gat gaa cta      1249
Asn Leu Lys Thr Asn Thr Gln Leu Leu Ser Asn Lys Leu Asp Glu Leu
400                 405                 410                 415 ggt cag aga gaa tgt gaa tta agg aat cag gct gga gat tat gag aaa      1297
Gly Gln Arg Glu Cys Glu Leu Arg Asn Gln Ala Gly Asp Tyr Glu Lys
            420                 425                 430 gaa ttg act aaa ttc aaa tta tcg tgc aaa gaa tta caa cgt aag gca      1345
Glu Leu Thr Lys Phe Lys Leu Ser Cys Lys Glu Leu Gln Arg Lys Ala
            435                 440                 445 gaa ttt gag aat gaa tta cgg cgt aaa act gag tcc tta cta gtt gaa      1393
Glu Phe Glu Asn Glu Leu Arg Arg Lys Thr Glu Ser Leu Leu Val Glu
            450                 455                 460 aca aag aaa aga cta gac gaa gag cag aat aaa aga act aga gaa atg      1441
Thr Lys Lys Arg Leu Asp Glu Glu Gln Asn Lys Arg Thr Arg Glu Met
465                 470                 475 aat aat aat caa cag cac aat gac aaa ata aat atg tta gaa aaa caa      1489
Asn Asn Asn Gln Gln His Asn Asp Lys Ile Asn Met Leu Glu Lys Gln
480                 485                 490                 495 att aat gat tta caa gaa aaa ttg aaa ggt gaa tta gag cac aat cag      1537
Ile Asn Asp Leu Gln Glu Lys Leu Lys Gly Glu Leu Glu His Asn Gln
            500                 505                 510 aaa tta aag aag caa gct gtt gag ctt aga gtt gct cag tct gct act      1585
Lys Leu Lys Lys Gln Ala Val Glu Leu Arg Val Ala Gln Ser Ala Thr
            515                 520                 525 gaa caa ctg aat aat gaa tta cag gaa act atg cag ggt tta caa aca      1633
Glu Gln Leu Asn Asn Glu Leu Gln Glu Thr Met Gln Gly Leu Gln Thr
            530                 535                 540 caa aga gat gct tta caa caa gaa gta gca tct ctc caa ggc aaa ctt      1681
Gln Arg Asp Ala Leu Gln Gln Glu Val Ala Ser Leu Gln Gly Lys Leu
545                 550                 555 tct caa gag agg agc tct aga tca cag gct tct gat atg cag ata gaa      1729
Ser Gln Glu Arg Ser Ser Arg Ser Gln Ala Ser Asp Met Gln Ile Glu
560                 565                 570                 575 cta gaa gca aaa ttg cag gct ctc cat att gaa ctg gag cat gtc aga      1777
Leu Glu Ala Lys Leu Gln Ala Leu His Ile Glu Leu Glu His Val Arg
            580                 585                 590 aat tgt gaa gac aaa gtt acc caa gac aac aga caa cta ttg gaa agg      1825
Asn Cys Glu Asp Lys Val Thr Gln Asp Asn Arg Gln Leu Leu Glu Arg
            595                 600                 605 ata tca aca ttg gag aaa gaa tgt gct tct cta gaa tta gaa ttg aaa      1873
Ile Ser Thr Leu Glu Lys Glu Cys Ala Ser Leu Glu Leu Glu Leu Lys
            610                 615                 620 gca aca caa aac aaa tat gag caa gag gtc aaa gca cat cgc gaa act      1921
Ala Thr Gln Asn Lys Tyr Glu Gln Glu Val Lys Ala His Arg Glu Thr
            625                 630                 635 gaa aaa tca aga ctg gtc agt aaa gaa gaa gca aat atg gag gaa gtt      1969
Glu Lys Ser Arg Leu Val Ser Lys Glu Glu Ala Asn Met Glu Glu Val
640                 645                 650                 655 aaa gca ctc caa ata aaa tta aat gaa gag aaa tct gct cga cag aaa      2017
```

-continued

```
                                                                    2065
Lys Ala Leu Gln Ile Lys Leu Asn Glu Glu Lys Ser Ala Arg Gln Lys
                660                 665                 670
tct gat cag aat tct caa gaa aag gaa cga caa att tct atg tta tct    2065
Ser Asp Gln Asn Ser Gln Glu Lys Glu Arg Gln Ile Ser Met Leu Ser
            675                 680                 685
gtg gat tat cgt caa atc caa cag cgt ttg caa aag cta gaa gga gaa    2113
Val Asp Tyr Arg Gln Ile Gln Gln Arg Leu Gln Lys Leu Glu Gly Glu
        690                 695                 700
tat agg caa gag agt gaa aaa gtt aaa gct ctc cac agt cag att gag    2161
Tyr Arg Gln Glu Ser Glu Lys Val Lys Ala Leu His Ser Gln Ile Glu
    705                 710                 715
caa gag caa cta aaa aaa tca caa tta caa agc gaa ttg ggt gtt caa    2209
Gln Glu Gln Leu Lys Lys Ser Gln Leu Gln Ser Glu Leu Gly Val Gln
720                 725                 730                 735
agg tct cag act gca cat tta aca gcc agg gaa gct cag cta gtt gga    2257
Arg Ser Gln Thr Ala His Leu Thr Ala Arg Glu Ala Gln Leu Val Gly
                740                 745                 750
gaa gtt gct cat ctt aga gat gct aaa aga aat gtt gaa gaa gag tta    2305
Glu Val Ala His Leu Arg Asp Ala Lys Arg Asn Val Glu Glu Glu Leu
            755                 760                 765
cac aag tta aaa act gct cga tca gtg gat aat gct cag atg aaa gag    2353
His Lys Leu Lys Thr Ala Arg Ser Val Asp Asn Ala Gln Met Lys Glu
        770                 775                 780
ctt caa gaa caa gtt gaa gcc gag caa gtt ttc tcg act ctt tat aaa    2401
Leu Gln Glu Gln Val Glu Ala Glu Gln Val Phe Ser Thr Leu Tyr Lys
    785                 790                 795
aca cat tct aat gaa ctt aag gaa gaa ctt gag gaa aaa tct cgt cat    2449
Thr His Ser Asn Glu Leu Lys Glu Glu Leu Glu Glu Lys Ser Arg His
800                 805                 810                 815
att caa gaa atg gaa gaa gaa aga gaa agt ttg gtt cat cag cta caa    2497
Ile Gln Glu Met Glu Glu Glu Arg Glu Ser Leu Val His Gln Leu Gln
                820                 825                 830
att gca tta gct aga gct gat tca gag gca ttg gcg aga tca ata gct    2545
Ile Ala Leu Ala Arg Ala Asp Ser Glu Ala Leu Ala Arg Ser Ile Ala
            835                 840                 845
gat gaa agt ata gct gat tta gaa aag gaa aag act atg aag gaa tta    2593
Asp Glu Ser Ile Ala Asp Leu Glu Lys Glu Lys Thr Met Lys Glu Leu
        850                 855                 860
gaa cta aaa gaa tta tta aac aaa aat cgt act gaa ctt tcc cag aaa    2641
Glu Leu Lys Glu Leu Leu Asn Lys Asn Arg Thr Glu Leu Ser Gln Lys
    865                 870                 875
gac att tca ata agt gca ttg cgt gaa cga gaa aat gaa cag aag aaa    2689
Asp Ile Ser Ile Ser Ala Leu Arg Glu Arg Glu Asn Glu Gln Lys Lys
880                 885                 890                 895
ctt tta gaa caa atc tc                                             2706
Leu Leu Glu Gln Ile
                900

<210> SEQ ID NO 21
<211> LENGTH: 900
<212> TYPE: PRT
<213> ORGANISM: Ctenocephalides felis

<400> SEQUENCE: 21

Met Lys Ser Ile Glu Ala Tyr Thr Asn Arg Tyr Glu Ile Ile Ala Ser
1               5                   10                  15

Glu Ile Val Asn Leu Arg Met Lys Pro Asp Asp Phe Asn Leu Ile Lys
            20                  25                  30

Val Ile Gly Arg Gly Ala Phe Gly Glu Val Gln Leu Val Arg His Lys
        35                  40                  45
```

```
Ser Thr Ala Gln Val Phe Ala Met Lys Arg Leu Ser Lys Phe Glu Met
 50                  55                  60

Ile Lys Arg Pro Asp Ser Ala Phe Phe Trp Glu Glu Arg His Ile Met
 65                  70                  75                  80

Ala His Ala Lys Ser Glu Trp Ile Val Gln Leu His Phe Ala Phe Gln
                 85                  90                  95

Asp Gln Lys Tyr Leu Tyr Met Val Met Asp Tyr Met Pro Gly Gly Asp
                100                 105                 110

Leu Val Ser Leu Met Ser Asp Tyr Glu Ile Pro Glu Lys Trp Ala Met
                115                 120                 125

Phe Tyr Thr Met Glu Val Val Leu Ala Leu Asp Thr Ile His Ser Met
130                 135                 140

Gly Phe Val His Arg Asp Val Lys Pro Asp Asn Met Leu Leu Asp Lys
145                 150                 155                 160

Tyr Gly His Leu Lys Leu Ala Asp Phe Gly Thr Cys Met Lys Met Asp
                165                 170                 175

Thr Asp Gly Leu Val Arg Ser Asn Asn Ala Val Gly Thr Pro Asp Tyr
                180                 185                 190

Ile Ser Pro Glu Val Leu Gln Ser Gln Gly Gly Glu Gly Val Tyr Gly
                195                 200                 205

Arg Glu Cys Asp Trp Trp Ser Val Gly Ile Phe Leu Tyr Glu Met Leu
210                 215                 220

Phe Gly Glu Thr Pro Phe Tyr Ala Asp Ser Leu Val Gly Thr Tyr Ser
225                 230                 235                 240

Lys Ile Met Asp His Arg Asn Ser Leu Thr Phe Pro Pro Glu Val Glu
                245                 250                 255

Ile Ser Gln Tyr Ala Arg Ser Leu Ile Gln Gly Phe Leu Thr Asp Arg
                260                 265                 270

Thr Gln Arg Leu Gly Arg Asn Glu Val Glu Ile Lys Arg His Pro
                275                 280                 285

Phe Phe Ile Asn Asp Gln Trp Thr Phe Asp Asn Leu Arg Asp Ser Ala
                290                 295                 300

Pro Pro Val Val Pro Glu Leu Ser Gly Asp Asp Thr Arg Asn Phe
305                 310                 315                 320

Asp Asp Ile Glu Arg Asp Glu Thr Pro Glu Glu Asn Phe Pro Ile Pro
                325                 330                 335

Lys Thr Phe Ala Gly Asn His Leu Pro Phe Val Gly Phe Thr Tyr Asn
                340                 345                 350

Gly Asp Tyr Gln Leu Leu Thr Asn Gly Gly Val Arg Asn Ser Asp Met
                355                 360                 365

Val Asp Thr Lys Leu Asn Asn Ile Cys Val Ser Ser Lys Asp Asp Val
370                 375                 380

Leu Asn Leu Gln Asn Leu Leu Glu Gln Glu Lys Gly Asn Ser Glu Asn
385                 390                 395                 400

Leu Lys Thr Asn Thr Gln Leu Leu Ser Asn Lys Leu Asp Glu Leu Gly
                405                 410                 415

Gln Arg Glu Cys Glu Leu Arg Asn Gln Ala Gly Asp Tyr Glu Lys Glu
                420                 425                 430

Leu Thr Lys Phe Lys Leu Ser Cys Lys Glu Leu Gln Arg Lys Ala Glu
                435                 440                 445

Phe Glu Asn Glu Leu Arg Arg Lys Thr Glu Ser Leu Leu Val Glu Thr
450                 455                 460
```

-continued

```
Lys Lys Arg Leu Asp Glu Glu Gln Asn Lys Arg Thr Arg Glu Met Asn
465                 470                 475                 480

Asn Asn Gln Gln His Asn Asp Lys Ile Asn Met Leu Glu Lys Gln Ile
            485                 490                 495

Asn Asp Leu Gln Glu Lys Leu Lys Gly Glu Leu Glu His Asn Gln Lys
        500                 505                 510

Leu Lys Lys Gln Ala Val Glu Leu Arg Val Ala Gln Ser Ala Thr Glu
    515                 520                 525

Gln Leu Asn Asn Glu Leu Gln Glu Thr Met Gln Gly Leu Gln Thr Gln
530                 535                 540

Arg Asp Ala Leu Gln Gln Glu Val Ala Ser Leu Gln Gly Lys Leu Ser
545                 550                 555                 560

Gln Glu Arg Ser Ser Arg Ser Gln Ala Ser Asp Met Gln Ile Glu Leu
            565                 570                 575

Glu Ala Lys Leu Gln Ala Leu His Ile Glu Leu Glu His Val Arg Asn
        580                 585                 590

Cys Glu Asp Lys Val Thr Gln Asp Asn Arg Gln Leu Leu Glu Arg Ile
    595                 600                 605

Ser Thr Leu Glu Lys Glu Cys Ala Ser Leu Glu Leu Glu Leu Lys Ala
610                 615                 620

Thr Gln Asn Lys Tyr Glu Gln Glu Val Lys Ala His Arg Glu Thr Glu
625                 630                 635                 640

Lys Ser Arg Leu Val Ser Lys Glu Glu Ala Asn Met Glu Glu Val Lys
            645                 650                 655

Ala Leu Gln Ile Lys Leu Asn Glu Glu Lys Ser Ala Arg Gln Lys Ser
        660                 665                 670

Asp Gln Asn Ser Gln Glu Lys Glu Arg Gln Ile Ser Met Leu Ser Val
    675                 680                 685

Asp Tyr Arg Gln Ile Gln Gln Arg Leu Gln Lys Leu Glu Gly Glu Tyr
690                 695                 700

Arg Gln Glu Ser Glu Lys Val Lys Ala Leu His Ser Gln Ile Glu Gln
705                 710                 715                 720

Glu Gln Leu Lys Lys Ser Gln Leu Gln Ser Glu Leu Gly Val Gln Arg
            725                 730                 735

Ser Gln Thr Ala His Leu Thr Ala Arg Glu Ala Gln Leu Val Gly Glu
        740                 745                 750

Val Ala His Leu Arg Asp Ala Lys Arg Asn Val Glu Glu Leu His
    755                 760                 765

Lys Leu Lys Thr Ala Arg Ser Val Asp Asn Ala Gln Met Lys Glu Leu
770                 775                 780

Gln Glu Gln Val Glu Ala Glu Gln Val Phe Ser Thr Leu Tyr Lys Thr
785                 790                 795                 800

His Ser Asn Glu Leu Lys Glu Glu Leu Glu Glu Lys Ser Arg His Ile
            805                 810                 815

Gln Glu Met Glu Glu Glu Arg Glu Ser Leu Val His Gln Leu Gln Ile
        820                 825                 830

Ala Leu Ala Arg Ala Asp Ser Glu Ala Leu Ala Arg Ser Ile Ala Asp
    835                 840                 845

Glu Ser Ile Ala Asp Leu Glu Lys Glu Lys Thr Met Lys Glu Leu Glu
    850                 855                 860

Leu Lys Glu Leu Leu Asn Lys Asn Arg Thr Glu Leu Ser Gln Lys Asp
865                 870                 875                 880

Ile Ser Ile Ser Ala Leu Arg Glu Arg Glu Asn Glu Gln Lys Lys Leu
```

Leu Glu Gln Ile
        900

<210> SEQ ID NO 22
<211> LENGTH: 414
<212> TYPE: DNA
<213> ORGANISM: Ctenocephalides felis
<220> FEATURE:
<221> NAME/KEY: CDS
<222> LOCATION: (3)..(413)

<400> SEQUENCE: 22

```
ga gct gat gag aat gga aat gtg att agc att act gat gaa aat gga        47
   Ala Asp Glu Asn Gly Asn Val Ile Ser Ile Thr Asp Glu Asn Gly
   1               5                  10                  15 aac att att agt act act gat gag aat gga aat gtg att agc att act       95
Asn Ile Ile Ser Thr Thr Asp Glu Asn Gly Asn Val Ile Ser Ile Thr
                20                  25                  30 gat gag aat gga aac att att agt act act gat gag aat gga aat gtg      143
Asp Glu Asn Gly Asn Ile Ile Ser Thr Thr Asp Glu Asn Gly Asn Val
            35                  40                  45 att agc att act gat gaa aat gga aac att att agt act act gat gag      191
Ile Ser Ile Thr Asp Glu Asn Gly Asn Ile Ile Ser Thr Thr Asp Glu
        50                  55                  60 aat gga aat gtg att agc att act gat gag aat gga aat gtg att agc      239
Asn Gly Asn Val Ile Ser Ile Thr Asp Glu Asn Gly Asn Val Ile Ser
65                  70                  75 att act gat gaa aat gga aac tcg aat agc act act agt gtt ttc aat      287
Ile Thr Asp Glu Asn Gly Asn Ser Asn Ser Thr Thr Ser Val Phe Asn
80                  85                  90                  95 gaa act gaa aat atg act ggt gct gct gat aca aat gaa tat tca att      335
Glu Thr Glu Asn Met Thr Gly Ala Ala Asp Thr Asn Glu Tyr Ser Ile
                100                 105                 110 ggt tct act gac gga aat gga aat ttt ata agt act ttt agt gat cat      383
Gly Ser Thr Asp Gly Asn Gly Asn Phe Ile Ser Thr Phe Ser Asp His
            115                 120                 125 gat tac gta agt aat act gaa gaa aat gaa a                            414
Asp Tyr Val Ser Asn Thr Glu Glu Asn Glu
        130                 135
```

<210> SEQ ID NO 23
<211> LENGTH: 137
<212> TYPE: PRT
<213> ORGANISM: Ctenocephalides felis

<400> SEQUENCE: 23

Ala Asp Glu Asn Gly Asn Val Ile Ser Ile Thr Asp Glu Asn Gly Asn
1               5                  10                  15

Ile Ile Ser Thr Thr Asp Glu Asn Gly Asn Val Ile Ser Ile Thr Asp
            20                  25                  30

Glu Asn Gly Asn Ile Ile Ser Thr Thr Asp Glu Asn Gly Asn Val Ile
        35                  40                  45

Ser Ile Thr Asp Glu Asn Gly Asn Ile Ile Ser Thr Thr Asp Glu Asn
    50                  55                  60

Gly Asn Val Ile Ser Ile Thr Asp Glu Asn Gly Asn Val Ile Ser Ile
65                  70                  75                  80

Thr Asp Glu Asn Gly Asn Ser Asn Ser Thr Thr Ser Val Phe Asn Glu
                85                  90                  95

Thr Glu Asn Met Thr Gly Ala Ala Asp Thr Asn Glu Tyr Ser Ile Gly

```
                    100                 105                 110
Ser Thr Asp Gly Asn Gly Asn Phe Ile Ser Thr Phe Ser Asp His Asp
    115                 120                 125

Tyr Val Ser Asn Thr Glu Glu Asn Glu
    130                 135

<210> SEQ ID NO 24
<211> LENGTH: 273
<212> TYPE: DNA
<213> ORGANISM: Ctenocephalides felis
<220> FEATURE:
<221> NAME/KEY: CDS
<222> LOCATION: (3)..(272)

<400> SEQUENCE: 24 at gag aat gga aat gtg att agc tat act gat gaa aat gga aac att       47
   Glu Asn Gly Asn Val Ile Ser Tyr Thr Asp Glu Asn Gly Asn Ile
   1               5                   10                  15 atc agt act act gat gag aat gga aat gtg att agc att act gat gaa      95
Ile Ser Thr Thr Asp Glu Asn Gly Asn Val Ile Ser Ile Thr Asp Glu
                20                  25                  30 aat gga aat gtg att agc att act gat gaa aat gga aac att atc agt     143
Asn Gly Asn Val Ile Ser Ile Thr Asp Glu Asn Gly Asn Ile Ile Ser
            35                  40                  45 act act gat gag aat gga aat gtg att agc att act gat gaa aat gga     191
Thr Thr Asp Glu Asn Gly Asn Val Ile Ser Ile Thr Asp Glu Asn Gly
        50                  55                  60 aat gtg att agc att act gat gaa aat gga aac att att agt act act     239
Asn Val Ile Ser Ile Thr Asp Glu Asn Gly Asn Ile Ile Ser Thr Thr
65                  70                  75 gat gag aat gga aat gtg att agc aat act cga g                       273
Asp Glu Asn Gly Asn Val Ile Ser Asn Thr Arg
80                  85                  90

<210> SEQ ID NO 25
<211> LENGTH: 90
<212> TYPE: PRT
<213> ORGANISM: Ctenocephalides felis

<400> SEQUENCE: 25

Glu Asn Gly Asn Val Ile Ser Tyr Thr Asp Glu Asn Gly Asn Ile Ile
1               5                   10                  15

Ser Thr Thr Asp Glu Asn Gly Asn Val Ile Ser Ile Thr Asp Glu Asn
            20                  25                  30

Gly Asn Val Ile Ser Ile Thr Asp Glu Asn Gly Asn Ile Ile Ser Thr
        35                  40                  45

Thr Asp Glu Asn Gly Asn Val Ile Ser Ile Thr Asp Glu Asn Gly Asn
    50                  55                  60

Val Ile Ser Ile Thr Asp Glu Asn Gly Asn Ile Ile Ser Thr Thr Asp
65                  70                  75                  80

Glu Asn Gly Asn Val Ile Ser Asn Thr Arg
                85                  90

<210> SEQ ID NO 26
<211> LENGTH: 1704
<212> TYPE: DNA
<213> ORGANISM: Ctenocephalides felis
<220> FEATURE:
<221> NAME/KEY: CDS
<222> LOCATION: (24)..(1406)

<400> SEQUENCE: 26
```

```
cagaaacccg acattctcaa aat atg gaa cct caa tcg ctg tct tgg caa ctt      53
                      Met Glu Pro Gln Ser Leu Ser Trp Gln Leu
                       1               5                  10 ccg act caa gta gtt cag cca gtt ttt gaa caa caa atg cag att cct     101
Pro Thr Gln Val Val Gln Pro Val Phe Glu Gln Gln Met Gln Ile Pro
             15                  20                  25 gga tat aat atg caa att caa tct aat tat tat caa att cac cca gaa     149
Gly Tyr Asn Met Gln Ile Gln Ser Asn Tyr Tyr Gln Ile His Pro Glu
             30                  35                  40 atg ttg gat cca aat ttg aac aat cct cag cag tta atg ttt aat tat     197
Met Leu Asp Pro Asn Leu Asn Asn Pro Gln Gln Leu Met Phe Asn Tyr
             45                  50                  55 atg caa tta caa caa ttg cag gaa cta caa cat tta agt caa caa cag     245
Met Gln Leu Gln Gln Leu Gln Glu Leu Gln His Leu Ser Gln Gln Gln
             60                  65                  70 cca atg cat cat gaa ttt gaa cat cat atc ccc att cca caa gaa gca     293
Pro Met His His Glu Phe Glu His His Ile Pro Ile Pro Gln Glu Ala
75                  80                  85                  90 act tca act aat tac ggt cca tcc gga cag tat att act agt gac gca     341
Thr Ser Thr Asn Tyr Gly Pro Ser Gly Gln Tyr Ile Thr Ser Asp Ala
             95                 100                 105 aca tct tat caa tca att gcc caa caa ttt gta cca caa cca cca att     389
Thr Ser Tyr Gln Ser Ile Ala Gln Gln Phe Val Pro Gln Pro Pro Ile
            110                 115                 120 gaa act acc acc acg aaa ata cct gaa act gaa att caa att ggc gtt     437
Glu Thr Thr Thr Thr Lys Ile Pro Glu Thr Glu Ile Gln Ile Gly Val
            125                 130                 135 tcg aat caa tat gcc caa aat ata act tat aat tca aat atc agt cct     485
Ser Asn Gln Tyr Ala Gln Asn Ile Thr Tyr Asn Ser Asn Ile Ser Pro
        140                 145                 150 gaa gtg att gga ttc cga gaa cat tat gtt gcg gaa cag cct tct ggt     533
Glu Val Ile Gly Phe Arg Glu His Tyr Val Ala Glu Gln Pro Ser Gly
155                 160                 165                 170 gac gtg ctt cac aaa agt cat tta aca gaa caa cca gca gat aaa agc     581
Asp Val Leu His Lys Ser His Leu Thr Glu Gln Pro Ala Asp Lys Ser
            175                 180                 185 aca cgt ggt gat cag gaa cct gtt agt gag aca ggc tct ggt ttt tcg     629
Thr Arg Gly Asp Gln Glu Pro Val Ser Glu Thr Gly Ser Gly Phe Ser
            190                 195                 200 tat gca caa att tta tca cag gga ctt aag cct acc cag cca tcc aac     677
Tyr Ala Gln Ile Leu Ser Gln Gly Leu Lys Pro Thr Gln Pro Ser Asn
            205                 210                 215 tca gtt aat ttg ctt gca gat cga tcg aga tca cct cta gat acg aaa     725
Ser Val Asn Leu Leu Ala Asp Arg Ser Arg Ser Pro Leu Asp Thr Lys
        220                 225                 230 acg aaa gaa aat tat aaa tct cct ggt cgt gtg cag gat atc acg aaa     773
Thr Lys Glu Asn Tyr Lys Ser Pro Gly Arg Val Gln Asp Ile Thr Lys
235                 240                 245                 250 ata ata gat gag aaa caa aag tcg tca aaa gac aca gag tgg cat aat     821
Ile Ile Asp Glu Lys Gln Lys Ser Ser Lys Asp Thr Glu Trp His Asn
            255                 260                 265 aag aaa gtg aaa gaa cat aaa aaa gtg aaa gat atc aaa cct gat ttc     869
Lys Lys Val Lys Glu His Lys Lys Val Lys Asp Ile Lys Pro Asp Phe
            270                 275                 280 gaa tct tct caa agg aat aag aaa agc aag aat att cct aag caa att     917
Glu Ser Ser Gln Arg Asn Lys Lys Ser Lys Asn Ile Pro Lys Gln Ile
            285                 290                 295 gaa aat atc aca cct caa ctt gac agc tta cga tca cga gat ata gta     965
Glu Asn Ile Thr Pro Gln Leu Asp Ser Leu Arg Ser Arg Asp Ile Val
```

-continued

```
                300                 305                 310
att aag gga gaa tta cta aca aaa gat act aca aaa agt tta act act    1013
Ile Lys Gly Glu Leu Leu Thr Lys Asp Thr Thr Lys Ser Leu Thr Thr
315                 320                 325                 330 gtt aat gtt gat agt gaa tta gat agt gta aaa cct aaa gat gaa aaa    1061
Val Asn Val Asp Ser Glu Leu Asp Ser Val Lys Pro Lys Asp Glu Lys
                335                 340                 345 cct gaa cct tct gaa cct agt aaa acg ttt att gat act tca gtt gca    1109
Pro Glu Pro Ser Glu Pro Ser Lys Thr Phe Ile Asp Thr Ser Val Ala
            350                 355                 360 aag gat gtt gat aat tct aca cag gcg aac cat aaa aag aag aaa agt    1157
Lys Asp Val Asp Asn Ser Thr Gln Ala Asn His Lys Lys Lys Lys Ser
        365                 370                 375 aaa tct aag ccg agg aaa acg gaa ccg gaa gat gaa att gaa aaa gct    1205
Lys Ser Lys Pro Arg Lys Thr Glu Pro Glu Asp Glu Ile Glu Lys Ala
    380                 385                 390 ttg aaa gaa att caa gct agt gag aaa aaa ctt acg aag tct atc gat    1253
Leu Lys Glu Ile Gln Ala Ser Glu Lys Lys Leu Thr Lys Ser Ile Asp
395                 400                 405                 410 aac att gtg aat aaa ttt aat aca cca ctt gct agt gtt aaa gcc gat    1301
Asn Ile Val Asn Lys Phe Asn Thr Pro Leu Ala Ser Val Lys Ala Asp
                415                 420                 425 gat tcc aat tct acc aag gat aat gta cca gca aag aag aaa aaa cct    1349
Asp Ser Asn Ser Thr Lys Asp Asn Val Pro Ala Lys Lys Lys Lys Pro
            430                 435                 440 tcg aag tca tct gtt tct tta cct gag aat gta gta caa aat cta ttg    1397
Ser Lys Ser Ser Val Ser Leu Pro Glu Asn Val Val Gln Asn Leu Leu
        445                 450                 455 ata cta aca taactactag tagcgacaag attgaaaaca tgccgcaacc             1446
Ile Leu Thr
    460 gcaaccaaaa agagaagatt tacaagatgc agctaaggaa gtattgactt caatagagtc   1506 agtaatgatg cagtctgttg agactattcc tattacgaag aaaagagtaa ataagaaaaa   1566 gaataccact caacagacga aggaatttgt ggaacacgaa atatgcgata catcaaaaaa   1626 tgaaacttta aaaatattg aaaagaatc gcatgagaat atggctatat tgcaaacaag    1686 tccgaaaccg ccactaag                                                 1704

<210> SEQ ID NO 27
<211> LENGTH: 461
<212> TYPE: PRT
<213> ORGANISM: Ctenocephalides felis

<400> SEQUENCE: 27

Met Glu Pro Gln Ser Leu Ser Trp Gln Leu Pro Thr Gln Val Val Gln
1               5                   10                  15

Pro Val Phe Glu Gln Gln Met Gln Ile Pro Gly Tyr Asn Met Gln Ile
                20                  25                  30

Gln Ser Asn Tyr Tyr Gln Ile His Pro Glu Met Leu Asp Pro Asn Leu
            35                  40                  45

Asn Asn Pro Gln Gln Leu Met Phe Asn Tyr Met Gln Leu Gln Gln Leu
        50                  55                  60

Gln Glu Leu Gln His Leu Ser Gln Gln Pro Met His His Glu Phe
65                  70                  75                  80

Glu His His Ile Pro Ile Pro Gln Glu Ala Thr Ser Thr Asn Tyr Gly
                85                  90                  95

Pro Ser Gly Gln Tyr Ile Thr Ser Asp Ala Thr Ser Tyr Gln Ser Ile
```

```
        100                 105                 110
Ala Gln Gln Phe Val Pro Gln Pro Pro Ile Glu Thr Thr Thr Lys
        115                 120                 125
Ile Pro Glu Thr Glu Ile Gln Ile Gly Val Ser Asn Gln Tyr Ala Gln
130                 135                 140
Asn Ile Thr Tyr Asn Ser Asn Ile Ser Pro Glu Val Ile Gly Phe Arg
145                 150                 155                 160
Glu His Tyr Val Ala Glu Gln Pro Ser Gly Asp Val Leu His Lys Ser
                165                 170                 175
His Leu Thr Glu Gln Pro Ala Asp Lys Ser Thr Arg Gly Asp Gln Glu
                180                 185                 190
Pro Val Ser Glu Thr Gly Ser Gly Phe Ser Tyr Ala Gln Ile Leu Ser
                195                 200                 205
Gln Gly Leu Lys Pro Thr Gln Pro Ser Asn Ser Val Asn Leu Leu Ala
        210                 215                 220
Asp Arg Ser Arg Ser Pro Leu Asp Thr Lys Thr Lys Glu Asn Tyr Lys
225                 230                 235                 240
Ser Pro Gly Arg Val Gln Asp Ile Thr Lys Ile Ile Asp Glu Lys Gln
                245                 250                 255
Lys Ser Ser Lys Asp Thr Glu Trp His Asn Lys Lys Val Lys Glu His
                260                 265                 270
Lys Lys Val Lys Asp Ile Lys Pro Asp Phe Glu Ser Ser Gln Arg Asn
                275                 280                 285
Lys Lys Ser Lys Asn Ile Pro Lys Gln Ile Glu Asn Ile Thr Pro Gln
        290                 295                 300
Leu Asp Ser Leu Arg Ser Arg Asp Ile Val Ile Lys Gly Glu Leu Leu
305                 310                 315                 320
Thr Lys Asp Thr Thr Lys Ser Leu Thr Thr Val Asn Val Asp Ser Glu
                325                 330                 335
Leu Asp Ser Val Lys Pro Lys Asp Glu Lys Pro Glu Pro Ser Glu Pro
                340                 345                 350
Ser Lys Thr Phe Ile Asp Thr Ser Val Ala Lys Asp Val Asp Asn Ser
                355                 360                 365
Thr Gln Ala Asn His Lys Lys Lys Ser Lys Ser Lys Pro Arg Lys
        370                 375                 380
Thr Glu Pro Glu Asp Glu Ile Glu Lys Ala Leu Lys Glu Ile Gln Ala
385                 390                 395                 400
Ser Glu Lys Lys Leu Thr Lys Ser Ile Asp Asn Ile Val Asn Lys Phe
                405                 410                 415
Asn Thr Pro Leu Ala Ser Val Lys Ala Asp Asp Ser Asn Ser Thr Lys
                420                 425                 430
Asp Asn Val Pro Ala Lys Lys Lys Pro Ser Lys Ser Ser Val Ser
        435                 440                 445
Leu Pro Glu Asn Val Val Gln Asn Leu Leu Ile Leu Thr
450                 455                 460

<210> SEQ ID NO 28
<211> LENGTH: 1383
<212> TYPE: DNA
<213> ORGANISM: Ctenocephalides felis

<400> SEQUENCE: 28
atggaacctc aatcgctgtc ttggcaactt ccgactcaag tagttcagcc agtttttgaa      60
caacaaatgc agattcctgg atataatatg caaattcaat ctaattatta tcaaattcac     120
```

```
ccagaaatgt tggatccaaa tttgaacaat cctcagcagt taatgtttaa ttatatgcaa    180
ttacaacaat tgcaggaact acaacattta agtcaacaac agccaatgca tcatgaattt    240
gaacatcata tccccattcc acaagaagca acttcaacta attacggtcc atccggacag    300
tatattacta gtgacgcaac atcttatcaa tcaattgccc aacaatttgt accacaacca    360
ccaattgaaa ctaccaccac gaaaatacct gaaactgaaa ttcaaattgg cgtttcgaat    420
caatatgccc aaaatataac ttataattca aatatcagtc ctgaagtgat tggattccga    480
gaacattatg ttgcggaaca gccttctggt gacgtgcttc acaaaagtca tttaacagaa    540
caaccagcag ataaaagcac acgtggtgat caggaacctg ttagtgagac aggctctggt    600
ttttcgtatg cacaaatttt atcacaggga cttaagccta cccagccatc caactcagtt    660
aatttgcttg cagatcgatc gagatcacct ctagatacga aaacgaaaga aaattataaa    720
tctcctggtc gtgtgcagga tatcacgaaa ataatagatg agaaacaaaa gtcgtcaaaa    780
gacacagagt ggcataataa gaaagtgaaa gaacataaaa aagtgaaaga tatcaaacct    840
gatttcgaat cttctcaaag gaataagaaa agcaagaata ttcctaagca aattgaaaat    900
atcacacctc aacttgacag cttacgatca cgagatatag taattaaggg agaattacta    960
acaaaagata ctacaaaaag tttaactact gttaatgttg atagtgaatt agatagtgta   1020
aaacctaaag atgaaaaacc tgaaccttct gaacctagta aaacgtttat tgatacttca   1080
gttgcaaagg atgttgataa ttctacacag gcgaaccata aaagaagaa aagtaaatct   1140 aagccgagga aaacggaacc ggaagatgaa attgaaaaag ctttgaaaga aattcaagct   1200
agtgagaaaa aacttacgaa gtctatcgat aacattgtga ataaatttaa tacaccactt   1260
gctagtgtta aagccgatga ttccaattct accaaggata atgtaccagc aaagaagaaa   1320
aaaccttcga agtcatctgt ttctttacct gagaatgtag tacaaaatct attgatacta   1380
aca                                                                 1383

<210> SEQ ID NO 29
<211> LENGTH: 1758
<212> TYPE: DNA
<213> ORGANISM: Ctenocephalides felis
<220> FEATURE:
<221> NAME/KEY: CDS
<222> LOCATION: (1)..(1758)
<221> NAME/KEY: misc_feature
<222> LOCATION: (1136)..()
<223> OTHER INFORMATION: W = A or T/U
<221> NAME/KEY: misc_feature
<222> LOCATION: (379)..()
<223> OTHER INFORMATION: Xaa = Met or Lys

<400> SEQUENCE: 29 cta gag atg gct aaa ttt ctg acg gaa aca tta gac gac atg act cta    48
Leu Glu Met Ala Lys Phe Leu Thr Glu Thr Leu Asp Asp Met Thr Leu
1               5                   10                  15 caa cac aaa gat cac aga tca gaa ttg gct aaa gag ttt tca att tgg    96
Gln His Lys Asp His Arg Ser Glu Leu Ala Lys Glu Phe Ser Ile Trp
            20                  25                  30 ttt acg aaa atg aga cag tct ggc gct caa gcc agt aac gaa gaa atc   144
Phe Thr Lys Met Arg Gln Ser Gly Ala Gln Ala Ser Asn Glu Glu Ile
        35                  40                  45 atg aaa ttt tca aaa ttg ttt gaa gat gaa atc act ctt gac tcg ctg   192
Met Lys Phe Ser Lys Leu Phe Glu Asp Glu Ile Thr Leu Asp Ser Leu
    50                  55                  60 gcg agg ccg caa ctt gtt gct ttg tgc agg gta cta gaa atc agt act   240
```

-continued

```
Ala Arg Pro Gln Leu Val Ala Leu Cys Arg Val Leu Glu Ile Ser Thr
 65              70                  75                  80 tta gga aca aca aat ttc tta agg ttt caa ctg cga atg aaa ctg cgt      288
Leu Gly Thr Thr Asn Phe Leu Arg Phe Gln Leu Arg Met Lys Leu Arg
                 85                  90                  95 tca tta gct gct gat gat aaa atg att caa aaa gaa ggc ata gtt tct      336
Ser Leu Ala Ala Asp Asp Lys Met Ile Gln Lys Glu Gly Ile Val Ser
            100                 105                 110 atg act tat tcg gag gtg caa cag gcc tgc aga gct cgt gga atg cga      384
Met Thr Tyr Ser Glu Val Gln Gln Ala Cys Arg Ala Arg Gly Met Arg
        115                 120                 125 gct tat ggt atg cct gaa cat agg ttg agg agg caa ttg gaa gac tgg      432
Ala Tyr Gly Met Pro Glu His Arg Leu Arg Arg Gln Leu Glu Asp Trp
    130                 135                 140 att aat tta agc ttg aat gaa aag gtt cca cca tca tta ttg ctt ttg      480
Ile Asn Leu Ser Leu Asn Glu Lys Val Pro Pro Ser Leu Leu Leu Leu
145                 150                 155                 160 tca agg gcg ctg atg ttg ccc gag aat gtt cca gtg tct gat aaa ctt      528
Ser Arg Ala Leu Met Leu Pro Glu Asn Val Pro Val Ser Asp Lys Leu
                165                 170                 175 aaa gca aca ata aat gct ctt cct gaa act att gta act cag aca aag      576
Lys Ala Thr Ile Asn Ala Leu Pro Glu Thr Ile Val Thr Gln Thr Lys
            180                 185                 190 gct gct att gga gaa aga gaa gga aag att gac aat aag acc aaa att      624
Ala Ala Ile Gly Glu Arg Glu Gly Lys Ile Asp Asn Lys Thr Lys Ile
        195                 200                 205 gag gtc atc aaa gag gaa gaa cgc aaa att cgc gaa gag cgc caa gaa      672
Glu Val Ile Lys Glu Glu Glu Arg Lys Ile Arg Glu Glu Arg Gln Glu
    210                 215                 220 gca cgt gag gaa gag gaa caa cgc aag caa gcc gaa ctt gct ctt aat      720
Ala Arg Glu Glu Glu Glu Gln Arg Lys Gln Ala Glu Leu Ala Leu Asn
225                 230                 235                 240 gcc agt tct gca gca gct gag gcc tct tca gct cag gaa ctt ttg ata      768
Ala Ser Ser Ala Ala Ala Glu Ala Ser Ser Ala Gln Glu Leu Leu Ile
                245                 250                 255 gat aca gct cct gta ata gat gca gaa aag aca cca aag gtg gca aca      816
Asp Thr Ala Pro Val Ile Asp Ala Glu Lys Thr Pro Lys Val Ala Thr
            260                 265                 270 tca cct gtt gaa tca cca ttg gca cca cca gaa gtt ctg att atg ggt      864
Ser Pro Val Glu Ser Pro Leu Ala Pro Pro Glu Val Leu Ile Met Gly
        275                 280                 285 gct cct aaa aca cct gtt gca acc gaa gtg gat aag aat gct gat gag      912
Ala Pro Lys Thr Pro Val Ala Thr Glu Val Asp Lys Asn Ala Asp Glu
    290                 295                 300 gtg gaa ttc acc aag aaa gat ctt gag gtt gtt gaa gat gca ttg gat      960
Val Glu Phe Thr Lys Lys Asp Leu Glu Val Val Glu Asp Ala Leu Asp
305                 310                 315                 320 aca cta tcg aaa gac aaa aat aat ttg gtg att gaa aag gaa gtt att     1008
Thr Leu Ser Lys Asp Lys Asn Asn Leu Val Ile Glu Lys Glu Val Ile
                325                 330                 335 aaa gac att aag gaa gaa att gct gat tac caa gaa gat gta gaa gaa     1056
Lys Asp Ile Lys Glu Glu Ile Ala Asp Tyr Gln Glu Asp Val Glu Glu
            340                 345                 350 ttg aaa gaa gcc ata gtt gct gct gag aaa cca aag gat gag ata aaa     1104
Leu Lys Glu Ala Ile Val Ala Ala Glu Lys Pro Lys Asp Glu Ile Lys
        355                 360                 365 gaa act aaa gga gct caa cga ttg ttg aag awg gtt aac aag atg ata     1152
Glu Thr Lys Gly Ala Gln Arg Leu Leu Lys Xaa Val Asn Lys Met Ile
    370                 375                 380
```

-continued

```
acg aaa atg gat act gtt gta caa gaa att gaa agc aaa gaa tct gag      1200
Thr Lys Met Asp Thr Val Val Gln Glu Ile Glu Ser Lys Glu Ser Glu
385                 390                 395                 400 aag aaa gcc aaa aca ttg cca ctt gaa gct cct agg agc gct act gaa      1248
Lys Lys Ala Lys Thr Leu Pro Leu Glu Ala Pro Arg Ser Ala Thr Glu
                405                 410                 415 act caa gaa tta gat gta agg aaa gaa aga gga gag att tta att gac      1296
Thr Gln Glu Leu Asp Val Arg Lys Glu Arg Gly Glu Ile Leu Ile Asp
            420                 425                 430 gaa tta atg gac gct att aag aaa gtt aaa aat gtg cca gac gaa aat      1344
Glu Leu Met Asp Ala Ile Lys Lys Val Lys Asn Val Pro Asp Glu Asn
        435                 440                 445 cgc ttg aaa tta att gag aac att ttg ggc agg atc gat act gac aaa      1392
Arg Leu Lys Leu Ile Glu Asn Ile Leu Gly Arg Ile Asp Thr Asp Lys
    450                 455                 460 gat agg cat atc aaa gtt gaa gat gta ttg aag gtt att gac att gtg      1440
Asp Arg His Ile Lys Val Glu Asp Val Leu Lys Val Ile Asp Ile Val
465                 470                 475                 480 gaa aaa gaa gat ggt atc atg agt aca aaa caa tta gat gag ttg gtt      1488
Glu Lys Glu Asp Gly Ile Met Ser Thr Lys Gln Leu Asp Glu Leu Val
                485                 490                 495 cag ctt ttg aaa aag gag gaa gtt att gaa ttg gaa gaa aag aaa gaa      1536
Gln Leu Leu Lys Lys Glu Glu Val Ile Glu Leu Glu Glu Lys Lys Glu
            500                 505                 510 aag caa gag tct caa cag aaa agt ttt gta cca cca agt gaa act ttg      1584
Lys Gln Glu Ser Gln Gln Lys Ser Phe Val Pro Pro Ser Glu Thr Leu
        515                 520                 525 cat ctt gaa tca tca cag cag aag agt aca gtt cct agc tcg gga cat      1632
His Leu Glu Ser Ser Gln Gln Lys Ser Thr Val Pro Ser Ser Gly His
    530                 535                 540 gaa gct aag gtg tcc gaa gat gac tta aat gtt aaa aat aaa aat ttg      1680
Glu Ala Lys Val Ser Glu Asp Asp Leu Asn Val Lys Asn Lys Asn Leu
545                 550                 555                 560 gaa gaa tcg acc aaa act gaa tgt gga gca att gac gaa gag cac aga      1728
Glu Glu Ser Thr Lys Thr Glu Cys Gly Ala Ile Asp Glu Glu His Arg
                565                 570                 575 aga gag cat tgc cag tac cca gac att aca                              1758
Arg Glu His Cys Gln Tyr Pro Asp Ile Thr
            580                 585
```

<210> SEQ ID NO 30
<211> LENGTH: 586
<212> TYPE: PRT
<213> ORGANISM: Ctenocephalides felis
<220> FEATURE:
<221> NAME/KEY: misc_feature
<222> LOCATION: (1136)..()
<223> OTHER INFORMATION: W = A or T/U
<221> NAME/KEY: misc_feature
<222> LOCATION: (379)..()
<223> OTHER INFORMATION: Xaa = Met or Lys

<400> SEQUENCE: 30

Leu Glu Met Ala Lys Phe Leu Thr Glu Thr Leu Asp Asp Met Thr Leu
1               5                   10                  15

Gln His Lys Asp His Arg Ser Glu Leu Ala Lys Glu Phe Ser Ile Trp
                20                  25                  30

Phe Thr Lys Met Arg Gln Ser Gly Ala Gln Ala Ser Asn Glu Glu Ile
            35                  40                  45

Met Lys Phe Ser Lys Leu Phe Glu Asp Glu Ile Thr Leu Asp Ser Leu
        50                  55                  60

```
Ala Arg Pro Gln Leu Val Ala Leu Cys Arg Val Leu Glu Ile Ser Thr
 65                  70                  75                  80

Leu Gly Thr Thr Asn Phe Leu Arg Phe Gln Leu Arg Met Lys Leu Arg
                 85                  90                  95

Ser Leu Ala Ala Asp Asp Lys Met Ile Gln Lys Glu Gly Ile Val Ser
            100                 105                 110

Met Thr Tyr Ser Glu Val Gln Gln Ala Cys Arg Ala Arg Gly Met Arg
        115                 120                 125

Ala Tyr Gly Met Pro Glu His Arg Leu Arg Arg Gln Leu Glu Asp Trp
130                 135                 140

Ile Asn Leu Ser Leu Asn Glu Lys Val Pro Ser Leu Leu Leu Leu
145                 150                 155                 160

Ser Arg Ala Leu Met Leu Pro Glu Asn Val Pro Val Ser Asp Lys Leu
                165                 170                 175

Lys Ala Thr Ile Asn Ala Leu Pro Glu Thr Ile Val Thr Gln Thr Lys
            180                 185                 190

Ala Ala Ile Gly Glu Arg Glu Gly Lys Ile Asp Asn Lys Thr Lys Ile
        195                 200                 205

Glu Val Ile Lys Glu Glu Arg Lys Ile Arg Glu Arg Gln Glu
210                 215                 220

Ala Arg Glu Glu Glu Gln Arg Lys Gln Ala Glu Leu Ala Leu Asn
225                 230                 235                 240

Ala Ser Ser Ala Ala Glu Ala Ser Ser Ala Gln Glu Leu Leu Ile
            245                 250                 255

Asp Thr Ala Pro Val Ile Asp Ala Glu Lys Thr Pro Lys Val Ala Thr
        260                 265                 270

Ser Pro Val Glu Ser Pro Leu Ala Pro Glu Val Leu Ile Met Gly
                275                 280                 285

Ala Pro Lys Thr Pro Val Ala Thr Glu Val Asp Lys Asn Ala Asp Glu
        290                 295                 300

Val Glu Phe Thr Lys Lys Asp Leu Glu Val Val Glu Asp Ala Leu Asp
305                 310                 315                 320

Thr Leu Ser Lys Asp Lys Asn Asn Leu Val Ile Glu Lys Glu Val Ile
                325                 330                 335

Lys Asp Ile Lys Glu Glu Ile Ala Asp Tyr Gln Glu Asp Val Glu Glu
            340                 345                 350

Leu Lys Glu Ala Ile Val Ala Ala Glu Lys Pro Lys Asp Glu Ile Lys
        355                 360                 365

Glu Thr Lys Gly Ala Gln Arg Leu Leu Lys Xaa Val Asn Lys Met Ile
370                 375                 380

Thr Lys Met Asp Thr Val Gln Glu Ile Glu Ser Lys Glu Ser Glu
385                 390                 395                 400

Lys Lys Ala Lys Thr Leu Pro Leu Glu Ala Pro Arg Ser Ala Thr Glu
                405                 410                 415

Thr Gln Glu Leu Asp Val Arg Lys Glu Arg Gly Glu Ile Leu Ile Asp
            420                 425                 430

Glu Leu Met Asp Ala Ile Lys Lys Val Lys Asn Val Pro Asp Glu Asn
        435                 440                 445

Arg Leu Lys Leu Ile Glu Asn Ile Leu Gly Arg Ile Asp Thr Asp Lys
        450                 455                 460

Asp Arg His Ile Lys Val Glu Asp Val Leu Lys Val Ile Asp Ile Val
465                 470                 475                 480

Glu Lys Glu Asp Gly Ile Met Ser Thr Lys Gln Leu Asp Glu Leu Val
```

```
                485             490                 495
Gln Leu Leu Lys Lys Glu Val Ile Glu Leu Glu Lys Lys Glu
                500             505             510

Lys Gln Glu Ser Gln Lys Ser Phe Val Pro Ser Glu Thr Leu
        515             520             525

His Leu Glu Ser Ser Gln Lys Ser Thr Val Pro Ser Ser Gly His
    530             535             540

Glu Ala Lys Val Ser Glu Asp Asp Leu Asn Val Lys Asn Lys Asn Leu
545             550             555             560

Glu Glu Ser Thr Lys Thr Glu Cys Gly Ala Ile Asp Glu Glu His Arg
            565             570             575

Arg Glu His Cys Gln Tyr Pro Asp Ile Thr
            580             585
```

<210> SEQ ID NO 31
<211> LENGTH: 293
<212> TYPE: DNA
<213> ORGANISM: Ctenocephalides felis

<400> SEQUENCE: 31

```
cccgggctgc aggaattcgg cacgagatga gaatggaaat gtgattagct atactgatga    60
aaatggaaac attatcagta ctactgatga gaatggaaat gtgattagca ttactgatga   120
aaatggaaat gtgattagca ttactgatga aaatggaaac attatcagta ctactgatga   180
gaatggaaat gtgattagca ttactgatga aaatggaaat gtgattagca ttactgatga   240
aaatggaaac attattagta ctactgatga gaatggaaat gtgattagca ata           293
```

<210> SEQ ID NO 32
<211> LENGTH: 335
<212> TYPE: DNA
<213> ORGANISM: Ctenocephalides felis

<400> SEQUENCE: 32

```
ttggaaacag ctatgaccat gattacccca agctcgaaag ttaavccctc actharaggg    60
gaacaaaagt ctggagctcc acccgcggat ggcggccgcb tctagaacct agtggactcc   120
cccggsgctg caggaattcg ggcacgagct ccagctagcc atatacattc atccaaaatg   180
aagttgsaat gtgtcctacc cggcaacggg atgccagaaa ttgtktcgaa atktgtggac   240
gagcacaagc ttcgtgtctk tctatgaaaa acgtatggga gcagaagtcg agggccgaca   300
tcctcggcga tgaatggara ggttatgtgc tccga                              335
```

<210> SEQ ID NO 33
<211> LENGTH: 396
<212> TYPE: DNA
<213> ORGANISM: Ctenocephalides felis

<400> SEQUENCE: 33

```
atagctttta atatttttaa ttgatgtatt gctcaatggt gatttctgtt tattaaactg    60
agttaccaat atgctcgctt caatagacat agcaaatgaa agcattccgt atcctcaagc   120
gttaccaaac taacattaag gagttaaata atgttgtttt ccaataaata taatgggaaa   180
aacatttaat atttgttcca atttgtattt atttttacta caattatata caataaaata   240
ttttttatata tattttataa agtttatgat gcaggagaga aaataatgtt aagaatatag   300
gtaatgtgta tatataaatg tttgacaagc atgttctagt taaataataa atacaatgtt   360
aaatctactt aaaaaaaaaa aaaaaaaaaa aaaaaa                             396
```

<210> SEQ ID NO 34
<211> LENGTH: 285
<212> TYPE: DNA
<213> ORGANISM: Ctenocephalides felis

<400> SEQUENCE: 34

```
ggaaagcgaa gaatgaaaag gggaaacaaa aaaagaaaag acgaaggagt ggagagataa      60
aacggaggca agaagaaaaa tgaggatgca aagaaaggt aataaaagag atgaaaagaa      120
ggaaaaagga aataagaaag aaagagtgag ggaaaaataa agacagaggc gaagcaaaaa      180
aggaggagaa atagagatta aaaagaaat acagcgaaga aaccaggaaa gcgataaaga      240
aaaaaaaaga aaaaaagaga gcagtgaaaa aaaaaaaaaa aaaaa                     285
```

<210> SEQ ID NO 35
<211> LENGTH: 228
<212> TYPE: DNA
<213> ORGANISM: Ctenocephalides felis
<220> FEATURE:
<221> NAME/KEY: misc_feature
<222> LOCATION: (192)..()
<223> OTHER INFORMATION: n = any

<400> SEQUENCE: 35

```
cagatattta ctaaayattg tgaaayaaat cattttcaaa atggtstcca aagtgtttgt      60
tgctcttgcc atcaatggct ttataggggg ctscacaagy ctttttttcga acaagatgmc    120 gtcttagata asatsgtaga tracatctct grctsmatat gagaacarca ttgsmagaat    180
tagccaaggr tngcraaatt gatatgmtts cygctgtaat tcgaaaaa                  228
```

<210> SEQ ID NO 36
<211> LENGTH: 339
<212> TYPE: DNA
<213> ORGANISM: Ctenocephalides felis
<220> FEATURE:
<221> NAME/KEY: CDS
<222> LOCATION: (1)..(339)

<400> SEQUENCE: 36

```
ctt cgt gtc aac cgc tgg gtc aga cct gtt att gct atg cac cca acc       48
Leu Arg Val Asn Arg Trp Val Arg Pro Val Ile Ala Met His Pro Thr
1               5                   10                  15 atg act ctt gct gaa cgt ctc ggc aaa aaa gct ttg cgc gac caa tat       96
Met Thr Leu Ala Glu Arg Leu Gly Lys Lys Ala Leu Arg Asp Gln Tyr
                20                  25                  30 gct ccc gtt tgc tcc att gga caa cgt aac atc aac acc ttt gac aac      144
Ala Pro Val Cys Ser Ile Gly Gln Arg Asn Ile Asn Thr Phe Asp Asn
            35                  40                  45 atg acc ttc ccc gct caa ttc gga aaa tgc tgg cac gct ttg ttg caa      192
Met Thr Phe Pro Ala Gln Phe Gly Lys Cys Trp His Ala Leu Leu Gln
        50                  55                  60 act gtt ccc caa aag tat tcc gaa gaa cgt gaa tac agc gaa gaa caa      240
Thr Val Pro Gln Lys Tyr Ser Glu Glu Arg Glu Tyr Ser Glu Glu Gln
65                  70                  75                  80 caa tac gac cgt caa atg tcc gtc ctc gtt cgt gaa aac ggc gaa gaa      288
Gln Tyr Asp Arg Gln Met Ser Val Leu Val Arg Glu Asn Gly Glu Glu
                85                  90                  95 aaa aga cgt tat gat tgt ctt ggg caa ccg tta caa caa ttg aat tgc      336
Lys Arg Arg Tyr Asp Cys Leu Gly Gln Pro Leu Gln Gln Leu Asn Cys
            100                 105                 110 aat                                                                   339
```

Asn

<210> SEQ ID NO 37
<211> LENGTH: 113
<212> TYPE: PRT
<213> ORGANISM: Ctenocephalides felis

<400> SEQUENCE: 37

```
Leu Arg Val Asn Arg Trp Val Arg Pro Val Ile Ala Met His Pro Thr
1               5                   10                  15

Met Thr Leu Ala Glu Arg Leu Gly Lys Lys Ala Leu Arg Asp Gln Tyr
            20                  25                  30

Ala Pro Val Cys Ser Ile Gly Gln Arg Asn Ile Asn Thr Phe Asp Asn
        35                  40                  45

Met Thr Phe Pro Ala Gln Phe Gly Lys Cys Trp His Ala Leu Leu Gln
    50                  55                  60

Thr Val Pro Gln Lys Tyr Ser Glu Glu Arg Glu Tyr Ser Glu Glu Gln
65                  70                  75                  80

Gln Tyr Asp Arg Gln Met Ser Val Leu Val Arg Glu Asn Gly Glu Glu
                85                  90                  95

Lys Arg Arg Tyr Asp Cys Leu Gly Gln Pro Leu Gln Gln Leu Asn Cys
            100                 105                 110

Asn
```

<210> SEQ ID NO 38
<211> LENGTH: 493
<212> TYPE: DNA
<213> ORGANISM: Ctenocephalides felis
<220> FEATURE:
<221> NAME/KEY: CDS
<222> LOCATION: (1)..(390)

<400> SEQUENCE: 38

```
tcc agc tcc tcc agc tcc agc agt gac tct tcc agc tcc agc agc tct        48
Ser Ser Ser Ser Ser Ser Ser Ser Asp Ser Ser Ser Ser Ser Ser Ser
1               5                   10                  15 tcc tct tcc agc tcc agc agc tcc tct tct gaa tct tcc gaa gaa aaa        96
Ser Ser Ser Ser Ser Ser Ser Ser Ser Glu Ser Ser Glu Glu Lys
            20                  25                  30 acc tcc cac aaa aaa tcc gaa aag aag gaa cac aaa tcc tgc tcc atc       144
Thr Ser His Lys Lys Ser Glu Lys Lys Glu His Lys Ser Cys Ser Ile
            35                  40                  45 aag aag caa gta caa ttc gta gaa aaa gac ggt aaa ctc tgc ttc agc       192
Lys Lys Gln Val Gln Phe Val Glu Lys Asp Gly Lys Leu Cys Phe Ser
    50                  55                  60 atc cgt ccc ttg gcc gct tgc caa aaa cac tgc aaa gcc act gaa acc       240
Ile Arg Pro Leu Ala Ala Cys Gln Lys His Cys Lys Ala Thr Glu Thr
65                  70                  75                  80 act caa atg gaa gtc gaa gta tac tgc ccc tct ggc agc ctt gct gaa       288
Thr Gln Met Glu Val Glu Val Tyr Cys Pro Ser Gly Ser Leu Ala Glu
                85                  90                  95 ctt tac aaa caa aag atc ctt aag gga gcc aac ccc gac ttg agc gac       336
Leu Tyr Lys Gln Lys Ile Leu Lys Gly Ala Asn Pro Asp Leu Ser Asp
            100                 105                 110 aag act cct tcc aga atc ttg aaa ttc aag gtt ccc aaa gct tgc acc       384
Lys Thr Pro Ser Arg Ile Leu Lys Phe Lys Val Pro Lys Ala Cys Thr
            115                 120                 125 gct tac taaatctgaa ataaattaca tggattagtt catttctgat gtagtgcaat        440
Ala Tyr
        130
```
tagttcgata ataaattatt caatgagcat ttaaaaaaaa aaaaaaaaaa aac                493

<210> SEQ ID NO 39
<211> LENGTH: 130
<212> TYPE: PRT
<213> ORGANISM: Ctenocephalides felis

<400> SEQUENCE: 39

Ser Ser Ser Ser Ser Ser Ser Asp Ser Ser Ser Ser Ser Ser Ser Ser
1               5                   10                  15

Ser Ser Ser Ser Ser Ser Ser Ser Ser Glu Ser Ser Glu Glu Lys
            20                  25                  30

Thr Ser His Lys Lys Ser Glu Lys Lys Glu His Lys Ser Cys Ser Ile
            35                  40                  45

Lys Lys Gln Val Gln Phe Val Glu Lys Asp Gly Lys Leu Cys Phe Ser
        50                  55                  60

Ile Arg Pro Leu Ala Ala Cys Gln Lys His Cys Lys Ala Thr Glu Thr
65                  70                  75                  80

Thr Gln Met Glu Val Glu Val Tyr Cys Pro Ser Gly Ser Leu Ala Glu
                85                  90                  95

Leu Tyr Lys Gln Lys Ile Leu Lys Gly Ala Asn Pro Asp Leu Ser Asp
            100                 105                 110

Lys Thr Pro Ser Arg Ile Leu Lys Phe Lys Val Pro Lys Ala Cys Thr
            115                 120                 125

Ala Tyr
    130

<210> SEQ ID NO 40
<211> LENGTH: 306
<212> TYPE: DNA
<213> ORGANISM: Ctenocephalides felis

<400> SEQUENCE: 40
gtagtgccat cattcgtaaa csttytgacg gtkgggcgct gtatwggtgc tgcctggaaa       60
ttgcatcgat gcactwccgt gtcgggcgca watagtgckk tggsccctgt ctgmttatag      120
acattcaggg cgcsggsakt agccatgttc atggctcmca awmtgcattc acagtggggt      180
cacatttcag tcgcatgatt kmtcaartta gtatmwgada tatatttta tcatactaag      240 tagtgagcda ataacacgcg arwwacraac accgaatatc ttkagttttt gcacagatat      300 ktgtaa                                                                  306

<210> SEQ ID NO 41
<211> LENGTH: 490
<212> TYPE: DNA
<213> ORGANISM: Ctenocephalides felis

<400> SEQUENCE: 41
accggatacg ttgccaatga ctacgtcacc accaatgttg tttccactcc agttactgga       60
tacaccaccg gacatcttgc taatgactac gtcaccacca atgttgtatc cactccagtt      120
actggataca ccaccggaca tcttgccaat gactacgtca ccaccaacgt agtttccgca      180
ccagtcacca ctggatacac cactggctat accaccggta atgtcggata caccaccgga      240
gttactggtt acaccaacgg agttagtgga tataccaatg gacttaatgg ttataccact      300
ggtagctatg tcagctcccc aggatacact tcttctggac ttgtcaacgt tttctagatt      360
tatgatttcg tctgccctca atgatgatga ccacactttt tacttttat gatatttgga      420 aaaaataaat aactggaaga atatataata atttcaaaat aaaaaaaaaa aaaaaaaaaa 480
ctcgaggggg 490

<210> SEQ ID NO 42
<211> LENGTH: 616
<212> TYPE: DNA
<213> ORGANISM: Ctenocephalides felis

<400> SEQUENCE: 42
aaaaaatcga agaaggcgt aaaccaaaa tgggcacaga aggatattcg ggattttagt 60
gatgccgaca tggagaggtt actggatcaa tgggaagaag atgaagaccc ccttccagaa 120
gacgaattgc ccgaacatct cagacctgat ccaaagatcg acataagcaa catcgatatg 180
agcaatcccb aaaacatact aaaggcttcc aaaaaggca agactttgat ggcattcgta 240
caagtcagtg gaaatccaac acaagaagaa gccgaaacca tcactaaatt gtggcaaggc 300
agtctatgga atagtcatat acaagccgaa agatatatgg ttagcgatga cagggctata 360
tttatgttta aagatggttc tcaagcttgg cctgctaaag acttttagt ggaacaagaa 420 aggtgtaaag atgttacaat tgaaaataaa atatatcctg gtaaatattc ttcgactaaa 480
gaagaattat aatataatat attataatta taatctataa aatagatttg aaattctaca 540
ttcatgatct actatgtatg atattaattt attaaaaata atgttttttc aagtaaaaaa 600
aaaaaaaaaa aaaaaa 616

<210> SEQ ID NO 43
<211> LENGTH: 475
<212> TYPE: DNA
<213> ORGANISM: Ctenocephalides felis

<400> SEQUENCE: 43
ctcgtgcggg acagatatag gaccggattc gttaattgat ttgagtgaag tggcttctgg 60
tggttctgat attgacacaa aattttccaa tttaaaaata gataaaaagc ctgttgcaac 120
ttcacaacaa ggaattgatg aatttgatat gtttgcacaa tcgagaaaca tttctagtga 180
gggatcaacc agtgctatga aggaaggaca cggtttggac ttattatcaa atacacataa 240
aaatgtacca ccaacaattc cacaagccgg acaacttcca agggattctg agtttgatga 300
aattgctgct tggcttgatg aaaaggttga agacaaagcc caagttcccg aagcacagtat 360 tacaagcagt gaatttgata aattcctggc agaacgggca gctgttgctg aaactttgcc 420
aaatattcca ccgactacac aaagtaatca ttcaaatatt gaagcaaacg ataaa 475

<210> SEQ ID NO 44
<211> LENGTH: 295
<212> TYPE: DNA
<213> ORGANISM: Ctenocephalides felis

<400> SEQUENCE: 44
ccggcacggg aggtagtgac gaaaaataac gatacgggac tcatccgagg ccccgtaatc 60
ggaatgagta cactttaaat cctttaacga ggatctatta gagggccagt ctgtgtgcca 120
gcagccgcgg taattccagc tctaatagcg tatattaaag ttgttgcggt taaaaagctc 180
gtagttgaat ctgtgtccca cactgtyggt tcaccgctcg cggtgttcaa ctggcatgtc 240
tgtgggacgt cctaccggtg ggcttagccc gtcaaaaggc ggcccaactc aaaat 295

<210> SEQ ID NO 45

-continued

```
<211> LENGTH: 372
<212> TYPE: DNA
<213> ORGANISM: Ctenocephalides felis

<400> SEQUENCE: 45
ctgactaatc ccaggactcc tttatcctgt ttgcgcaatg tcgataccca tctcacaatg      60
gttaatgatt tatcggctaa acagaagagt cctaagaagg ttgttaaagg tgtttctaga     120
ataccgactt ttagacccaa ggctatgaat gctgatgttg agaattttga ttcgatgagg     180
tgcgatgttt ggacaaaga caccagtgtt gttatataat tactaaagca atccacatgt      240
agctaatttt tttttttacaa ttttatttgt aactatgtgt atttatatga attcttgtgg    300
aatataattt taagttttta aatgaaatat agatattatt ctaaaaaaaa aaaacaaaaa     360
aaaaaaaaaa aa                                                         372

<210> SEQ ID NO 46
<211> LENGTH: 252
<212> TYPE: DNA
<213> ORGANISM: Ctenocephalides felis

<400> SEQUENCE: 46
ggattcggca cgagaattta ttaagcgcat tatttgcaag tgtaatttgc tcctttaacg      60
cggaagtaca aaatcgaatc gttggtggca atgatgtaag tatttcaaaa attgggtggc     120
aagtatctat tcaaagtaat aaccaacatt tctgtggtgg ttcaatcatt gctaaagatt     180
gggtactgac ttcttctcaa tgcgtcgtgg acaaacaaag tccaccgaag gatttaactg     240
ttcgtgttgg aa                                                         252

<210> SEQ ID NO 47
<211> LENGTH: 613
<212> TYPE: DNA
<213> ORGANISM: Ctenocephalides felis

<400> SEQUENCE: 47
attcctgctg ttaatagtac taatgcagta attgctgcha gctgctgcac agaggttttt      60
aaaatggcaa caagttgtta cacccacatg aacaactaca tggtattcaa tgataccgat     120
gggatttata catatactta cgaagctgaa agaaaacctg actgtttagc ttgttcacaa     180
attccaaaaa ctatagaagt ttctaatcct gaaaatatga ctctccaaga cttgattact     240
ttgttgtgtg aagggctga atatcaaatg aagagcccag gtattgtagc ctcaatcgaa      300
ggcaaaaaca aaaccttata catgtcaaca gtagcaagta tagaagaaaa gactaaacag     360
aatctaacaa agtctctaaa agaattaaat ctagaaaatg gaatggaact gatggttgca     420
gatgtgacga caccaaacac aatattactt aaattaaaat ataagaatgt aattgaaaac     480
gatgttgaga tgacttgata tttacttaaa aatgttatct acaataatt gataatttat      540 atttaatact tttggaactt tgtatttaat gataataaat tattataaga attaaaaaaa     600
aaaaaaaaaa aaa                                                        613

<210> SEQ ID NO 48
<211> LENGTH: 538
<212> TYPE: DNA
<213> ORGANISM: Ctenocephalides felis
<220> FEATURE:
<221> NAME/KEY: CDS
<222> LOCATION: (3)..(536)

<400> SEQUENCE: 48
```

```
tt gat att tgc tct gtt gag ggt gcc tta gga ttt tta gtg gaa atg        47
   Asp Ile Cys Ser Val Glu Gly Ala Leu Gly Phe Leu Val Glu Met
    1               5                  10                  15 tta aaa tat aag gcc cca agt aaa act cta gct att gta gag aat gct       95
Leu Lys Tyr Lys Ala Pro Ser Lys Thr Leu Ala Ile Val Glu Asn Ala
                    20                  25                  30 ggt gga ata tta cga aat gta tct agt cat ata gcc ctt aga gag gac      143
Gly Gly Ile Leu Arg Asn Val Ser Ser His Ile Ala Leu Arg Glu Asp
                35                  40                  45 tac aga gaa ata ctt cga cat cat aat tgc tta aca ata tta cta caa      191
Tyr Arg Glu Ile Leu Arg His His Asn Cys Leu Thr Ile Leu Leu Gln
            50                  55                  60 caa tta aaa tca cca agc ctc ata att gtc agt aat gct tgt ggg aca      239
Gln Leu Lys Ser Pro Ser Leu Ile Ile Val Ser Asn Ala Cys Gly Thr
 65                 70                  75 tta tgg aat tta tct gct agg aat tca aca gat caa caa ttt tta tgg      287
Leu Trp Asn Leu Ser Ala Arg Asn Ser Thr Asp Gln Gln Phe Leu Trp
 80              85                  90                  95 gag aat ggt gct gtc cct tta tta aga agt ttg ata tat tct aag cat      335
Glu Asn Gly Ala Val Pro Leu Leu Arg Ser Leu Ile Tyr Ser Lys His
                100                 105                 110 aaa atg ata tct atg gga tca agt gca gct ctc aaa aat ttg tta aat      383
Lys Met Ile Ser Met Gly Ser Ser Ala Ala Leu Lys Asn Leu Leu Asn
            115                 120                 125 gca aaa cct gag tgc atc aat ttc tta agt gat tct tct tct aaa gga      431
Ala Lys Pro Glu Cys Ile Asn Phe Leu Ser Asp Ser Ser Ser Lys Gly
        130                 135                 140 gtt cca aat cta act aca ttg ggt gta aga aaa caa aaa tct cta cat      479
Val Pro Asn Leu Thr Thr Leu Gly Val Arg Lys Gln Lys Ser Leu His
145                 150                 155 gag tta ata gat caa aat ctt tca gaa act tgt gat aat ata gat agt      527
Glu Leu Ile Asp Gln Asn Leu Ser Glu Thr Cys Asp Asn Ile Asp Ser
160                 165                 170                 175 gtg gcc gct aa                                                       538
Val Ala Ala
```

<210> SEQ ID NO 49
<211> LENGTH: 178
<212> TYPE: PRT
<213> ORGANISM: Ctenocephalides felis

<400> SEQUENCE: 49

```
Asp Ile Cys Ser Val Glu Gly Ala Leu Gly Phe Leu Val Glu Met Leu
 1               5                  10                  15

Lys Tyr Lys Ala Pro Ser Lys Thr Leu Ala Ile Val Glu Asn Ala Gly
                20                  25                  30

Gly Ile Leu Arg Asn Val Ser Ser His Ile Ala Leu Arg Glu Asp Tyr
            35                  40                  45

Arg Glu Ile Leu Arg His His Asn Cys Leu Thr Ile Leu Leu Gln Gln
        50                  55                  60

Leu Lys Ser Pro Ser Leu Ile Ile Val Ser Asn Ala Cys Gly Thr Leu
 65                 70                  75                  80

Trp Asn Leu Ser Ala Arg Asn Ser Thr Asp Gln Gln Phe Leu Trp Glu
                85                  90                  95

Asn Gly Ala Val Pro Leu Leu Arg Ser Leu Ile Tyr Ser Lys His Lys
                100                 105                 110

Met Ile Ser Met Gly Ser Ser Ala Ala Leu Lys Asn Leu Leu Asn Ala
            115                 120                 125
```

```
Lys Pro Glu Cys Ile Asn Phe Leu Ser Asp Ser Ser Lys Gly Val
    130                 135                 140

Pro Asn Leu Thr Thr Leu Gly Val Arg Lys Gln Lys Ser Leu His Glu
145                 150                 155                 160

Leu Ile Asp Gln Asn Leu Ser Glu Thr Cys Asp Asn Ile Asp Ser Val
                165                 170                 175

Ala Ala

<210> SEQ ID NO 50
<211> LENGTH: 432
<212> TYPE: DNA
<213> ORGANISM: Ctenocephalides felis
<220> FEATURE:
<221> NAME/KEY: CDS
<222> LOCATION: (1)..(387)

<400> SEQUENCE: 50 gtt ctt ctt aaa cag ttg gac tct gga ttg tta ctt gtt aca ggt ccc      48
Val Leu Leu Lys Gln Leu Asp Ser Gly Leu Leu Val Thr Gly Pro
1               5                   10                  15 ttc tta atc aat gca tgc cca ttg cgt cgc att tcc caa aac tat gtc      96
Phe Leu Ile Asn Ala Cys Pro Leu Arg Arg Ile Ser Gln Asn Tyr Val
                20                  25                  30 att gcc acc tct acc cga tta gac gtt agt gga gtt aaa tta cca gaa     144
Ile Ala Thr Ser Thr Arg Leu Asp Val Ser Gly Val Lys Leu Pro Glu
            35                  40                  45 cac atc aat gat gat tat ttc aaa agg caa aag aac aag cgt gca aag     192
His Ile Asn Asp Asp Tyr Phe Lys Arg Gln Lys Asn Lys Arg Ala Lys
        50                  55                  60 aaa gag gaa ggt gat att ttt gct gcc aag aaa gag gct tat aaa cca     240
Lys Glu Glu Gly Asp Ile Phe Ala Ala Lys Lys Glu Ala Tyr Lys Pro
65                  70                  75                  80 act gag caa agg aag aat gac caa aag ctt gta gac aaa atg gtt tta     288
Thr Glu Gln Arg Lys Asn Asp Gln Lys Leu Val Asp Lys Met Val Leu
                85                  90                  95 gga gta atc aag aag cac cca gac cac aaa ctt ttg tat aca tat ttg     336
Gly Val Ile Lys Lys His Pro Asp His Lys Leu Leu Tyr Thr Tyr Leu
            100                 105                 110 tca gct atg ttt ggt ttg aaa tct tcc caa tat cca cat cgt atg aag     384
Ser Ala Met Phe Gly Leu Lys Ser Ser Gln Tyr Pro His Arg Met Lys
        115                 120                 125 ttc taaatactat attcataaaa taaattgaac ttctcaaaaa aaaaa              432
Phe

<210> SEQ ID NO 51
<211> LENGTH: 129
<212> TYPE: PRT
<213> ORGANISM: Ctenocephalides felis

<400> SEQUENCE: 51

Val Leu Leu Lys Gln Leu Asp Ser Gly Leu Leu Val Thr Gly Pro
1               5                   10                  15

Phe Leu Ile Asn Ala Cys Pro Leu Arg Arg Ile Ser Gln Asn Tyr Val
                20                  25                  30

Ile Ala Thr Ser Thr Arg Leu Asp Val Ser Gly Val Lys Leu Pro Glu
            35                  40                  45

His Ile Asn Asp Asp Tyr Phe Lys Arg Gln Lys Asn Lys Arg Ala Lys
        50                  55                  60

Lys Glu Glu Gly Asp Ile Phe Ala Ala Lys Lys Glu Ala Tyr Lys Pro
65                  70                  75                  80
```

```
Thr Glu Gln Arg Lys Asn Asp Gln Lys Leu Val Asp Lys Met Val Leu
            85                  90                  95

Gly Val Ile Lys Lys His Pro Asp His Lys Leu Leu Tyr Thr Tyr Leu
            100                 105                 110

Ser Ala Met Phe Gly Leu Lys Ser Ser Gln Tyr Pro His Arg Met Lys
        115                 120                 125

Phe

<210> SEQ ID NO 52
<211> LENGTH: 595
<212> TYPE: DNA
<213> ORGANISM: Ctenocephalides felis
<220> FEATURE:
<221> NAME/KEY: CDS
<222> LOCATION: (47)..(313)

<400> SEQUENCE: 52
tggaaattca atattttgtt ttaacattaa attttcaaa ttcgat atg aaa ttt        55
                                                  Met Lys Phe
                                                   1 tta ctg gca att tgc gtg ttg tgt gtt tta tta aat caa gta tct atg    103
Leu Leu Ala Ile Cys Val Leu Cys Val Leu Leu Asn Gln Val Ser Met
     5                  10                  15 tca aaa atg gtc act gaa aag tgt aaa tcg gga gga aat aat cca agt    151
Ser Lys Met Val Thr Glu Lys Cys Lys Ser Gly Gly Asn Asn Pro Ser
 20                 25                  30                  35 aca aaa gag gtg tca ata cca tct ggg aag ctt act att gaa gat ttt    199
Thr Lys Glu Val Ser Ile Pro Ser Gly Lys Leu Thr Ile Glu Asp Phe
                40                  45                  50 tgt att gga aat cat caa agt tgc aaa ata ttt tgc aaa agt caa tgt    247
Cys Ile Gly Asn His Gln Ser Cys Lys Ile Phe Cys Lys Ser Gln Cys
            55                  60                  65 gga ttt gga ggt ggt gct tgt gga aac ggt ggt tca aca cga cca aat    295
Gly Phe Gly Gly Gly Ala Cys Gly Asn Gly Gly Ser Thr Arg Pro Asn
        70                  75                  80 caa aaa cac tgt tat tgc gaataaccat attccggatg aaagaccaaa           343
Gln Lys His Cys Tyr Cys
    85 ttgatataaa ttactaaaat tatgctagat agcaatcata aaattttgaa gttttcaatg  403 atcctaacat gttttgcctc caatttattt taacagcaaa ttgctgggaa cttaccgtac  463 cgtaacaaaa tgttcaagaa atactgaatg tttacaaata gattattata aatattgtaa  523 cattgtctaa tatttataag aattatataa actgaattgc aaaagttgaa aaaaaaaaa   583 aaaaaaaaaa aa                                                      595

<210> SEQ ID NO 53
<211> LENGTH: 89
<212> TYPE: PRT
<213> ORGANISM: Ctenocephalides felis

<400> SEQUENCE: 53

Met Lys Phe Leu Leu Ala Ile Cys Val Leu Cys Val Leu Leu Asn Gln
 1               5                  10                  15

Val Ser Met Ser Lys Met Val Thr Glu Lys Cys Lys Ser Gly Gly Asn
            20                  25                  30

Asn Pro Ser Thr Lys Glu Val Ser Ile Pro Ser Gly Lys Leu Thr Ile
        35                  40                  45

Glu Asp Phe Cys Ile Gly Asn His Gln Ser Cys Lys Ile Phe Cys Lys
```

```
                   50                  55                  60
Ser Gln Cys Gly Phe Gly Gly Ala Cys Gly Asn Gly Gly Ser Thr
 65                  70                  75                  80

Arg Pro Asn Gln Lys His Cys Tyr Cys
                 85

<210> SEQ ID NO 54
<211> LENGTH: 595
<212> TYPE: DNA
<213> ORGANISM: Ctenocephalides felis

<400> SEQUENCE: 54 ttttttttttt tttttttttt ttttcaactt tgcaattca gtttatataa ttcttataaa      60
tattagacaa tgttacaata tttataataa tctatttgta aacattcagt atttcttgaa     120
cattttgtta cggtacggta agttcccagc aatttgctgt taaataaat tggaggcaaa      180 acatgttagg atcattgaaa acttcaaaat tttatgattg ctatctagca taattttagt     240
aatttatatc aatttggtct ttcatccgga atatggttat tcgcaataac agtgtttttg     300
atttggtcgt gttgaaccac cgtttccaca agcaccacct ccaaatccac attgactttt     360
gcaaaatatt ttgcaacttt gatgatttcc aatacaaaaa tcttcaatag taagcttccc     420
agatggtatt gacacctctt ttgtacttgg attatttcct cccgatttac acttttcagt     480
gaccattttt gacatagata cttgatttaa taaaacacac aacacgcaaa ttgccagtaa     540
aaatttcata tcgaatttga aaatttaat gttaaaacaa aatattgaat ttcca           595

<210> SEQ ID NO 55
<211> LENGTH: 270
<212> TYPE: DNA
<213> ORGANISM: Ctenocephalides felis
<220> FEATURE:
<221> NAME/KEY: CDS
<222> LOCATION: (1)..(270)

<400> SEQUENCE: 55 atg aaa ttt tta ctg gca att tgc gtg ttg tgt gtt tta tta aat caa       48
Met Lys Phe Leu Leu Ala Ile Cys Val Leu Cys Val Leu Leu Asn Gln
  1               5                  10                  15 gta tct atg tca aaa atg gtc act gaa aag tgt aaa tcg gga gga aat       96
Val Ser Met Ser Lys Met Val Thr Glu Lys Cys Lys Ser Gly Gly Asn
             20                  25                  30 aat cca agt aca aaa gag gtg tca ata cca tct ggg aag ctt act att      144
Asn Pro Ser Thr Lys Glu Val Ser Ile Pro Ser Gly Lys Leu Thr Ile
         35                  40                  45 gaa gat ttt tgt att gga aat cat caa agt tgc aaa ata ttt tgc aaa      192
Glu Asp Phe Cys Ile Gly Asn His Gln Ser Cys Lys Ile Phe Cys Lys
     50                  55                  60 agt caa tgt gga ttt gga ggt ggt gct tgt gga aac ggt ggt tca aca      240
Ser Gln Cys Gly Phe Gly Gly Gly Ala Cys Gly Asn Gly Gly Ser Thr
 65                  70                  75                  80 cga cca aat caa aaa cac tgt tat tgc gaa                              270
Arg Pro Asn Gln Lys His Cys Tyr Cys Glu
                 85                  90

<210> SEQ ID NO 56
<211> LENGTH: 90
<212> TYPE: PRT
<213> ORGANISM: Ctenocephalides felis

<400> SEQUENCE: 56
```

```
Met Lys Phe Leu Leu Ala Ile Cys Val Leu Cys Val Leu Leu Asn Gln
1               5                   10                  15

Val Ser Met Ser Lys Met Val Thr Glu Lys Cys Lys Ser Gly Gly Asn
            20                  25                  30

Asn Pro Ser Thr Lys Glu Val Ser Ile Pro Ser Gly Lys Leu Thr Ile
            35                  40                  45

Glu Asp Phe Cys Ile Gly Asn His Gln Ser Cys Lys Ile Phe Cys Lys
        50                  55                  60

Ser Gln Cys Gly Phe Gly Gly Gly Ala Cys Gly Asn Gly Gly Ser Thr
65                  70                  75                  80

Arg Pro Asn Gln Lys His Cys Tyr Cys Glu
                85                  90

<210> SEQ ID NO 57
<211> LENGTH: 270
<212> TYPE: DNA
<213> ORGANISM: Ctenocephalides felis

<400> SEQUENCE: 57
ttcgcaataa cagtgttttt gatttggtcg tgttgaacca ccgtttccac aagcaccacc      60
tccaaatcca cattgacttt tgcaaaatat tttgcaactt tgatgatttc caatacaaaa    120
atcttcaata gtaagcttcc cagatggtat tgacacctct tttgtacttg gattatttcc    180
tcccgattta cacttttcag tgaccatttt tgacatagat acttgattta ataaaacaca    240
caacacgcaa attgccagta aaatttcat                                       270

<210> SEQ ID NO 58
<211> LENGTH: 213
<212> TYPE: DNA
<213> ORGANISM: Ctenocephalides felis
<220> FEATURE:
<221> NAME/KEY: CDS
<222> LOCATION: (1)..(213)

<400> SEQUENCE: 58 tca aaa atg gtc act gaa aag tgt aaa tcg gga gga aat aat cca agt       48
Ser Lys Met Val Thr Glu Lys Cys Lys Ser Gly Gly Asn Asn Pro Ser
1               5                   10                  15 aca aaa gag gtg tca ata cca tct ggg aag ctt act att gaa gat ttt       96
Thr Lys Glu Val Ser Ile Pro Ser Gly Lys Leu Thr Ile Glu Asp Phe
            20                  25                  30 tgt att gga aat cat caa agt tgc aaa ata ttt tgc aaa agt caa tgt      144
Cys Ile Gly Asn His Gln Ser Cys Lys Ile Phe Cys Lys Ser Gln Cys
        35                  40                  45 gga ttt gga ggt ggt gct tgt gga aac ggt ggt tca aca cga cca aat      192
Gly Phe Gly Gly Gly Ala Cys Gly Asn Gly Gly Ser Thr Arg Pro Asn
50                  55                  60 caa aaa cac tgt tat tgc gaa                                          213
Gln Lys His Cys Tyr Cys Glu
65                  70

<210> SEQ ID NO 59
<211> LENGTH: 71
<212> TYPE: PRT
<213> ORGANISM: Ctenocephalides felis

<400> SEQUENCE: 59

Ser Lys Met Val Thr Glu Lys Cys Lys Ser Gly Gly Asn Asn Pro Ser
1               5                   10                  15

Thr Lys Glu Val Ser Ile Pro Ser Gly Lys Leu Thr Ile Glu Asp Phe
```

```
                    20                  25                  30
Cys Ile Gly Asn His Gln Ser Cys Lys Ile Phe Cys Lys Ser Gln Cys
                35                  40                  45

Gly Phe Gly Gly Gly Ala Cys Gly Asn Gly Gly Ser Thr Arg Pro Asn
    50                  55                  60

Gln Lys His Cys Tyr Cys Glu
65                  70

<210> SEQ ID NO 60
<211> LENGTH: 213
<212> TYPE: DNA
<213> ORGANISM: Ctenocephalides felis

<400> SEQUENCE: 60
ttcgcaataa cagtgttttt gatttggtcg tgttgaacca ccgtttccac aagcaccacc      60
tccaaatcca cattgacttt tgcaaaatat tttgcaactt tgatgatttc caatacaaaa     120
atcttcaata gtaagcttcc cagatggtat tgacacctct tttgtacttg gattatttcc     180
tcccgattta cacttttcag tgaccatttt tga                                  213

<210> SEQ ID NO 61
<211> LENGTH: 1007
<212> TYPE: DNA
<213> ORGANISM: Ctenocephalides felis
<220> FEATURE:
<221> NAME/KEY: CDS
<222> LOCATION: (1)..(465)

<400> SEQUENCE: 61 tgg aaa gtt aat aaa aaa tgt aca tca ggt gga aaa aat caa gat aga        48
Trp Lys Val Asn Lys Lys Cys Thr Ser Gly Gly Lys Asn Gln Asp Arg
1               5                  10                  15 aaa ctc gat caa ata att caa aaa ggc caa caa gtt aaa atc caa aat        96
Lys Leu Asp Gln Ile Ile Gln Lys Gly Gln Gln Val Lys Ile Gln Asn
                20                  25                  30 att tgc aaa tta ata cga gat aaa cca cat aca aat caa gag aaa gaa       144
Ile Cys Lys Leu Ile Arg Asp Lys Pro His Thr Asn Gln Glu Lys Glu
            35                  40                  45 aaa tgt atg aaa ttt tgc aaa aaa gtt tgc aaa ggt tat aga gga gct       192
Lys Cys Met Lys Phe Cys Lys Lys Val Cys Lys Gly Tyr Arg Gly Ala
        50                  55                  60 tgt gat ggc aat att tgc tac tgc agc agg cca agt aat tta ggt cct       240
Cys Asp Gly Asn Ile Cys Tyr Cys Ser Arg Pro Ser Asn Leu Gly Pro
65                  70                  75                  80 gat tgg aaa gta agc aaa gaa tgc aaa gat ccc aat aac aaa gat tct       288
Asp Trp Lys Val Ser Lys Glu Cys Lys Asp Pro Asn Asn Lys Asp Ser
                85                  90                  95 cgt cct acg gaa ata gtt cca tat cga caa caa tta gca aat cca aat       336
Arg Pro Thr Glu Ile Val Pro Tyr Arg Gln Gln Leu Ala Asn Pro Asn
                100                 105                 110 att tgc aaa cta aaa aat tca gag acc aat gaa gat tcc aaa tgc aaa       384
Ile Cys Lys Leu Lys Asn Ser Glu Thr Asn Glu Asp Ser Lys Cys Lys
            115                 120                 125 aaa cat tgc aaa gaa aaa tgt cgt ggt gga aat gat gct gga tgt gat       432
Lys His Cys Lys Glu Lys Cys Arg Gly Gly Asn Asp Ala Gly Cys Asp
        130                 135                 140 gga aac ttt tgt tat tgt cga cca aaa aat aaa taataattat aataaataaa     485
Gly Asn Phe Cys Tyr Cys Arg Pro Lys Asn Lys
145                 150                 155 ttgttatagt tattagttat cccatcacat attagaaaag tggcttataa tttatgaaca     545
```

-continued

```
atataacaca taaattagtt gtgtaatttc gaatgttttt ttcaaatata aggcgttttt      605
ctagaatatc ttgatattag aaactaactt agattatttt gttgtgtata aaatattcaa      665
atacgtaagt tatattgaac aaagcattta gaagctacat tagatatact aaataagtgc      725
aaaattgcat ggaaacccct tactggattta ctacatattt tcttcctaaa tattgtcttg     785
gtattactct tattatataa aaattaatat aaaattgtag acagagacga attggggtat      845
tgttatatat aaaaaagtag tggattattt aattctaaaa aagtttgcaa aatgtttcat      905
acataataac cgaatatttt caaatatata aatattgtaa tgaataaatg cgcatctgta      965
tgcttaatat aaaaaaaaaa aaaaaaaaaa aaaaaaaaaa aa                        1007
```

<210> SEQ ID NO 62
<211> LENGTH: 155
<212> TYPE: PRT
<213> ORGANISM: Ctenocephalides felis

<400> SEQUENCE: 62

```
Trp Lys Val Asn Lys Cys Thr Ser Gly Gly Lys Asn Gln Asp Arg
1               5                   10                  15

Lys Leu Asp Gln Ile Ile Gln Lys Gly Gln Gln Val Lys Ile Gln Asn
            20                  25                  30

Ile Cys Lys Leu Ile Arg Asp Lys Pro His Thr Asn Gln Glu Lys Glu
        35                  40                  45

Lys Cys Met Lys Phe Cys Lys Lys Val Cys Lys Gly Tyr Arg Gly Ala
    50                  55                  60

Cys Asp Gly Asn Ile Cys Tyr Cys Ser Arg Pro Ser Asn Leu Gly Pro
65                  70                  75                  80

Asp Trp Lys Val Ser Lys Glu Cys Lys Asp Pro Asn Asn Lys Asp Ser
                85                  90                  95

Arg Pro Thr Glu Ile Val Pro Tyr Arg Gln Gln Leu Ala Asn Pro Asn
            100                 105                 110

Ile Cys Lys Leu Lys Asn Ser Glu Thr Asn Glu Asp Ser Lys Cys Lys
        115                 120                 125

Lys His Cys Lys Glu Lys Cys Arg Gly Gly Asn Asp Ala Gly Cys Asp
    130                 135                 140

Gly Asn Phe Cys Tyr Cys Arg Pro Lys Asn Lys
145                 150                 155
```

<210> SEQ ID NO 63
<211> LENGTH: 1007
<212> TYPE: DNA
<213> ORGANISM: Ctenocephalides felis

<400> SEQUENCE: 63

```
tttttttttt tttttttttt tttttttttt ttatattaag catacagatg cgcatttatt       60
cattacaata tttatatatt tgaaaatatt cggttattat gtatgaaaca ttttgcaaac      120
ttttttagaa ttaaataatc cactactttt ttatatataa caatacccca attcgtctct      180
gtctacaatt ttatattaat ttttatataa taagagtaat accaagacaa tatttaggaa      240
gaaaatatgt agtaaatcca gtaagggttt ccatgcaatt ttgcacttat ttagtatatc      300
taatgtagct tctaaatgct ttgttcaata taacttacgt atttgaatat tttatacaca      360
acaaaataat ctaagttagt ttctaatatc aagatattct agaaaaacgc cttatatttg      420
aaaaaaacat tcgaaattac acaactaatt tatgtgttat attgttcata aattataagc      480
```

-continued

```
cacttttcta atatgtgatg ggataactaa taactataac aatttattta ttataattat      540
tatttatttt ttggtcgaca ataacaaaag tttccatcac atccagcatc atttccacca      600 cgacatttt ctttgcaatg tttttttgcat ttggaatctt cattggtctc tgaattttt       660 agtttgcaaa tatttggaat tgctaattgt tgtcgatatg aactatttc cgtaggacga      720 gaatctttgt tattgggatc tttgcattct ttgcttactt tccaatcagg acctaaatta     780
cttggcctgc tgcagtagca aatattgcca tcacaagctc ctctataacc tttgcaaact     840
tttttgcaaa atttcataca tttttctttc tcttgatttg tatgtggttt atctcgtatt     900
aatttgcaaa tatttggat tttaacttgt tggccttttt gaattatttg atcgagtttt     960
ctatcttgat ttttccacc tgatgtacat tttttattaa ctttcca                    1007

<210> SEQ ID NO 64
<211> LENGTH: 1205
<212> TYPE: DNA
<213> ORGANISM: Ctenocephalides felis
<220> FEATURE:
<221> NAME/KEY: CDS
<222> LOCATION: (4)..(1062)

<400> SEQUENCE: 64 gca gaa ttg aaa ttt gtg ttt gcg act gca cga ggt atg tca cat aca        48
    Glu Leu Lys Phe Val Phe Ala Thr Ala Arg Gly Met Ser His Thr
    1               5                   10                  15 cct tgt gat tat cca ggc ggt cca aaa att aca cac aag tct gaa gat        96
Pro Cys Asp Tyr Pro Gly Gly Pro Lys Ile Thr His Lys Ser Glu Asp
                20                  25                  30 tca agc caa ttg aca ccg gca ggt caa gaa gag gca tta aaa att ggc       144
Ser Ser Gln Leu Thr Pro Ala Gly Gln Glu Glu Ala Leu Lys Ile Gly
            35                  40                  45 aaa tta tta tcc gaa cat tac aga act aat tta aaa gtt gac aaa tgg       192
Lys Leu Leu Ser Glu His Tyr Arg Thr Asn Leu Lys Val Asp Lys Trp
        50                  55                  60 gat tca aat aaa aat tat tgg aca tta gct agt gct acg aga aga tct       240
Asp Ser Asn Lys Asn Tyr Trp Thr Leu Ala Ser Ala Thr Arg Arg Ser
65                  70                  75 caa gaa gga gcg ctt atc att ggt tct ggt cta gaa gaa aag gaa aag       288
Gln Glu Gly Ala Leu Ile Ile Gly Ser Gly Leu Glu Glu Lys Glu Lys
80                  85                  90                  95 gca gtt tgg aca aaa gag aaa gga gat aaa acc ata ttt tct tcg ttt       336
Ala Val Trp Thr Lys Glu Lys Gly Asp Lys Thr Ile Phe Ser Ser Phe
                100                 105                 110 ggt gaa tat gct aaa ttt tat agt cca aaa act tgt cca aac ttc ata       384
Gly Glu Tyr Ala Lys Phe Tyr Ser Pro Lys Thr Cys Pro Asn Phe Ile
            115                 120                 125 gca caa cag aaa ata gca gta aga gac ttg tta aca aaa agt gca aaa       432
Ala Gln Gln Lys Ile Ala Val Arg Asp Leu Leu Thr Lys Ser Ala Lys
        130                 135                 140 gat tat aaa aat tca ctt gca aaa tta aaa gaa gcg tat aaa ata gat       480
Asp Tyr Lys Asn Ser Leu Ala Lys Leu Lys Glu Ala Tyr Lys Ile Asp
145                 150                 155 gcg acg aca agc cct cag aat gtt tgg ctg gca tat gaa act ttg aat       528
Ala Thr Thr Ser Pro Gln Asn Val Trp Leu Ala Tyr Glu Thr Leu Asn
160                 165                 170                 175 tta caa agc aag caa aat aac gct cca aca tgg tgg aat act gta aac       576
Leu Gln Ser Lys Gln Asn Asn Ala Pro Thr Trp Trp Asn Thr Val Asn
                180                 185                 190 aaa gat cta aaa caa ttc tct gag aaa tat tta tgg acc gcc ttg act       624
Lys Asp Leu Lys Gln Phe Ser Glu Lys Tyr Leu Trp Thr Ala Leu Thr
```

-continued

```
                         195                 200                 205
tct aat gat aat ctt aga aag atg tca gga ggt cgt atg att aac gat      672
Ser Asn Asp Asn Leu Arg Lys Met Ser Gly Gly Arg Met Ile Asn Asp
                210                 215                 220 ata ttg aac gat atc gaa aac ata aag aaa gga gag gga caa ccg ggt      720
Ile Leu Asn Asp Ile Glu Asn Ile Lys Lys Gly Glu Gly Gln Pro Gly
            225                 230                 235 gct cca gga gga aag gaa aac aaa tta tca gtg ctg acc gtt cct caa      768
Ala Pro Gly Gly Lys Glu Asn Lys Leu Ser Val Leu Thr Val Pro Gln
240                 245                 250                 255 gct atc tta gca gca ttt gtt tca gca ttt gct ccc gaa ggt aca aaa      816
Ala Ile Leu Ala Ala Phe Val Ser Ala Phe Ala Pro Glu Gly Thr Lys
                260                 265                 270 att gaa aat aag gac ctt gat ccg tct act tta tat cct ggc caa gga      864
Ile Glu Asn Lys Asp Leu Asp Pro Ser Thr Leu Tyr Pro Gly Gln Gly
            275                 280                 285 gca ctt cac gtt att gaa cta cac caa gat aag agc gat tgg agc ata      912
Ala Leu His Val Ile Glu Leu His Gln Asp Lys Ser Asp Trp Ser Ile
        290                 295                 300 aaa gtt ctc tat aga aac aat gac caa atg aag ctg aaa cca atg aaa      960
Lys Val Leu Tyr Arg Asn Asn Asp Gln Met Lys Leu Lys Pro Met Lys
    305                 310                 315 ctt gca caa tgc ggt gac aag tgt tct tat ggt act ttc aaa tca atg     1008
Leu Ala Gln Cys Gly Asp Lys Cys Ser Tyr Gly Thr Phe Lys Ser Met
320                 325                 330                 335 cta caa aaa tat aac atg gag aag gaa gct cat gat aaa tta tgt aaa     1056
Leu Gln Lys Tyr Asn Met Glu Lys Glu Ala His Asp Lys Leu Cys Lys
                340                 345                 350 acg tcg taaaaattaa aaataaaaac ttttcaatat attttccgct aaaataaata     1112
Thr Ser aatatgtttg tatatttaaa cttatcaaaa taatagtagt gttttaataa agattttaaa  1172
taaataattg taaaaaaaaa aaaaaaaaaa aaa                                1205

<210> SEQ ID NO 65
<211> LENGTH: 353
<212> TYPE: PRT
<213> ORGANISM: Ctenocephalides felis

<400> SEQUENCE: 65

Glu Leu Lys Phe Val Phe Ala Thr Ala Arg Gly Met Ser His Thr Pro
1               5                   10                  15

Cys Asp Tyr Pro Gly Gly Pro Lys Ile Thr His Lys Ser Glu Asp Ser
            20                  25                  30

Ser Gln Leu Thr Pro Ala Gly Gln Glu Glu Ala Leu Lys Ile Gly Lys
        35                  40                  45

Leu Leu Ser Glu His Tyr Arg Thr Asn Leu Lys Val Asp Lys Trp Asp
    50                  55                  60

Ser Asn Lys Asn Tyr Trp Thr Leu Ala Ser Ala Thr Arg Arg Ser Gln
65                  70                  75                  80

Glu Gly Ala Leu Ile Ile Gly Ser Gly Leu Glu Lys Glu Lys Ala
                85                  90                  95

Val Trp Thr Lys Glu Lys Gly Asp Lys Thr Ile Phe Ser Ser Phe Gly
            100                 105                 110

Glu Tyr Ala Lys Phe Tyr Ser Pro Lys Thr Cys Pro Asn Phe Ile Ala
        115                 120                 125

Gln Gln Lys Ile Ala Val Arg Asp Leu Leu Thr Lys Ser Ala Lys Asp
    130                 135                 140
```

```
Tyr Lys Asn Ser Leu Ala Lys Leu Lys Glu Ala Tyr Lys Ile Asp Ala
145                 150                 155                 160

Thr Thr Ser Pro Gln Asn Val Trp Leu Ala Tyr Glu Thr Leu Asn Leu
                165                 170                 175

Gln Ser Lys Gln Asn Asn Ala Pro Thr Trp Trp Asn Thr Val Asn Lys
            180                 185                 190

Asp Leu Lys Gln Phe Ser Glu Lys Tyr Leu Trp Thr Ala Leu Thr Ser
        195                 200                 205

Asn Asp Asn Leu Arg Lys Met Ser Gly Gly Arg Met Ile Asn Asp Ile
    210                 215                 220

Leu Asn Asp Ile Glu Asn Ile Lys Lys Gly Glu Gly Gln Pro Gly Ala
225                 230                 235                 240

Pro Gly Gly Lys Glu Asn Lys Leu Ser Val Leu Thr Val Pro Gln Ala
                245                 250                 255

Ile Leu Ala Ala Phe Val Ser Ala Phe Ala Pro Glu Gly Thr Lys Ile
            260                 265                 270

Glu Asn Lys Asp Leu Asp Pro Ser Thr Leu Tyr Pro Gly Gln Gly Ala
        275                 280                 285

Leu His Val Ile Glu Leu His Gln Asp Lys Ser Asp Trp Ser Ile Lys
    290                 295                 300

Val Leu Tyr Arg Asn Asn Asp Gln Met Lys Leu Lys Pro Met Lys Leu
305                 310                 315                 320

Ala Gln Cys Gly Asp Lys Cys Ser Tyr Gly Thr Phe Lys Ser Met Leu
                325                 330                 335

Gln Lys Tyr Asn Met Glu Lys Glu Ala His Asp Lys Leu Cys Lys Thr
            340                 345                 350

Ser

<210> SEQ ID NO 66
<211> LENGTH: 1205
<212> TYPE: DNA
<213> ORGANISM: Ctenocephalides felis

<400> SEQUENCE: 66
tttttttttt tttttttttt ttacaattat ttatttaaaa tctttattaa aacactacta      60
ttattttgat aagtttaaat atacaaacat atttatttat tttagcggaa aatatattga     120
aaagttttta tttttaattt ttacgacgtt ttacataatt tatcatgagc ttccttctcc     180
atgttatatt tttgtagcat tgatttgaaa gtaccataag aacacttgtc accgcattgt     240
gcaagtttca ttggtttcag cttcatttgg tcattgtttc tatagagaac ttttatgctc     300
caatcgctct tatcttggtg tagttcaata acgtgaagtg ctccttggcc aggatataaa     360
gtagacggat caaggtcctt attttcaatt tttgtacctt cgggagcaaa tgctgaaaca     420
aatgctgcta agatagcttg aggaacggtc agcactgata atttgttttc ctttcctcct     480
ggagcacccg gttgtccctc tcctttcttt atgttttcga tatcgttcaa tatatcgtta     540
atcatacgac ctcctgacat ctttctaaga ttatcattag aagtcaaggc ggtccataaa     600
tatttctcag agaattgttt tagatctttg tttacagtat tccaccatgt tggagcgtta     660
ttttgcttgc tttgtaaatt caaagtttca tatgccagcc aaacattctg agggcttgtc     720
gtcgcatcta ttttatacgc ttctttaat tttgcaagtg aattttttata atcttttgca     780
cttttttgtta acaagtctct tactgctatt ttctgttgtg ctatgaagtt tggacaagtt     840
tttggactat aaaatttagc atattcacca aacgaagaaa atatggtttt atctcctttc     900
```

-continued

```
tcttttgtcc aaactgcctt ttccttttct tctagaccag aaccaatgat aagcgctcct      960
tcttgagatc ttctcgtagc actagctaat gtccaataat ttttatttga atcccatttg     1020
tcaactttta aattagttct gtaatgttcg gataataatt tgccaatttt taatgcctct     1080
tcttgacctg ccggtgtcaa ttggcttgaa tcttcagact tgtgtgtaat ttttggaccg     1140
cctggataat cacaaggtgt atgtgacata cctcgtgcag tcgcaaacac aaatttcaat     1200
tctgc                                                                 1205

<210> SEQ ID NO 67
<211> LENGTH: 1059
<212> TYPE: DNA
<213> ORGANISM: Ctenocephalides felis
<220> FEATURE:
<221> NAME/KEY: CDS
<222> LOCATION: (1)..(1059)

<400> SEQUENCE: 67 gaa ttg aaa ttt gtg ttt gcg act gca cga ggt atg tca cat aca cct       48
Glu Leu Lys Phe Val Phe Ala Thr Ala Arg Gly Met Ser His Thr Pro
1               5                  10                  15 tgt gat tat cca ggc ggt cca aaa att aca cac aag tct gaa gat tca       96
Cys Asp Tyr Pro Gly Gly Pro Lys Ile Thr His Lys Ser Glu Asp Ser
            20                  25                  30 agc caa ttg aca ccg gca ggt caa gaa gag gca tta aaa att ggc aaa      144
Ser Gln Leu Thr Pro Ala Gly Gln Glu Glu Ala Leu Lys Ile Gly Lys
        35                  40                  45 tta tta tcc gaa cat tac aga act aat tta aaa gtt gac aaa tgg gat      192
Leu Leu Ser Glu His Tyr Arg Thr Asn Leu Lys Val Asp Lys Trp Asp
    50                  55                  60 tca aat aaa aat tat tgg aca tta gct agt gct acg aga aga tct caa      240
Ser Asn Lys Asn Tyr Trp Thr Leu Ala Ser Ala Thr Arg Arg Ser Gln
65                  70                  75                  80 gaa gga gcg ctt atc att ggt tct ggt cta gaa gaa aag gaa aag gca      288
Glu Gly Ala Leu Ile Ile Gly Ser Gly Leu Glu Glu Lys Glu Lys Ala
                85                  90                  95 gtt tgg aca aaa gag aaa gga gat aaa acc ata ttt tct tcg ttt ggt      336
Val Trp Thr Lys Glu Lys Gly Asp Lys Thr Ile Phe Ser Ser Phe Gly
            100                 105                 110 gaa tat gct aaa ttt tat agt cca aaa act tgt cca aac ttc ata gca      384
Glu Tyr Ala Lys Phe Tyr Ser Pro Lys Thr Cys Pro Asn Phe Ile Ala
        115                 120                 125 caa cag aaa ata gca gta aga gac ttg tta aca aaa agt gca aaa gat      432
Gln Gln Lys Ile Ala Val Arg Asp Leu Leu Thr Lys Ser Ala Lys Asp
    130                 135                 140 tat aaa aat tca ctt gca aaa tta aaa gaa gcg tat aaa ata gat gcg      480
Tyr Lys Asn Ser Leu Ala Lys Leu Lys Glu Ala Tyr Lys Ile Asp Ala
145                 150                 155                 160 acg aca agc cct cag aat gtt tgg ctg gca tat gaa act ttg aat tta      528
Thr Thr Ser Pro Gln Asn Val Trp Leu Ala Tyr Glu Thr Leu Asn Leu
                165                 170                 175 caa agc aag caa aat aac gct cca aca tgg tgg aat act gta aac aaa      576
Gln Ser Lys Gln Asn Asn Ala Pro Thr Trp Trp Asn Thr Val Asn Lys
            180                 185                 190 gat cta aaa caa ttc tct gag aaa tat tta tgg acc gcc ttg act tct      624
Asp Leu Lys Gln Phe Ser Glu Lys Tyr Leu Trp Thr Ala Leu Thr Ser
        195                 200                 205 aat gat aat ctt aga aag atg tca gga ggt cgt atg att aac gat ata      672
Asn Asp Asn Leu Arg Lys Met Ser Gly Gly Arg Met Ile Asn Asp Ile
    210                 215                 220
```

-continued

```
ttg aac gat atc gaa aac ata aag aaa gga gag gga caa ccg ggt gct      720
Leu Asn Asp Ile Glu Asn Ile Lys Lys Gly Glu Gly Gln Pro Gly Ala
225                 230                 235                 240 cca gga gga aag gaa aac aaa tta tca gtg ctg acc gtt cct caa gct      768
Pro Gly Gly Lys Glu Asn Lys Leu Ser Val Leu Thr Val Pro Gln Ala
                245                 250                 255 atc tta gca gca ttt gtt tca gca ttt gct ccc gaa ggt aca aaa att      816
Ile Leu Ala Ala Phe Val Ser Ala Phe Ala Pro Glu Gly Thr Lys Ile
            260                 265                 270 gaa aat aag gac ctt gat ccg tct act tta tat cct ggc caa gga gca      864
Glu Asn Lys Asp Leu Asp Pro Ser Thr Leu Tyr Pro Gly Gln Gly Ala
        275                 280                 285 ctt cac gtt att gaa cta cac caa gat aag agc gat tgg agc ata aaa      912
Leu His Val Ile Glu Leu His Gln Asp Lys Ser Asp Trp Ser Ile Lys
    290                 295                 300 gtt ctc tat aga aac aat gac caa atg aag ctg aaa cca atg aaa ctt      960
Val Leu Tyr Arg Asn Asn Asp Gln Met Lys Leu Lys Pro Met Lys Leu
305                 310                 315                 320 gca caa tgc ggt gac aag tgt tct tat ggt act ttc aaa tca atg cta     1008
Ala Gln Cys Gly Asp Lys Cys Ser Tyr Gly Thr Phe Lys Ser Met Leu
                325                 330                 335 caa aaa tat aac atg gag aag gaa gct cat gat aaa tta tgt aaa acg     1056
Gln Lys Tyr Asn Met Glu Lys Glu Ala His Asp Lys Leu Cys Lys Thr
            340                 345                 350 tcg                                                                  1059
Ser
```

<210> SEQ ID NO 68
<211> LENGTH: 353
<212> TYPE: PRT
<213> ORGANISM: Ctenocephalides felis

<400> SEQUENCE: 68

```
Glu Leu Lys Phe Val Phe Ala Thr Ala Arg Gly Met Ser His Thr Pro
1               5                   10                  15

Cys Asp Tyr Pro Gly Gly Pro Lys Ile Thr His Lys Ser Glu Asp Ser
            20                  25                  30

Ser Gln Leu Thr Pro Ala Gly Gln Glu Glu Ala Leu Lys Ile Gly Lys
        35                  40                  45

Leu Leu Ser Glu His Tyr Arg Thr Asn Leu Lys Val Asp Lys Trp Asp
50                  55                  60

Ser Asn Lys Asn Tyr Trp Thr Leu Ala Ser Ala Thr Arg Arg Ser Gln
65                  70                  75                  80

Glu Gly Ala Leu Ile Ile Gly Ser Gly Leu Glu Glu Lys Glu Lys Ala
                85                  90                  95

Val Trp Thr Lys Glu Lys Gly Asp Lys Thr Ile Phe Ser Ser Phe Gly
            100                 105                 110

Glu Tyr Ala Lys Phe Tyr Ser Pro Lys Thr Cys Pro Asn Phe Ile Ala
        115                 120                 125

Gln Gln Lys Ile Ala Val Arg Asp Leu Leu Thr Lys Ser Ala Lys Asp
    130                 135                 140

Tyr Lys Asn Ser Leu Ala Lys Leu Lys Glu Ala Tyr Lys Ile Asp Ala
145                 150                 155                 160

Thr Thr Ser Pro Gln Asn Val Trp Leu Ala Tyr Glu Thr Leu Asn Leu
                165                 170                 175

Gln Ser Lys Gln Asn Asn Ala Pro Thr Trp Trp Asn Thr Val Asn Lys
            180                 185                 190
```

```
Asp Leu Lys Gln Phe Ser Glu Lys Tyr Leu Trp Thr Ala Leu Thr Ser
            195                 200                 205

Asn Asp Asn Leu Arg Lys Met Ser Gly Gly Arg Met Ile Asn Asp Ile
        210                 215                 220

Leu Asn Asp Ile Glu Asn Ile Lys Lys Gly Glu Gly Gln Pro Gly Ala
225                 230                 235                 240

Pro Gly Gly Lys Glu Asn Lys Leu Ser Val Leu Thr Val Pro Gln Ala
                245                 250                 255

Ile Leu Ala Ala Phe Val Ser Ala Phe Ala Pro Glu Gly Thr Lys Ile
            260                 265                 270

Glu Asn Lys Asp Leu Asp Pro Ser Thr Leu Tyr Pro Gly Gln Gly Ala
        275                 280                 285

Leu His Val Ile Glu Leu His Gln Asp Lys Ser Asp Trp Ser Ile Lys
290                 295                 300

Val Leu Tyr Arg Asn Asn Asp Gln Met Lys Leu Lys Pro Met Lys Leu
305                 310                 315                 320

Ala Gln Cys Gly Asp Lys Cys Ser Tyr Gly Thr Phe Lys Ser Met Leu
                325                 330                 335

Gln Lys Tyr Asn Met Glu Lys Glu Ala His Asp Lys Leu Cys Lys Thr
            340                 345                 350

Ser
```

```
<210> SEQ ID NO 69
<211> LENGTH: 1059
<212> TYPE: DNA
<213> ORGANISM: Ctenocephalides felis

<400> SEQUENCE: 69
cgacgtttta cataatttat catgagcttc cttctccatg ttatattttt gtagcattga      60
tttgaaagta ccataagaac acttgtcacc gcattgtgca agtttcattg gtttcagctt     120
catttggtca ttgtttctat agagaacttt tatgctccaa tcgctcttat cttggtgtag     180
ttcaataacg tgaagtgctc cttggccagg atataaagta gacggatcaa ggtccttatt     240
ttcaattttt gtaccttcgg gagcaaatgc tgaaacaaat gctgctaaga tagcttgagg     300
aacggtcagc actgataatt tgttttcctt cctcctgga gcacccggtt gtccctctcc      360
tttctttatg ttttcgatat cgttcaatat atcgttaatc atacgacctc ctgacatctt     420
tctaagatta tcattagaag tcaaggcggt ccataaatat ttctcagaga attgttttag    480
atctttgttt acagtattcc accatgttgg agcgttattt tgcttgcttt gtaaattcaa     540
agtttcatat gccagccaaa cattctgagg gcttgtcgtc gcatctattt tatacgcttc     600
ttttaatttt gcaagtgaat ttttataatc ttttgcactt tttgttaaca agtctcttac     660
tgctattttc tgttgtgcta tgaagtttgg acaagttttt ggactataaa atttagcata     720
ttcaccaaac gaagaaaata tggttttatc ccttttctct tttgtccaaa ctgccttttc     780
cttttcttct agaccagaac caatgataag cgctccttct tgagatcttc tcgtagcact     840
agctaatgtc caataatttt tatttgaatc ccatttgtca acttttaaat tagttctgta     900
atgttcggat aataatttgc caattttttaa tgcctcttct tgacctgccg gtgtcaattg     960
gcttgaatct tcagacttgt gtgtaatttt tggaccgcct ggataatcac aaggtgtatg    1020
tgacataacct cgtgcagtcg caaacacaaa tttcaattc                          1059
```

```
<210> SEQ ID NO 70
<211> LENGTH: 25
<212> TYPE: PRT
<213> ORGANISM: Ctenocephalides felis
<220> FEATURE:
<221> NAME/KEY: misc_feature
<222> LOCATION: (1)..()
<223> OTHER INFORMATION: Xaa = any amino acid
<221> NAME/KEY: misc_feature
<222> LOCATION: (24)..()
<223> OTHER INFORMATION: Xaa = any amino acid

<400> SEQUENCE: 70

Xaa Glu Leu Lys Phe Val Phe Val Met Val Lys Gly Pro Asp His Glu
1               5                   10                  15

Ala Cys Asn Tyr Ala Gly Gly Xaa Gln
            20                  25

<210> SEQ ID NO 71
<211> LENGTH: 406
<212> TYPE: DNA
<213> ORGANISM: Ctenocephalides felis
<220> FEATURE:
<221> NAME/KEY: CDS
<222> LOCATION: (1)..(405)

<400> SEQUENCE: 71 atg gtt aaa ggt cca gat cac gaa gct tgt aac tat gca gga ggt cct        48
Met Val Lys Gly Pro Asp His Glu Ala Cys Asn Tyr Ala Gly Gly Pro
1               5                   10                  15 cag tta act act ctt caa gaa aaa gat agt gtt cta act gaa gat ggc        96
Gln Leu Thr Thr Leu Gln Glu Lys Asp Ser Val Leu Thr Glu Asp Gly
            20                  25                  30 aag aca gaa gca tac gaa ttg gga aaa ctt ttg gac aag gta tat aaa       144
Lys Thr Glu Ala Tyr Glu Leu Gly Lys Leu Leu Asp Lys Val Tyr Lys
        35                  40                  45 aaa caa tta aaa gtt gac aaa tgg gat gcc acg aaa acc tac tgg gct       192
Lys Gln Leu Lys Val Asp Lys Trp Asp Ala Thr Lys Thr Tyr Trp Ala
    50                  55                  60 gtg tcc aca aaa gct atg cgt act aaa gaa gca gcc tta att gta gga       240
Val Ser Thr Lys Ala Met Arg Thr Lys Glu Ala Ala Leu Ile Val Gly
65                  70                  75                  80 gca gga ttg gaa aat aat cct gca aaa gct aaa ggt aat tgg aca caa       288
Ala Gly Leu Glu Asn Asn Pro Ala Lys Ala Lys Gly Asn Trp Thr Gln
                85                  90                  95 caa cag ctc gat tca aca cat ttt gat gcg atg cct ggc ttt tct aga       336
Gln Gln Leu Asp Ser Thr His Phe Asp Ala Met Pro Gly Phe Ser Arg
            100                 105                 110 ttt tgg aat cct caa caa tgt ccg gca tat ttc aga gcg ctc tcg cta       384
Phe Trp Asn Pro Gln Gln Cys Pro Ala Tyr Phe Arg Ala Leu Ser Leu
        115                 120                 125 caa aat cag aaa ata aag aaa t                                         406
Gln Asn Gln Lys Ile Lys Lys
    130                 135

<210> SEQ ID NO 72
<211> LENGTH: 135
<212> TYPE: PRT
<213> ORGANISM: Ctenocephalides felis

<400> SEQUENCE: 72

Met Val Lys Gly Pro Asp His Glu Ala Cys Asn Tyr Ala Gly Gly Pro
1               5                   10                  15

Gln Leu Thr Thr Leu Gln Glu Lys Asp Ser Val Leu Thr Glu Asp Gly
```

```
                    20                  25                  30
Lys Thr Glu Ala Tyr Glu Leu Gly Lys Leu Leu Asp Lys Val Tyr Lys
            35                  40                  45

Lys Gln Leu Lys Val Asp Lys Trp Asp Ala Thr Lys Thr Tyr Trp Ala
        50                  55                  60

Val Ser Thr Lys Ala Met Arg Thr Lys Glu Ala Ala Leu Ile Val Gly
 65                  70                  75                  80

Ala Gly Leu Glu Asn Asn Pro Ala Lys Ala Lys Gly Asn Trp Thr Gln
                85                  90                  95

Gln Gln Leu Asp Ser Thr His Phe Asp Ala Met Pro Gly Phe Ser Arg
            100                 105                 110

Phe Trp Asn Pro Gln Cys Pro Ala Tyr Phe Arg Ala Leu Ser Leu
        115                 120                 125

Gln Asn Gln Lys Ile Lys Lys
        130             135

<210> SEQ ID NO 73
<211> LENGTH: 406
<212> TYPE: DNA
<213> ORGANISM: Ctenocephalides felis

<400> SEQUENCE: 73
atttctttat tttctgattt tgtagcgaga gcgctctgaa atatgccgga cattgttgag      60
gattccaaaa tctagaaaag ccaggcatcg catcaaaatg tgttgaatcg agctgttgtt     120
gtgtccaatt acctttagct tttgcaggat tattttccaa tcctgctcct acaattaagg     180
ctgcttcttt agtacgcata gcttttgtgg acacagccca gtaggttttc gtggcatccc     240
atttgtcaac ttttaattgt tttttatata ccttgtccaa aagttttccc aattcgtatg     300
cttctgtctt gccatcttca gttagaacac tatcttttc ttgaagagta gttaactgag      360
gacctcctgc atagttacaa gcttcgtgat ctggaccttt aaccat                    406

<210> SEQ ID NO 74
<211> LENGTH: 420
<212> TYPE: DNA
<213> ORGANISM: Ctenocephalides felis
<220> FEATURE:
<221> NAME/KEY: CDS
<222> LOCATION: (1)..(216)

<400> SEQUENCE: 74 gaa gtt atg gat aaa ttg cga aaa cag gca cct cct aaa act gat ggc       48
Glu Val Met Asp Lys Leu Arg Lys Gln Ala Pro Pro Lys Thr Asp Gly
 1               5                  10                  15 aat cct cca aaa aca acc ata atg agt aca ctt caa aag caa caa ata       96
Asn Pro Pro Lys Thr Thr Ile Met Ser Thr Leu Gln Lys Gln Gln Ile
            20                  25                  30 agt tgc aca gaa gtg aaa gcg gtt aac tta gaa agt cat gtt tgt gct      144
Ser Cys Thr Glu Val Lys Ala Val Asn Leu Glu Ser His Val Cys Ala
        35                  40                  45 tat gat tgt agt caa cct gaa act gca gga att aca tgc aaa gga aat      192
Tyr Asp Cys Ser Gln Pro Glu Thr Ala Gly Ile Thr Cys Lys Gly Asn
    50                  55                  60 aag tgt gat tgt cct aaa aaa cgc taaaaattta ttcaaaacat ttacattttt     246
Lys Cys Asp Cys Pro Lys Lys Arg
 65                 70 tattaatatt caactatcaa aaattctgtg ttgattgtta ttatatttat catagttact     306
agaaataaaa ttttataaca ttgttaattc gaattgaat acacataata ttataattag      366
```

```
tgaggttaaa agaaataaac cgaatatcca aatcaaaaaa aaaaaaaaaa aaaa        420
```

<210> SEQ ID NO 75
<211> LENGTH: 72
<212> TYPE: PRT
<213> ORGANISM: Ctenocephalides felis

<400> SEQUENCE: 75

Glu Val Met Asp Lys Leu Arg Lys Gln Ala Pro Pro Lys Thr Asp Gly
1               5                   10                  15

Asn Pro Pro Lys Thr Thr Ile Met Ser Thr Leu Gln Lys Gln Gln Ile
            20                  25                  30

Ser Cys Thr Glu Val Lys Ala Val Asn Leu Glu Ser His Val Cys Ala
        35                  40                  45

Tyr Asp Cys Ser Gln Pro Glu Thr Ala Gly Ile Thr Cys Lys Gly Asn
    50                  55                  60

Lys Cys Asp Cys Pro Lys Lys Arg
65                  70

<210> SEQ ID NO 76
<211> LENGTH: 420
<212> TYPE: DNA
<213> ORGANISM: Ctenocephalides felis

<400> SEQUENCE: 76

```
tttttttttt tttttttttt gatttggata ttcggtttat ttcttttaac ctcactaatt   60
ataatattat gtgtattcaa tttcgaatta acaatgttat aaaattttat ttctagtaac  120
tatgataaat ataataacaa tcaacacaga attttttgata gttgaatatt aataaaaaat  180
gtaaatgttt tgaataaatt tttagcgttt tttaggacaa tcacacttat ttcctttgca  240
tgtaattcct gcagtttcag gttgactaca atcataagca caaacatgac tttctaagtt  300
aaccgctttc acttctgtgc aacttatttg ttgcttttga agtgtactca ttatggttgt  360
ttttggagga ttgccatcag ttttaggagg tgcctgtttt cgcaatttat ccataacttc  420
```

<210> SEQ ID NO 77
<211> LENGTH: 71
<212> TYPE: PRT
<213> ORGANISM: Ctenocephalides felis

<400> SEQUENCE: 77

Ser Lys Met Val Thr Glu Lys Cys Lys Ser Gly Gly Asn Asn Pro Ser
1               5                   10                  15

Thr Lys Glu Val Ser Ile Pro Ser Gly Lys Leu Thr Ile Glu Asp Phe
            20                  25                  30

Cys Ile Gly Asn His Gln Ser Cys Lys Ile Phe Cys Lys Ser Gln Cys
        35                  40                  45

Gly Phe Gly Gly Gly Ala Cys Gly Asn Gly Gly Ser Thr Arg Pro Asn
    50                  55                  60

Gln Lys His Cys Tyr Cys Glu
65                  70

<210> SEQ ID NO 78
<211> LENGTH: 25
<212> TYPE: PRT
<213> ORGANISM: Ctenocephalides felis

<400> SEQUENCE: 78

```
Asn Asp Lys Leu Gln Phe Val Phe Val Met Ala Arg Gly Pro Asp His
 1           5                  10                  15

Glu Ala Cys Asn Tyr Pro Gly Gly Pro
            20              25
```

<210> SEQ ID NO 79
<211> LENGTH: 26
<212> TYPE: DNA
<213> ORGANISM: Ctenocephalides felis
<220> FEATURE:
<221> NAME/KEY: misc_feature
<222> LOCATION: (1)..(26)
<223> OTHER INFORMATION: primer

<400> SEQUENCE: 79
agtggatccg tcaaaaatgg tcactg                                    26

<210> SEQ ID NO 80
<211> LENGTH: 28
<212> TYPE: DNA
<213> ORGANISM: Ctenocephalides felis
<220> FEATURE:
<221> NAME/KEY: misc_feature
<222> LOCATION: (1)..(28)
<223> OTHER INFORMATION: primer

<400> SEQUENCE: 80
ccggaattcg gttattcgca ataacagt                                  28

<210> SEQ ID NO 81
<211> LENGTH: 54
<212> TYPE: DNA
<213> ORGANISM: Ctenocephalides felis
<220> FEATURE:
<221> NAME/KEY: misc_feature
<222> LOCATION: (1)..(54)
<223> OTHER INFORMATION: primer

<400> SEQUENCE: 81
gcgcggatcc gcatatggaa gacatctgga aagttaataa aaaatgtaca tcag      54

<210> SEQ ID NO 82
<211> LENGTH: 45
<212> TYPE: DNA
<213> ORGANISM: Ctenocephalides felis
<220> FEATURE:
<221> NAME/KEY: misc_feature
<222> LOCATION: (1)..(45)
<223> OTHER INFORMATION: primer

<400> SEQUENCE: 82
ccggaattct tatttatttt ttggtcgaca ataacaaaag tttcc                45

<210> SEQ ID NO 83
<211> LENGTH: 41
<212> TYPE: DNA
<213> ORGANISM: Ctenocephalides felis
<220> FEATURE:
<221> NAME/KEY: misc_feature
<222> LOCATION: (1)..(41)
<223> OTHER INFORMATION: primer

<400> SEQUENCE: 83
aaatttgtwt ttgtwatggt waaaggwccw gatcatgaag c                   41

<210> SEQ ID NO 84

```
<211> LENGTH: 29
<212> TYPE: DNA
<213> ORGANISM: Ctenocephalides felis
<220> FEATURE:
<221> NAME/KEY: misc_feature
<222> LOCATION: (1)..(29)
<223> OTHER INFORMATION: primer

<400> SEQUENCE: 84
catgaaccwg gwaatacwcg waarathas                                    29

<210> SEQ ID NO 85
<211> LENGTH: 17
<212> TYPE: DNA
<213> ORGANISM: Ctenocephalides felis
<220> FEATURE:
<221> NAME/KEY: misc_feature
<222> LOCATION: (1)..(17)
<223> OTHER INFORMATION: primer

<400> SEQUENCE: 85
gtaaaacgac ggccagt                                                 17

<210> SEQ ID NO 86
<211> LENGTH: 26
<212> TYPE: DNA
<213> ORGANISM: Ctenocephalides felis
<220> FEATURE:
<221> NAME/KEY: misc_feature
<222> LOCATION: (1)..(26)
<223> OTHER INFORMATION: primer

<400> SEQUENCE: 86
gaagtwatgg ayaaattrag rcargc                                       26

<210> SEQ ID NO 87
<211> LENGTH: 19
<212> TYPE: PRT
<213> ORGANISM: Ctenocephalides felis
<220> FEATURE:
<221> NAME/KEY: PEPTIDE
<222> LOCATION: (1)..(19)

<400> SEQUENCE: 87

Tyr Phe Asn Lys Leu Val Gln Ser Trp Thr Glu Pro Met Val Phe Lys
 1               5                  10                  15

Tyr Pro Tyr

<210> SEQ ID NO 88
<211> LENGTH: 24
<212> TYPE: DNA
<213> ORGANISM: Ctenocephalides felis
<220> FEATURE:
<221> NAME/KEY: misc_feature
<222> LOCATION: (1)..(24)
<223> OTHER INFORMATION: primer

<400> SEQUENCE: 88
gtaatacgac tcactatata gggc                                         24

<210> SEQ ID NO 89
<211> LENGTH: 1300
<212> TYPE: DNA
<213> ORGANISM: Ctenocephalides felis
<220> FEATURE:
<221> NAME/KEY: CDS
<222> LOCATION: (12)..(1136)
```

<400> SEQUENCE: 89

```
catatttcaa a atg ttt gcg atc ttg tta aca gga ata ttg gcg cta aca        50
            Met Phe Ala Ile Leu Leu Thr Gly Ile Leu Ala Leu Thr
             1               5                  10 tta agt gct gaa tgt agt gaa ctt aag ttt gta ttt gtg atg gtg aaa         98
Leu Ser Ala Glu Cys Ser Glu Leu Lys Phe Val Phe Val Met Val Lys
 15              20                  25 ggg ccg gat cat gaa gct tgt aac tat gca gga ggt cct cag tta act        146
Gly Pro Asp His Glu Ala Cys Asn Tyr Ala Gly Gly Pro Gln Leu Thr
 30              35                  40                  45 act ctt caa gaa aaa gat agt gtt cta act gaa gat ggc aag aca gaa        194
Thr Leu Gln Glu Lys Asp Ser Val Leu Thr Glu Asp Gly Lys Thr Glu
                 50                  55                  60 gca tac gaa ttg gga aaa ctc ttg gac aag gta tat aaa aaa caa tta        242
Ala Tyr Glu Leu Gly Lys Leu Leu Asp Lys Val Tyr Lys Lys Gln Leu
                 65                  70                  75 aaa gtt gac aaa tgg gat gcc acg aaa acc tac tgg gct gtg tcc aca        290
Lys Val Asp Lys Trp Asp Ala Thr Lys Thr Tyr Trp Ala Val Ser Thr
             80                  85                  90 aaa gct atg cgt act aaa gaa gca gcc tta att gta gga gca gga ttg        338
Lys Ala Met Arg Thr Lys Glu Ala Ala Leu Ile Val Gly Ala Gly Leu
 95              100                 105 gaa aat aat cct gca aaa gct aaa ggt aat tgg aca caa caa cag ctc        386
Glu Asn Asn Pro Ala Lys Ala Lys Gly Asn Trp Thr Gln Gln Gln Leu
110             115                 120                 125 gat tca aca cat ttt gat gcg atg cct ggc ttt tct aga ttt tgg aat        434
Asp Ser Thr His Phe Asp Ala Met Pro Gly Phe Ser Arg Phe Trp Asn
                130                 135                 140 cct caa caa tgt ccg gca tat ttc aga gcg ctc tcg cta caa aat cag        482
Pro Gln Gln Cys Pro Ala Tyr Phe Arg Ala Leu Ser Leu Gln Asn Gln
                145                 150                 155 aaa ata aag aaa ctt ctc gag aaa tat caa act act att aaa gaa gtt        530
Lys Ile Lys Lys Leu Leu Glu Lys Tyr Gln Thr Thr Ile Lys Glu Val
                160                 165                 170 act gcc aag ttt cca tct att gat ggt aca aaa gcg caa cat ata tgg        578
Thr Ala Lys Phe Pro Ser Ile Asp Gly Thr Lys Ala Gln His Ile Trp
175                 180                 185 atc gcc tac gag act ttt aag aga atg aaa caa caa ggc aga aaa gaa        626
Ile Ala Tyr Glu Thr Phe Lys Arg Met Lys Gln Gln Gly Arg Lys Glu
190                 195                 200                 205 gta gaa ggg ata aat act gca act atg caa aaa ctt aaa gaa ttt tca        674
Val Glu Gly Ile Asn Thr Ala Thr Met Gln Lys Leu Lys Glu Phe Ser
                210                 215                 220 tct gag ttc gtg ctg att gct ttg aca tcc aca gat caa atg aga aaa        722
Ser Glu Phe Val Leu Ile Ala Leu Thr Ser Thr Asp Gln Met Arg Lys
                225                 230                 235 tta gca gga ggt tta ata ttg aag gac tta ttt aat gat att gat gag        770
Leu Ala Gly Gly Leu Ile Leu Lys Asp Leu Phe Asn Asp Ile Asp Glu
                240                 245                 250 ctg aca aaa gac cat gcg caa cca cat gcg ccg ggt ggc att aag aat        818
Leu Thr Lys Asp His Ala Gln Pro His Ala Pro Gly Gly Ile Lys Asn
                255                 260                 265 aaa atg aat ata ttt gtg gta cca caa gca att tta gcc gca caa atg        866
Lys Met Asn Ile Phe Val Val Pro Gln Ala Ile Leu Ala Ala Gln Met
270                 275                 280                 285 gct gta ttt atg cca gaa ggt acc aaa ttg aga gat caa cca ata aca        914
Ala Val Phe Met Pro Glu Gly Thr Lys Leu Arg Asp Gln Pro Ile Thr
                290                 295                 300 gct tca aat ttc tat cct gat gat cag tct tat gta atc ata gaa ttg        962
Ala Ser Asn Phe Tyr Pro Asp Asp Gln Ser Tyr Val Ile Ile Glu Leu
```

```
Ala Ser Asn Phe Tyr Pro Asp Asp Gln Ser Tyr Val Ile Ile Glu Leu
            305                 310                 315 tac caa gat aaa aac aag tgg aac gta caa tta caa tat aaa aac aac       1010
Tyr Gln Asp Lys Asn Lys Trp Asn Val Gln Leu Gln Tyr Lys Asn Asn
            320                 325                 330 aaa aat agc gga tgg ctg cca att aaa gtg caa ggt tgc aat tca cct       1058
Lys Asn Ser Gly Trp Leu Pro Ile Lys Val Gln Gly Cys Asn Ser Pro
            335                 340                 345 atg tgt ccg tat gat aca tta aaa aaa tca ctg aat aaa tat ata ata       1106
Met Cys Pro Tyr Asp Thr Leu Lys Lys Ser Leu Asn Lys Tyr Ile Ile
350                 355                 360                 365 gat gat gct aga cat aag caa gcc tgt aaa taattattgg tcctggccat         1156
Asp Asp Ala Arg His Lys Gln Ala Cys Lys
                370                 375 aataattaaa taaaaaaaag attttattta cttctcaaaa ttagtataca aagctctata     1216 ataataataat ataataatat ttttgttgta aactataat caaatatat ttgctatta       1276 taaggaaaaa aaaaaaaaaa aaaa                                            1300

<210> SEQ ID NO 90
<211> LENGTH: 375
<212> TYPE: PRT
<213> ORGANISM: Ctenocephalides felis

<400> SEQUENCE: 90

Met Phe Ala Ile Leu Leu Thr Gly Ile Leu Ala Leu Thr Leu Ser Ala
1               5                   10                  15

Glu Cys Ser Glu Leu Lys Phe Val Phe Val Met Val Lys Gly Pro Asp
            20                  25                  30

His Glu Ala Cys Asn Tyr Ala Gly Gly Pro Gln Leu Thr Thr Leu Gln
        35                  40                  45

Glu Lys Asp Ser Val Leu Thr Glu Asp Gly Lys Thr Glu Ala Tyr Glu
    50                  55                  60

Leu Gly Lys Leu Leu Asp Lys Val Tyr Lys Lys Gln Leu Lys Val Asp
65                  70                  75                  80

Lys Trp Asp Ala Thr Lys Thr Tyr Trp Ala Val Ser Thr Lys Ala Met
                85                  90                  95

Arg Thr Lys Glu Ala Ala Leu Ile Val Gly Ala Gly Leu Glu Asn Asn
            100                 105                 110

Pro Ala Lys Ala Lys Gly Asn Trp Thr Gln Gln Gln Leu Asp Ser Thr
        115                 120                 125

His Phe Asp Ala Met Pro Gly Phe Ser Arg Phe Trp Asn Pro Gln Gln
    130                 135                 140

Cys Pro Ala Tyr Phe Arg Ala Leu Ser Leu Gln Asn Gln Lys Ile Lys
145                 150                 155                 160

Lys Leu Leu Glu Lys Tyr Gln Thr Thr Ile Lys Glu Val Thr Ala Lys
                165                 170                 175

Phe Pro Ser Ile Asp Gly Thr Lys Ala Gln His Ile Trp Ile Ala Tyr
            180                 185                 190

Glu Thr Phe Lys Arg Met Lys Gln Gln Gly Arg Lys Glu Val Glu Gly
        195                 200                 205

Ile Asn Thr Ala Thr Met Gln Lys Leu Lys Glu Phe Ser Ser Glu Phe
    210                 215                 220

Val Leu Ile Ala Leu Thr Ser Thr Asp Gln Met Arg Lys Leu Ala Gly
225                 230                 235                 240

Gly Leu Ile Leu Lys Asp Leu Phe Asn Asp Ile Asp Glu Leu Thr Lys
```

```
                245               250                 255
Asp His Ala Gln Pro His Ala Pro Gly Gly Ile Lys Asn Lys Met Asn
                    260                 265                 270

Ile Phe Val Val Pro Gln Ala Ile Leu Ala Ala Gln Met Ala Val Phe
            275                 280                 285

Met Pro Glu Gly Thr Lys Leu Arg Asp Gln Pro Ile Thr Ala Ser Asn
        290                 295                 300

Phe Tyr Pro Asp Asp Gln Ser Tyr Val Ile Ile Glu Leu Tyr Gln Asp
305                 310                 315                 320

Lys Asn Lys Trp Asn Val Gln Leu Gln Tyr Lys Asn Asn Lys Asn Ser
                    325                 330                 335

Gly Trp Leu Pro Ile Lys Val Gln Gly Cys Asn Ser Pro Met Cys Pro
                340                 345                 350

Tyr Asp Thr Leu Lys Lys Ser Leu Asn Lys Tyr Ile Ile Asp Asp Ala
                355                 360                 365

Arg His Lys Gln Ala Cys Lys
                370                 375

<210> SEQ ID NO 91
<211> LENGTH: 1300
<212> TYPE: DNA
<213> ORGANISM: Ctenocephalides felis

<400> SEQUENCE: 91
tttttttttt ttttttttc cttataaata gcaaatatat tttgattata gttttacaac    60
aaaaatatta ttatattatt atattataga gctttgtata ctaattttga gaagtaaata   120
aaatcttttt tttatttaat tattatggcc aggaccaata attatttaca ggcttgctta   180
tgtctagcat catctattat atatttattc agtgattttt ttaatgtatc atacggacac   240
ataggtgaat tgcaaccttg cactttaatt ggcagccatc cgctattttt gttgttttta   300
tattgtaatt gtacgttcca cttgttttta tcttggtaca attctatgat tacataagac   360
tgatcatcag gatagaaatt tgaagctgtt attggttgat ctctcaattt ggtaccttct   420
ggcataaata cagccatttg tgcggctaaa attgcttgtg gtaccacaaa tatattcatt   480
ttattcttaa tgccacccgg cgcatgtggt tgcgcatggt ctttttgtcag ctcatcaata   540
tcattaaata agtccttcaa tattaaacct cctgctaatt ttctcatttg atctgtggat   600
gtcaaagcaa tcagcacgaa ctcagatgaa aattctttaa gttttttgcat agttgcagta   660
tttatccctt ctacttcttt tctgccttgt tgtttcattc tcttaaaagt ctcgtaggcg   720
atccatatat gttgcgcttt tgtaccatca atagatggaa acttggcagt aacttcttta   780
atagtagttt gatatttctc gagaagtttc tttattttct gattttgtag cgagagcgct   840
ctgaaatatg ccggacattg ttgaggattc caaaatctag aaaagccagg catcgcatca   900
aaatgtgttg aatcgagctg ttgttgtgtc caattacctt tagcttttgc aggattattt   960
tccaatcctg ctcctacaat taaggctgct tctttagtac gcatagcttt tgtggacaca  1020
gcccagtagg ttttcgtggc atcccatttg tcaactttta attgtttttt atataccttg  1080
tccaagagtt ttcccaattc gtatgcttct gtcttgccat cttcagttag aacactatct  1140
ttttcttgaa gagtagttaa ctgaggacct cctgcatagt tacaagcttc atgatccggc  1200
cctttcacca tcacaaatac aaacttaagt tcactacatt cagcacttaa tgttagcgcc  1260
aatattcctg ttaacaagat cgcaaacatt ttgaaatatg                        1300
```

<210> SEQ ID NO 92
<211> LENGTH: 1125
<212> TYPE: DNA
<213> ORGANISM: Ctenocephalides felis

<400> SEQUENCE: 92

| | | | | | |
|---|---|---|---|---|---|
| atgtttgcga | tcttgttaac | aggaatattg | gcgctaacat | taagtgctga | atgtagtgaa | 60 |
| cttaagtttg | tatttgtgat | ggtgaaaggg | ccggatcatg | aagcttgtaa | ctatgcagga | 120 |
| ggtcctcagt | taactactct | tcaagaaaaa | gatagtgttc | taactgaaga | tggcaagaca | 180 |
| gaagcatacg | aattgggaaa | actcttggac | aaggtatata | aaaaacaatt | aaaagttgac | 240 |
| aaatgggatg | ccacgaaaac | ctactgggct | gtgtccacaa | aagctatgcg | tactaaagaa | 300 |
| gcagccttaa | ttgtaggagc | aggattggaa | ataatcctg | caaaagctaa | aggtaattgg | 360 |
| acacaacaac | agctcgattc | aacacatttt | gatgcgatgc | ctggcttttc | tagattttgg | 420 |
| aatcctcaac | aatgtccggc | atatttcaga | gcgctctcgc | tacaaaatca | gaaaataaag | 480 |
| aaacttctcg | agaaatatca | aactactatt | aagaagtta | ctgccaagtt | tccatctatt | 540 |
| gatggtacaa | aagcgcaaca | tatatggatc | gcctacgaga | cttttaagag | aatgaaacaa | 600 |
| caaggcagaa | aagaagtaga | agggataaat | actgcaacta | tgcaaaaact | taagaatttt | 660 |
| tcatctgagt | tcgtgctgat | tgctttgaca | tccacagatc | aaatgagaaa | attagcagga | 720 |
| ggtttaatat | tgaaggactt | atttaatgat | attgatgagc | tgacaaaaga | ccatgcgcaa | 780 |
| ccacatgcgc | cgggtggcat | taagaataaa | atgaatatat | ttgtggtacc | acaagcaatt | 840 |
| ttagccgcac | aaatggctgt | atttatgcca | gaaggtacca | aattgagaga | tcaaccaata | 900 |
| acagcttcaa | atttctatcc | tgatgatcag | tcttatgtaa | tcatagaatt | gtaccaagat | 960 |
| aaaaacaagt | ggaacgtaca | attacaatat | aaaaacaaca | aaaatagcgg | atggctgcca | 1020 |
| attaaagtgc | aaggttgcaa | ttcacctatg | tgtccgtatg | atacattaaa | aaaatcactg | 1080 |
| aataaatata | taatagatga | tgctagacat | aagcaagcct | gtaaa | | 1125 |

<210> SEQ ID NO 93
<211> LENGTH: 1125
<212> TYPE: DNA
<213> ORGANISM: Ctenocephalides felis

<400> SEQUENCE: 93

| | | | | | |
|---|---|---|---|---|---|
| tttacaggct | tgcttatgtc | tagcatcatc | tattatatat | ttattcagtg | atttttttaa | 60 |
| tgtatcatac | ggacacatag | gtgaattgca | accttgcact | ttaattggca | gccatccgct | 120 |
| attttttgttg | ttttttatatt | gtaattgtac | gttccacttg | tttttatctt | ggtacaattc | 180 |
| tatgattaca | taagactgat | catcaggata | gaaatttgaa | gctgttattg | gttgatctct | 240 |
| caatttggta | ccttctggca | taaatacagc | catttgtgcg | gctaaaattg | cttgtggtac | 300 |
| cacaaatata | ttcattttat | tcttaatgcc | acccggcgca | tgtggttgcg | catggtcttt | 360 |
| tgtcagctca | tcaatatcat | taataagtc | cttcaatatt | aaacctcctg | ctaattttct | 420 |
| catttgatct | gtggatgtca | aagcaatcag | cacgaactca | gatgaaaatt | ctttaagttt | 480 |
| ttgcatagtt | gcagtattta | tcccttctac | ttcttttctg | ccttgttgtt | tcattctctt | 540 |
| aaaagtctcg | taggcgatcc | atatatgttg | cgcttttgta | ccatcaatag | atggaaactt | 600 |
| ggcagtaact | tctttaatag | tagtttgata | tttctcgaga | agtttctta | ttttctgatt | 660 |
| ttgtagcgag | agcgctctga | aatatgccgg | acattgttga | ggattccaaa | atctagaaaa | 720 |
| gccaggcatc | gcatcaaaat | gtgttgaatc | gagctgttgt | tgtgtccaat | tacctttagc | 780 |

-continued

```
ttttgcagga ttattttcca atcctgctcc tacaattaag gctgcttctt tagtacgcat      840
agcttttgtg gacacagccc agtaggtttt cgtggcatcc catttgtcaa cttttaattg      900 tttttatat accttgtcca agagttttcc caattcgtat gcttctgtct tgccatcttc       960
agttagaaca ctatctttt  cttgaagagt agttaactga ggacctcctg catagttaca     1020
agcttcatga tccggccctt tcaccatcac aaatacaaac ttaagttcac tacattcagc     1080
acttaatgtt agcgccaata ttcctgttaa caagatcgca aacat                     1125
```

<210> SEQ ID NO 94
<211> LENGTH: 356
<212> TYPE: PRT
<213> ORGANISM: Ctenocephalides felis

<400> SEQUENCE: 94

```
Glu Leu Lys Phe Val Phe Val Met Val Lys Gly Pro Asp His Glu Ala
 1               5                  10                  15

Cys Asn Tyr Ala Gly Gly Pro Gln Leu Thr Thr Leu Gln Glu Lys Asp
            20                  25                  30

Ser Val Leu Thr Glu Asp Gly Lys Thr Glu Ala Tyr Glu Leu Gly Lys
        35                  40                  45

Leu Leu Asp Lys Val Tyr Lys Lys Gln Leu Lys Val Asp Lys Trp Asp
    50                  55                  60

Ala Thr Lys Thr Tyr Trp Ala Val Ser Thr Lys Ala Met Arg Thr Lys
65                  70                  75                  80

Glu Ala Ala Leu Ile Val Gly Ala Gly Leu Glu Asn Asn Pro Ala Lys
                85                  90                  95

Ala Lys Gly Asn Trp Thr Gln Gln Leu Asp Ser Thr His Phe Asp
            100                 105                 110

Ala Met Pro Gly Phe Ser Arg Phe Trp Asn Pro Gln Gln Cys Pro Ala
        115                 120                 125

Tyr Phe Arg Ala Leu Ser Leu Gln Asn Gln Lys Ile Lys Lys Leu Leu
    130                 135                 140

Glu Lys Tyr Gln Thr Thr Ile Lys Glu Val Thr Ala Lys Phe Pro Ser
145                 150                 155                 160

Ile Asp Gly Thr Lys Ala Gln His Ile Trp Ile Ala Tyr Glu Thr Phe
                165                 170                 175

Lys Arg Met Lys Gln Gln Gly Arg Lys Glu Val Glu Gly Ile Asn Thr
            180                 185                 190

Ala Thr Met Gln Lys Leu Lys Glu Phe Ser Ser Glu Phe Val Leu Ile
        195                 200                 205

Ala Leu Thr Ser Thr Asp Gln Met Arg Lys Leu Ala Gly Gly Leu Ile
    210                 215                 220

Leu Lys Asp Leu Phe Asn Asp Ile Asp Glu Leu Thr Lys Asp His Ala
225                 230                 235                 240

Gln Pro His Ala Pro Gly Gly Ile Lys Asn Lys Met Asn Ile Phe Val
                245                 250                 255

Val Pro Gln Ala Ile Leu Ala Ala Gln Met Ala Val Phe Met Pro Glu
            260                 265                 270

Gly Thr Lys Leu Arg Asp Gln Pro Ile Thr Ala Ser Asn Phe Tyr Pro
        275                 280                 285

Asp Asp Gln Ser Tyr Val Ile Ile Glu Leu Tyr Gln Asp Lys Asn Lys
    290                 295                 300

Trp Asn Val Gln Leu Gln Tyr Lys Asn Asn Lys Asn Ser Gly Trp Leu
```

```
                305                 310                 315                 320
           Pro Ile Lys Val Gln Gly Cys Asn Ser Pro Met Cys Pro Tyr Asp Thr
                           325                 330                 335

Leu Lys Ser Leu Asn Lys Tyr Ile Ile Asp Asp Ala Arg His Lys
                           340                 345                 350

Gln Ala Cys Lys
                   355

<210> SEQ ID NO 95
<211> LENGTH: 1068
<212> TYPE: DNA
<213> ORGANISM: Ctenocephalides felis

<400> SEQUENCE: 95
gaacttaagt ttgtatttgt gatggtgaaa gggccggatc atgaagcttg taactatgca      60
ggaggtcctc agttaactac tcttcaagaa aaagatagtg ttctaactga agatggcaag     120
acagaagcat acgaattggg aaaactcttg acaaggtat ataaaaaaca attaaaagtt     180
gacaaatggg atgccacgaa aacctactgg gctgtgtcca caaaagctat gcgtactaaa     240
gaagcagcct taattgtagg agcaggattg gaaaataatc ctgcaaaagc taaggtaat     300
tggacacaac aacagctcga ttcaacacat tttgatgcga tgcctggctt ttctagattt     360
tggaatcctc aacaatgtcc ggcatatttc agagcgctct cgctacaaaa tcagaaaata     420
aagaaacttc tcgagaaata tcaaactact attaaagaag ttactgccaa gtttccatct     480
attgatggta caaaagcgca acatatatgg atcgcctacg agacttttaa gagaatgaaa     540
caacaaggca gaaagaagt agaagggata aatactgcaa ctatgcaaaa acttaaagaa     600
ttttcatctg agttcgtgct gattgctttg acatccacag atcaaatgag aaaattagca     660
ggaggtttaa tattgaagga cttatttaat gatattgatg agctgacaaa agaccatgcg     720
caaccacatg cgccgggtgg cattaagaat aaaatgaata tatttgtggt accacaagca     780
attttagccg cacaaatggc tgtatttatg ccagaaggta ccaaattgag agatcaacca     840
ataacagctt caaatttcta tcctgatgat cagtcttatg taatcataga attgtaccaa     900
gataaaaaca gtggaacgt acaattacaa tataaaaaca caaaaatag cggatggctg     960
ccaattaaag tgcaaggttg caattcacct atgtgtccgt atgatacatt aaaaaaatca    1020
ctgaataaat atataataga tgatgctaga cataagcaag cctgtaaa              1068

<210> SEQ ID NO 96
<211> LENGTH: 1068
<212> TYPE: DNA
<213> ORGANISM: Ctenocephalides felis

<400> SEQUENCE: 96
tttacaggct tgcttatgtc tagcatcatc tattatatat ttattcagtg atttttttaa      60
tgtatcatac ggacacatag gtgaattgca accttgcact ttaattggca gccatccgct     120
attttttgttg ttttttatatt gtaattgtac gttccacttg ttttttatctt ggtacaattc     180
tatgattaca taagactgat catcaggata gaaatttgaa gctgttattg gttgatctct     240
caatttggta ccttctggca taaatacagc catttgtgcg gctaaaattg cttgtggtac     300
cacaaatata ttcattttat tcttaatgcc acccggcgca tgtggttgcg catggtcttt     360
tgtcagctca tcaatatcat taataagtc cttcaatatt aaacctcctg ctaattttct     420
catttgatct gtggatgtca aagcaatcag cacgaactca gatgaaaatt ctttaagttt     480
```

| | |
|---|---|
| ttgcatagtt gcagtattta tcccttctac ttcttttctg ccttgttgtt tcattctctt | 540 |
| aaaagtctcg taggcgatcc atatatgttg cgcttttgta ccatcaatag atggaaactt | 600 |
| ggcagtaact tctttaatag tagtttgata tttctcgaga agtttcttta ttttctgatt | 660 |
| ttgtagcgag agcgctctga aatatgccgg acattgttga ggattccaaa atctagaaaa | 720 |
| gccaggcatc gcatcaaaat gtgttgaatc gagctgttgt tgtgtccaat tacctttagc | 780 |
| ttttgcagga ttattttcca atcctgctcc tacaattaag gctgcttctt tagtacgcat | 840 |
| agcttttgtg gacacagccc agtaggtttt cgtggcatcc catttgtcaa cttttaattg | 900 |
| tttttatat accttgtcca agagttttcc caattcgtat gcttctgtct tgccatcttc | 960 |
| agttagaaca ctatcttttt cttgaagagt agttaactga ggacctcctg catagttaca | 1020 |
| agcttcatga tccggccctt tcaccatcac aaatacaaac ttaagttc | 1068 |

<210> SEQ ID NO 97
<211> LENGTH: 1071
<212> TYPE: DNA
<213> ORGANISM: Ctenocephalides felis

<400> SEQUENCE: 97

| | |
|---|---|
| atggaactta agtttgtatt tgtgatggtg aaagggccgg atcatgaagc ttgtaactat | 60 |
| gcaggaggtc tcagttaac tactcttcaa gaaaaagata gtgttctaac tgaagatggc | 120 |
| aagacagaag catacgaatt gggaaaactc ttggacaagg tatataaaaa acaattaaaa | 180 |
| gttgacaaat gggatgccac gaaaacctac tgggctgtgt ccacaaaagc tatgcgtact | 240 |
| aaagaagcag ccttaattgt aggagcagga ttggaaaata tcctgcaaa agctaaaggt | 300 |
| aattggacac aacaacagct cgattcaaca cattttgatg cgatgcctgg cttttctaga | 360 |
| ttttggaatc ctcaacaatg tccggcatat ttcagagcgc tctcgctaca aaatcagaaa | 420 |
| ataaagaaac ttctcgagaa atatcaaact actattaaag aagttactgc caagtttcca | 480 |
| tctattgatg gtacaaaagc gcaacatata tggatcgcct acgagacttt taagagaatg | 540 |
| aaacaacaag gcagaaaaga agtagaaggg ataaatactg caactatgca aaaacttaaa | 600 |
| gaattttcat ctgagttcgt gctgattgct ttgacatcca cagatcaaat gagaaaatta | 660 |
| gcaggaggtt taatattgaa ggacttattt aatgatattg atgagctgac aaaagaccat | 720 |
| gcgcaaccac atgcgccggg tggcattaag aataaaatga atatatttgt ggtaccacaa | 780 |
| gcaattttag ccgcacaaat ggctgtattt atgccagaag gtaccaaatt gagagatcaa | 840 |
| ccaataacag cttcaaattt ctatcctgat gatcagtctt atgtaatcat agaattgtac | 900 |
| caagataaaa acaagtggaa cgtacaatta caatataaaa acaacaaaaa tagcggatgg | 960 |
| ctgccaatta aagtgcaagg ttgcaattca cctatgtgtc cgtatgatac attaaaaaaa | 1020 |
| tcactgaata aatatataat agatgatgct agacataagc aagcctgtaa a | 1071 |

<210> SEQ ID NO 98
<211> LENGTH: 47
<212> TYPE: DNA
<213> ORGANISM: Ctenocephalides felis
<220> FEATURE:
<221> NAME/KEY: misc_feature
<222> LOCATION: (1)..(47)
<223> OTHER INFORMATION: primer

<400> SEQUENCE: 98

| | |
|---|---|
| gatgcggatc cgcatatgga actgaagttt gtatttgtga tgaaagg | 47 |

```
<210> SEQ ID NO 99
<211> LENGTH: 48
<212> TYPE: DNA
<213> ORGANISM: Ctenocephalides felis
<220> FEATURE:
<221> NAME/KEY: misc_feature
<222> LOCATION: (1)..(48)
<223> OTHER INFORMATION: primer

<400> SEQUENCE: 99
gatcatccgc tgcagttatt tacaggcttg cttatgtcta gcatcatc                48

<210> SEQ ID NO 100
<211> LENGTH: 606
<212> TYPE: DNA
<213> ORGANISM: Ctenocephalides felis
<220> FEATURE:
<221> NAME/KEY: CDS
<222> LOCATION: (43)..(384)

<400> SEQUENCE: 100
```

| | | | | | | |
|---|---|---|---|---|---|---|
| atatttttat actaccattc aataaacgac atttgactaa aa atg aag cag ttg | | | | | | 54 |
| | | | | Met Lys Gln Leu | | |
| | | | | 1 | | |

| tca | tta | aat | att | act | acc | tta | gta | gtt | tta | act | gca | ttt | gtt | gta | att | 102 |
|---|---|---|---|---|---|---|---|---|---|---|---|---|---|---|---|---|
| Ser | Leu | Asn | Ile | Thr | Thr | Leu | Val | Val | Leu | Thr | Ala | Phe | Val | Val | Ile | |
| 5 | | | | 10 | | | | | 15 | | | | | | 20 | |

| caa | gaa | act | tcg | gcc | gaa | att | aaa | aga | aat | tca | cat | gaa | cct | ggc | aat | 150 |
|---|---|---|---|---|---|---|---|---|---|---|---|---|---|---|---|---|
| Gln | Glu | Thr | Ser | Ala | Glu | Ile | Lys | Arg | Asn | Ser | His | Glu | Pro | Gly | Asn | |
| | | | 25 | | | | | 30 | | | | | 35 | | | |

| acg | aga | aaa | ata | aga | gaa | gtt | atg | gat | aaa | tta | aga | aaa | caa | gca | cct | 198 |
|---|---|---|---|---|---|---|---|---|---|---|---|---|---|---|---|---|
| Thr | Arg | Lys | Ile | Arg | Glu | Val | Met | Asp | Lys | Leu | Arg | Lys | Gln | Ala | Pro | |
| | | 40 | | | | | 45 | | | | | 50 | | | | |

| cct | aaa | act | gat | ggc | aat | cct | cca | aaa | aca | acc | ata | atg | agt | aca | ctt | 246 |
|---|---|---|---|---|---|---|---|---|---|---|---|---|---|---|---|---|
| Pro | Lys | Thr | Asp | Gly | Asn | Pro | Pro | Lys | Thr | Thr | Ile | Met | Ser | Thr | Leu | |
| | 55 | | | | | 60 | | | | | 65 | | | | | |

| caa | aag | caa | caa | ata | agt | tgc | aca | gaa | gtg | aaa | gcg | gtt | aac | tta | gaa | 294 |
|---|---|---|---|---|---|---|---|---|---|---|---|---|---|---|---|---|
| Gln | Lys | Gln | Gln | Ile | Ser | Cys | Thr | Glu | Val | Lys | Ala | Val | Asn | Leu | Glu | |
| 70 | | | | | 75 | | | | | 80 | | | | | | |

| agt | cat | gtt | tgt | gct | tat | gat | tgt | agt | caa | cct | gaa | act | gca | gga | att | 342 |
|---|---|---|---|---|---|---|---|---|---|---|---|---|---|---|---|---|
| Ser | His | Val | Cys | Ala | Tyr | Asp | Cys | Ser | Gln | Pro | Glu | Thr | Ala | Gly | Ile | |
| 85 | | | | 90 | | | | | 95 | | | | | 100 | | |

| aca | tgc | aaa | gga | aat | aag | tgt | gat | tgt | cct | aaa | aaa | cgc | taa | | | 384 |
|---|---|---|---|---|---|---|---|---|---|---|---|---|---|---|---|---|
| Thr | Cys | Lys | Gly | Asn | Lys | Cys | Asp | Cys | Pro | Lys | Lys | Arg | | | | |
| | | | 105 | | | | | 110 | | | | | | | | |

```
aaatttattc aaaacattta cattttttat taatattcaa ctatcaaaaa ttctgtgttg     444
attgttatta tatttatcat agttactaga aataaaattt tataacattg ttaattcgaa     504
attgaataca cataatatta taattagtga ggttaaaaga aataaaccga atatccaaat     564 caaaaaaaa aaaaaaaaaa aaaaaaaaaa aaaaaaaaaa aa                         606

<210> SEQ ID NO 101
<211> LENGTH: 113
<212> TYPE: PRT
<213> ORGANISM: Ctenocephalides felis

<400> SEQUENCE: 101

Met Lys Gln Leu Ser Leu Asn Ile Thr Thr Leu Val Val Leu Thr Ala
1               5                   10                  15

Phe Val Val Ile Gln Glu Thr Ser Ala Glu Ile Lys Arg Asn Ser His
            20                  25                  30

Glu Pro Gly Asn Thr Arg Lys Ile Arg Glu Val Met Asp Lys Leu Arg
```

```
            35                  40                  45
Lys Gln Ala Pro Pro Lys Thr Asp Gly Asn Pro Pro Lys Thr Thr Ile
            50                  55                  60

Met Ser Thr Leu Gln Lys Gln Gln Ile Ser Cys Thr Glu Val Lys Ala
65                  70                  75                  80

Val Asn Leu Glu Ser His Val Cys Ala Tyr Asp Cys Ser Gln Pro Glu
                85                  90                  95

Thr Ala Gly Ile Thr Cys Lys Gly Asn Lys Cys Asp Cys Pro Lys Lys
                100                 105                 110

Arg

<210> SEQ ID NO 102
<211> LENGTH: 606
<212> TYPE: DNA
<213> ORGANISM: Ctenocephalides felis

<400> SEQUENCE: 102
tttttttttt tttttttttt tttttttttt tttttttttt tgatttggat attcggttta    60
tttcttttaa cctcactaat tataatatta tgtgtattca atttcgaatt aacaatgtta   120
taaaatttta tttctagtaa ctatgataaa tataataaca atcaacacag aattttttgat  180 agttgaatat taataaaaaa tgtaaatgtt ttgaataaat ttttagcgtt ttttaggaca   240
atcacactta tttcctttgc atgtaattcc tgcagtttca ggttgactac aatcataagc   300
acaaacatga ctttctaagt taaccgcttt cacttctgtg caacttattt gttgcttttg   360
aagtgtactc attatggttg tttttggagg attgccatca gttttaggag gtgcttgttt   420
tcttaattta tccataactt ctcttatttt tctcgtattg ccaggttcat gtgaatttct   480
tttaatttcg gccgaagttt cttgaattac aacaaatgca gttaaaacta ctaaggtagt   540
aatatttaat gacaactgct tcattttttag tcaaatgtcg tttattgaat ggtagtataa   600
aaatat                                                              606

<210> SEQ ID NO 103
<211> LENGTH: 339
<212> TYPE: DNA
<213> ORGANISM: Ctenocephalides felis

<400> SEQUENCE: 103
atgaagcagt tgtcattaaa tattactacc ttagtagttt taactgcatt tgttgtaatt    60
caagaaactt cggccgaaat taaagaaatt tcacatgaac ctggcaatac gagaaaaata   120
agagaagtta tggataaatt aagaaaacaa gcacctccta aaactgatgg caatcctcca   180
aaacaaccaa taatgagtac acttcaaaag caacaaataa gttgcacaga agtgaaagcg   240
gttaacttag aaagtcatgt tgtgcttat gattgtagtc aacctgaaac tgcaggaatt   300
acatgcaaag gaaataagtg tgattgtcct aaaaaacgc                          339

<210> SEQ ID NO 104
<211> LENGTH: 339
<212> TYPE: DNA
<213> ORGANISM: Ctenocephalides felis

<400> SEQUENCE: 104 gcgttttta ggacaatcac acttatttcc tttgcatgta attcctgcag tttcaggttg    60
actacaatca taagcacaaa catgactttc taagttaacc gctttcactt ctgtgcaact   120
tatttgttgc ttttgaagtg tactcattat ggttgttttt ggaggattgc catcagtttt   180
```

```
aggaggtgct tgttttctta atttatccat aacttctctt attttttctcg tattgccagg      240 ttcatgtgaa tttctttttaa tttcggccga agtttcttga attacaacaa atgcagttaa    300
aactactaag gtagtaatat ttaatgacaa ctgcttcat                             339
```

<210> SEQ ID NO 105
<211> LENGTH: 88
<212> TYPE: PRT
<213> ORGANISM: Ctenocephalides felis

<400> SEQUENCE: 105

```
Glu Ile Lys Arg Asn Ser His Glu Pro Gly Asn Thr Arg Lys Ile Arg
1               5                   10                  15

Glu Val Met Asp Lys Leu Arg Lys Gln Ala Pro Pro Lys Thr Asp Gly
            20                  25                  30

Asn Pro Pro Lys Thr Thr Ile Met Ser Thr Leu Gln Lys Gln Gln Ile
        35                  40                  45

Ser Cys Thr Glu Val Lys Ala Val Asn Leu Glu Ser His Val Cys Ala
    50                  55                  60

Tyr Asp Cys Ser Gln Pro Glu Thr Ala Gly Ile Thr Cys Lys Gly Asn
65                  70                  75                  80

Lys Cys Asp Cys Pro Lys Lys Arg
                85
```

<210> SEQ ID NO 106
<211> LENGTH: 264
<212> TYPE: DNA
<213> ORGANISM: Ctenocephalides felis

<400> SEQUENCE: 106

```
gaaattaaaa gaaattcaca tgaacctggc aatacgagaa aaataagaga agttatggat     60
aaattaagaa acaagcacc tcctaaaact gatggcaatc ctccaaaaac aaccataatg    120
agtacacttc aaaagcaaca aataagttgc acagaagtga aagcggttaa cttagaaagt    180
catgtttgtg cttatgattg tagtcaacct gaaactgcag gaattacatg caaaggaaat    240
aagtgtgatt gtcctaaaaa acgc                                           264
```

<210> SEQ ID NO 107
<211> LENGTH: 264
<212> TYPE: DNA
<213> ORGANISM: Ctenocephalides felis

<400> SEQUENCE: 107

```
gcgttttttta ggacaatcac acttatttcc tttgcatgta attcctgcag tttcaggttg     60
actacaatca taagcacaaa catgactttc taagttaacc gctttcactt ctgtgcaact    120
tatttgttgc ttttgaagtg tactcattat ggttgttttt ggaggattgc catcagtttt    180
aggaggtgct tgttttctta atttatccat aacttctctt attttttctcg tattgccagg    240 ttcatgtgaa tttctttttaa tttc                                          264
```

<210> SEQ ID NO 108
<211> LENGTH: 25
<212> TYPE: PRT
<213> ORGANISM: Ctenocephalides felis
<220> FEATURE:
<221> NAME/KEY: misc_feature
<222> LOCATION: (22)..()
<223> OTHER INFORMATION: Xaa = any amino acid
<221> NAME/KEY: misc_feature

```
<222> LOCATION: (24)..()
<223> OTHER INFORMATION: Xaa = any amino acid
<221> NAME/KEY: misc_feature
<222> LOCATION: (25)..()
<223> OTHER INFORMATION: Xaa = any amino acid

<400> SEQUENCE: 108

Val Asn Val Lys Pro Lys Pro Asn Gln Asp Asp Tyr Cys Asn Leu Asn
1               5                   10                  15

Cys Tyr Asn Gly Pro Xaa Val Xaa Xaa
            20              25

<210> SEQ ID NO 109
<211> LENGTH: 28
<212> TYPE: DNA
<213> ORGANISM: Ctenocephalides felis
<220> FEATURE:
<221> NAME/KEY: misc_feature
<222> LOCATION: (1)..(28)
<223> OTHER INFORMATION: primer
<221> NAME/KEY: misc_feature
<222> LOCATION: (6)..(28)
<223> OTHER INFORMATION: W = A or T
<221> NAME/KEY: misc_feature
<222> LOCATION: (12)..()
<223> OTHER INFORMATION: W = A or T
<221> NAME/KEY: misc_feature
<222> LOCATION: (17)..()
<223> OTHER INFORMATION: Y = C or T
<221> NAME/KEY: misc_feature
<222> LOCATION: (18)..()
<223> OTHER INFORMATION: W = A or T
<221> NAME/KEY: misc_feature
<222> LOCATION: (21)..()
<223> OTHER INFORMATION: Y = C or T

<400> SEQUENCE: 109
aatgtwaaac cwaaaccwaa ycaagayg                                      28

<210> SEQ ID NO 110
<211> LENGTH: 26
<212> TYPE: DNA
<213> ORGANISM: Ctenocephalides felis
<220> FEATURE:
<221> NAME/KEY: misc_feature
<222> LOCATION: (1)..(26)
<223> OTHER INFORMATION: primer
<221> NAME/KEY: misc_feature
<222> LOCATION: (3)..()
<223> OTHER INFORMATION: W = A or T
<221> NAME/KEY: misc_feature
<222> LOCATION: (9)..()
<223> OTHER INFORMATION: W = A or T
<221> NAME/KEY: misc_feature
<222> LOCATION: (12)..()
<223> OTHER INFORMATION: Y = C or T
<221> NAME/KEY: misc_feature
<222> LOCATION: (18)..()
<223> OTHER INFORMATION: Y = C or T
<221> NAME/KEY: misc_feature
<222> LOCATION: (21)..()
<223> OTHER INFORMATION: Y = C or T

<400> SEQUENCE: 110
ccwaaaccwa aycaagayga ytattg                                        26

<210> SEQ ID NO 111
<211> LENGTH: 878
<212> TYPE: DNA
<213> ORGANISM: Ctenocephalides felis

<400> SEQUENCE: 111
```

-continued

```
cctaaaccta accaagacga ttattgtaat ctaaattgta caaatggacc aaatgtagga        60
tgcacaaaac cggatgtacc tagagactgc caaaacttta aacttgtgaa tataacagaa       120
cgtatgaaaa aggcattttt aaatgcacac aatagaaaga gaagacttgt tgcagccgga       180
aaaggtcttc tgaaagatgg tgtacacact ccaattgctg caaagatgcc caacttaacg       240
tggaatatag cgctcgccaa gttagcagaa ataacgtgaa gcaatgcga atgaagcac          300 gattgtgcta aactagaca tggtcacact ggtcaaaacc tatttttta tggcactact          360 ctcagcccca taaaaaactc aactatagcc aaaatgcag ttgatggttg gtatgctgaa         420
agcaaagata caagattgga agatatcaag aaattgacca ctatctaccc aaatggtaaa       480
cccattggac attatacccca attgatctgg ggtaatacaa caaaagtagg atgtgctgtc       540
agtacttata aaaacactc aaatggaaat atgtttaata tgactcttgt ggcttgcaac        600
tatagaggtg gaaatatgct tgaggaagca gtatatcaaa tcaaagatgc aaaaaatcca       660
aaatccaaaa atcaaactaa gaacaacaaa aaccaaaac aaaaaatgcc aaaatagagc        720
ttcttgaaaa ccagcaatag agttttttact gctaaattga gactgagaaa acagttttt      780 aaacgttta taaatatatt tttatgaaaa atattattta ttaagtagtt gttattgtgt        840
ttgaaataaa tttgaattta caaaaaaaaa aaaaaaaa                                878
```

<210> SEQ ID NO 112
<211> LENGTH: 238
<212> TYPE: PRT
<213> ORGANISM: Ctenocephalides felis

<400> SEQUENCE: 112

```
Pro Lys Pro Asn Gln Asp Asp Tyr Cys Asn Leu Asn Cys Thr Asn Gly
1               5                   10                  15

Pro Asn Val Gly Cys Thr Lys Pro Asp Val Pro Arg Asp Cys Gln Asn
            20                  25                  30

Phe Lys Leu Val Asn Ile Thr Glu Arg Met Lys Lys Ala Phe Leu Asn
        35                  40                  45

Ala His Asn Arg Lys Arg Arg Leu Val Ala Ala Gly Lys Gly Leu Leu
    50                  55                  60

Lys Asp Gly Val His Thr Pro Ile Ala Lys Met Pro Asn Leu Thr
65                  70                  75                  80

Trp Asn Ile Ala Leu Ala Lys Leu Ala Glu Tyr Asn Val Lys Gln Cys
                85                  90                  95

Glu Met Lys His Asp Cys Ala Lys Thr Arg His Gly His Thr Gly Gln
            100                 105                 110

Asn Leu Phe Phe Tyr Gly Thr Thr Leu Ser Pro Ile Lys Asn Ser Thr
        115                 120                 125

Ile Ala Lys Met Ala Val Asp Gly Trp Tyr Ala Glu Ser Lys Asp Thr
    130                 135                 140

Arg Leu Glu Asp Ile Lys Lys Leu Thr Ile Tyr Pro Asn Gly Lys
145                 150                 155                 160

Pro Ile Gly His Tyr Thr Gln Leu Ile Trp Gly Asn Thr Thr Lys Val
                165                 170                 175

Gly Cys Ala Val Ser Thr Tyr Lys His Ser Asn Gly Asn Met Phe
            180                 185                 190

Asn Met Thr Leu Val Ala Cys Asn Tyr Arg Gly Gly Asn Met Leu Glu
        195                 200                 205

Glu Ala Val Tyr Gln Ile Lys Asp Ala Lys Asn Pro Lys Ser Lys Asn
```

Gln Thr Lys Asn Asn Lys Lys Pro Lys Gln Lys Met Pro Lys
225                 230                 235

<210> SEQ ID NO 113
<211> LENGTH: 878
<212> TYPE: DNA
<213> ORGANISM: Ctenocephalides felis

<400> SEQUENCE: 113

```
tttttttttt ttttttgta aattcaaatt tatttcaaac acaataacaa ctacttaata    60
aataatattt ttcataaaaa tatatttata aaacgtttaa aaactgtttt tctcagtctc   120
aatttagcag taaaaactct attgctggtt ttcaagaagc tctattttgg cattttttgt   180
tttggttttt tgttgttctt agtttgattt ttggattttg gattttttgc atctttgatt   240
tgatatactg cttcctcaag catatttcca cctctatagt tgcaagccac aagagtcata   300
ttaaacatat ttccatttga gtgttttta taagtactga cagcacatcc tacttttgtt   360
gtattacccc agatcaattg gtataatgt ccaatgggtt taccatttgg gtagatagtg    420
gtcaatttct tgatatcttc caatcttgta tctttgcttt cagcatacca accatcaact   480
gccattttgg ctagttga gttttttatg gggctgagag tagtgccata aaaaatagg     540
ttttgaccag tgtgaccatg tctagtttta gcacaatcgt gcttcatttc gcattgcttc   600
acgttatatt ctgctaactt ggcgagcgct atattccacg ttaagttggg catctttgca   660
gcaattggag tgtgtacacc atctttcaga agacctttt cggctgcaac aagtcttctc    720
tttctattgt gtgcatttaa aaatgccttt ttcatacgtt ctgttatatt cacaagttta   780
aagttttggc agtctctagg tacatccggt tttgtgcatc ctacatttgg tccatttgta   840
caatttagat tacaataatc gtcttggtta ggtttagg                          878
```

<210> SEQ ID NO 114
<211> LENGTH: 1297
<212> TYPE: DNA
<213> ORGANISM: Ctenocephalides felis
<220> FEATURE:
<221> NAME/KEY: CDS
<222> LOCATION: (341)..(1135)

<400> SEQUENCE: 114

```
cattagcatt ttctaaaata gcttggtagc ttggtgtatt cttgccaatt ttcaatacac    60
aacgccattt ggcaaagtgg catccatcct ttttgtattg tgcacagcgg gcagccaaat   120
catccaatcc ttgagtagtg cattcattct cactgcccat caagtcaact acacctttgt   180
cgactttgat tcctgggatg atgttttgc gtttcaaaag ttctacgaat ggagctcgtg    240
ccgaattcgg cacgagatga ttgaacttaa taatgaattc atactgattt cacccaatat   300
tgaaatgaat acgaaattgg atgaatttgg tgaaatcagt atg aat tca tta tta    355
                                              Met Asn Ser Leu Leu
                                              1               5 agt tca atc att att gtg gta ttt tcg gta tgg tta agt gta att ttt    403
Ser Ser Ile Ile Ile Val Val Phe Ser Val Trp Leu Ser Val Ile Phe
             10                  15                  20 gca gtt aac gta aag ccc aaa cca aat caa gat gat tac tgt aat cta    451
Ala Val Asn Val Lys Pro Lys Pro Asn Gln Asp Asp Tyr Cys Asn Leu
             25                  30                  35 aat tgt aca aat gga cca aat gta gga tgc aca aaa ccg gat gta cct    499
Asn Cys Thr Asn Gly Pro Asn Val Gly Cys Thr Lys Pro Asp Val Pro
         40                  45                  50
```

```
aga gac tgc caa aac ttt aaa ctt gtg aat ata aca gaa cgt atg aaa      547
Arg Asp Cys Gln Asn Phe Lys Leu Val Asn Ile Thr Glu Arg Met Lys
     55                  60                  65 aag gca ttt tta aat gca cac aat aga aag aga ctt gtt gca gcc          595
Lys Ala Phe Leu Asn Ala His Asn Arg Lys Arg Leu Val Ala Ala
 70              75                  80                  85 gga aaa ggt ctt ctg aaa gat ggt gta cac act cca att gct gca aag      643
Gly Lys Gly Leu Leu Lys Asp Gly Val His Thr Pro Ile Ala Ala Lys
                 90                  95                 100 atg ccc aac tta acg tgg aat ata gcg ctc gcc aag tta gca gaa tat      691
Met Pro Asn Leu Thr Trp Asn Ile Ala Leu Ala Lys Leu Ala Glu Tyr
                105                 110                 115 aac gtg aag caa tgc gaa atg aag cac gat tgt gct aaa act aga cat      739
Asn Val Lys Gln Cys Glu Met Lys His Asp Cys Ala Lys Thr Arg His
            120                 125                 130 ggt cac act ggt caa aac cta ttt ttt tat ggc act act ctc agc ccc      787
Gly His Thr Gly Gln Asn Leu Phe Phe Tyr Gly Thr Thr Leu Ser Pro
        135                 140                 145 ata aaa aac tca act ata gcc aaa atg gca gtt gat ggt tgg tat gct      835
Ile Lys Asn Ser Thr Ile Ala Lys Met Ala Val Asp Gly Trp Tyr Ala
150                 155                 160                 165 gaa agc aaa gat aca aga ttg gaa gat atc aag aaa ttg acc act atc      883
Glu Ser Lys Asp Thr Arg Leu Glu Asp Ile Lys Lys Leu Thr Thr Ile
                170                 175                 180 tac cca aat ggt aaa ccc att gga cat tat acc caa ttg atc tgg ggt      931
Tyr Pro Asn Gly Lys Pro Ile Gly His Tyr Thr Gln Leu Ile Trp Gly
                185                 190                 195 aat aca aca aaa gta gga tgt gct gtc agt act tat aaa aaa cac tca      979
Asn Thr Thr Lys Val Gly Cys Ala Val Ser Thr Tyr Lys Lys His Ser
            200                 205                 210 aat gga aat atg ttt aat atg act ctt gtg gct tgc aac tat aga ggt     1027
Asn Gly Asn Met Phe Asn Met Thr Leu Val Ala Cys Asn Tyr Arg Gly
        215                 220                 225 gga aat atg ctt gag gaa gca gta tat caa atc aaa gat gca aaa aat     1075
Gly Asn Met Leu Glu Glu Ala Val Tyr Gln Ile Lys Asp Ala Lys Asn
230                 235                 240                 245 cca aaa tcc aaa aat caa act aag aac aac aaa aaa cca aaa caa aaa     1123
Pro Lys Ser Lys Asn Gln Thr Lys Asn Asn Lys Lys Pro Lys Gln Lys
                250                 255                 260 atg cca aaa tag agcttcttga aaaccagcaa tagagttttt actgctaaat         1175
Met Pro Lys tgagactgag aaaaacagtt tttaaacgtt ttataaatat attttttatga aaatattat   1235 ttattaagta gttgttattg tgtttgaaat aaatttgaat ttacaaaaaa aaaaaaaaaa   1295
aa                                                                   1297

<210> SEQ ID NO 115
<211> LENGTH: 264
<212> TYPE: PRT
<213> ORGANISM: Ctenocephalides felis

<400> SEQUENCE: 115

Met Asn Ser Leu Leu Ser Ser Ile Ile Ile Val Val Phe Ser Val Trp
1               5                   10                  15

Leu Ser Val Ile Phe Ala Val Asn Val Lys Pro Lys Pro Asn Gln Asp
            20                  25                  30

Asp Tyr Cys Asn Leu Asn Cys Thr Asn Gly Pro Asn Val Gly Cys Thr
        35                  40                  45
```

```
Lys Pro Asp Val Pro Arg Asp Cys Gln Asn Phe Lys Leu Val Asn Ile
 50                  55                  60
Thr Glu Arg Met Lys Lys Ala Phe Leu Asn Ala His Asn Arg Lys Arg
 65                  70                  75                  80
Arg Leu Val Ala Ala Gly Lys Gly Leu Leu Lys Asp Gly Val His Thr
                 85                  90                  95
Pro Ile Ala Ala Lys Met Pro Asn Leu Thr Trp Asn Ile Ala Leu Ala
                100                 105                 110
Lys Leu Ala Glu Tyr Asn Val Lys Gln Cys Glu Met Lys His Asp Cys
                115                 120                 125
Ala Lys Thr Arg His Gly His Thr Gly Gln Asn Leu Phe Phe Tyr Gly
                130                 135                 140
Thr Thr Leu Ser Pro Ile Lys Asn Ser Thr Ile Ala Lys Met Ala Val
145                 150                 155                 160
Asp Gly Trp Tyr Ala Glu Ser Lys Asp Thr Arg Leu Glu Asp Ile Lys
                165                 170                 175
Lys Leu Thr Thr Ile Tyr Pro Asn Gly Lys Pro Ile Gly His Tyr Thr
                180                 185                 190
Gln Leu Ile Trp Gly Asn Thr Thr Lys Val Gly Cys Ala Val Ser Thr
                195                 200                 205
Tyr Lys Lys His Ser Asn Gly Asn Met Phe Asn Met Thr Leu Val Ala
                210                 215                 220
Cys Asn Tyr Arg Gly Gly Asn Met Leu Glu Glu Ala Val Tyr Gln Ile
225                 230                 235                 240
Lys Asp Ala Lys Asn Pro Lys Ser Lys Asn Gln Thr Lys Asn Asn Lys
                245                 250                 255
Lys Pro Lys Gln Lys Met Pro Lys
                260

<210> SEQ ID NO 116
<211> LENGTH: 1297
<212> TYPE: DNA
<213> ORGANISM: Ctenocephalides felis

<400> SEQUENCE: 116
tttttttttt ttttttttgt aaattcaaat ttatttcaaa cacaataaca actacttaat     60 aataatatt tttcataaaa atatatttat aaaacgttta aaaactgttt ttctcagtct    120
caatttagca gtaaaaactc tattgctggt tttcaagaag ctctattttg gcatttttg    180 ttttggtttt ttgttgttct tagtttgatt tttggatttt ggattttttg catctttgat    240
ttgatatact gcttcctcaa gcatatttcc acctctatag ttgcaagcca caagagtcat    300
attaaacata tttccatttg agtgtttttt ataagtactg acagcacatc ctactttgt    360 tgtattaccc cagatcaatt gggtataatg tccaatgggt ttaccatttg ggtagatagt    420
ggtcaatttc ttgatatctt ccaatcttgt atctttgctt tcagcatacc aaccatcaac    480
tgccattttg gctatagttg agttttttat ggggctgaga gtagtgccat aaaaaaatag    540
gttttgacca gtgtgaccat gtctagtttt agcacaatcg tgcttcattt cgcattgctt    600
cacgttatat tctgctaact tggcgagcgc tatattccac gttaagttgg gcatctttgc    660
agcaattgga gtgtgtacac catctttcag aagacctttt ccggctgcaa caagtcttct    720
ctttctattg tgtgcattta aaaatgcctt tttcatacgt tctgttatat tcacaagttt    780
aaagttttgg cagtctctag gtacatccgg ttttgtgcat cctacatttg gtccatttgt    840
acaatttaga ttacagtaat catcttgatt tggtttgggc tttacgttaa ctgcaaaaat    900
```

| | |
|---|---|
| tacacttaac cataccgaaa ataccacaat aatgattgaa cttaataatg aattcatact | 960 |
| gatttcacca aattcatcca atttcgtatt catttcaata ttgggtgaaa tcagtatgaa | 1020 |
| ttcattatta agttcaatca tctcgtgccg aattcggcac gagctccatt cgtagaactt | 1080 |
| ttgaaacgca aaacatcat cccaggaatc aaagtcgaca aggtgtagt tgacttgatg | 1140 |
| ggcagtgaga atgaatgcac tactcaagga ttggatgatt tggctgcccg ctgtgcacaa | 1200 |
| tacaaaaagg atggatgcca ctttgccaaa tggcgttgtg tattgaaaat tggcaagaat | 1260 |
| acaccaagct accaagctat tttagaaaat gctaatg | 1297 |

<210> SEQ ID NO 117
<211> LENGTH: 792
<212> TYPE: DNA
<213> ORGANISM: Ctenocephalides felis

<400> SEQUENCE: 117

| | |
|---|---|
| atgaattcat tattaagttc aatcattatt gtggtatttt cggtatggtt aagtgtaatt | 60 |
| tttgcagtta acgtaaagcc caaaccaaat caagatgatt actgtaatct aaattgtaca | 120 |
| aatggaccaa atgtaggatg cacaaaaccg gatgtaccta gagactgcca aaactttaaa | 180 |
| cttgtgaata taacagaacg tatgaaaaag gcatttttaa atgcacacaa tagaaagaga | 240 |
| agacttgttg cagccggaaa aggtcttctg aaagatggtg tacacactcc aattgctgca | 300 |
| aagatgccca acttaacgtg gaatatagcg ctcgccaagt tagcagaata taacgtgaag | 360 |
| caatgcgaaa tgaagcacga ttgtgctaaa actagacatg gtcacactgg tcaaaaccta | 420 |
| tttttttatg gcactactct cagccccata aaaaactcaa ctatagccaa aatggcagtt | 480 |
| gatggttggt atgctgaaag caaagataca agattggaag atatcaagaa attgaccact | 540 |
| atctacccaa atggtaaacc cattggacat tatacccaat tgatctgggg taatacaaca | 600 |
| aaagtaggat gtgctgtcag tacttataaa aaacactcaa atggaaatat gtttaatatg | 660 |
| actcttgtgg cttgcaacta tagaggtgga aatatgcttg aggaagcagt atatcaaatc | 720 |
| aaagatgcaa aaaatccaaa atccaaaaat caaactaaga caacaaaaa accaaaacaa | 780 |
| aaaatgccaa aa | 792 |

<210> SEQ ID NO 118
<211> LENGTH: 792
<212> TYPE: DNA
<213> ORGANISM: Ctenocephalides felis

<400> SEQUENCE: 118

| | |
|---|---|
| ttttggcatt ttttgttttg gttttttgtt gttcttagtt tgattttttgg attttggatt | 60 |
| ttttgcatct ttgatttgat atactgcttc ctcaagcata tttccacctc tatagttgca | 120 |
| agccacaaga gtcatattaa acatatttcc atttgagtgt ttttttataag tactgacagc | 180 |
| acatcctact tttgttgtat taccccagat caattgggta taatgtccaa tgggtttacc | 240 |
| atttgggtag atagtggtca atttcttgat atcttccaat cttgtatctt tgctttcagc | 300 |
| ataccaacca tcaactgcca ttttggctat agttgagttt tttatggggc tgagagtagt | 360 |
| gccataaaaa aataggtttt gaccagtgtg accatgtcta gttttagcac aatcgtgctt | 420 |
| catttcgcat tgcttcacgt tatattctgc taacttggcg agcgctatat tccacgttaa | 480 |
| gttgggcatc tttgcagcaa ttggagtgtg tacaccatct ttcagaagac cttttccggc | 540 |
| tgcaacaagt cttctctttc tattgtgtgc atttaaaaat gccttttca tacgttctgt | 600 |

```
tatattcaca agtttaaagt tttggcagtc tctaggtaca tccggttttg tgcatcctac    660
atttggtcca tttgtacaat ttagattaca gtaatcatct tgatttggtt tgggctttac    720
gttaactgca aaaattacac ttaaccatac cgaaaatacc acaataatga ttgaacttaa    780
taatgaattc at                                                        792
```

<210> SEQ ID NO 119
<211> LENGTH: 242
<212> TYPE: PRT
<213> ORGANISM: Ctenocephalides felis

<400> SEQUENCE: 119

```
Val Asn Val Lys Pro Lys Pro Asn Gln Asp Asp Tyr Cys Asn Leu Asn
1               5                   10                  15

Cys Thr Asn Gly Pro Asn Val Gly Cys Thr Lys Pro Asp Val Pro Arg
            20                  25                  30

Asp Cys Gln Asn Phe Lys Leu Val Asn Ile Thr Glu Arg Met Lys Lys
        35                  40                  45

Ala Phe Leu Asn Ala His Asn Arg Lys Arg Leu Val Ala Ala Gly
    50                  55                  60

Lys Gly Leu Leu Lys Asp Gly Val His Thr Pro Ile Ala Ala Lys Met
65                  70                  75                  80

Pro Asn Leu Thr Trp Asn Ile Ala Leu Ala Lys Leu Ala Glu Tyr Asn
                85                  90                  95

Val Lys Gln Cys Glu Met Lys His Asp Cys Ala Lys Thr Arg His Gly
            100                 105                 110

His Thr Gly Gln Asn Leu Phe Phe Tyr Gly Thr Thr Leu Ser Pro Ile
        115                 120                 125

Lys Asn Ser Thr Ile Ala Lys Met Ala Val Asp Gly Trp Tyr Ala Glu
    130                 135                 140

Ser Lys Asp Thr Arg Leu Glu Asp Ile Lys Lys Leu Thr Thr Ile Tyr
145                 150                 155                 160

Pro Asn Gly Lys Pro Ile Gly His Tyr Thr Gln Leu Ile Trp Gly Asn
                165                 170                 175

Thr Thr Lys Val Gly Cys Ala Val Ser Thr Tyr Lys Lys His Ser Asn
            180                 185                 190

Gly Asn Met Phe Asn Met Thr Leu Val Ala Cys Asn Tyr Arg Gly Gly
        195                 200                 205

Asn Met Leu Glu Glu Ala Val Tyr Gln Ile Lys Asp Ala Lys Asn Pro
    210                 215                 220

Lys Ser Lys Asn Gln Thr Lys Asn Asn Lys Lys Pro Lys Gln Lys Met
225                 230                 235                 240

Pro Lys
```

<210> SEQ ID NO 120
<211> LENGTH: 726
<212> TYPE: DNA
<213> ORGANISM: Ctenocephalides felis

<400> SEQUENCE: 120

```
gttaacgtaa agcccaaacc aaatcaagat gattactgta atctaaattg tacaaatgga    60
ccaaatgtag gatgcacaaa accggatgta cctagagact gccaaaactt taaacttgtg   120
aatataacag aacgtatgaa aaaggcattt ttaaatgcac acaatagaaa gagaagactt   180
gttgcagccg gaaaaggtct tctgaaagat ggtgtacaca ctccaattgc tgcaaagatg   240
```

| | |
|---|---|
| cccaacttaa cgtggaatat agcgctcgcc aagttagcag aatataacgt gaagcaatgc | 300 |
| gaaatgaagc acgattgtgc taaaactaga catggtcaca ctggtcaaaa cctatttttt | 360 |
| tatggcacta ctctcagccc cataaaaaac tcaactatag ccaaaatggc agttgatggt | 420 |
| tggtatgctg aaagcaaaga tacaagattg gaagatatca agaaattgac cactatctac | 480 |
| ccaaatggta aacccattgg acattatacc caattgatct ggggtaatac aacaaaagta | 540 |
| ggatgtgctg tcagtactta taaaaaacac tcaaatggaa atatgtttaa tatgactctt | 600 |
| gtggcttgca actatagagg tggaaatatg cttgaggaag cagtatatca aatcaaagat | 660 |
| gcaaaaaatc caaatccaa aaatcaaact aagaacaaca aaaaaccaaa acaaaaaatg | 720 |
| ccaaaa | 726 |

<210> SEQ ID NO 121
<211> LENGTH: 726
<212> TYPE: DNA
<213> ORGANISM: Ctenocephalides felis

<400> SEQUENCE: 121

| | |
|---|---|
| ttttggcatt ttttgttttg gttttttgtt gttcttagtt tgattttttgg attttggatt | 60 |
| ttttgcatct tgatttgat atactgcttc ctcaagcata tttccacctc tatagttgca | 120 |
| agccacaaga gtcatattaa acatatttcc atttgagtgt ttttttataag tactgacagc | 180 |
| acatcctact tttgttgtat taccccagat caattgggta taatgtccaa tgggtttacc | 240 |
| atttgggtag atagtggtca atttcttgat atcttccaat cttgtatctt tgctttcagc | 300 |
| ataccaacca tcaactgcca ttttggctat agttgagttt tttatggggc tgagagtagt | 360 |
| gccataaaaa aataggtttt gaccagtgtg accatgtcta gttttagcac aatcgtgctt | 420 |
| catttcgcat tgcttcacgt tatattctgc taacttggcg agcgctatat tccacgttaa | 480 |
| gttgggcatc tttgcagcaa ttggagtgtg tacaccatct ttcagaagac cttttccggc | 540 |
| tgcaacaagt cttctctttc tattgtgtgc atttaaaaat gccttttttca tacgttctgt | 600 |
| tatattcaca agtttaaagt tttggcagtc tctaggtaca tccggttttg tgcatcctac | 660 |
| atttggtcca tttgtacaat ttagattaca gtaatcatct tgatttggtt tgggctttac | 720 |
| gttaac | 726 |

<210> SEQ ID NO 122
<211> LENGTH: 23
<212> TYPE: DNA
<213> ORGANISM: Ctenocephalides felis
<220> FEATURE:
<221> NAME/KEY: misc_feature
<222> LOCATION: (1)..(23)
<223> OTHER INFORMATION: primer
<221> NAME/KEY: misc_feature
<222> LOCATION: (3)..()
<223> OTHER INFORMATION: Y = C or T
<221> NAME/KEY: misc_feature
<222> LOCATION: (15)..()
<223> OTHER INFORMATION: W = A or T
<221> NAME/KEY: misc_feature
<222> LOCATION: (18)..()
<223> OTHER INFORMATION: W = A or T

<400> SEQUENCE: 122

| | |
|---|---|
| aaygataaag aaccwggwaa cac | 23 |

<210> SEQ ID NO 123
<211> LENGTH: 29
<212> TYPE: DNA

```
<213> ORGANISM: Ctenocephalides felis
<220> FEATURE:
<221> NAME/KEY: misc_feature
<222> LOCATION: (1)..(29)
<223> OTHER INFORMATION: primer
<221> NAME/KEY: misc_feature
<222> LOCATION: (6)..()
<223> OTHER INFORMATION: W = A or T
<221> NAME/KEY: misc_feature
<222> LOCATION: (12)..()
<223> OTHER INFORMATION: Y = C or T
<221> NAME/KEY: misc_feature
<222> LOCATION: (18)..()
<223> OTHER INFORMATION: R = A or G
<221> NAME/KEY: misc_feature
<222> LOCATION: (21)..()
<223> OTHER INFORMATION: R = A or G
<221> NAME/KEY: misc_feature
<222> LOCATION: (24)..()
<223> OTHER INFORMATION: R = A or G
<221> NAME/KEY: misc_feature
<222> LOCATION: (27)..()
<223> OTHER INFORMATION: R = A or G

<400> SEQUENCE: 123
gaagtwatgg ayaaattrag raarcargc                                   29

<210> SEQ ID NO 124
<211> LENGTH: 26
<212> TYPE: DNA
<213> ORGANISM: Ctenocephalides felis
<220> FEATURE:
<221> NAME/KEY: misc_feature
<222> LOCATION: (1)..(26)
<223> OTHER INFORMATION: primer
<221> NAME/KEY: misc_feature
<222> LOCATION: (9)..()
<223> OTHER INFORMATION: W = A or T
<221> NAME/KEY: misc_feature
<222> LOCATION: (15)..()
<223> OTHER INFORMATION: W = A or T
<221> NAME/KEY: misc_feature
<222> LOCATION: (21)..()
<223> OTHER INFORMATION: W = A or T
<221> NAME/KEY: misc_feature
<222> LOCATION: (18)..()
<223> OTHER INFORMATION: Y = C or T
<221> NAME/KEY: misc_feature
<222> LOCATION: (25)..()
<223> OTHER INFORMATION: M = A or C

<400> SEQUENCE: 124
gcacaaccwa gaacwgaygg wcaamg                                      26

<210> SEQ ID NO 125
<211> LENGTH: 18
<212> TYPE: DNA
<213> ORGANISM: Ctenocephalides felis
<220> FEATURE:
<221> NAME/KEY: misc_feature
<222> LOCATION: (1)..(18)
<223> OTHER INFORMATION: primer

<400> SEQUENCE: 125
gaattgggta ccgggccc                                               18

<210> SEQ ID NO 126
<211> LENGTH: 500
<212> TYPE: DNA
<213> ORGANISM: Ctenocephalides felis
<220> FEATURE:
<221> NAME/KEY: CDS
<222> LOCATION: (1)..(183)
```

<400> SEQUENCE: 126

```
gca caa cct aga aca gac ggt caa cgt ccg aaa act acc ata atg agt     48
Ala Gln Pro Arg Thr Asp Gly Gln Arg Pro Lys Thr Thr Ile Met Ser
1               5                   10                  15 gaa ctt cta aag caa aaa ata agt tgc aaa gaa gtg aaa gca gct aaa     96
Glu Leu Leu Lys Gln Lys Ile Ser Cys Lys Glu Val Lys Ala Ala Lys
            20                  25                  30 tta gaa agt gct gtt tgt gct tat gat tgc agt caa cat gaa aac act    144
Leu Glu Ser Ala Val Cys Ala Tyr Asp Cys Ser Gln His Glu Asn Thr
        35                  40                  45 gga att aat tgt gaa gga aat gcg tgt aaa tgc ccc aag taaccttaaa    193
Gly Ile Asn Cys Glu Gly Asn Ala Cys Lys Cys Pro Lys
    50                  55                  60 gcaccaaaaa aatgcttgac gcattactaa aaaaatattt ataaatttta aaatagact    253 aataaaataa aattaataaa tcgaaattta atacgctctt caataagtaa acttgaaaca    313
agtaaatatt tatttataat attgataata tgaatcatgc atcactgtat gccgatattt    373
ttaaattatt aactcaaatc atatacattt ttatttttta ttaattatta aaattataat    433
aaatgttact aaaatattac aagaaacaaa atgtaataaa attattattt caaaaaaaa    493 aaaaaaa                                                             500
```

<210> SEQ ID NO 127
<211> LENGTH: 61
<212> TYPE: PRT
<213> ORGANISM: Ctenocephalides felis

<400> SEQUENCE: 127

```
Ala Gln Pro Arg Thr Asp Gly Gln Arg Pro Lys Thr Thr Ile Met Ser
1               5                   10                  15

Glu Leu Leu Lys Gln Lys Ile Ser Cys Lys Glu Val Lys Ala Ala Lys
            20                  25                  30

Leu Glu Ser Ala Val Cys Ala Tyr Asp Cys Ser Gln His Glu Asn Thr
        35                  40                  45

Gly Ile Asn Cys Glu Gly Asn Ala Cys Lys Cys Pro Lys
    50                  55                  60
```

<210> SEQ ID NO 128
<211> LENGTH: 500
<212> TYPE: DNA
<213> ORGANISM: Ctenocephalides felis

<400> SEQUENCE: 128

```
ttttttttt tttttgaaa taataatttt attacatttt gtttcttgta atatttagt      60 aacatttatt ataattttaa taattaataa aaaataaaaa tgtatatgat ttgagttaat   120
aatttaaaaa tatcggcata cagtgatgca tgattcatat tatcaatatt ataaataaat   180
atttacttgt ttcaagttta cttattgaag agcgtattaa atttcgattt attaatttta   240
ttttattagt ctatttttaa aatttataaa tatttttta gtaatgcgtc aagcattttt    300
ttggtgcttt aaggttactt ggggcattta cacgcatttc cttcacaatt aattccagtg   360
ttttcatgtt gactgcaatc ataagcacaa acagcacttt ctaatttagc tgctttcact   420
tctttgcaac ttattttttg ctttagaagt tcactcatta tggtagtttt cggacgttga   480
ccgtctgttc taggttgtgc                                               500
```

<210> SEQ ID NO 129

<211> LENGTH: 183
<212> TYPE: DNA
<213> ORGANISM: Ctenocephalides felis

<400> SEQUENCE: 129

```
gcacaaccta gaacagacgg tcaacgtccg aaaactacca taatgagtga acttctaaag    60
caaaaaataa gttgcaaaga agtgaaagca gctaaattag aaagtgctgt ttgtgcttat   120
gattgcagtc aacatgaaaa cactggaatt aattgtgaag gaaatgcgtg taaatgcccc   180
aag                                                                 183
```

<210> SEQ ID NO 130
<211> LENGTH: 183
<212> TYPE: DNA
<213> ORGANISM: Ctenocephalides felis

<400> SEQUENCE: 130

```
cttggggcat ttacacgcat ttccttcaca attaattcca gtgttttcat gttgactgca    60
atcataagca caaacagcac tttctaattt agctgctttc acttctttgc aacttatttt   120
ttgctttaga agttcactca ttatggtagt tttcggacgt tgaccgtctg ttctaggttg   180
tgc                                                                 183
```

<210> SEQ ID NO 131
<211> LENGTH: 71
<212> TYPE: PRT
<213> ORGANISM: Ctenocephalides felis

<400> SEQUENCE: 131

```
Ser Lys Met Val Thr Glu Lys Cys Lys Ser Gly Gly Asn Asn Pro Ser
1               5                   10                  15

Thr Glu Glu Val Ser Ile Pro Ser Gly Lys Leu Thr Ile Glu Asp Phe
            20                  25                  30

Cys Ile Gly Asn His Gln Ser Cys Lys Ile Phe Tyr Lys Ser Gln Cys
        35                  40                  45

Gly Phe Gly Gly Gly Ala Cys Gly Asn Gly Gly Ser Thr Arg Pro Asn
    50                  55                  60

Gln Lys His Cys Tyr Cys Glu
65                  70
```

<210> SEQ ID NO 132
<211> LENGTH: 22
<212> TYPE: PRT
<213> ORGANISM: Ctenocephalides felis
<220> FEATURE:
<221> NAME/KEY: misc_feature
<222> LOCATION: (1)..()
<223> OTHER INFORMATION: Xaa = Tyr, Gln, Ser or Arg
<221> NAME/KEY: misc_feature
<222> LOCATION: (2)..()
<223> OTHER INFORMATION: Xaa = Gly or Tyr
<221> NAME/KEY: misc_feature
<222> LOCATION: (3)..()
<223> OTHER INFORMATION: Xaa = Lys or Ser
<221> NAME/KEY: misc_feature
<222> LOCATION: (9)..()
<223> OTHER INFORMATION: Xaa = Gly or Ser
<221> NAME/KEY: misc_feature
<222> LOCATION: (10)..()
<223> OTHER INFORMATION: Xaa = Gly or Lys
<221> NAME/KEY: misc_feature
<222> LOCATION: (14)..()
<223> OTHER INFORMATION: Xaa = Arg or Ile
<221> NAME/KEY: misc_feature
<222> LOCATION: (17)..()

```
-continued

<223> OTHER INFORMATION: Xaa = Ile or Leu
<221> NAME/KEY: misc_feature
<222> LOCATION: (19)..()
<223> OTHER INFORMATION: Xaa = Lys or Asp
<221> NAME/KEY: misc_feature
<222> LOCATION: (21)..()
<223> OTHER INFORMATION: Xaa = Gly or Leu

<400> SEQUENCE: 132

Xaa Xaa Xaa Gln Tyr Ser Glu Lys Xaa Xaa Arg Gly Gln Xaa His Gln
1               5                   10                  15

Xaa Leu Xaa Lys Xaa Lys
            20

<210> SEQ ID NO 133
<211> LENGTH: 10
<212> TYPE: PRT
<213> ORGANISM: Ctenocephalides felis
<220> FEATURE:
<221> NAME/KEY: misc_feature
<222> LOCATION: (1)..()
<223> OTHER INFORMATION: Xaa = Ser or Gln
<221> NAME/KEY: misc_feature
<222> LOCATION: (8)..()
<223> OTHER INFORMATION: Xaa = any amino acid
<221> NAME/KEY: misc_feature
<222> LOCATION: (9)..()
<223> OTHER INFORMATION: Xaa = Gly or Lys

<400> SEQUENCE: 133

Xaa Gly Lys Gln Tyr Ser Glu Xaa Xaa Lys
1               5                   10

<210> SEQ ID NO 134
<211> LENGTH: 6
<212> TYPE: PRT
<213> ORGANISM: Ctenocephalides felis

<400> SEQUENCE: 134

Asp Arg Arg Val Ser Lys
1               5

<210> SEQ ID NO 135
<211> LENGTH: 78
<212> TYPE: PRT
<213> ORGANISM: Ctenocephalides felis
<220> FEATURE:
<221> NAME/KEY: misc_feature
<222> LOCATION: (27)..()
<223> OTHER INFORMATION: Xaa = His or Tyr

<400> SEQUENCE: 135

Asp Arg Arg Val Ser Lys Thr Cys Gln Ser Gly Gly Lys Ile Gln Ser
1               5                   10                  15

Glu Xaa Gln Val Val Ile Lys Ser Gly Gln Xaa Ile Leu Glu Asn Tyr
            20                  25                  30

Xaa Ser Asp Gly Arg Asn Asn Asn Pro Cys His Leu Phe Cys Met
        35                  40                  45

Arg Glu Cys Arg Ser Gly Asn Gly Cys Gly Asn Gly Gly Arg Thr
    50                  55                  60

Arg Pro Asp Ser Lys His Cys Tyr Cys Glu Ala Pro Tyr Ser
65                  70                  75

<210> SEQ ID NO 136
<211> LENGTH: 12
<212> TYPE: PRT
```

<213> ORGANISM: Ctenocephalides felis

<400> SEQUENCE: 136

Asp Ser Lys His Cys Tyr Cys Glu Ala Pro Tyr Ser
1               5                  10

<210> SEQ ID NO 137
<211> LENGTH: 37
<212> TYPE: PRT
<213> ORGANISM: Ctenocephalides felis

<400> SEQUENCE: 137

Asp Gly Arg Asn Asn Asn Pro Cys His Leu Phe Cys Met Arg Glu
1               5                  10                  15

Cys Arg Ser Gly Asn Gly Gly Cys Gly Asn Gly Arg Thr Arg Pro
            20                  25                  30

Asp Ser Lys His Cys
        35

<210> SEQ ID NO 138
<211> LENGTH: 11
<212> TYPE: PRT
<213> ORGANISM: Ctenocephalides felis

<400> SEQUENCE: 138

Asp Arg Arg Val Ser Lys Thr Cys Gln Ser Gly
1               5                  10

<210> SEQ ID NO 139
<211> LENGTH: 37
<212> TYPE: PRT
<213> ORGANISM: Ctenocephalides felis
<220> FEATURE:
<221> NAME/KEY: misc_feature
<222> LOCATION: (8)..()
<223> OTHER INFORMATION: Xaa = any amino acid
<221> NAME/KEY: misc_feature
<222> LOCATION: (18)..()
<223> OTHER INFORMATION: Xaa = any amino acid
<221> NAME/KEY: misc_feature
<222> LOCATION: (27)..()
<223> OTHER INFORMATION: Xaa = any amino acid
<221> NAME/KEY: misc_feature
<222> LOCATION: (33)..()
<223> OTHER INFORMATION: Xaa = any amino acid

<400> SEQUENCE: 139

Asp Arg Arg Val Ser Lys Thr Xaa Gln Ser Gly Gly Lys Ile Gln Ser
1               5                  10                  15

Glu Xaa Gln Val Val Ile Lys Ser Gly Gln Xaa Ile Leu Glu Asn Tyr
            20                  25                  30

Xaa Ser Asp Gly Arg
        35

<210> SEQ ID NO 140
<211> LENGTH: 23
<212> TYPE: PRT
<213> ORGANISM: Ctenocephalides felis
<220> FEATURE:
<221> NAME/KEY: misc_feature
<222> LOCATION: (8)..()
<223> OTHER INFORMATION: Xaa = any amino acid

<400> SEQUENCE: 140

Ser Lys Met Val Thr Glu Lys Xaa Lys Ser Gly Gly Asn Asn Pro Ser
1               5                  10                  15

```
Thr Lys Glu Val Ser Ile Pro
            20

<210> SEQ ID NO 141
<211> LENGTH: 20
<212> TYPE: PRT
<213> ORGANISM: Ctenocephalides felis
<220> FEATURE:
<221> NAME/KEY: misc_feature
<222> LOCATION: (15)..()
<223> OTHER INFORMATION: Xaa = any amino acid

<400> SEQUENCE: 141

Glu Val Ser Ile Pro Ser Gly Lys Leu Thr Ile Glu Asp Phe Xaa Ile
1               5                   10                  15

Gly Asn His Gln
            20

<210> SEQ ID NO 142
<211> LENGTH: 38
<212> TYPE: PRT
<213> ORGANISM: Ctenocephalides felis
<220> FEATURE:
<221> NAME/KEY: misc_feature
<222> LOCATION: (10)..()
<223> OTHER INFORMATION: Xaa = any amino acid
<221> NAME/KEY: misc_feature
<222> LOCATION: (32)..()
<223> OTHER INFORMATION: Xaa = any amino acid
<221> NAME/KEY: misc_feature
<222> LOCATION: (33)..()
<223> OTHER INFORMATION: Xaa = any amino acid
<221> NAME/KEY: misc_feature
<222> LOCATION: (36)..()
<223> OTHER INFORMATION: Xaa = any amino acid
<221> NAME/KEY: misc_feature
<222> LOCATION: (37)..()
<223> OTHER INFORMATION: Xaa = any amino acid

<400> SEQUENCE: 142

Glu Asp Ile Trp Lys Val Asn Lys Lys Xaa Thr Ser Gly Gly Lys Asn
1               5                   10                  15

Gln Asp Arg Lys Leu Asp Gln Ile Ile Gln Lys Gly Gln Gln Val Xaa
            20                  25                  30

Xaa Gln Asn Xaa Xaa Lys
            35

<210> SEQ ID NO 143
<211> LENGTH: 23
<212> TYPE: PRT
<213> ORGANISM: Ctenocephalides felis

<400> SEQUENCE: 143

Asn Ser His Glu Pro Gly Asn Thr Arg Lys Ile Arg Glu Val Met Asp
1               5                   10                  15

Lys Leu Arg Lys Gln His Pro
            20

<210> SEQ ID NO 144
<211> LENGTH: 27
<212> TYPE: PRT
<213> ORGANISM: Ctenocephalides felis

<400> SEQUENCE: 144

Glu Ile Lys Arg Asn Ser His Glu Pro Gly Asn Thr Arg Lys Ile Arg
1               5                   10                  15
```

Glu Val Met Asp Lys Leu Arg Lys Gln His Pro
            20                  25

<210> SEQ ID NO 145
<211> LENGTH: 36
<212> TYPE: PRT
<213> ORGANISM: Ctenocephalides felis
<220> FEATURE:
<221> NAME/KEY: misc_feature
<222> LOCATION: (34)..()
<223> OTHER INFORMATION: Xaa = any amino acid

<400> SEQUENCE: 145

Asn Asp Lys Glu Pro Gly Asn Thr Arg Lys Ile Arg Glu Val Met Asp
1               5                   10                  15

Lys Leu Arg Lys Gln Ala Gln Pro Arg Thr Asp Gly Gln Arg Pro Lys
            20                  25                  30

Thr Xaa Ile Met
        35

<210> SEQ ID NO 146
<211> LENGTH: 21
<212> TYPE: PRT
<213> ORGANISM: Ctenocephalides felis
<220> FEATURE:
<221> NAME/KEY: misc_feature
<222> LOCATION: (1)..()
<223> OTHER INFORMATION: Xaa = any amino acid
<221> NAME/KEY: misc_feature
<222> LOCATION: (3)..()
<223> OTHER INFORMATION: Xaa = any amino acid

<400> SEQUENCE: 146

Xaa Leu Xaa Arg Asn Asp Lys Glu Pro Gly Asn Thr Arg Lys Ile Arg
1               5                   10                  15

Glu Val Met Asp Lys
            20

<210> SEQ ID NO 147
<211> LENGTH: 12
<212> TYPE: PRT
<213> ORGANISM: Ctenocephalides felis

<400> SEQUENCE: 147

Asn Asp Glu Leu Lys Phe Val Phe Val Met Ala Lys
1               5                   10

<210> SEQ ID NO 148
<211> LENGTH: 23
<212> TYPE: PRT
<213> ORGANISM: Ctenocephalides felis
<220> FEATURE:
<221> NAME/KEY: misc_feature
<222> LOCATION: (1)..()
<223> OTHER INFORMATION: Xaa = any amino acid
<221> NAME/KEY: misc_feature
<222> LOCATION: (16)..()
<223> OTHER INFORMATION: Xaa = any amino acid
<221> NAME/KEY: misc_feature
<222> LOCATION: (19)..()
<223> OTHER INFORMATION: Xaa = any amino acid

<400> SEQUENCE: 148

Xaa Asp Glu Leu Lys Phe Val Phe Val Met Ala Lys Gly Pro Ser Xaa
1               5                   10                  15

Gln Ala Xaa Asp Tyr Pro Cys

-continued

```
<210> SEQ ID NO 149
<211> LENGTH: 20
<212> TYPE: PRT
<213> ORGANISM: Ctenocephalides felis

<400> SEQUENCE: 149

Glu Leu Lys Phe Val Phe Ala Thr Ala Arg Gly Met Ser His Thr Pro
1               5                   10                  15

Cys Asp Tyr Pro
            20

<210> SEQ ID NO 150
<211> LENGTH: 25
<212> TYPE: PRT
<213> ORGANISM: Ctenocephalides felis

<400> SEQUENCE: 150

Asp Ile Glu Asn Ile Lys Lys Gly Glu Gly Gln Pro Gly Ala Pro Gly
1               5                   10                  15

Gly Lys Glu Asn Asn Leu Ser Val Leu
            20                  25
```

ECTOPARASITE SALIVA PROTEINS AND APPARATUS TO COLLECT SUCH PROTEINS

This application is a National Stage of PCT Application No. PCT/US97/18669, having an international filing date of Oct. 15, 1997, and claims priority under 35 U.S.C. §365(c) to PCT Application No. PCT/US97/05959, having an international filing date of Apr. 10, 1997. PCT Application No. PCT/US97/05959 claims priority to U.S. patent application Ser. No. 08/630,822, filed Apr. 10, 1996, which issued as U.S. Pat. No. 5,840,695 on Nov. 24, 1998. U.S. patent application Ser. No. 08/630,822 is a continuation-in-part of PCT application Ser. No. PCT/US95/13200, filed Oct. 6, 1995, which is a continuation-in-part application of U.S. patent application Ser. No. 08/487,001, filed Jun. 7, 1995, which issued as U.S. Pat. No. 5,795,862 on Aug. 18, 1998, and of U.S. patent application Ser. No. 08/487,608, filed Jun. 7, 1995, which are continuation-in-part applications of U.S. patent application Ser. No. 08/319,590, filed Oct. 7, 1994, which issued as U.S. Pat. No. 5,646,115 on Jul. 8, 1997. The present application claims priority under 35 U.S.C. §371 to PCT/US97/18669, and is a continuation-in-part under 35 U.S.C. §365(c) to PCT Application No. PCT/US97/05959 as a continuation in part of U.S. Ser. No. 08/630,822 filed Apr. 10, 1996, U.S. Pat. No. 5,840,695 filed Apr. 10, 1997, and under 35 U.S.C. §120 to U.S. patent application Ser. No. 08/630,822, which is continuation in part of U.S. patent application Ser. No. 08/487,001, which is a continuation in part of now U.S. Pat No. 5,795,862 filed Jun. 7, 1995 and U.S. patent application Ser. No. 08/319,590 filed on Oct. 7, 1994, now U.S. Pat. No. 5,646,115.

FIELD OF THE INVENTION

The present invention relates to a novel product and method for isolating ectoparasite saliva proteins, and a novel product and method for detecting and/or treating allergic dermatitis in an animal.

BACKGROUND OF THE INVENTION

Bites from ectoparasites, in particular fleas, can cause a hypersensitive response in animals. In particular, hypersensitive responses to fleabites is manifested in a disease called flea allergy dermatitis (FAD). Hypersensitivity refers to a state of altered reactivity in which an animal, having been previously exposed to a compound, exhibits an allergic response to the compound upon subsequent exposures. Hypersensitive responses include immediate and delayed-type hypersensitivity, and in particular Type I, Type II, Type III and Type IV hypersensitivities (described in detail in Janeway et al., *Immunobiology*, Garland Publishing, New York, 1994, which is incorporated in its entirety by this reference).

Foreign compounds that induce symptoms of immediate and/or delayed hypersensitivity are herein referred to as allergens. The term "allergen" primarily refers to foreign compounds capable of causing an allergic response. The term can be used interchangeably with the term "antigen," especially with respect to a foreign compound capable of inducing symptoms of immediate and/or delayed hypersensitivity. Factors that influence an animal's susceptibility to an allergen can include a genetic component and/or environmental exposure to an allergen. Animals can be de-sensitized to an allergen by repeated injections of the allergen to which an animal is hypersensitive.

FAD can have manifestations of both immediate and delayed-type hypersensitivity (described in detail in Janeway et al., ibid.). Effective treatment of FAD has been difficult if not impossible to achieve. FAD afflicts about 15%, of cats and dogs in flea endemic areas and the frequency is increasing each year. In a geographical area, effective flea control requires treatment of all animals. One treatment investigators have proposed includes desensitization of animals using flea allergens. However, reliable, defined preparations of flea allergens are needed for such treatments.

Until the discovery of the novel formulations of the present invention, flea allergens responsible for FAD had not been clearly defined. Whole flea antigen preparations have been used to diagnose and desensitize animals with FAD (Benjamini et al., 1960, pp. 214–222, *Experimental Parasitology*, Vol. 10; Keep et al., 1967, pp. 425–426, *Australian Veterinary Journal*, Vol. 43; Kristensen et al., 1978, pp. 414–423, *Nord. Vet-Med*, Vol. 30; Van Winkle, 1981, pp. 343–354, *J. Amer. Animal Hosp. Assoc.*, Vol. 17; Haliwell et al., 1987, pp. 203–213, *Veterinary Immunology and Immunopathology*, Vol. 15; Greene et al., 1993, pp. 69–74, *Parasite Immunology*, Vol. 15); PCT Publication No. WO 93/18788 by Opdebeeck et al.; and Van Winkle, pp. 343–354, 1981, *J. Am. Anim. Hosp. Assoc.*, vol. 32. Available commercial whole flea extracts, however, are unpredictable and, therefore, have limited usefulness.

Prior investigators have suggested that products contained in flea saliva might be involved in FAD and have also suggested methods to isolate such products: Benjamini et al., 1963, pp. 143–154, *Experimental Parasitology*, Vol. 13; Young et al., 1963, pp. 155–166, *Experimental Parasitology* 13, Vol. 13; Michaeli et al., 1965, pp. 162–170, *J. Immunol.*, Vol. 95; and Michaeli et al., 1996, pp. 402–406, *J. Immunol.*, Vol. 97. These investigators, however, have characterized the allergenic factors of flea saliva as being haptens having molecular weights of less than 6 kilodaltons (kD). That they are not proteins is also supported by the finding that they are not susceptible to degradation when exposed to strong acids (e.g., 6 N hydrochloric acid) or heat. Some of the particular low molecular weight allergenic factors have also been characterized as being a highly fluorescent aromatic fraction (Young et al., ibid.). In addition, studies by such investigators have indicated that in order to be allergenic, such factors need to be associated with adjuvants and/or carriers, such as collagen or portions of the membrane used to collect the oral secretions. Moreover, the methods described to collect flea saliva factors were difficult and unpredictable. Furthermore the factors isolated by these methods were typically contaminated with material from the fleas, their culture medium or the skin-based membranes used to allow the fleas to feed.

Thus, there remains a need to more clearly define flea saliva allergens capable of inducing a hypersensitive response in animals. In addition, there remains a need to develop a method to collect substantially pure flea saliva allergens which provide predictable and less expensive preparations of allergens useful for desensitizing animals subject to, or having, FAD.

SUMMARY OF THE INVENTION

One embodiment of the present invention is an isolated nucleic acid molecule that hybridizes under stringent conditions with a gene including a flea saliva gene comprising a nucleic acid sequence including SEQ ID NO:89, SEQ ID NO:91, SEQ ID NO:92, SEQ ID NO:93, SEQ ID NO:95, SEQ ID NO:96, SEQ ID NO:97, SEQ ID NO:100, SEQ ID NO:102, SEQ ID NO:103, SEQ ID NO:104, SEQ ID NO:106, SEQ ID NO:107, SEQ ID NO:11, SEQ ID NO:113, SEQ ID NO:114, SEQ ID NO:116, SEQ ID NO:117, SEQ ID NO:118, SEQ ID NO:120, SEQ ID NO:121, SEQ ID NO:126, SEQ ID NO:128, SEQ ID NO:129 and SEQ ID NO:130.

The present invention also includes a nucleic acid molecule that hybridizes under stringent hybridization conditions with a nucleic acid molecule having a nucleic acid sequence encoding a protein comprising an amino acid sequence including SEQ ID NO:90, SEQ ID NO:94, SEQ ID NO:101 and SEQ ID NO:105, SEQ ID NO:112, SEQ ID NO:115, SEQ ID NO:119 and SEQ ID NO:127.

Another embodiment of the present invention includes an isolated protein encoded by a nucleic acid molecule that hybridizes under stringent hybridization conditions with a nucleic acid molecule having a nucleic acid sequence encoding a protein comprising an amino acid sequence including SEQ ID NO:90, SEQ ID NO:94, SEQ ID NO:101 and SEQ ID NO:105, SEQ ID NO:112, SEQ ID NO:115, SEQ ID NO:119 and SEQ ID NO:127.

Also included in the present invention are recombinant molecules and cells having a nucleic acid molecule of the present invention.

Another aspect of the present invention includes an antibody capable of selectively binding to an ectoparasite protein, or mimetope.

Yet another embodiment of the present invention is a therapeutic composition for treating allergic dermatitis comprising a formulation comprising at least one isolated ectoparasite saliva protein, in which the ectoparasite saliva protein comprises at least a portion of an amino acid sequence, in which the portion is encoded by a nucleic acid molecule that hybridizes under stringent hybridization conditions with a nucleic acid molecule having a nucleic acid sequence including SEQ ID NO:89, SEQ ID NO:91, SEQ ID NO:92, SEQ ID NO:93, SEQ ID NO:95, SEQ ID NO:96, SEQ ID NO:97, SEQ ID NO:100, SEQ ID NO:102, SEQ ID NO:103, SEQ ID NO:104, SEQ ID NO:106, SEQ ID NO:107, SEQ ID NO:111, SEQ ID NO:113, SEQ ID NO:114, SEQ ID NO:116, SEQ ID NO:117, SEQ ID NO:118, SEQ ID NO:120, SEQ ID NO:121, SEQ ID NO:126, SEQ ID NO:128, SEQ ID NO:129 and SEQ ID NO:130. A preferred therapeutic composition of the present invention also includes an excipient, an adjuvant and/or a carrier. Also included in the present invention is a method to desensitize a host animal to allergic dermatitis. The method includes the step of administering to the animal a therapeutic composition of the present invention.

Other embodiments of the present invention include methods to identify an animal susceptible to or having allergic dermatitis, using in vivo or in vitro methods. In one embodiment, an animal susceptible to or having allergic dermatitis is identified in vivo by the method comprising: (a) administering to a site on the animal a formulation comprising at least one isolated ectoparasite saliva protein, in which the ectoparasite saliva protein comprises an amino acid sequence including SEQ ID NO:90, SEQ ID NO:94, SEQ ID NO:101 and SEQ ID NO:105, SEQ ID NO:112, SEQ ID NO:115, SEQ ID NO:119 and SEQ ID NO:127 and SEQ ID; and (b) comparing a reaction resulting from administration of the formulation with a reaction resulting from administration of a control solution, in which the animal is determined to be susceptible to or to have allergic dermatitis if the reaction to the formulation is at least as large as said reaction to the positive control solution, and in which the animal is determined not to be susceptible to or not to have allergic dermatitis if the reaction to the formulation is about the same size as said reaction to the negative control solution.

In another embodiment, an animal susceptible to or having allergic dermatitis is identified in vitro by measuring the presence of antibodies indicative of allergic dermatitis in the animal using the method comprising: (a) contacting a formulation with a body fluid from an animal under conditions sufficient for formation of an immunocomplex between the formulation and the antibodies, if present, in the body fluid, the formulation comprising at least one isolated ectoparasite saliva protein, in which the ectoparasite saliva protein comprises an amino acid sequence including SEQ ID NO:90, SEQ ID NO:94, SEQ ID NO:101 and SEQ ID NO:105, SEQ ID NO:112, SEQ ID NO:115, SEQ ID NO:119 and SEQ ID NO:127; and (b) determining the amount of immunocomplex formed, in which formation of the immunocomplex indicates that the animal is susceptible to or has allergic dermatitis.

The present invention further relates to an assay kit for testing if an animal is susceptible to or has allelic dermatitis, the kit comprising: (a) a formulation comprising at least one isolated ectoparasite saliva protein, in which the ectoparasite saliva protein comprises an amino acid sequence including SEQ ID SEQ ID NO:90, SEQ ID NO:94, SEQ ID NO:101 and SEQ ID NO:105, SEQ ID NO:112, SEQ ID NO:115, SEQ ID NO:119 and SEQ ID NO:127; and (b) a means for determining if the animal is susceptible to or has allergic dermatitis, in which the means comprises use of the formulation to identify animals susceptible to or having allergic dermatitis.

DETAILED DESCRIPTION OF THE INVENTION

Figure 1A:
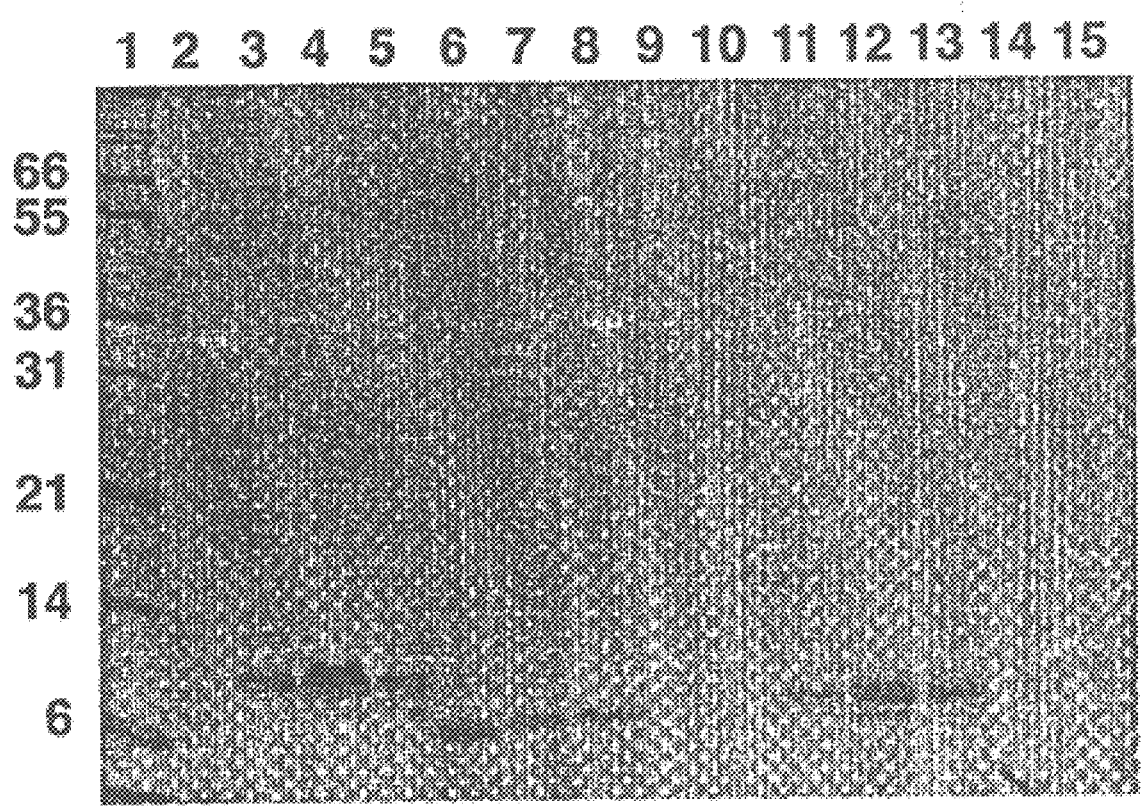
FIG. 1A illustrates the resolution of flea saliva proteins by reducing 16% Tris glycine SDS-PAGE.

The present invention includes a novel product and method for diagnosing and treating allergic dermatitis of animals to ectoparasites.

According to the present invention, ectoparasites are external living parasites that attach and feed through the skin of a host animal. Ectoparasites include parasites that live on a host animal and parasites that attach temporarily to an animal in order to feed. Also, according to the present invention, ectoparasite saliva refers to the material released from the mouth of an ectoparasite when the ectoparasite attempts to feed in response to a temperature differential. Ectoparasite saliva includes ectoparasite saliva products.

One embodiment of the present invention is a formulation that contains ectoparasite saliva products that can be used to diagnose and/or treat animals susceptible to or having (i.e., suffering from) allergic dermatitis. Preferred types of allergic dermatitis to diagnose and/or treat using ectoparasite saliva products of the present invention include flea allergy dermatitis, Culicoides allergy dermatitis and mosquito allergy dermatitis. A preferred type of allergic dermatitis to diagnose and/or treat using ectoparasite saliva products of the present invention is flea allergy dermatitis. As used herein, an animal that is susceptible to allergic dermatitis refers to an animal that is genetically pre-disposed to developing allergic dermatitis and/or to an animal that has been primed with an antigen in such a manner that re-exposure to the antigen results in symptoms of allergy that can be perceived by, for example, observing the animal or measuring antibody production by the animal to the antigen. As such, animals susceptible to allergic dermatitis can include animals having sub-clinical allergic dermatitis. Sub-clinical allergic dermatitis refers to a condition in which allergy symptoms cannot be detected by simply observing an animal (i.e., manifestation of the disease can include the presence of anti-ectoparasite saliva protein antibodies within an affected animal but no dermatitis). For example, sub-clinical allergic dermatitis can be detected using in vivo or in vitro assays of the present invention, as described in detail below. Reference to animals having allergic dermatitis includes animals that do display allergy symptoms that can be detected by simply observing an animal and/or by using in vivo or in vitro assays of the present invention, as described in detail below.

One embodiment of the present invention is a formulation that includes one or more isolated ectoparasite saliva proteins. According to the present invention, an isolated protein is a protein that has been removed from its natural milieu. An isolated ectoparasite saliva protein can, for example, be obtained from its natural source, be produced using recombinant DNA technology, or be synthesized chemically. As used herein, an isolated ectoparasite saliva protein can be a full-length ectoparasite saliva protein or any homologue of such a protein, such as an ectoparasite saliva protein in which amino acids have been deleted (e.g., a truncated version of the protein, such as a peptide), inserted, inverted, substituted and/or derivatized (e.g., by glycosylation, phosphorylation, acetylation, myristylation, prenylation, palmitation, amidation and/or addition of glycosylphosphatidyl inositol). A homologue of an ectoparasite saliva protein is a protein having an amino acid sequence that is sufficiently similar to a natural ectoparasite saliva protein amino acid sequence that a nucleic acid sequence encoding the homologue is capable of hybridizing under stringent conditions to (i.e., with) a nucleic acid molecule encoding the natural ectoparasite saliva protein (i.e., the complement of a nucleic acid sequence encoding the natural ectoparasite saliva protein amino acid sequence). A nucleic acid sequence complement of any nucleic acid sequence of the present invention refers to the nucleic acid sequence of the nucleic acid strand that is complementary to (i.e., can form a complete double helix with) the strand for which the sequence is cited. It is to be noted that a double-stranded nucleic acid molecule of the present invention for which a nucleic acid sequence has been determined for one strand that represented by a SEQ ID NO also comprises a complementary strand having a sequence that is a complement of that SEQ ID NO. As such, nucleic acid molecules of the present invention, which can be either double-stranded or single-stranded, include those nucleic acid molecules that form stable hybrids under stringent hybridization conditions with either a given SEQ ID NO denoted herein and/or with the complement of that SEQ ID NO, which may or may not be denoted herein. Methods to deduce a complementary sequence are known to those skilled in the art.

As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., *Molecular Cloning: A Laboratory Manual*, Cold Spring Harbor Labs Press, 1989; Sambrook et al., ibid., is incorporated by reference herein in its entirety. Stringent hybridization conditions typically permit isolation of nucleic acid molecules having at least about 70% nucleic acid sequence identity with the nucleic acid molecule being used to probe in the hybridization reaction. Formulae to calculate the appropriate hybridization and wash conditions to achieve hybridization permitting 30% or less mismatch of nucleotides are disclosed, for example, in Meinkoth et al., 1984, *Anal. Biochem.* 138, 267–284; Meinkoth et al., ibid., is incorporated by reference herein in its entirety.

The minimal size of a protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode an ectoparasite saliva protein homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of an ectoparasite saliva protein homologue of the present invention is from about 4 to about 6 amino acids in length, with preferred sizes depending on whether a full-length, multivalent (i.e., fusion protein having more than one domain each of which has a function), or functional portions of such proteins are desired.

Ectoparasite saliva protein homologues can be the result of allelic variation of a natural gene encoding an ectoparasite saliva protein. A natural gene refers to the form of the gene found most often in nature. Ectoparasite saliva protein homologues can be produced using techniques known in the art including, but not limited to, direct modifications to a gene encoding a protein using, for example, classic or recombinant DNA techniques to effect random or targeted mutagenesis.

Preferred ectoparasite saliva proteins of the present invention, including homologues thereof, are capable of detecting and/or treating allergic dermatitis resulting from the bites of ectoparasites. A preferred ectoparasite saliva protein homologue includes at least one epitope capable of eliciting a hypersensitive response to the natural ectoparasite saliva protein counterpart. An ectoparasite saliva protein homologue can also include an epitope capable of hyposensitizing an animal to the natural form of the protein. The ability of an ectoparasite saliva protein homologue to detect and/or treat (i.e., immunomodulate or regulate by, for example, desensitizing) the hypersensitivity of an animal susceptible to or having allergic dermatitis, can be tested using techniques known to those skilled in the art. Such techniques include skin tests and immunoabsorbent assays as described in detail below. Additional preferred ectoparasite saliva proteins of the present invention have other activities that include activities important for feeding and survival of the ectoparasite.

In one embodiment, a formulation of the present invention can comprise a protein having at least a portion of an isolated ectoparasite saliva protein. According to the present invention, "at least a portion of an ectoparasite saliva protein" refers to a portion of an ectoparasite saliva protein encoded by a nucleic acid molecule that is capable of hybridizing, under stringent conditions, with a nucleic acid encoding a full-length ectoparasite saliva protein of the present invention. Preferred portions of ectoparasite saliva proteins are useful for detecting and/or treating allergic dermatitis resulting from the bites of ectoparasites. Additional preferred portions have activities important for flea feeding and survival. Suitable sizes for portions of an ectoparasite saliva protein of the present invention are as disclosed for saliva protein homologues of the present invention.

As will be apparent to one of skill in the art, the present invention is intended to apply to all ectoparasites. A formulation of the present invention can include saliva products from any ectoparasites. A preferred ectoparasite of the present invention from which to isolate saliva products (including proteins), and/or from which to identify proteins that can then be produced recombinantly or synthetically, include arachnids, insects and leeches. More preferred ectoparasites from which to obtain saliva products include fleas; ticks, including both hard ticks of the family Ixodidae (e.g., Ixodes and Amblyomma) and soft ticks of the family Argasidae (e.g., Ornithodoros, such as *O. parkeri* and *O. turicata*); flies, such as midges (e.g., Culicoides), mosquitos, sand flies, black flies, horse flies, horn flies, deer flies, tsetse flies, stable flies, myiasis-causing flies and biting gnats; ants; spiders, lice; mites; and true bugs, such as bed bugs and kissing bugs, including those carrying Chagas disease. Even more preferred ectoparasite saliva products include those from fleas, mosquitos, midges, sandflies, blackflies, ticks and Rhodnius, with products from fleas, mosquitos and Culicoides being even more preferred.

A particularly preferred formulation of the present invention includes flea saliva proteins. Preferred flea saliva products include those from Ctenocephalides, Xenopsylla, Pulex, Tunga, Nosopsyllus, Diamanus, Ctopsyllus and *Echidnophaga fleas*, With saliva products from *Ctenocephalides canis* and *Ctenocephalides felis* fleas being even more preferred. For the purposes of illustration, many of the following embodiments discuss flea saliva proteins. Such discussion of flea saliva proteins is not intended, in any way, to limit the scope of the present invention.

In another embodiment, a formulation of the present invention includes at least a portion of an ectoparasite saliva protein homologue having at least a portion of one of the following amino acid sequences:SEQ ID NO:90, SEQ ID NO:94, SEQ ID NO:101 and SEQ ID NO:105, SEQ ID NO:112, SEQ ID NO:115, SEQ ID NO:119 and SEQ ID NO:127 and/or other sequences disclosed herein.

In one embodiment, a formulation of the present invention can include at least one isolated protein having (i.e., including) at least a portion of one of the amino acid sequences identified in the Sequence ID Listing, and more specifically an amino acid sequence selected from the group consisting of SEQ ID NO:90, SEQ ID NO:94, SEQ ID NO:101 and SEQ ID NO:105, SEQ ID NO:112, SEQ ID NO:115, SEQ ID NO:119 and SEQ ID NO:127.

It is to be appreciated that ectoparasite saliva proteins of the present invention include, but are not limited to, full-length proteins, hybrid proteins, fusion proteins, multivalent proteins, and proteins that are truncated homologues of, or are proteolytic products of, at least a portion of a protein having at least a portion of one of the following amino acid sequences: SEQ ID NO:90, SEQ ID NO:94, SEQ ID NO:101 and SEQ ID NO:105, SEQ ID NO:112, SEQ ID NO:115, SEQ ID NO:119 and SEQ ID NO:127. As used herein, the term hybrid protein refers to a single protein produced from two different proteins.

The foregoing SEQ ID NO's represent amino acid sequences deduced according to methods disclosed in the Examples. It should be noted that since amino acid sequencing technology is not entirely error-free, the foregoing SEQ ID NO's, at best, represent an apparent amino acid sequence of the ectoparasite saliva proteins of the present invention. In addition, the variation seen in the foregoing SEQ ID NO's can also be due, at least in part, to allelic variation since the proteins being sequenced were derived from populations of fleas.

According to the present invention, a formulation of the present invention can include flea saliva proteins that have undergone post-translational modification. Such modification can include, for example, glycosylation. Glycosylation can include addition of N-linked and/or O-linked oligosaccharides. It is to be appreciated that post-translational modification of a protein of the present invention can contribute to an epitope's ability to induce an allergic response against the protein in an immediate or delayed hypersensitivity response.

Another embodiment of the present invention is an isolated nucleic acid molecule capable of hybridizing, under stringent conditions, with an ectoparasite saliva protein gene encoding an ectoparasite saliva protein of the present invention. In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

An isolated nucleic acid molecule of the present invention can be obtained from its natural source either as an entire (i.e., complete) gene or a portion thereof capable of forming a stable hybrid with that gene. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid with the corresponding gene under stringent hybridization conditions. An isolated nucleic acid molecule of the present invention can also be produced using recombinant DNA technology (e.g., polymerase chain reaction (PCR) amplification, cloning) or chemical synthesis. Isolated ectoparasite saliva protein nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode an ectoparasite saliva protein of the present invention or to form stable hybrids under stringent conditions with natural nucleic acid molecule isolates.

An isolated nucleic acid molecule of the present invention can include a nucleic acid sequence that encodes at least one ectoparasite saliva protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding an ectoparasite saliva protein. As heretofore disclosed, ectoparasite saliva proteins of the present invention include, but are not limited to, proteins having full-length ectoparasite saliva protein coding regions, portions thereof, and other ectoparasite saliva protein homologues.

It is to be appreciated that an ectoparasite saliva protein of the present invention can be encoded by a full-length nucleic acid sequence which encodes a polyprotein. The polyprotein can be post-translationally processed into multiple proteins which are found in saliva. As used herein, an ectoparasite saliva protein gene includes all nucleic acid sequences related to a natural ectoparasite saliva protein gene such as regulatory regions that control production of an ectoparasite saliva protein encoded by that gene (such as, but not limited to, transcription, translation or post-translation control regions) as well as the coding region itself. A nucleic acid molecule of the present invention can be an isolated natural ectoparasite saliva protein nucleic acid molecule or a homologue thereof. A nucleic acid molecule of the present invention can include one or more regulatory regions, full-length or partial coding regions, or combinations thereof. The minimal size of an ectoparasite saliva protein nucleic acid molecule of the present invention is the minimal size capable of forming a stable hybrid under stringent hybridization conditions with a corresponding natural gene.

An ectoparasite saliva protein nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by'screening for the function of the protein encoded by the nucleic acid (e.g., the ability of a homologue to elicit an allergic response in animals having allergic dermatitis or the ability of a homologue to act as an anti-coagulant) and/or by hybridization with isolated ectoparasite saliva protein nucleic acids under stringent conditions.

One embodiment of the present invention is an ectoparasite saliva protein nucleic acid molecule that encodes a protein having at least a portion of one or more of the following amino acid sequences: SEQ ID NO:90, SEQ ID NO:94, SEQ ID NO:101 and SEQ ID NO:105, SEQ ID NO:112, SEQ ID NO:115, SEQ ID NO:119 and SEQ ID NO:127.

A preferred nucleic acid molecule of the present invention is capable of hybridizing under stringent conditions to the coding strand and/or to the strand complementary to the coding strand of a nucleic acid molecule that encodes at least a portion of such a flea saliva protein or homologue thereof. A particularly preferred nucleic acid sequence is a nucleic acid sequence having at least about 65 percent, preferably at least about 75 percent, more preferably at least about 85 percent, and even more preferably at least about 95 percent homology with a nucleic acid sequence encoding at least a portion of one or more of the following amino acid sequences: SEQ ID NO:90, SEQ ID NO:94, SEQ ID NO:101 and SEQ ID NO:105, SEQ ID NO:112, SEQ ID NO:115, SEQ ID NO:119 and SEQ ID NO:127.

Such nucleic acid molecules can be a full-length gene and/or a nucleic acid molecule encoding a full-length protein, a hybrid protein, a fusion protein, a multivalent protein or a truncation fragment. More preferred nucleic acid molecules of the present invention comprise isolated nucleic acid molecules having a nucleic acid sequence as represented by SEQ ID NO:89, SEQ ID NO:91, SEQ ID NO:92, SEQ ID NO:93, SEQ ID NO:95, SEQ ID NO:96, SEQ ID NO:97, SEQ ID NO:100, SEQ ID NO:102, SEQ ID NO:103, SEQ ID NO:104, SEQ ID NO:106, SEQ ID NO:107, SEQ ID NO:111, SEQ ID NO:113, SEQ ID NO:114, SEQ ID NO:116, SEQ ID NO:117, SEQ ID NO:118, SEQ ID NO:120, SEQ ID NO:121, SEQ ID NO:126, SEQ ID NO:128, SEQ ID NO:129 and SEQ ID NO:130, or other sequences disclosed herein.

SEQ ID NO:114, a nucleic acid sequence that includes about 1297 nucleotides of the apparent gene encoding a flea saliva protein fspM(N) (denoted nfspM(N)$_{1297}$), encodes a protein of about 264 amino acids (denoted as PfspM(N)$_{264}$), represented by SEQ ID NO:115. SEQ ID NO:126, a nucleic acid sequence that includes about 500 nucleotides of the apparent gene encoding flea saliva protein fspL3 (denoted nfspL3$_{500}$), encodes a protein of about 61 amino acids (denoted PfspL3$_{61}$), which is denoted SEQ ID NO:127. SEQ ID NO:100, a nucleic acid sequence that includes about 606 nucleotides of the apparent gene encoding a flea saliva protein fspJ1 (denoted nfspJ1$_{606}$), encodes a protein of about 113 amino acids (denoted PfspJ1$_{113}$), which is denoted SEQ ID NO:101. SEQ ID NO:89, a nucleic acid sequence that includes about 1300 nucleotides of the apparent gene encoding a fspN6 flea saliva protein (denoted nfspN6$_{1300}$), encodes a protein of about 375 amino acids (denoted PfspN6$_{375}$), which is denoted SEQ ID NO:90.

Knowing a nucleic acid molecule of an ectoparasite saliva protein of the present invention allows one skilled in the art to make copies of that nucleic acid molecule as well as to obtain a nucleic acid molecule including additional portions of ectoparasite saliva protein-encoding genes (e.g., nucleic acid molecules that include the translation start site and/or transcription and/or translation control regions), and/or ectoparasite saliva protein nucleic acid molecule homologues. Knowing a portion of an amino acid sequence of an ectoparasite saliva protein of the present invention allows one skilled in the art to clone nucleic acid sequences encoding such an ectoparasite saliva protein. In addition, a desired ectoparasite saliva protein nucleic acid molecule can be obtained in a variety of ways including screening appropriate expression libraries with antibodies which bind to ectoparasite saliva proteins of the present invention; traditional cloning techniques using oligonucleotide probes of the present invention to screen appropriate libraries or DNA; and PCR amplification of appropriate libraries, or RNA or DNA using oligonucleotide primers of the present invention (genomic and/or cDNA libraries can be used). To isolate flea saliva protein nucleic acid molecules, preferred cDNA libraries include cDNA libraries made from unfed whole flea, fed whole flea, fed flea midgut, unfed flea midgut, and flea salivary gland. Techniques to clone and amplify genes are disclosed, for example, in Sambrook et al., ibid. The Examples section includes examples of the isolation of cDNA sequences encoding flea saliva proteins of the present invention.

The present invention also includes nucleic acid molecules that are oligonucleotides capable of hybridizing, under stringent conditions, with complementary regions of other, preferably longer, nucleic acid molecules of the present invention that encode at least a portion of one or more of the following amino acid sequences: SEQ ID NO:90, SEQ ID NO:94, SEQ ID NO:101 and SEQ ID NO:105, SEQ ID NO:112, SEQ ID NO:115, SEQ ID NO:119 and SEQ ID NO:127, or homologues thereof, such oligonucleotides can hybridize to the coding or non-coding strand of a double-stranded nucleic acid molecule. Certain preferred oligonucleotides are capable of hybridizing to nucleic acid molecules including nucleic acid sequences represented by SEQ ID NO:89, SEQ ID NO:100, SEQ ID NO:114 and SEQ ID NO:126.

Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit, for example, expression of saliva proteins by ectoparasites. Such therapeutic applications include the use of such oligonucleotides in, for example, antisense-, triplex formation-, ribozyme- and/or RNA drug-based technologies. The present invention, therefore, includes such oligonucleotides and methods to interfere with the production of ectoparasite saliva proteins by use of one or more of such technologies.

The present invention also includes a recombinant vector, which includes an ectoparasite saliva protein nucleic acid molecule of the present invention inserted into any vector capable of delivering the nucleic acid molecule into a host cell. Such a vector contains heterologous nucleic acid sequences, that is nucleic acid sequences that are not naturally found adjacent to ectoparasite saliva protein nucleic acid molecules of the present invention. The vector can be either RNA or DNA, either prokaryotic or eukaryotic, and typically is a virus or a plasmid. Recombinant vectors can be used in the cloning, sequencing, and/or otherwise manipulating of ectoparasite saliva protein nucleic acid molecules of the present invention. One type of recombinant vector, herein referred to as a recombinant molecule and described in more detail below, can be used in the expression of nucleic acid molecules of the present invention. Preferred recombinant vectors are capable of replicating in the transformed cell.

A preferred nucleic acid molecule to include in a recombinant vector of the present invention is a nucleic acid molecule that encodes at least a portion of one or more of the following amino acid sequences: SEQ ID NO:90, SEQ ID NO:94, SEQ ID NO:101 and SEQ ID NO:105, SEQ ID NO:112, SEQ ID NO:115, SEQ ID NO:119 and SEQ ID NO:127, or other sequences disclosed herein, or homologues thereof, and nucleic acid molecules including at least a portion of a nucleic acid sequence represented by SEQ ID NO:89, SEQ ID NO:100, SEQ ID NO:114 and SEQ ID NO:126, or other sequences disclosed herein, or complements thereof. A more preferred sequences to include in a recombinant vector include nfspI$_{1007}$, nfspI$_{477}$, nfspN6$_{1300}$ nfspN6$_{1125}$, nfspN6$_{1068}$, nfspN6$_{1071}$, nfspM (N)$_{1297}$, nfspM (N)$_{792}$, nfspM (N)$_{726}$, nfspM(N)$_{878}$, nfspL3$_{500}$, nfspL3$_{183}$, nfspJ1$_{606}$ nfspJ1$_{339}$ and nfsJ1$_{264}$.

A Preferred nucleic acid molecule of the present invention includes, pCro-nfspN6$_{1071}$, the production of which is described in detail in the Examples section.

In one embodiment, an isolated ectoparasite saliva protein of the present invention is produced by culturing a cell capable of expressing the protein under conditions effective to produce the protein, and recovering the protein. A preferred cell to culture is a recombinant cell that is capable of expressing the ectoparasite saliva protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a host cell include one or more nucleic acid molecules that are as disclosed herein for including in recombinant vectors of the present invention.

Suitable host cells to transform include any cell that can be transformed and that can express the introduced ectoparasite saliva protein. Such cells are, therefore, capable of producing ectoparasite saliva proteins of the present invention after being transformed with at least one nucleic acid molecule of the present invention. Host cells can be either untransformed cells or cells that are already transformed with at least one nucleic acid molecule. Suitable host cells of the present invention can include bacterial, fungal (including yeast), insect, animal and plant cells. Preferred host cells include bacterial, yeast, insect and mammalian cells, with bacterial (e.g., *E. coli*) and insect (e.g., Spodoptera) cells being particularly preferred.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, insect, animal, and/or plant cells. As such, nucleic acid molecules of the present invention can be operatively linked to expression vectors containing regulatory sequences such as promoters, operators, repressors, enhancers, termination sequences, origins of replication, and other regulatory sequences that are compatible with the recombinant cell and that control the expression of nucleic acid molecules of the present invention. As used herein, a transcription control sequence includes a sequence which is capable of controlling the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to thhe art. Preferred transcription control sequences include those which function in bacterial, yeast, helminth, insect and mammalian cells, such as, but not limited to, tac, lac, trp, trc, oxy-pro, omp/lpp, rrnB, bacteriophage lambda ($\lambda$) (such as $\lambda p_L$ and $\lambda p_R$ and fusions that include such promoters), bacteriophage T7, T7lac, bacteriophage T3, bacteriophage SP6, bacteriophage SP01, metallothionein, alpha mating factor, Pichia alcohol oxidase, alphavirus subgenomic promoters (such as Sindbis virus subgenomic promoters), baculovirus, *Heliothis zea* insect virus, vaccinia virus, herpesvirus, poxvirus, adenovirus, simian virus 40, retrovirus actin, retroviral long terminal repeat, *Rous sarcoma* virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a DNA sequence encoding an ectoparasite saliva protein.

Expression vectors of the present invention may also contain secretory signals (i.e., signal segment nucleic acid sequences) to enable an expressed ectoparasite saliva protein to be secreted from the cell that produces the protein. Suitable signal segments include an ectoparasite saliva protein signal segment or any heterologous signal segment capable of directing the secretion of an ectoparasite saliva protein, including fusion proteins, of the present invention. Preferred signal segments include, but are not limited to, tissue plasminogen activator (t-PA), interferon, interleukin, growth hormone, histocompatibility and viral envelope glycoprotein signal segments.

Expression vectors of the present invention may also contain fusion sequences which lead to the expression of inserted nucleic acid molecules of the present invention as fusion proteins. Inclusion of a fusion sequence as part of an ectoparasite nucleic acid molecule of the present invention can enhance the stability during production, storage and/or use of the protein encoded by the nucleic acid molecule. Furthermore, a fusion segment can function as a tool to simplify purification of an ectoparasite saliva protein, such as to enable purification of the resultant fusion protein using affinity chromatography. A suitable fusion segment can be a domain of any size that has the desired function (e.g., increased stability and/or purification tool). It is within the scope of the present invention to use one or more fusion segments. Fusion segments can be joined to amino and/or carboxyl termini of an ectoparasite saliva protein. Linkages between fusion segments and ectoparasite saliva proteins can be constructed to be susceptible to cleavage to enable straight-forward recovery of the ectoparasite saliva proteins. Fusion proteins are preferably produced by culturing a recombinant cell transformed with a fusion nucleic acid sequence that encodes a protein including the fusion segment attached to either the carboxyl and/or amino terminal end of an ectoparasite saliva protein.

A recombinant molecule of the present invention is a molecule that can include at least one of any nucleic acid molecule heretofore described operatively linked to at least one of any transcription control sequence capable of regulating expression of the nucleic acid molecule(s) in the cell to be transformed. A preferred recombinant molecule includes one or more nucleic acid molecules that are as disclosed herein for including in a recombinant vector of the present invention.

A recombinant cell of the present invention includes any cells transformed with at least one of any nucleic acid molecules of the present invention. A preferred recombinant cell is a cell transformed with at least one nucleic acid molecule that encode a protein having at least a portion of one or more of the following amino acid sequences: SEQ ID NO:90, SEQ ID NO:94, SEQ ID NO:101 and SEQ ID NO:105, SEQ ID NO:112, SEQ ID NO:115, SEQ ID NO:119 and SEQ ID NO:127, or other sequences disclosed herein, or homologues thereof, and nucleic acid molecules including at least a portion of a nucleic acid sequence represented by SEQ ID NO:89, SEQ ID NO:100, SEQ ID NO:114 and SEQ ID NO:126, or other sequences disclosed herein, or complements thereof. Particularly preferred recombinant cells include *E. coli* transformed with at least one of the aforementioned nucleic acid molecules. Preferred recombinant cells of the present invention include *E. coli*:pCro-nfspN6$_{1071}$.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant protein production during fermentation. The activity of an expressed recombinant protein of the present invention may be improved by fragmenting, modifying, or derivatizing the resultant protein.

In accordance with the present invention, recombinant cells can be used to produce an ectoparasite saliva protein of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing an ectoparasite saliva protein. Such a medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium.

Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant ectoparasite saliva proteins may either remain within the recombinant cell; be secreted into the fermentation medium; be secreted into a space between two cellular membranes, such as the periplasmic space in *E. coli*; or be retained on the outer surface of a cell or viral membrane. The phrase "recovering the protein" refers simply to collecting the whole fermentation medium containing the protein and need not imply additional steps of separation or purification. Ectoparasite saliva proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, chromatofocusing and differential solubilization.

Ectoparasite saliva proteins are preferably retrieved in "substantially pure" form. As used herein, "substantially pure" refers to a purity that allows for the effective use of the protein as a therapeutic composition or diagnostic. For example, an animal being administered dosages of ectoparasite saliva protein isolated from a recombinant cell of the present invention should exhibit no substantial toxicity from contaminants mixed with the protein.

Ectoparasite saliva that is substantially free of contaminating material can be collected using a saliva collection apparatus of the present invention (disclosed in related PCT Patent Publication No. WO 96/11,271, published Apr. 18, 1996, by Frank et al.; this publication is incorporated by reference herein in its entirety). The interior diameter of a preferred chamber of the present invention is preferably about 7.5 cm. The size of a collection means of the present invention is preferably larger than the open end of the 7.5 cm chamber, the size of the collection means is more preferably about 8 cm.

According to the present invention, ectoparasite saliva products can be extracted from a collection means (described in related PCT Patent Publication No. WO 96/11, 271) by contacting a collection means with a Tris buffer containing sodium chloride, alcohol and Tris. A suitable extraction buffer includes 2.5 M NaCl, 5% IPA and 20 mM Tris, about pH 8.0 to about pH 8.3. Suitable extraction times for eluting proteins and other products from the collection means using the Tris buffer are described in detail in the Examples.

Further concentration of saliva proteins extracted from a collection means of the present invention can be performed by concentrating the extracted flea saliva product-containing solution using hydrophobic interaction chromatographic (HIC) resins. Suitable HIC resins include any resins that bind protein at high salt concentrations. Preferred HIC resins include, for example, butyl-, octyl- and phenyl-substrate conjugated resins. A more preferred resin includes a phenyl-sepharose resin. In a preferred embodiment, extracted flea saliva proteins contained in a Tris buffer of the present invention can be contacted with a HIC resin to bind the flea saliva proteins to the resin.

In accordance with the present invention, a "mimetope" refers to any compound that is able to mimic the ability of an isolated ectoparasite saliva protein of the present invention to carry out its function (e.g., anti-coagulation, anti-complement, vasodialators, proteases, acid phosphatases or detecting and/or treating the hypersensitivity of an animal susceptible to or having allergic dermatitis). A mimetope can be a peptide that has been modified to decrease its susceptibility to degradation but that still retains the desired activity. Other examples of mimetopes include, but are not limited to, carbohydrate-based compounds, lipid-based compounds, nucleic acid-based compounds, natural organic compounds, synthetically derived organic compounds, anti-idiotypic antibodies and/or catalytic antibodies, or fragments thereof. Mimetopes of the present invention can also include non-proteinaceous portions of ectoparasite saliva products having allergenic and/or antigenic activity (e.g., carbohydrate moieties associated with ectoparasite saliva proteins). A mimetope can be obtained by, for example, screening libraries of synthetic compounds for compounds capable of altering the ability of ectoparasites to feed, or of detecting and/or treating allergic dermatitis resulting from the bites of ectoparasites. A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modeling. The predicted mimetope structures can then be produced by, for example, chemical synthesis, recombinant DNA technology, or by isolating a mimetope from a natural source (e.g., plants, animals, bacteria and fungi).

One embodiment of the present invention is an in vivo test that is capable of detecting whether an animal is hypersensitive to ectoparasite saliva products. An in vivo test of the present invention can initially be used to determine if an animal is hypersensitive to ectoparasite saliva products and then used to determine if an animal is hypersensitive to a particular ectoparasite saliva component, in particular to an ectoparasite saliva protein. An in vivo hypersensitivity test of the present invention is particularly useful for identifying animals susceptible to or having allergic dermatitis. An in vivo hypersensitivity test of the present invention is even more useful for identifying animals susceptible to or having FAD. A suitable in vivo hypersensitivity test of the present invention can be, but is not limited to, a skin test comprising administering (e.g., intradermally injecting or superficial scratching) an effective amount of a formulation containing at least one ectoparasite saliva product, or a mimetope thereof. Methods to conduct skin tests of the present invention are known to those of skill in the art and are briefly disclosed herein.

Suitable formulations to use in an in vivo skin test include one or more isolated ectoparasite saliva proteins of the present invention.

A suitable amount of ectoparasite saliva protein for use in a skin test of the present invention can vary widely depending on the allergenicity of the product used in the test and on the site at which the product is delivered. Suitable amounts of ectoparasite saliva proteins for use in a skin test of the present invention include an amount capable of forming reaction, such as a detectable wheal or induration (hardness) resulting from an allergic reaction to the product. Preferred amounts of ectoparasite saliva proteins for use in a skin test of the present invention range from about 1 nanogram (ng) to about 500 micrograms ($\mu$g), more preferably from about 5 ng to about 300 $\mu$g, and even more preferably from about 10 ng to about 50 $\mu$g of ectoparasite saliva proteins. It is to be appreciated by those of skill in the art that such amounts will vary depending upon the allergenicity of the protein(s) being administered.

According to the present invention, ectoparasite saliva proteins of the present invention can be combined with an immunopotentiator (e.g., carriers or adjuvants of the present invention as defined in detail below). A novel aspect, however, of the present invention is that an ectoparasite saliva protein of the present invention can induce a hypersensitive response in the absence of an immunopotentiator.

A skin test of the present invention further comprises administering a control solution to an animal. A control solution can include a negative control solution and/or a positive control solution. A positive control solution of the present invention contains an effective amount of at least one compound known to induce a hypersensitive response when administered to an animal. A preferred compound for use as positive control solution includes, but is not limited to, histamine. A negative control solution of the present invention can comprise a solution that is known not to induce a hypersensitive response when administered to an animal. As such, a negative control solution can comprise a solution having compounds essentially incapable of inducing a hypersensitive response or simply a buffer used to prepare the formulation, such as saline. An example of a preferred negative control solution is phenolated phosphate buffered saline (available from Greer Laboratories, Inc., Lenoir, N.C.).

Hypersensitivity of an animal to one or more formulations of the present invention can be evaluated by measuring reactions (e.g., wheal size, induration or hardness; using techniques known to those skilled in the art) resulting from administration of one or more experimental sample(s) and control sample(s) into an animal and comparing the reactions to the experimental sample(s) with reactions resulting from administration of one or more control solution. Preferred devices for intradermal injections include individual syringes. Preferred devices for scratching include devices that permit the administration of a number of samples at one time. The hypersensitivity of an animal can be evaluated by determining if the reaction resulting from administration of a formulation of the present invention is larger than the reaction resulting from administration of a negative control, and/or by determining if the reaction resulting from administration of the formulation is at least about the same size as the reaction resulting from administration of a positive control solution. As such, if an experimental sample produces a reaction greater than or equal to the size of a wheal produced by administration of a positive control sample to an animal, then that animal is hypersensitive to the experimental sample. Conversely, if an experimental sample produces a reaction similar to the reaction produced by administration of a negative control sample to an animal, then that animal is not hypersensitive to the experimental sample.

Preferred wheal sizes for evaluation of the hypersensitivity of an animal range from about 16 mm to about 8 mm, more preferably from about 15 mm to about 9 mm, and even more preferably from about 14 mm to about 10 mm in diameter.

Preferably, the ability or inability of an animal to exhibit an immediate hypersensitive response to a formulation of the present invention is determined by measuring wheal sizes from about 2 minutes to about 30 minutes after administration of a sample, more preferably from about 10 minutes to about 25 minutes after administration of a sample, and even more preferably about 15 minutes after administration of a sample.

Preferably, the ability or inability of an animal to exhibit a delayed hypersensitive response to a formulation of the present invention is determined by measuring induration and/or erythema from about 18 hours to about 30 hours after administration of a sample, more preferably from about 20 hours to about 28 hours after administration of a sample, and even more preferably at about 24 hours after administration of a sample. A delayed hypersensitivity response can also be measured using other techniques such as by determining, using techniques known to those of skill in the art, the extent of cell infiltrate at the site of administration during the time periods defined directly above.

In a preferred embodiment, a skin test of the present invention comprises intradermally injecting into an animal at a given site an effective amount of a formulation that includes at least one flea saliva protein of the present invention, and intradermally injecting an effective amount of a control solution into the same animal at a different site. It is within the scope of one of skill in the art to use devices capable of delivering multiple samples simultaneously at a number of sites, preferably enabling concurrent evaluation of numerous formulations. One preferred formulation comprises flea saliva products collected in accordance with the present invention. Also preferred are formulations comprising one or more recombinantly produced flea saliva proteins.

Suitable flea saliva proteins for use with a skin test of the present invention include proteins having an amino acid sequence such as is listed in the Sequence Listing herein, or homologues thereof. A preferred positive control sample can be a sample comprising histamine. A preferred negative control sample can be a sample comprising diluent.

Animals suitable and preferred to test for hypersensitivity to ectoparasite saliva proteins using a skin test of the present invention are disclosed herein. Particularly preferred animals to test with a skin test of the present invention include dogs, cats and horses, with dogs and cats being even more preferred.

Another embodiment of the present invention is an in vitro immunoabsorbent test that is capable of detecting the presence of an antibody capable of binding to one or more ectoparasite saliva proteins of the present invention by contacting a putative antibody-containing solution with a solution containing ectoparasite saliva proteins in such a manner that immunocomplexes can form and be detected. Thus, an in vitro immunoabsorbent test of the present invention is particularly useful for identifying animals susceptible to or having allergic dermatitis by demonstrating that an animal has been previously exposed to an ectoparasite saliva antigen and, therefore may be hypersensitive to further exposure to an ectoparasite saliva antigen.

According to the present invention, an in vitro hypersensitivity test of the present invention can be, but is not limited to, an immunoabsorbent test comprising: (a) contacting a formulation of the present invention with a body fluid from an animal under conditions sufficient for formation of an immunocomplex between the formulation and antibodies, if present, in the body fluid; and (b) determining the amount of immunocomplex formed, wherein formation of the immunocomplex indicates that the animal is susceptible to or has allergic dermatitis. The immunoabsorbent test is particularly useful for the detection of IgE antibodies in the body fluid, thereby indicating immediate hypersensitivity in the animal. Determining the amount of immunocomplex formed can include the step of separating depending on the mode of detection. Immunoabsorbent assays can be a variety of protocols and can be set-up by those of skill in the art.

A preferred immunoabsorbent test of the present invention comprises a first step of coating one or more portions of a solid substrate with a suitable amount of one or more ectoparasite saliva proteins of the present invention or a mimetope thereof, and of coating one or more other portions of the (or another) solid substrate with a suitable amount of positive and/or negative control solutions of the present invention. A preferred solid substrate of the present invention can include, but is not limited to, an ELISA plate, a dipstick, a radioimmunoassay plate, agarose beads, plastic beads, immunoblot membranes and paper; a more preferred solid substrate includes an ELISA plate, a dipstick or a radioimmunoassay plate, with an ELISA plate and a dipstick being even more preferred. As used herein, a dipstick refers to any solid material having a surface to which antibodies can be bound, such solid material having a stick-like shape capable if being inserted into a test tube. Suitable and preferred flea saliva proteins for use with an in vitro hypersensitivity test of the present invention are as disclosed for a skin test of the present invention.

A second step of a preferred in vitro hypersensitivity test of the present invention comprises contacting the coated substrate with a body fluid, such as serum, plasma or whole blood, from an animal susceptible to allergic dermatitis in such a manner as to allow antibodies contained in the body fluid that are capable of binding to ectoparasite saliva products to bind to such products bound to the substrate to form immunocomplexes. Excess body fluid and antibodies are then washed from the substrate. In a preferred embodiment in which IgE antibodies in the body fluid are to be measured, the body fluid can be pretreated to remove at least some of the other isotypes of immunoglobulin and/or other proteins, such as albumin, present in the fluid. Such removal can include, but is not limited to, contacting the body fluid with a material, such a Protein G, to remove IgG antibodies and/or affinity purifying the IgE antibodies from other components of the body fluid by exposing the fluid to, for example, Concanavalin A (Con-A).

A third step of a preferred in vitro hypersensitivity test of the present invention comprises contacting the immunocomplexes bound to the substrate with a compound capable of binding to the immunocomplexes, such as a secondary antibody or other compound that is capable of binding to the heavy chain of allergy-related antibodies produced by animals allergic to ectoparasites, in such a manner that the compound(s) can bind to the immunocomplexes. Preferred binding compounds include, but are not limited to, secondary antibodies capable of binding to the heavy chain of IgE antibodies and Fc receptors (FcR) that bind to IgE antibodies (i.e., epsilon FcR), including single chains of an FcR (e.g., the alpha chain of an epsilon FcR), as well as truncated forms with or without transmembrane domains. Preferred animals to test are disclosed herein. Compounds capable of binding to immunocomplexes are usually tagged with a label which enables the amount of compound bound to the antibody from the body fluid to be measured. Such labels include, but are not limited to, a radioactive label, an enzyme capable of producing a color reaction upon contact with a substrate, a fluorescent label, a chemiluminescent label, a chromophoric label or a compound capable of being bound by another compound. Preferred labels include, but are not limited to, fluorescein, radioisotopes, alkaline phosphatases, biotin, avidin, or peroxidases.

A fourth step of a preferred in vitro hypersensitivity test of the present invention comprises measuring the amount of detectable label bound to the solid substrate using techniques known to those of skill in the art. It is within the scope of the present invention that the amount of antibody from the body fluid bound to the substrate can be determined using one or more layers of secondary antibodies or other binding compounds. For example, an untagged secondary antibody can be bound to a serum antibody and the untagged secondary antibody can then be bound by a tagged tertiary antibody.

A hypersensitive animal is identified by comparing the level of immunocomplex formation using samples of body fluid with the level of immunocomplex formation using control samples. An immunocomplex refers to a complex comprising an antibody and its ligand (i.e., antigen). As such, immunocomplexes form using positive control samples and do not form using negative control samples. As such, if a body fluid sample results in immunocomplex formation greater than or equal to immunocomplex formation using a positive control sample, then the animal from which the fluid was taken is hypersensitive to the ectoparasite saliva product bound to the substrate. Conversely, if a body fluid sample results in immunocomplex formation similar to immunocomplex formation using a negative control sample, then the animal from which the fluid was taken is not hypersensitive to the ectoparasite saliva product bound to the substrate.

A preferred embodiment of an in vitro hypersensitivity test of the present invention comprises the steps of: (a) contacting an ELISA plate, which is coated with a suitable amount of flea saliva extract (disclosed in related PCT Patent Publication No. WO 96/11,271, published Apr. 18, 1996, by Frank et al.; this publication is incorporated by reference herein in its entirety), including FS-1, FS-2, FS-3 and/or one or more flea saliva proteins (disclosed in related PCT Patent Publication No. WO 96/11,271 and disclosed herein), with serum, plasma or whole blood from an animal being tested for susceptibility to allergic dermatitis; and (b) identifying whether immunocomplexes are formed by step (a) by assaying for the presence of such immunocomplexes by (i) contacting the plate with an antibody that specifically binds to IgE or other compounds capable of binding to such immunocomplexes, such as an epsilon Fc receptor, and (ii) determining whether such an antibody or other compound is bound thereto. It should be noted that citing of specific embodiments does not preclude the use of a variety of other immunoassay protocols, including those in which a compound that binds IgE is coated onto a substrate; the substrate is then contacted with serum, plasma or whole blood; and binding of IgE by the compound is detected by the ability to bind flea saliva extracts or proteins of the present invention.

One embodiment of the present invention is a kit useful for identification of an animal susceptible to or having allergic dermatitis. As used herein, a suspect animal is an animal to be tested. A kit of the present invention comprises a formulation of the present invention and a means for determining if an animal is susceptible to or has allergic dermatitis, in which the formulation is used to identify animals susceptible to or having allergic dermatitis. A means for determining if an animal is susceptible to or has allergic dermatitis can include an in vivo or in vitro hypersensitivity test of the present invention as described in detail above. A kit of the present invention further comprises at least one control solution such as those disclosed herein.

A preferred kit of the present invention comprises the elements useful for performing an immunoassay. A kit of the present invention can comprise one or more experimental samples (i.e., formulations of the present invention) and one or more control samples bound to at least one pre-packed dipstick or ELISA plate, and the necessary means for detecting immunocomplex formation (e.g., labeled secondary antibodies or other binding compounds and any necessary solutions needed to resolve such labels, as described in detail above) between antibodies contained in the bodily fluid of the animal being tested and the proteins bound to the dipstick or ELISA plate. It is within the scope of the invention that the kit can comprise simply a formulation of the present invention and that the detecting means can be provided in another way.

An alternative preferred kit of the present invention comprises elements useful for performing a skin test. A kit of the present invention can comprise at least one pre-packed syringe and needle apparatus containing one or more experimental samples and/or one or more control samples.

It is within the scope of the present invention that two or more different in vivo and/or in vitro tests can be used in combination for diagnostic purposes. For example, the immediate hypersensitivity of an animal to an ectoparasite saliva allergen can be tested using an in vitro immunoabsorbent test capable of detecting IgE antibodies specific for an ectoparasite saliva allergen in the animal's bodily fluid. While most animals that display delayed hypersensitivity to an ectoparasite saliva allergen also display immediate hypersensitivity to the allergen, a small number of animals that display delayed hypersensitivity to an allergen do not display immediate hypersensitivity to the allergen. In such cases, following negative results from the IgE-specific in vitro test, the delayed hypersensitivity of the animal to an ectoparasite saliva allergen can be tested using an in vivo test of the present invention.

Another aspect of the present invention includes treating animals susceptible to or having allergic dermatitis, with a formulation of the present invention. According to the present invention, the term treatment can refer to the regulation of a hypersensitive response by an animal to bites from ectoparasites. Regulation can include, for example, immunomodulation of cells involved in the animal's hypersensitive response or alteration of the ability of an ectoparasite to introduce allergens into an animal, for example by inhibiting the anti-coagulation activity of a saliva enzyme, thereby impairing the ability of the arthropod to penetrate the dermis of an animal and feed. Immunomodulation can include modulating the activity of molecules typically involved in an immune response (e.g., antibodies, antigens, major histocompatibility molecules (MHC) and molecules co-reactive with MHC molecules). In particular, immunomodulation refers to modulation of antigen:antibody interactions resulting in inflammatory responses, immunosuppression, and immunotolerization of cells involved in a hypersensitive response. Immunosuppression refers to inhibiting an immune response by, for example, killing particular cells involved in the immune response. Immunotolerization refers to inhibiting an immune response by anergizing (i.e., diminishing reactivity of a T cell to an antigen) particular cells involved in the immune response. Suitable and preferred ectoparasites against which to treat an animal are disclosed herein. A particularly preferred formulation of the present invention is used to treat FAD.

One embodiment of the present invention is a therapeutic composition that, when administered to an animal in an effective manner, is useful for immunomodulating the immune response of the animal (i.e., immunomodulating the animal) so as to block (i.e., to inhibit, reduce or substantially prevent) a hypersensitive response by the animal upon subsequent exposure to allergenic components transmitted through bites from ectoparasites. Such a therapeutic composition is useful for immunomodulating animals known to be hypersensitive to ectoparasite saliva products and animals susceptible to hypersensitive responses against ectoparasite saliva products.

One embodiment of the present invention is a therapeutic composition that includes de-sensitizing compounds capable of inhibiting an immune response to an ectoparasite saliva protein of the present invention. Such de-sensitizing compounds include blocking compounds, toleragens and/or suppressor compounds. Blocking compounds comprise compounds capable of modulating antigen:antibody interactions that can result in inflammatory responses, toleragens are compounds capable of immunotolerizing an animal, and suppressor compounds are capable of immunosuppressing an animal. A de-sensitizing compound of the present invention can be soluble or membrane-bound. Membrane-bound de-sensitizing compounds can be associated with biomembranes, including cells, liposomes, planar membranes, cochleates or micelles. A soluble de-sensitizing compound of the present invention is useful for: (1) inhibiting a Type I hypersensitivity reaction by blocking IgE:antigen mediated de-granulation of mast cells; (2) inhibiting a Type III hypersensitivity reaction by blocking IgG:antigen complex formation leading to complement destruction of cells; and (3) inhibiting a Type IV hypersensitivity reaction by blocking T helper cell stimulation of cytokine secretion by macrophages. A membrane-bound de-sensitizing compound of the present invention is useful for: (1) inhibiting a Type II hypersensitivity reaction by blocking IgG:antigen complex formation on the surface of cells leading to complement destruction of cells; (2) inhibiting a Type II hypersensitivity reaction by blocking IgG regulated signal transduction in immune cells; and (3) inhibiting a Type IV hypersensitivity reaction by blocking T cytotoxic cell killing of antigen-bearing cells.

A de-sensitizing compound of the present invention can also be covalently linked to a ligand molecule capable of targeting the de-sensitizing compound to a specific cell involved in a hypersensitive response to ectoparasite saliva products. Appropriate ligands with which to link a de-sensitizing compound include, for example, at least a portion of an immunoglobulin molecule, cytokines, lectins, heterologous allergens, CD8 molecules, CD4 molecules or major histocompatibility molecules (e.g., MHC class I or MHC class II molecules). Preferred portions of immunoglobulin molecules to link to a de-sensitizing compound include variable regions capable of binding to immune cell specific surface molecules and constant regions capable of binding to Fc receptors on immune cells, in particular IgE constant regions. Preferred CD8 molecules include at least the extracellular functional domains of the β chain of CD8. Preferred CD4 molecules include at least the extracellular functional domains of CD4. An immune cell refers to a cell involved in an immune response, in particular, cells having MHC class I or MHC class II molecules. Preferred immune cells include antigen presenting cells, T cells and B cells.

In one embodiment, a therapeutic composition of the present invention includes ectoparasite saliva products of the present invention, or mimetopes thereof. Preferred therapeutic compositions include formulations comprising ectoparasite saliva extracts or at least one ectoparasite saliva product (preferably protein) of the present invention or mimetopes thereof.

In one embodiment, an ectoparasite saliva protein of the present invention is modified in such a manner that the protein does not induce an anaphylactic response in an animal being de-sensitized using the protein. Preferably, an ectoparasite saliva protein of the present invention useful for de-sensitizing an animal is a protein in which T cell epitopes of the protein remain intact while the IgE binding epitopes of the protein are disrupted. A preferred modification includes removing one or more cysteine residues, more preferably all of the cysteines, from an ectoparasite saliva protein of the present invention. Such cysteine can be deleted or replaced with another amino acid residue of choice.

Suitable therapeutic compositions of the present invention for treating flea allergy dermatitis include flea saliva extracts (such as those disclosed in related PCT Patent Publication No. WO 96/11,271) and other formulations including at least one flea saliva protein, or a mimetope thereof. Preferred therapeutic compositions include FS-1, FS-2 and/or FS-3 (such as those disclosed in related PCT Patent Publication No. WO 96/11,271) as well as at least a portion of at least one flea saliva protein that can be isolated from FS-1, FS-2 and/or FS-3. As such, preferred formulations for use as therapeutic compositions include FS-1, FS-2, FS-3, and/or at least a portion of one or more of the proteins having an amino acid sequence including SEQ ID NO:90, SEQ ID NO:94, SEQ ID NO:101 and SEQ ID NO:105, SEQ ID NO:112, SEQ ID NO:115, SEQ ID NO:119 and SEQ ID NO:127.

In another embodiment, a therapeutic composition can include ectoparasite products of the present invention associated with a suitable excipient. A therapeutic composition of the present invention can be formulated in an excipient that the animal to be treated can tolerate. Preferred excipients are capable of maintaining a product of the present invention in a form that is capable of being bound by cells involved in an allergic response in an animal such that the cells are stimulated to initiate or enhance an immune response. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran.

Excipients can also contain minor amounts of additives, such as substances that enhance isotonicity and chemical stability. Examples of buffers include phosphate buffer, bicarbonate buffer and Tris buffer, while examples of preservatives include thimerosal, - or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In another embodiment, a therapeutic composition of the present invention can also comprise a carrier or adjuvant, although it is to be appreciated that an advantage of saliva products of the present invention is that adjuvants and/or carriers are not required for administration. Adjuvants are typically substances that generally enhance the immune response of an animal to a specific antigen. Suitable adjuvants include, but are not limited to, cytokines, chemokines, and compounds that induce the production of cytokines and chemokines (e.g., granulocyte macrophage colony stimulating factor [GM-CSF], macrophage colony stimulating factor [M-CSF], granulocyte colony stimulating factor [G-CSF], colony stimulating factor [CSF], erythropoietin [EPO], interleukin-2 [IL-2], interleukin-3 [IL-3], interleukin-5 [IL-5], interleukin-6 [IL-6], interleukin-7 [IL-7], interleukin-8 [IL-8], interleukin-10 [IL-10], interleukin-12 [IL-12], gamma interferon [IFN-γ], interferon gamma inducing factor [IGIF], transforming growth factor beta, RANTES [regulated upon activation, normal T cell expressed and presumably secreted], macrophage inflammatory proteins [e.g., MIP1α and MIP1β], and Leishmania elongation initiating factor [LeIF]; bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant [Vaxcel™, Inc. Norcross, Ga.], Ribi adjuvants [Ribi ImmunoChem Research, Inc., Hamilton, Mont.]; and saponins and their derivatives (e.g., Quil A [Superfos Biosector A/S, Denmark]. Protein adjuvants of the present invention can be delivered in the form of the protein themselves or of nucleic acid molecules encoding such proteins using the methods described herein.

Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

One embodiment of the present invention is a controlled release formulation that is capable of slowly releasing a therapeutic composition of the present invention into the bloodstream of an animal. Suitable controlled release formulations include, but are not limited to, biocompatible (including biodegradable) polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ.

The present invention also includes a recombinant virus particle therapeutic composition. Such a composition includes a recombinant molecule of the present invention that is packaged in a viral coat and that can be expressed in an animal after administration. Preferably, the recombinant molecule is packaging-deficient. A number of recombinant virus particles can be used, including, but not limited to, those based on alphaviruses, poxviruses, adenoviruses, herpesviruses, and retroviruses. Preferred recombinant particle viruses are those based on alphaviruses (such as Sindbis virus), herpesviruses and poxviruses. Methods to produce and use recombinant virus particle vaccines are disclosed in U.S. patent application Ser. No. 08/015,414, filed Feb. 8, 1993, entitled "Recombinant Virus Particle Vaccines", U.S. Pat. No. 5,266,313, by Esposito et al., issued Nov. 30, 1993 and U.S. patent application Ser. No. 08/602,010, by Haanes et al., filed Jan. 15, 1996, entitled "Recombinant Canine Herpesvirus", each of the patents and patent application referred to in this section is incorporated by reference herein in its entirety.

When administered to an animal, a recombinant virus particle therapeutic composition of the present invention infects cells within the immunized animal and directs the production of a protective protein or RNA nucleic acid molecule that is capable of protecting the animal from allergic dermatitis caused by the bites of ectoparasites. For example, a recombinant virus particle comprising a nucleic acid molecule encoding one or more ectoparasite saliva protein of the present invention is administered according to a protocol that results in the tolerization of an animal against ectoparasite saliva allergens.

According to one embodiment, a nucleic acid molecule of the present invention can be delivered to an animal as a naked (i.e., not packaged in a viral coat or cellular membrane) nucleic acid vaccine (e.g., as naked DNA or RNA molecules, such as is taught, for example in Wolff et al., 1990, *Science* 247, 1465–1468). A naked nucleic acid vaccine of the present invention includes a nucleic acid molecule of the present invention and preferably includes a recombinant molecule of the present invention that preferably is replication, or otherwise amplification, competent. A naked nucleic acid vaccine of the present invention can comprise one or more nucleic acid molecules of the present invention in the form of, for example, a dicistronic recombinant molecule. Preferred naked nucleic acid vaccines include at least a portion of a viral genome (i.e., a viral vector). Preferred viral vectors include those based on alphaviruses, poxviruses, adenoviruses, herpesviruses, and retroviruses, with those based on alphaviruses (such as Sindbis or Semliki virus), species-specific herpesviruses and species-specific poxviruses being particularly preferred. Any suitable transcription control sequence can be used, including those disclosed as suitable for protein production. Particularly preferred transcription control sequence include cytomegalovirus intermediate early (preferably in conjunction with Intron-A), *Rous Sarcoma* Virus long terminal repeat, and tissue-specific transcription control sequences, as well as transcription control sequences endogenous to viral vectors if viral vectors are used. The incorporation of "strong" poly(A) sequences are also preferred.

Naked nucleic acid vaccines of the present invention can be administered in a variety of ways, with intramuscular, subcutaneous, intradermal, transdermal, intranasal and oral routes of administration being preferred. An example of one embodiment is disclosed in PCT Patent Publication No. WO 95/05853, published Mar. 2, 1995. A preferred single dose of a naked nucleic acid vaccine ranges from about 1 nanogram (ng) to about 100 μg, depending on the route of administration and/or method of delivery, as can be determined by those skilled in the art. Suitable delivery methods include, for example, by injection, as drops, aerosolized, oral and/or topical. Naked DNA of the present invention can be contained in an aqueous excipient (e.g., phosphate buffered saline) alone or a carrier (e.g., lipid-based vehicles).

Therapeutic compositions of the present invention can be sterilized by conventional methods which do not result in protein degradation (e.g., filtration) and/or lyophilized.

A therapeutic composition of the present invention can be administered to any animal susceptible to ectoparasite infestation as herein described. Acceptable protocols by which to administer therapeutic compositions of the present invention in an effective manner can vary according to individual dose size, number of doses, frequency of dose administration, and mode of administration. Determination of such protocols can be accomplished by those skilled in the art. An effective dose refers to a dose capable of treating an animal against hypersensitivity to ectoparasite saliva allergens. Effective doses can vary depending upon, for example, the therapeutic composition used, the arthropod from which the composition was derived, and the size and type of the recipient animal. Effective doses to immunomodulate an animal against ectoparasite saliva allergens include doses administered over time that are capable of alleviating a hypersensitive response by an animal to ectoparasite saliva allergens. For example, a first tolerizing dose can comprise an amount of a therapeutic composition of the present invention that causes a minimal hypersensitive response when administered to a hypersensitive animal. A second tolerizing dose can comprise a greater amount of the same therapeutic composition than the first dose. Effective tolerizing doses can comprise increasing concentrations of the therapeutic composition necessary to tolerize an animal such that the animal does not have a hypersensitive response to the bite of an ectoparasite. An effective dose to desensitize an animal can comprise a concentration of a therapeutic composition of the present invention sufficient to block an animal from having a hypersensitive response to the bite of an ectoparasite. Effective desensitizing doses can include repeated doses having concentrations of a therapeutic composition that cause a minimal hypersensitive response when administered to a hypersensitive animal.

A suitable single dose is a dose that is capable of treating an animal against hypersensitivity to ectoparasite saliva allergens when administered one or more times over a suitable time period. For example, a preferred single dose of an ectoparasite saliva product, or mimetope therapeutic composition is from about 0.5 ng to about 1 g of the therapeutic composition per kilogram body weight of the animal. Further treatments with the therapeutic composition can be administered from about 1 hour to 1 year after the original administration. Further treatments with the therapeutic composition preferably are administered when the animal is no longer protected from hypersensitive responses to ectoparasite. Particular administration doses and schedules can be developed by one of skill in the art based upon the parameters discussed above. Modes of administration can include, but are not limited to, subcutaneous, intradermal, intravenous, nasal, oral, transdermal and intramuscular routes.

A therapeutic composition of the present invention can be used in conjunction with other compounds capable of modifying an animal's hypersensitivity to ectoparasite bites. For example, an animal can be treated with compounds capable of modifying the function of a cell involved in a hypersensitive response, compounds that reduce allergic reactions, such as by systemic agents or anti-inflammatory agents (e.g., anti-histamines, anti-steroid reagents, anti-inflammatory reagents and reagents that drive immunoglobulin heavy chain class switching from IgE to IgG). Suitable compounds useful for modifying the function of a cell involved in a hypersensitive response include, but are not limited to, antihistamines, cromolyn sodium, theophylline, cyclosporin A, adrenalin, cortisone, compounds capable of regulating cellular signal transduction, compounds capable of regulating adenosine 3',5'-cyclic phosphate (cAMP) activity, and compounds that block IgE activity, such as peptides from IgE or IgE specific Fc receptors, antibodies specific for peptides from IgE or IgE-specific Fc receptors, or antibodies capable of blocking binding of IgE to Fc receptors.

Another aspect of the present invention includes a method for prescribing treatment for animals susceptible to or having allergic dermatitis, using a formulation of the present invention. A preferred method for prescribing treatment for flea allergy dermatitis, for example, comprises: (1) intradermally injecting into an animal at one site an effective amount of a formulation containing at least one flea saliva antigen of the present invention, or a mimetope thereof (suitable and preferred formulations are,disclosed herein); (2) intradermally injecting into the animal at a second site an effective amount of a control solution; (3) evaluating if the animal has flea allergy dermatitis by measuring and comparing the wheal size resulting from injection of the formulation with the wheal size resulting from injection of the control solution; and (4) prescribing a treatment for the flea allergy dermatitis.

An alternative preferred method for prescribing treatment for flea allergy dermatitis comprises: (1) contacting a first portion of a sample of bodily fluid obtained from an animal to be tested with an effective amount of a formulation containing at least one flea saliva antigen, or a mimetope thereof (suitable and preferred formulations are disclosed herein) to form a first immunocomplex solution; (2) contacting a positive control antibody to form a second immunocomplex solution; (3) evaluating if the animal has flea allergy dermatitis by measuring and comparing the amount of immunocomplex formation in the first and second immunocomplex solutions; and (4) prescribing a treatment for the flea allergy dermatitis. It is to be noted that similar methods can be used to prescribe treatment for allergies caused by other ectoparasites using ectoparasite saliva product formulations as disclosed herein.

Another aspect of the present invention includes a method for monitoring animals susceptible to or having allergic dermatitis, using a formulation of the present invention. In vivo and in vitro tests of the present invention can be used to test animals for allergic dermatitis prior to and following any treatment for allergic dermatitis. A preferred method to monitor treatment of flea allergy dermatitis (which can also be adapted to monitor treatment of other ectoparasite allergies) comprises: (1) intradermally injecting an animal at one site with an effective amount of a formulation containing at least one flea saliva protein, or a mimetope thereof (suitable and preferred formulations are disclosed herein); (2) intradermally injecting an effective amount of a control solution into the animal at a second site; and (3) determining if the animal is desensitized to flea saliva antigens by measuring and comparing the wheal size resulting from injection of the formulation with the wheal size resulting from injection of the control solution.

An alternative preferred method to monitor treatment of flea allergy dermatitis (which can be adapted to monitor treatments of other ectoparasite allergies) comprises: (1) contacting a first portion of a sample of bodily fluid obtained from an animal to be tested with an effective amount of a formulation containing at least one flea saliva protein or mimetope thereof (suitable and preferred formulations are disclosed herein) to form a first immunocomplex solution; (2) contacting a positive control antibody to form a second immunocomplex solution; and (3) determining if the animal is desensitized to flea saliva antigens by measuring and comparing the amount of immunocomplex formation in the first and second immunocomplex solutions.

The present invention also includes antibodies capable of selectively binding to an ectoparasite saliva protein, or mimetope thereof. Such an antibody is herein referred to as an anti-ectoparasite saliva protein antibody. As used herein, the term "selectively binds to" refers to the ability of such an antibody to preferentially bind to ectoparasite saliva proteins and mimetopes thereof. In particular, the present invention includes antibodies capable of selectively binding to flea saliva proteins. Binding can be measured using a variety of methods known to those skilled in the art including immunoblot assays, immunoprecipitation assays, enzyme immunoassays (e.g., ELISA), radioimmunoassays, immunofluorescent antibody assays and immunoelectron microscopy; see, for example, Sambrook et al., ibid.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Preferably, an antibody of the present invention has a single site binding affinity of from about $10^3$ $M^{-1}$ to about $10^{12}$ $M^{-1}$ for a flea saliva product of the present invention.

A preferred method to produce antibodies of the present invention includes administering to an animal an effective amount of an ectoparasite saliva protein or mimetope thereof to produce the antibody and recovering the antibodies. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as vaccines to passively immunize an animal in order to protect the animal from allergic dermatitis, (b) as positive controls in test kits, and/or (c) as tools to recover desired ectoparasite saliva proteins from a mixture of proteins and other contaminants.

The following examples are provided for the purposes of illustration and are not intended to limit the scope of the present invention.

EXAMPLE 1

This example describes the amino acid sequence analysis of additional isolated flea saliva proteins from FS-1 extract and eluted from DE-81 filters.

FS-1 flea saliva extract and flea saliva product eluted from DE-81 filters were collected using techniques described in Example 2 of related PCT Publication No. WO 96/11,271. Using standard purification techniques (e.g., C4 reverse phase chromatography; SDS-PAGE gel electrophoresis and blotting; and/or flow through electrophoresis), several proteins were isolated from peak M and partial amino acid sequences were determined as described in Example 4 of related PCT Publication No. WO 96/11,271. Partial N-terminal amino acid sequencing indicated that peak M contained fspj, fspL and fspN proteins (as described in Example 4 of related PCT Publication No. WO 96/11,271) as well as newly identified proteins referred to herein as fspM(G), fspM(H), fspM(I), fspM(J), fspM(K), fspM(L) and fspM(M). Flea saliva protein fspM(G), having a molecular weight of about 37 kD, had an N-terminal partial amino acid sequence of MRGNHVFLEDGMADMTGGQQMGRDLY, denoted SEQ ID NO:1. Flea saliva protein fspM(H), having a molecular weight of about 34 kD, had an N-terminal partial amino acid sequence of KYRN(Y/D)XTNDPQY, denoted SEQ ID NO:2. Flea saliva protein fspM(I), having a molecular weight of about 10 kD had an N-terminal partial amino acid sequence of E IKRNDREPGNLSKIRTVMDKVIKQTQ, denoted SEQ ID NO:3. Flea saliva protein fspM(J), having a molecular weight of about 25 kD, had an N-terminal partial amino acid sequence of LKDNDIY(A/H)(A/H)RDINEILRVLDPSK, denoted SEQ ID NO:4. Flea saliva protein fspM(K), having a molecular weight of about 30 kD, had an N-terminal partial amino acid sequence of NYGRVQIEDYTXSNHKDXEEKDQINGL, denoted SEQ ID NO:5. Flea saliva protein fspM(L), having a molecular weight of about 37 kD, had an N-terminal partial amino acid sequence of KYRNXYTNDPQLKLLDEG, denoted SEQ ID NO:6. Flea saliva protein fspM(M) was recovered from peak M and subjected to amino acid sequence analysis as described in Example 4 of related PCT Publication No. WO 96/11,271. Flea saliva protein fsp(M), having a molecular weight of about 31 kD, had an N-terminal partial amino acid sequence of YFNDQIKSVMEPXVFKYPXAXL, denoted SEQ ID NO:7. A Genbank homology search revealed no significant homology between known amino acid sequences and those determined for fspM(G), fspM(H), fspM(I), fspM (J), fspM(K), fspM(L) and fspM(M).

EXAMPLE 2

This example describes the isolation of nucleic acid molecules encoding at least a portion of a fspG flea saliva protein. This example also describes expression of a fspG protein by bacteria.

A. Isolation of fspG4 Nucleic Acid Molecules

The partial N-terminal amino acid sequence of fspG2 (i.e., SEQ ID NO:29 of related PCT Publication No. WO 96/11, 271) was used to synthesize degenerate antisense Primer G2-2, having the nucleic acid sequence 5' TGR TTT CCW ATR AAR TCT TC 3', denoted SEQ ID NO:8. Primer G2-2 was used in combination with the M13 reverse primer (SEQ ID NO:40; described in Example 7 of related PCT Publication No. WO 96/11,271), to PCR amplify, using standard techniques, the 5'-terminal portion of the fspG4 gene from a salivary gland cDNA expression library as described above in Example 6A of related PCT Publication No. WO 96/11, 271. The resulting PCR product was approximately 225-bp when visualized on a 1% agarose gel. The nucleotide sequence of the 225-bp PCR fragment was obtained, named nfspG4$_{225}$ is presented as SEQ ID NO:9.

The nucleic acid sequence of nfspG4$_{225}$ was used to synthesize sense Primer G5, having nucleic acid sequence 5' AAT TCG GCA CGA GTG 3', denoted SEQ ID NO:10. Primer G5 was used in combination with the M13 universal primer (SEQ ID NO:19; described in Example 6 of related PCT Publication No. WO 96/11,271), to PCR amplify, as described above, the 3'-terminal portion of the fspG4 gene from the salivary gland cDNA expression library described above in Example 6A of related PCT Publication No. WO 96/11,271). The resulting PCR product, denoted nfspG4$_{610}$, was approximately 610-bp when visualized on a 1% agarose gel. The nucleotide sequence of the 610-bp PCR fragment was obtained, 565 nucleotides of which are presented as SEQ ID NO:11. The nucleic acid molecule containing nucleic acid sequence SEQ ID NO:11 is referred to herein as nfspG4$_{565}$. Translation of SEQ ID NO:11 suggests that nucleic acid molecule nfspG4$_{565}$ encodes a full-length fspG protein of about 90 amino acids, referred to herein as PfspG4$_{90}$, assuming an open reading frame having a start codon spanning from about nucleotide 45 through about nucleotide 47 of SEQ ID NO:11 and a stop codon spanning from about nucleotide 315 through about nucleotide 317 of SEQ ID NO:11. This open reading frame, excluding the stop codon, comprises nucleic acid molecule nfspG4$_{270}$ of the present invention, the nucleic acid sequence of which is represented herein by SEQ ID NO:13. PfspG4$_{90}$ is denoted herein as SEQ ID NO:12. Residues 20–42 of SEQ ID NO:12 appear to be identical to SEQ ID NO:29 of related PCT Publication No. WO 96/11,271 (N-terminal partial amino acid sequence of fspG2), except that residue 37 of SEQ ID NO:12 is a glutamic acid rather than a lysine. In addition, residues 38–57 of SEQ ID NO:12 appear to be identical to SEQ ID NO:30 of related PCT Publication No. WO 96/11, 271 (N-terminal partial amino acid sequence of fspG3). These similarities support the likelihood of a family of fspG proteins in flea saliva.

Analysis of SEQ ID NO:11 suggests that the sequence includes a leader segment of about 19 amino acids followed by a mature protein. The leader sequence is apparently cleaved to form a mature protein termed PfspG4$_{71}$, denoted SEQ ID NO:131. PfspG4$_{71}$ has a calculated molecular weight of 7536 daltons and calculated pI of about 9.0. PfspG4$_{90}$ has a calculated molecular weight of 9657 daltons and calculated pI of about 9.26. A Genbank homology search revealed no significant homology between SEQ ID NO:11 or SEQ ID NO:12 and known nucleic acid sequences or known amino acid sequences, respectively.

B. Expression

An about 216-bp DNA fragment of nfspG4 was PCR amplified from nucleic acid molecule nfspG4, using: Primer G7, a sense primer having the nucleic acid sequence 5' AGT GGA TCC GTC AAA AAT GGT CAC TG 3', denoted as (SEQ ID NO:15 (BamHI site in bold); and Primer G8, an antisense primer having the nucleic acid sequence 5' CCG GAA TTC GGT TAT TCG CAA TAA CAG T 3' (EcoRI site in bold), denoted SEQ ID NO:16. The PCR product, a fragment of about 216 nucleotides, denoted nfspG4$_{216}$, was digested with BamHI and EcoRI restriction endonucleases, gel purified, and subcloned into expression vector $P_R/T^2$ori/ S10HIS-RSET-A9 (described in Example 16 of related PCT Publication No. WO 96/11,271) that had been digested with BamHI and EcoRI to produce recombinant molecule pHis-nfspG4$_{216}$.

The recombinant molecule was transformed into E. coli to form recombinant cell E. coli:pHis-nfspG4$_{216}$. The recombinant cell was cultured and induced as described in Example 11A of related PCT Publication No. WO 96/11,271 to produce fusion protein PHIS-fspG4$_{72}$. The recombinant fusion protein was detected by immunoblot analysis using the T7 Tag monoclonal antibody as described in Example 11A of related PCT Publication No. WO 96/11,271.

EXAMPLE 3

This example describes the isolation of nucleic acid sequences encoding at least a portion of flea saliva proteins fspM(A), fspM(B), fspM(C), fspM(D), fspM(E), and fspM (F).

A. nfspM(A)$_{897}$ and nfspM(B)$_{2706}$.

A flea salivary gland cDNA library (prepared as described in Example 6 of related PCT Publication No. WO 96/11,271) was immunoscreened with antiserum collected from a rabbit that was immunized with the proteins in peak M2 of the HPLC separation of flea saliva extract described in Example 3 of related PCT Publication No. WO 96/11,271 (i.e., fspM2 proteins). Immunoscreening was performed as described in Example 12 of related PCT Publication No. WO 96/11,271.

A nucleotide sequence for a nfspM nucleic acid molecule named nfspM(A)$_{897}$ is denoted as SEQ ID NO:17. Translation of SEQ ID NO:17 suggests that nucleic acid molecule nfspM(A)$_{897}$ encodes a full-length fspM protein of about 157 amino acids, referred to herein as PfspM(A)$_{1571}$ assuming an open reading frame having a start codon spanning from about nucleotide 97 through about nucleotide 99 of SEQ ID NO:17 and a stop codon spanning from about nucleotide 568 through about nucleotide 570 of SEQ ID NO:17. This open reading frame, excluding the stop codon, comprises nucleic acid molecule nfspM(A)$_{471}$ of the present invention, the nucleic acid sequence of which is represented herein by SEQ ID NO:19. The amino acid sequence of PfspM(A)$_{157}$ is denoted SEQ ID NO:18. PfspM(A)$_{157}$ has a calculated molecular weight of about 18,291.68 daltons and calculated pI of about 10.3. A Genbank homology search revealed no significant homology between SEQ ID NO:17 or SEQ ID NO:18 and known nucleic acid or amino acid sequences, respectively.

A nucleotide sequence for another nfspM nucleic acid molecule named nfspM(B)$_{2706}$ is denoted as SEQ ID NO:20. Translation of SEQ ID NO:20 suggests that nucleic acid molecule nfspM(B)$_{2706}$ encodes a non-full-length fspM protein of about 900 amino acids, referred to herein as PfspM(B)$_{900}$, assuming an open reading frame having a start codon spanning from about nucleotide 5 through about nucleotide 7 of SEQ ID NO:20. The amino acid sequence of PfspM(B)$_{900}$ is denoted SEQ ID NO:21. PfspM(B)$_{900}$ has a calculated molecular weight of about 104,647 daltons and calculated pI of about 5.8.

The nucleic acid and amino acid sequences of the nfspM (B)$_{2706}$ nucleic acid molecule and PfspM(B)$_{900}$ protein, respectively, were compared to known nucleic acid and amino acid sequences using a Genbank homology search. SEQ ID NO:21 was found to be similar to the amino acid sequence of RhoA-binding alpha kinase (ROK). The most highly conserved region of continuous similarity between SEQ ID NO:21 and ROK amino acid sequences spans from about amino acid 32 through about amino acid 351 of SEQ ID NO:21 and from about amino acid 1 through about amino acid 900 of the ROK, there being about 75% identity between the two regions. Comparison of the nucleic acid sequence encoding amino acids from about 326 through about 1285 of the ROK kinase with the corresponding regions, spanning nucleotides from about 98 through about 1075 of nfspM(B)$_{2706}$ indicate that those regions are about 71% identical.

B. nfspM(C)$_{414}$ and nfspM(D)$_{273}$

A flea salivary gland cDNA library (prepared as described in Example 6 of related PCT Publication No. WO 96/11,271) was immunoscreened with antiserum collected from a rabbit that was immunized with the proteins in peak M1 of the HPLC separation of flea saliva extract described in Example 3 of related PCT Publication No. WO 96/11,271 (i.e., fspM1 proteins). Immunoscreening was performed as described in Example 12 of related PCT Publication No. WO 96/11,271.

Nucleotide sequence for a nfspM nucleic acid molecule named nfspM(C)$_{414}$ is denoted as SEQ ID NO:22. Translation of SEQ ID NO:22 suggests that nucleic acid molecule nfspM(C)$_{414}$ encodes a non-full-length fspM protein of about 137 amino acids, referred to herein as PfspM(C)$_{137}$, assuming the first residue spans from about nucleotide 2 through about nucleotide 4 of SEQ ID NO:22. The amino acid sequence of PfspM(C)$_{137}$ is denoted SEQ ID NO:23. PfspM(C)$_{137}$ has a calculated molecular weight of about 14,452 daltons and calculated pI of about 2.81. A Genbank homology search revealed no significant homology between SEQ ID NO:22 or SEQ ID NO:23 and known nucleic acid sequences or known amino acid sequences, respectively.

A nucleotide sequence for another nfspM nucleic acid molecule named nfspM(D)$_{273}$ is denoted as SEQ ID NO:24. Translation of SEQ ID NO:24 suggests that nucleic acid molecule nfspM(D)$_{273}$ encodes a non-full-length fspM protein of about 90 amino acids, referred to herein as PfspM (D)$_{90}$, assuming the first residue spans from about nucleotide 3 through about nucleotide 5 of SEQ ID NO:24. The amino acid sequence of PfspM(D)$_{90}$ is denoted SEQ ID NO:25. PfspM(D)$_{90}$ has a calculated molecular weight of about 9,503 daltons and calculated pI of about 3.01. SEQ ID NO:24 and SEQ ID NO:25 appear to be substantially similar to SEQ ID NO:22 and SEQ ID NO:23, respectively, suggesting a family of fspM proteins in flea saliva.

C. nfspM(E)$_{1704}$ and nfspM(F)$_{1758}$

A flea salivary gland cDNA library (prepared as described in Example 6 as described of related PCT Publication No. WO 96/11,271) was immunoscreened with antiserum collected from a rabbit that was immunized with the proteins in peak M2 of the HPLC separation of flea saliva extract described in Example 3 of related PCT Publication No. WO 96/11,271 (i.e., fspM2 proteins) Immunoscreening was performed as described in Example 12 of related PCT Publication No. WO 96/11,271.

A nucleotide sequence for another nfspM nucleic acid molecule named nfspM(E)$_{1704}$ is denoted as SEQ ID NO:26. Translation of SEQ ID NO:26 suggests that nucleic acid molecule nfspM(E)$_{1704}$ encodes a full-length fspM protein of about 461 amino acids, referred to herein as PfspM(E)$_{461}$, assuming the first residue spans from about nucleotide 24 through about nucleotide 26 of SEQ ID NO:26 and a stop codon spanning from about nucleotide 1407 through about nucleotide 1409 of SEQ ID NO:26. This open reading frame, excluding the stop codon, comprises nucleic acid molecule nfspM(E)$_{1383}$ of the present invention, the nucleic acid sequence of which is represented herein by SEQ ID NO:28. The amino acid sequence of PfspM(E)$_{461}$ is denoted SEQ ID NO:27. PfspM(E)$_{461}$ has a calculated molecular weight of about 54,139 daltons and calculated pI of about 7.00. A Genbank homology search revealed no significant homology between SEQ ID NO:26 or SEQ ID NO:27 and known nucleic acid sequences or known amino acid sequences, respectively.

A nucleotide sequence for another nfspM nucleic acid molecule named nfspM(F)$_{1758}$ is denoted as SEQ ID NO:29. Translation of SEQ ID NO:29 suggests that nucleic acid molecule nfspM(F)$_{1758}$ encodes a non-full-length fspM protein of about 586 amino acids, referred to herein as PfspM (F)$_{586}$, assuming an open reading frame having a start codon spanning from about nucleotide 1 through about nucleotide 3 of SEQ ID NO:29. The amino acid sequence of PfspM (F)$_{586}$ is denoted SEQ ID NO:30. PfspM(F)$_{586}$ has a calculated molecular weight of about 66,547 daltons and calculated pI of about 4.80. A Genbank homology search revealed no significant homology between SEQ ID NO:29 or SEQ ID NO:30 and known nucleic acid sequences or known amino acid sequences, respectively.

EXAMPLE 4

This Example demonstrates the expression of a fspM protein in E. coli cells.

Flea saliva protein PHIS-PfspM(D)go fusion protein was produced in the following manner. An about 305-bp DNA fragment, referred to herein as nfspM(D)$_{305}$, was isolated from nfspM(D)$_{293}$ (denoted SEQ ID NO:31) subcloned into pBluescript plasmid by digesting the nfspM(D)-containing plasmid with BamH1 and XhoI restriction endonucleases. The digestion product was gel purified and subcloned into expression vector pTrcHisB that had been digested with BamH1 and XhoI, and dephosphorylated. The resultant recombinant molecule, referred to herein as pHis-nfspM(D)$_{3051}$ was transformed into E. coli HB101 competent cells (available from Gibco BRL, Gaithersburg, Md.) to form recombinant cell E. coli:pHis-nfspM(D)$_{305}$. The recombinant cell was cultured and expression of nfspM$_{305}$induced using conditions described in Example 11A of related PCT Publication No. WO 96/11,271. Immunoblot analysis of recombinant cell E. coli:pHis-nfspM(D)$_{305}$ lysates using a T7 tag monoclonal antibody (Novagen, Inc) directed against the fusion portion of the recombinant PHis-nfspM(D)$_{305}$ fusion protein identified a protein of the appropriate size, namely an about 15,851 kD protein.

EXAMPLE 5

This example describes the isolation of nucleic acid sequences encoding at least a portion of flea saliva proteins fspN(C), fspN(D), fspN(E), fspN(F), fspN(G), fspN(H), fspN(I), fspN(J), fspN(K), fspN(L), fspN(M), fspN(N) and fspN(O).

A. Preparation of IgE Enriched Antiserum

Serum was obtained from the artificially sensitized dog CQQ2 (described in Example 8 of related PCT Publication No. WO 96/11,271). About 10 ml of antiserum was incubated with protein G-Sepharose (5 ml) over night at 4° C.

B. Immunoscreening with IgE Enriched Antiserum

About 2.4 ml of *Escherichia coli* (XL1 Blue, O.D.$_{.600}$= 0.5) was incubated with 6.48×10$^5$ pfu of phage from a flea salivary gland ZAP-CDNA library (1.8×10$^7$ pfu/ml), at 37° C. for 15 min and plated in 12 Luria-Bertani (LB) medium agar plates (150 mm). The plates were incubated at 37° C. over night. Each plate was then overlaid with an IPTG (10 mM) treated nitrocellulose filters for about 4 hours at 37° C. The filters were then removed and washed with TBST (20 mM Tris-HCl pH 7.5, 150 mM NaCl, 0.05% Tween-20). The filters were blocked with 5% dry milk in TBST for 2 hours at room temperature. Different filters were then incubated first with either IgE enriched CQQ2 antiserum or antiserum obtained from dogs infected with *Dirofilaria immitis*) at 4° C., overnight, then with a monoclonal anti-canine IgE antibody (D-9; gift from the laboratory of Dr. D. J. DeBoer, School of Veterinary Medicine, University of Wisconsin, Madison, Wis.), and then with a donkey anti-mouse IgG antibody conjugated to horseradish peroxidase (available from Jackson ImmunoResearch, West Grove, Pa.) for 2 hours at room temperature at each step. All of the filters were washed with TBST (3×15 min/wash) between each incubation. All of the filters were then treated to a final wash in TBS. Immunocomplexed plaques were identified by immersing the filters into the developing solution (TMB Peroxidase Substrate/TMB Peroxidase Solution/TMB Membrane Enhancer from Kirkegaard & Perry Laboratories) at 1/1/0.1 volume ratio to produce a color reaction. Eighteen plaques were identified and further plaque purified under the same immunoscreening condition as described above.

C. nfspN(C)$_{335}$, nfspN(D)$_{396}$, nfspN(E)$_{285}$, nfspN(F)$_{228}$, nfspN(G)$_{339}$, nfspN(G)$_{493}$, Single plaque of purified clones were isolated and stored in SM phage buffer (50mM Tris, pH 7.4, 0.58% NaCl, 0.2% MgCl$_2$.7H$_2$O and 0.01% Gelatin). The in vivo excision of the pBluescript phagemid from each positive clone was prepared by using ExAssist™/SOLR™ system (Stratagene). The pBluescript plasmid was purified by plasmid midi kit (Qiagen), and denatured with NaOH (0.4 N) at 37° C. for 15 min. The denatured plasmid was precipitated by ethanol and nucleic acid sequence obtained.

A nucleotide sequence for a nfspN nucleic acid molecule named nfspN(C)$_{335}$ is denoted as SEQ ID NO:32. A Genbank homology search revealed some similarity between SEQ ID NO:32 and ribosomal protein S6.

A nucleotide sequence for another nfspN nucleic acid molecule named nfspN(D)$_{396}$ is denoted as SEQ ID NO:33. A Genbank homology search revealed some similarity between SEQ ID NO:33 and erythropoietin.

A nucleotide sequence for another nfspN nucleic acid molecule named nfspN(E)$_{285}$ is denoted as SEQ ID NO:34. A Genbank homology search revealed some similarity between SEQ ID NO:34 and glutamic acid-rich protein or heat-shock protein, HSP81.

A nucleotide sequence for another nfspN nucleic acid molecule named nfspN(F)$_{228}$ is denoted as SEQ ID NO:35.

Nucleic acid sequence for portions of another nfspN nucleic acid molecule, denoted herein as nfspN(G), were obtained. The nucleic acid molecule representing a 5' portion of nfspN(G) named nfspN(G)$_{339}$ is denoted as SEQ ID NO:36. Translation of SEQ ID NO:36 suggests that nucleic acid molecule nfspN(G)$_{339}$ encodes a non-full-length fspN (G) protein of about 113 amino acids, referred to herein as PfspN(G)$_{113}$, assuming the first residue spans from about nucleotide 1 through about nucleotide 3 of SEQ ID NO:36. The amino acid sequence of PfspN(G)$_{113}$ is denoted SEQ ID NO:37.

The nucleic acid molecule representing a 3' portion of nfspN(G) named nfspN(G)$_{493}$ is denoted as SEQ ID NO:38. Translation of SEQ ID NO:38 suggests that nucleic acid molecule nfspN(G)$_{493}$ encodes a non-full-length fspN(G) protein of about 130 amino acids, referred to herein as PfspN(G)$_{130}$, assuming the first residue spans from about nucleotide 1 through about nucleotide 3 of SEQ ID NO:38 and a stop codon spanning from about nucleotide 391 through about nucleotide 393 of SEQ ID NO:38. The amino acid sequence of PfspN(G)$_{130}$ is denoted SEQ ID NO:39. A Genbank homology search revealed some similarity between SEQ ID NO:36 and SEQ ID NO:38 and vitellogenin.

A nucleotide sequence for another nfspN nucleic acid molecule named nfspN(H)$_{306}$is denoted as SEQ ID NO:40.

A nucleotide sequence for another nfspN nucleic acid molecule named nfspN(I)$_{490}$ is denoted as SEQ ID NO:41.

A nucleotide sequence for another nfspN nucleic acid molecule named nfspN(J)$_{616}$is denoted as SEQ ID NO:42.

A nucleotide sequence for another nfspN nucleic acid molecule named nfspN(K)$_{475}$ is denoted as SEQ ID NO:43.

A nucleotide sequence for another nfspN nucleic acid molecule named nfspN(L)$_{295}$ is denoted as SEQ ID NO:44.

A nucleotide sequence for another nfspN nucleic acid molecule named nfspN(M)$_{372}$ is denoted as SEQ ID NO:45.

Nucleic acid sequence for portions of another nfspN nucleic acid molecule, denoted herein as nfspN(N), were obtained. The nucleic acid molecule representing a 5' portion of nfspN(N) named nfspN(N)$_{252}$ is denoted as SEQ ID NO:46. The nucleic acid molecule representing a 3' portion of nfspN(N) named nfspN(N)$_{613}$ is denoted as SEQ ID NO:47.

Nucleic acid sequence for portions of another nfspN nucleic acid molecule, denoted herein as nfspN(O), were obtained. The nucleic acid molecule representing a 5' portion of nfspN(O) named nfspN(O)$_{538}$ is denoted as SEQ ID NO:48. Translation of SEQ ID NO:48 suggests that nucleic acid molecule nfspN(O)$_{538}$ encodes a non-full-length fspN (O) protein of about 178 amino acids, referred to herein as PfspN(O)$_{178}$, assuming the first residue spans from about nucleotide 1 through about nucleotide 3 of SEQ ID NO:48. The amino acid sequence of PfspN(N)$_{178}$ is denoted SEQ ID NO:49.

The nucleic acid molecule representing a 3' portion of nfspN(O) named nfspN(O)$_{432}$ is denoted as SEQ ID NO:50. Translation of SEQ ID NO:50 suggests that nucleic acid molecule nfspN(O)$_{432}$ encodes a non-full-length fspN(O) protein of about 129 amino acids, referred to herein as PfspN(O)$_{129}$, assuming the first residue spans from about nucleotide 1 through about nucleotide 3 of SEQ ID NO:50 and a stop codon spanning from about nucleotide 388 through about nucleotide 390 of SEQ ID NO:50. The amino acid sequence of PfspN(O)$_{129}$ is denoted SEQ ID NO:51.

EXAMPLE 6

This example describes studies confirming the specificity of IgE enriched antiserum from CQQ2 to fspN protein.

Three different petri dishes (100 mm) were overlaid with 300 microliter per plate of *E. coli* (XL1 Blue, O.D.$_{.600}$=500). A drop (about 100 pfu/drop) of each of the eighteen isolated phage clones was dropped onto each plate (18 phage clones/plate). Using the methods described in Example 5 above, the plates were incubated, filter lifted and the filters immunoscreened with IgE enriched antiserum from CQQ2, antiserum from a *D. Immitis* infected dog and antiserum from rabbits injected with flea saliva product from peak N (as described in Example 3 of related PCT Publication No. WO 96/11,271).

The results of the experiment indicate that both the IgE enriched CQQ2 antiserum and the antiserum specific for peak N flea saliva product bind to the products of the purified phage clones significantly better than the antiserum from a *D. Immitis* infected dog.

EXAMPLE 7

This example describes the isolation of nucleic acid molecules encoding a fspG flea saliva protein. This example also describes expression of a fspG protein by bacteria.

A DNA probe labeled with $^{32}$P comprising nucleotides from nfspG4$_{610}$ (described in Example 2) was used to screen a flea salivary gland cDNA library (described in Example 6 of related PCT Publication No. WO 96/11,706) using standard hybridization techniques. A clone was isolated having about a 595 nucleotide insert, referred to herein as nfspG5$_{595}$ having a nucleic acid sequence of the coding strand which is denoted hencodes a full-length flea salivary protein of about 90 amino acids, referred to herein as PfspG5$_{90}$, having amino acid sequence SEQ ID NO:56, assuming an open reading frame in which the initiation codon spans from about nucleotide 46 through about nucleotide 48 of SEQ ID NO:52 and the termination codon spans from about nucleotide 316 through about nucleotide 318 of SEQ ID NO:52. The complement of SEQ ID NO:52 is represented herein by SEQ ID NO:54. The coding region encoding PfspG5$_{90}$, is represented by nucleic acid molecule nfspG5$_{270}$, having a coding strand with the nucleic acid sequence represented by SEQ ID NO:55 and a complementary strand with nucleic acid sequence SEQ ID NO:57. The amino acid sequence of PfspG5$_{90}$ (i.e., SEQ ID NO:56) predicts that PfspG5$_{90}$ has an estimated molecular weight of about 9.6 kD and an estimated pI of about 9.28.

Analysis of SEQ ID NO:56 suggests the presence of a signal peptide encoded by a stretch of amino acids spanning from about amino acid 1 through about amino acid 19. The proposed mature protein, denoted herein as PfspG5$_{71}$, contains about 71 amino acids which is represented herein as SEQ ID NO:59. The complement of SEQ ID NO:58 is represented by SEQ ID NO:60. The amino acid sequence of PfspG5$_{71}$ (i.e., SEQ ID NO:59) predicts that PfspG5$_{71}$ has an estimated molecular weight of about 7.48 kD, and an estimated pI of about 8.28.

Comparison of amino acid sequence SEQ ID NO:56 with amino acid sequences reported in GenBank indicates that SEQ ID NO:56 showed the most homology, i.e., about 38% identity between SEQ ID NO:56 and a *Ctenocephalides felis* flea salivary protein FS-H precursor (GenBank accession U63544). Comparison of nucleic acid sequence SEQ ID NO:52 with nucleic acid sequences reported in GenBank indicates that SEQ ID NO:52 showed the most homology, i.e., about 63% identity between SEQ ID NO:52 and a *Ctenocephalides felis* flea salivary protein FS-H precursor gene (GenBank accession U63544).

Flea salivary protein PfspG5$_{71}$ was produced in the following manner. An about 213 bp nucleic acid molecule, referred to herein as nfspG5$_{213}$ and designated SEQ ID NO:58 (designed to encode an apparently mature flea salivary protein) was PCR amplified from nfspG5$_{595}$ using sense primer G7 having the nucleotide sequence 5' A GTG GAT CCG TCA AAA ATG GTC ACT G-3' (containing an BamHI-site shown in bold; denoted SEQ ID NO:79) and anti-sense primer G8 having the nucleotide sequence 5' CC GGA ATT CGG TTA TTC GCA ATA ACA GT-3' (containing a EcoRI shown in bold; denoted SEQ ID NO:80). The resulting PCR product nfspG5$_{213}$ was digested with BamHI and EcoRI restriction endonucleases, gel purified, and subcloned into expression vector lambdaP$_R$/T$^2$ori/S10HIS-RSET-A9, that had been digested with BamHI and EcoRI and dephosphorylated. The resultant recombinant molecule, referred to herein as pCro-nfspG5$_{2131}$ was transformed into *E. coli* BL-21 competent cells (available from Novagen, Madison, Wis.) to form recombinant cell *E. coli*:pCro-nfspG5$_{213}$. The recombinant cell was cultured and induced as described in Example 11A of related PCT Publication No. WO 96/11,271. Immunoblot analysis of the proteins using a T7 antibody showed expression of an about 12 kD protein in the induced sample but not in the uninduced sample.

EXAMPLE 8

This example describes the further sequencing of a nucleic acid sequence encoding a fspI flea saliva protein. This example also describes expression of a fspI protein by bacteria.

Another nucleic acid molecule was identified using the methods described in Example 6 of related PCT Publication No. WO 96/11,706. A nucleic acid molecule was identified of about 1007 nucleotides, referred to herein as nfspI$_{1007}$, the coding strand is denoted herein as SEQ ID NO:61. Translation of SEQ ID NO:61 suggests that SEQ ID NO:61 encodes a non-full-length flea salivary protein of about 155 amino acids, referred to herein as PfspI$_{155}$, having amino acid sequence SEQ ID NO:62, assuming the first codon spans from about nucleotide 1 through about nucleotide 3 of SEQ ID NO:61 and the termination codon spans from about nucleotide 466 through about nucleotide 468 of SEQ ID NO:61. The complement of SEQ ID NO:61 is represented herein by SEQ ID NO:63.

Flea salivary protein PfspI$_{158}$ was produced in the following manner. An about 474-bp nucleic acid molecule, referred to herein as nfspI$_{474}$ (designed to encode an apparently mature flea salivary protein) was PCR amplified from nfspI$_{1007}$ using sense primer I1 having the nucleotide sequence 5' GCG CGG ATC CGC ATA TGG AAG ACA TCr GGA AAG TTA ATA AAA AAT GTA CAT CAG-3' (containing an BamHI-site shown in bold as well as nucleic acid sequence encoding three amino acids, Glu-Asp-Isoleucine, shown in italics; denoted SEQ ID NO:81) and anti-sense primer I2 having the nucleotide sequence 5' CCG GAA TTC TTA TTT ATT TTT TGG TCG ACA ATA ACA AAA GTT TCC-3' (containing a EcoRI shown in bold; denoted SEQ ID NO:82). The resulting PCR product nfspI$_{474}$, which contained the nucleic acid sequences incorporated into primer I1 that encode three amino acids, was digested with BamHI and EcoRI restriction endonucleases, gel purified, and subcloned into expression vector lambdap$_R$/T$^2$ori/S 0HIS-RSET-A9, that had been digested with BamHI and XbaI and dephosphorylated. The resultant recombinant molecule, referred to herein as pCro-nfspI$_{474}$, was transformed into *E. coli* BL-21 competent cells (available from Novagen, Madison, Wis.) to form recombinant cell *E. coli*:pCro-nfspI$_{474}$. The recombinant cell was cultured and protein production resolved using the methods described in Example 11A of related PCT Publication No. WO 96/11,271. Immunoblot analysis of the proteins using a T7 antibody showed expression of an about 30 kD protein in the induced sample but not in the uninduced sample.

EXAMPLE 9

This example describes the isolation of nucleic acid molecules encoding a fspN flea saliva protein.

A DNA probe comprising nucleotides from nfspN(B)$_{612}$ (SEQ ID NO:52 of related PCT Publication No. WO 96/11, 706) was labeled with $^{32}$P and used to screen the flea salivary gland cDNA library using standard hybridization techniques. A clone was isolated having about a 1205 nucleotide insert, referred to herein as nfspN5$_{1205}$ having a nucleic acid sequence of the coding strand which is denoted herein as SEQ ID NO:64. Translation of SEQ ID NO:64 suggests that nucleic acid molecule nfspN5$_{1205}$ encodes a non-full-length flea salivary protein of about 353 amino acids, referred to herein as PfspN5$_{353}$, having amino acid sequence SEQ ID NO:65, assuming an open reading frame in which the initiation codon spans from about nucleotide 4 through about nucleotide 6 of SEQ ID NO:64 and the termination codon spans from about nucleotide 1060 through about nucleotide 1062 of SEQ ID NO:64. The complement of SEQ ID NO:64 is represented herein by SEQ ID NO:66. The coding region encoding PfspN5$_{353}$, is represented by nucleic acid molecule nfspN5$_{1059}$, having a coding strand with the nucleic acid sequence represented by SEQ ID NO:67 and a complementary strand with nucleic acid sequence SEQ ID NO:69. The amino acid sequence of PfspN5$_{353}$ (i.e., SEQ ID NO:65) predicts that PfspN5$_{353}$has an estimated molecular weight of about 39.7 kD and an estimated pI of about 9.45.

Comparison of amino acid sequence SEQ ID NO:65 with amino acid sequences reported in GenBank indicates that SEQ ID NO:65 showed the most homology, i.e., about 32% identity between SEQ ID NO:65 and a Human prostatic acid phosphatase precursor protein (GenBank accession P15309). A GenBank homology search revealed no significant homology between SEQ ID NO:64 and known nucleic acid sequences.

EXAMPLE 10

This example describes the isolation of nucleic acid molecules encoding a fspN flea saliva protein identified using IgE antibodies isolated from a pool of dogs having clinical flea allergy dermatitis.

A. PCR Clone

A pool of sera (referred to herein as Pool #4) was collected from numerous dogs known to have clinical flea allergy dermatitis (FAD). Pool #4 sera was used to identify flea saliva antigens that bind specifically to IgE antibodies in the FAD dog sera as follows. Flea saliva extract was collected using the general methods described in Examples 1 and 2 of related PCT Publication No. WO 96/11,706, except a carboxymethyl cation exchange (CM) membrane (available from Schleicher and Scheull, Keene, N. H.) was used rather than a Durapore® membrane. In addition, flea saliva extract was eluted from the membrane by contacting the membrane in an extraction buffer of 2.5 M NaCl, 5% isopropyl alcohol (IPA) and 20 mM Tris, pH 8.0. The membrane was eluted overnight at room temperature. The flea saliva extract was resolved by high pressure liquid chromatography (HPLC) using the method generally described in Example 2 of related PCT Publication No. WO 96/11,706. Proteins contained in the HPLC fractions were resolved on a 16% Tris-glycine SDS PAGE gel. Proteins on the gel were then blotted to an Immobilon P™ filter (available from Millipore Co., Bedford, Mass.) using standard Western Blot techniques. IgE antibodies bound to protein on the blot were then detected as follows. The blot was first incubated with about a 1:200 dilution of Pool #4 sera using standard antibody hybridization techniques, washed, and then incubated with about a 1:500 dilution of a 145 μg/milliliter solution of biotinylated human Fc R alpha chain protein using standard Western Blot techniques. Following washing, the blot was incubated with about a 1:5000 dilution of streptavidin conjugated to alkaline phosphatase (available from Sigma, St. Louis, Mo.). The blot was then incubated in about 10 milliliter of BCIP/NBT substrate (available from Gibco BRL, Gaithersburg, Md.) at room temperature until visible bands appeared and then rinsed in water to stop the reaction. Protein bands were detected in samples containing Fractions 34, 37, 38, 47, 49, 51, 52 and 53.

Amino (N-) terminal amino acid sequencing analysis was performed on protein contained in the about 40 kD protein band identified in the sample containing Fraction 52, using standard procedures known to those in the art (see, for example, Geisow et al., 1989, in *Protein Sequencing: A Practical Approach*, J B C Findlay and M J Geisow (eds.), IRL Press, Oxford, England, pp. 85–98; Hewick et al., 1981, *J. Biol. Chem.*, Vol. 256, pp. 7990–7997). The N-terminal partial amino acid sequence of the protein was determined to be Xaa Glu Leu Lys Phe Val Phe Val Met Val Lys Gly Pro Asp His Glu Ala Cys Asn Tyr Ala Gly Gly Xaa Gln (denoted herein as SEQ ID NO:70; wherein "Xaa" represents any amino acid residue).

Synthetic oligonucleotide primers were designed using SEQ ID NO:70 and used to isolate a nucleic acid molecule encoding SEQ ID NO:70 as follows. Sense primer 1 having the nucleotide sequence 5' AAA TTT GTW TTT GTW ATG GTW AAA GGW CCW GAT CAT GAA GC 3' (wherein W represents A or T), designated SEQ ID NO:83 was used in combination with the M13 forward universal standard primer 5' GTA AAA CGA CGG CCA GT 3' (denoted SEQ ID NO:85) to produce a PCR product from a flea salivary gland cDNA library (prepared as described in Example 6 of related PCT Publication No. WO 96/11,271). PCR amplification was conducted using standard techniques. The resulting PCR amplification product was a fragment of about 406 nucleotides, denoted herein as nfspN6$_{405}$. The PCR product was cloned into the InVitrogen, Corp., TA™ cloning vector (procedures provided by InVitrogen, Corp.) and subjected to DNA sequence analysis using standard techniques.

The nucleic acid sequence of the coding strand of nfspN6$_{405}$ is denoted herein as SEQ ID NO:71. Translation of SEQ ID NO:71 suggests that nucleic acid molecule nfspN6$_{405}$ encodes a non-full-length flea salivary protein of about 135 amino acids, referred to herein as PfspN6$_{135}$, having amino acid sequence SEQ ID NO:72, assuming the first codon spans from nucleotide 1 through nucleotide 3 of SEQ ID NO:71 and the last codon spans from nucleotide 403 through nucleotide 405 of SEQ ID NO:71. The amino acid sequence of PfspN6$_{135}$ (i.e. SEQ ID NO:72) predicts that PfspN6$_{135}$ has an estimated molecular weight of about 15.2 kD, and an estimated pI of about 9.49. The complement of SEQ ID NO:71 is represented herein by SEQ ID NO:73.

A Genbank homology search revealed no significant homology between amino acid sequence SEQ ID NO:72 and nucleic acid sequence SEQ ID NO:71 and known amino acid sequences or nucleic acid sequences, respectively.

B. CDNA Clone

A DNA probe comprising nucleotides from nfspN6$_{405}$, SEQ ID NO:71 was labeled with $^{32}$P and used to screen a whole flea CDNA library (prepared as described in Example 6 of related PCT Publication No. WO 96/11,271) using standard hybridization techniques. A clone was isolated having about a 1300 nucleotide insert, referred to herein as nfspN6$_{1300}$ having a nucleic acid sequence denoted herein as SEQ ID NO:89. The complement of SEQ ID NO:89 is represented herein by SEQ ID NO:91.

Translation of SEQ ID NO:89 suggests that nucleic acid molecule nfspN6$_{1300}$ encodes a full-length flea salivary protein of about 375 amino acids, referred to herein as PfspN6$_{375}$, having an amino acid sequence represented by SEQ ID NO:90, assuming the initiation codon spans from nucleotide 12 through nucleotide 14 of SEQ ID NO:89 and the termination codon spans from nucleotide 1137 through nucleotide 1139 of SEQ ID NO:89. The coding region encoding PfspN6$_{375}$, is represented by nucleic acid molecule nfspN6$_{1125}$, having a coding strand with the nucleic acid sequence represented by SEQ ID NO:92 and a complementary strand with nucleic acid sequence SEQ ID NO:93. The amino acid sequence of PfspN6$_{375}$ predicts that PfspN6$_{375}$ has an estimated molecular weight of about 42.4 kD and an estimated pI of about 9.36.

Analysis of SEQ ID NO:90 suggests the presence of a signal peptide encoded by a stretch of amino acids spanning from about amino acid 1 through about amino acid 19. The proposed mature protein, denoted herein as PfspN6$_{356}$, contains about 356 amino acids which is represented herein as SEQ ID NO:94. The amino acid sequence of PfspN6$_{356}$ (i.e. SEQ ID NO:94) predicts that PfspN6$_{356}$ has an estimated molecular weight of about 40.5, and an estimated pI of about 9.53. The coding region encoding PfspN6$_{356}$ is represented by nucleic acid molecule nfspN6$_{106}$8 having a coding strand with the nucleic acid sequence represented by SEQ ID NO:95 and a complementary strand with nucleic acid sequence SEQ ID NO:96.

A GenBank homology search revealed no significant homology between amino acid sequence SEQ ID NO:94 and nucleic acid sequence SEQ ID NO:92 and known amino acid sequences or nucleic acid sequences, respectively.

Flea salivary protein PfspN6$_{356}$ was produced in the following manner. An about 1071-bp nucleic acid molecule, referred to herein as nfspN6$_{1071}$ and designated SEQ ID NO:97 (designed to encode an apparently mature flea salivary protein) was PCR amplified from nfspN6$_{1300}$ using sense primer FSN6-Nde-S having the nucleotide sequence 5' GAT GCG GAT CCG CAT ATG GAA CTG AAG TTT GTA TTT GTG ATG AAA GG 3' (the NdeI site shown in bold; denoted SEQ ID NO:98) and anti-sense primer FSN6-Pst-A having the nucleotide sequence 5' GAT CAT CCG CTG CAG TTA TTT ACA GGC TTG CTT ATG TCT AGC ATC ATC 3' (the PstI site shown in bold; denoted SEQ ID NO:99). The resulting PCR product was digested with NdeI and PstI restriction endonucleases, gel purified, and subcloned into expression vector lambdaP$_R$/T$^2$ori/S10HIS-RSET-A9, that had been digested with NdeI and PstI and dephosphorylated as described herein in Example 7. The resultant recombinant molecule, referred to herein as pCro-nfspN6$_{1071}$, was transformed into E. coli BL-21 competent cells (available from Novagen, Madison, Wis.) to form recombinant cell E. coli:pCro-nfspN6$_{1071}$. The recombinant cell was cultured and induced as described in Example 11A of related PCT Publication No. WO 96/11,271. Immunoblot analysis using a rabbit anti-flea fs(N) polyclonal antibody identified an about 50 kD protein in the induced sample.

EXAMPLE 11

This example describes the isolation of nucleic acid molecules encoding a fspj flea saliva protein.

A. PCR Clone

Degenerate oligonucleotide primers were designed from the amino acid sequence deduced for fspj (described in Example 4 of related PCT Publication No. WO 96/11,706) and were used to isolate a fspj nucleic acid molecule as follows. Two synthetic oligonucleotides were synthesized that corresponded to the region of fspJ spanning from residues 7 through 26 of SEQ ID NO:8 of related PCT Publication No. WO 96/11,706. Primer 1, a "sense" primer corresponding to amino acid residue 7 to residue 16 of SEQ ID NO:8 of related PCT Publication No.WO 96/11,706, has the nucleotide sequence 5' CAT GAA CCW GGW AAT ACW CGW AAR ATH AS 3' (wherein W denotes A or T, R denotes A or G, H denotes A, C or T, and S denotes C or G), SEQ ID NO:84. Primer 2, a "sense" primer corresponding to amino acid residues from residue 17 through 26 of SEQ ID NO:8 of related PCT Publication No. WO 96/11,706, has the nucleic acid sequence 5' GAA GTW ATG GAY AAA TTR AGR CAR GC-3' (wherein W denotes A or T, R denotes A or G; and Y denotes C or T), SEQ ID NO:86.

PCR amplification of fragments from the flea salivary gland CDNA library (prepared as described in Example 6 of related PCT Publication No. WO 96/11,271) was conducted using standard techniques. PCR amplification products were generated using a combination of Primer 1 and M13 primer (denoted SEQ ID NO:85). The resultant PCR products were used for a nested PCR amplification using Primer 2 and the T7 standard primer 5' GTA ATA CGA CTC ACT ATA TAG GGC 3' (denoted SEQ ID NO:88). The resultant PCR product, a fragment of about 420 nucleotides, denoted herein as nfspJ$_{420}$. The PCR product was cloned into the InVitrogen, Corp., TA™ cloning vector and subjected to DNA sequence analysis using standard techniques.

The nucleic acid sequence of the coding strand of nfspJ$_{420}$ is denoted herein as SEQ ID NO:74. Translation of SEQ ID NO:74 suggests that nucleic acid molecule nfspJ$_{420}$ encodes a non-full-length flea salivary protein of about 72 amino acids, referred to herein as PfspJ$_7$2, having amino acid sequence SEQ ID NO:75, assuming the first codon spans from nucleotide 1 through nucleotide 3 of SEQ ID NO:74 and the last codon spans from nucleotide 214 through nucleotide 216 of SEQ ID NO:74. The complement of SEQ ID NO:74 is represented herein by SEQ ID NO:76.

A GenBank homology search revealed no significant homology between amino acid sequence SEQ ID NO:75 and nucleic acid sequence SEQ ID NO:74 and known amino acid sequences or nucleic acid sequences, respectively.

B. cDNA Clone

A DNA probe comprising nfspJ$_{420}$ was labeled with $^{32}$P and used to screen a whole flea cDNA library (prepared as described in Example 6 of related PCT Publication No. WO 96/11,271) using standard hybridization techniques. A clone was isolated having about a 606 nucleotide insert, referred to herein as nfspJ1$_{606}$, having a nucleic acid sequence denoted herein as SEQ ID NO:100. The complement of SEQ ID NO:100 is represented herein by SEQ ID NO:102.

Translation of SEQ ID NO:100 suggests that nucleic acid molecule nfspJ1$_{606}$ encodes a full-length flea salivary protein of about 113 amino acids, referred to herein as PfspJ1113, having amino acid sequence SEQ ID NO:101, assuming the initiation codon spans from nucleotide 43 through nucleotide 45 of SEQ ID NO:100 and the termination codon spans from nucleotide 382 through nucleotide 384 of SEQ ID NO:100. The coding region encoding PfspJ1$_{113}$, is represented by nucleic acid molecule nfspJ1$_{339}$, having a coding strand with the nucleic acid sequence represented by SEQ ID NO:103 and a complementary strand with nucleic acid sequence SEQ ID NO:104. The amino acid sequence of PfspJ1$_{113}$ predicts that PfspJ1$_{113}$ has an estimated molecular weight of about 12.5 kD and an estimated pI of about 9.34.

Analysis of SEQ ID NO:101 suggests the presence of a signal peptide encoded by a stretch of amino acids spanning from amino acid 1 through amino acid 17. The proposed mature protein, denoted herein as PfspJ1$_{971}$ contains about 97 amino acids which is represented herein as SEQ ID NO:105. The amino acid sequence of PfspJ1$_{97}$ (i.e. SEQ ID NO:105) predicts that PfspJ1$_{97}$ has an estimated molecular weight of about 9.8kD, and an estimated pI of about 9.41. The coding region encoding PfspJ1$_{97}$ is represented by nucleic acid molecule nfspJ1$_{291}$ having a coding strand with the nucleic acid sequence represented by SEQ ID NO:106 and a complementary strand with nucleic acid sequence SEQ ID NO:107.

A GenBank homology search revealed no significant homology between amino acid sequence SEQ ID NO:105 and nucleic acid sequence SEQ ID NO:103 and known amino acid sequences or nucleic acid sequences, respectively.

EXAMPLE 12

This example describes the amino acid sequence analysis of an isolated and HPLC purified fspN7 flea saliva protein.

Fractions of flea saliva proteins described above in Example 10 were tested for the ability to stimulate T cell clones that respond specifically to the flea saliva extract described in Exa-specific T cells). T cell activation were performed using standard methods such as those described in Current Protocols in Immunology, Vol. 1, Chapter 3 [3.13.2], ed. J. E. Coligan et al., pub. Wiley Interscience, 1993. Briefly, about $10^4$ FS-1-specific T cells (clone CPO2–7; isolated from dog CPO2 described in Example 8 of related PCT Patent Publication No. WO 96/11,271) were added to individual wells of a 96 well tissue culture plate, in the presence of about 2×104 autologous antigen presenting cells (isolated by ficoll gradient from dog CPO2) and about 100 units/milliliter of recombinant human interleukin-2 (Proleukin®; available from Chiron Inc., Emeryville, Calif.). About 1 microliter of each fraction of protein resolved by HPLC was to added to each well in triplicate. The cells were incubated for about 4 to about 6 days. About 16 hours prior to harvesting, about 1 $\mu$Ci of tritiated thymidine (available from Amersham Inc., Arlington Heights, Ill.) was added to each well. The cells were then harvested and the amount of tritium incorporated into the cellular protein was determined. The results indicated that protein contained in a HPLC fraction containing fspN protein (Fraction 51) stimulated the FS-specific T cells.

Amino (N-) terminal amino acid sequencing analysis was performed on protein contained in Fraction 51 using standard procedures known to those in the art (see, for example, Geisow et al., ibid.; Hewick et al., 1981, ibid.). The N-terminal partial amino acid sequence of the band was determined to be Asn Asp Lys Leu Gln Phe Val Phe Val Met Ala Arg Gly Pro Asp His Glu Ala Cys Asn Tyr Pro Gly Gly Pro (denoted herein as SEQ ID NO:78).

EXAMPLE 13

This example describes the amino acid sequence analysis of an isolated and HPLC purified fspM2 flea saliva protein.

Proteins contained within Fraction 47 described above in Example 10 were resolved on a 16% Tris-glycine SDS PAGE gel. A major band at about 34 kD was identified. Amino (N-) terminal amino acid sequencing analysis was performed on protein contained in the about 34 kD using standard procedures known to those in the art (see, for example, Geisow et al., ibid.; Hewick et al., 1981, ibid.). The N-terminal partial amino acid sequence of the band was determined to be Tyr Phe Asn Lys Leu Val Gln Ser Trp Thr Glu Pro Met Val Phe Lys Tyr Pro Tyr (denoted herein as SEQ ID NO:87).

EXAMPLE 14

This example describes the isolation of nucleic acid sequences encoding at least portions of flea saliva proteins fspM and fspL.

A. Isolation of Nucleic Acid Molecule Encoding fspM(N)

This example describes the isolation of nucleic acid molecules encoding a fspM flea saliva protein identified using IgE antibodies isolated from a pool of dogs having clinical flea allergy dermatitis.

1. PCR Clone

Pool number 4 was used to identify proteins in a flea extract using the methods described herein in Example 10.

Protein bands were detected in samples containing Fractions 39 and 40. Amino (N-) terminal amino acid sequencing analysis was performed on protein contained in the about 32 kD protein band identified in the sample containing Fraction 40, using standard procedures described herein in Example 10. The N-terminal partial amino acid sequence of the protein was determined to be Val Asn Val Lys Pro Lys Pro Asn Gln Asp Asp Tyr Cys Asn Leu Asn Cys Tyr Asn Gly Pro Xaa Val Xaa Xaa (denoted herein as SEQ ID NO:108; wherein "Xaa" represents any amino acid residue) Synthetic oligonucleotide primers were designed using SEQ ID NO:108 and used to isolate a nucleic acid molecule encoding SEQ ID NO:108 as follows. Sense primer 1, referred to as fsMvnv-1a, having the nucleotide sequence 5' AAT GTW AAA CCW AAA CCW AAY CAA GAY G 3' (wherein W denotes A or T and Y denotes C or T), and designated SEQ ID NO:109 was used in combination with the M13 forward universal standard primer (SEQ ID NO:85) to produce a PCR product from a whole fed flea cDNA library (prepared as described in Example 6 of related PCT Publication No. WO 96/11,271). PCR amplification was conducted using standard techniques. The resulting PCR amplification products were used for a nested PCR amplification using another degenerate synthetic primer referred to as fsMvnv-2a, having nucleotide sequence 5' CCW AAA CCW AAY CAA GAY GAY TAT TG 3' (wherein W denotes A or T and Y denotes C or T), SEQ ID NO:110 and the T7 standard primer (SEQ ID NO:88. The resulting PCR amplification product was a fragment of about 880 nucleotides, denoted herein as nfspM(N)$_{878}$ and represented herein by SEQ ID NO:111. The PCR product was cloned into the InVitrogen, Corp., TA™ cloning vector and subjected to DNA sequence analysis using standard techniques.

Translation of SEQ ID NO:111 suggests that nucleic acid molecule nfspM(N)$_{878}$ encodes a non-full-length flea salivary protein of about 238 amino acids, referred to herein as Pfsp(N)$_{238}$, having amino acid sequence SEQ ID NO:112, assuming the first codon spans from nucleotide 1 through nucleotide 3 of SEQ ID NO:111 and the last codon spans from nucleotide 712 through nucleotide 714 of SEQ ID NO:111. The complement of SEQ ID NO:111 is represented herein by SEQ ID NO:113.

Comparison of amino acid sequence SEQ ID NO:112 (i.e., the amino acid sequence of PfspM(N)$_{238}$) with amino acid sequences reported in GenBank indicates that SEQ ID NO:112, showed the most homology, i.e., about 25% identity, between SEQ ID NO:112 and SwissProt accession number p35778: Solenopsis invicta (red imported fire ant). Comparison of nucleic acid sequence SEQ ID NO:111 (i.e., the nucleic acid sequence of nfspM(N)$_{878}$ with nucleic acid sequences reported in GenBank revealed no significant homology.

2. cDNA Clone

A DNA probe comprising nucleotides from nfspM(N)$_{878}$, SEQ ID NO:111 was labeled with $^{32}$P and used to screen a whole flea cDNA library (prepared as described in Example 6 of related PCT Publication No. WO 96/11,271) using standard hybridization techniques. A clone was isolated having about a 1297 nucleotide insert, referred to herein as nfspM(N)$_{1297}$, denoted herein as SEQ ID NO:114. The complement of SEQ ID NO:114 is represented herein by SEQ ID NO:116.

Translation of SEQ ID NO:114 suggests that nucleic acid molecule nfspM(N)$_{1297}$encodes a full-length flea salivary protein of about 264 amino acids, referred to herein as PfspM(N)$_{264}$, having amino acid sequence SEQ ID NO:115, assuming the initiation codon spans from nucleotide 341 through nucleotide 343 of SEQ ID NO:114 and the termination codon spans from nucleotide 1133 through nucleotide 1135 of SEQ ID NO:114. The coding region encoding PfspM(N)$_{2641}$ is represented by nucleic acid molecule nfspM(N)$_{792}$, having a coding strand with the nucleic acid sequence represented by SEQ ID NO:117 and a complementary strand with nucleic acid sequence SEQ ID NO:118. The amino acid sequence of PfspM(N)$_{264}$ predicts that PfspM(N)$_{264}$ has an estimated molecular weight of about 29.6 kD and an estimated pI of about 10.16.

Analysis of SEQ ID NO:115 suggests the presence of a signal peptide encoded by a stretch of amino acids spanning from amino acid 1 through amino acid 22. The proposed mature protein, denoted herein as PfspM(N)$_{242}$, contains about 242 amino acids which is represented herein as SEQ ID NO:119. The amino acid sequence of PfspM(N)$_{242}$ (i.e. SEQ ID NO:119) predicts that PfspM(N)$_{242}$ has an estimated molecular weight of about 27.2 kD and an estimated pI of about 10.17. The coding region encoding PfspM(N)$_{242}$ is represented by nucleic acid molecule nfspM(N)$_{726}$ having a coding strand with the nucleic acid sequence represented by SEQ ID NO:120 and a complementary strand with nucleic acid sequence SEQ ID NO:121.

Comparison of amino acid sequence SEQ ID NO:119 (i.e., the amino acid sequence of PfspM(N)$_{242}$) with amino acid sequences reported in GenBank indicates that SEQ ID NO:119, showed the most homology, i.e., about 25% identity, between SEQ ID NO:119 and SwissProt accession number p35778: Solenopsis invicta (red imported fire ant). Comparison of nucleic acid sequence SEQ ID NO:117 (i.e., the nucleic acid sequence of nfspM(N)$_{792}$) with nucleic acid sequences reported in GenBank revealed no The partial N-terminal amino acid sequence of a fspL protein (SEQ ID NO:9 of related U.S. Pat. No. 5,646,115) was used to synthesize degenerate antisense Primer L1-B, having the nucleotide sequence 5' AAY GAT AAA GAA CCW GGW AAC AC 3' (wherein W denotes A or T and Y denotes C or T) and designated SEQ ID NO:122, was used in combination with the M13 forward universal standard primer (SEQ ID NO:85) to produce a PCR product from a whole fed flea cDNA library (prepared as described in Example 6 of related PCT Publication No. WO 96/11,271). PCR amplification was conducted using standard techniques. The resulting PCR amplification products were used for a nested PCR amplification as follows. Primer J2L2A, a sense primer having a nucleic acid sequence 5' GAA GTW ATG GAY AAA TTR AGR AAR CAR GC 3' (wherein W denotes A or T; R denotes A or G; and Y denotes C or T) and designated SEQ ID NO:123, was used in conjunction with T7 standard primer (SEQ ID NO:88) to produce a PCR product using standard techniques. This PCR amplification product was further amplified using primer L2-B having nucleic acid sequence 5' GCA CAA CCW AGA ACW GAY GGW CAA MG 3' (wherein W denotes A or T; Y denotes C or T; and M denotes A or C) and designated SEQ ID NO:124 used in combination with primer PBS-667 5' GAA TTG GGT ACC GGG CCC 3' (SEQ ID NO:125).

The resultant PCR product, a fragment of about 500 nucleotides designated nfspL3$_{5001}$ was cloned into the InVitrogen, Corp., TA™ cloning vector and subjected to DNA sequence analysis using standard techniques. The resulting nucleic acid sequence is denoted herein as SEQ ID NO:126. The complement of SEQ ID NO:126 is represented herein as SEQ ID NO:128.

Translation of SEQ ID NO:126 suggests that nucleic acid molecule nfspL3$_{500}$ encodes a non-full-length flea salivary protein of about 61 amino acids, referred to herein as PfspL3$_{61}$, having amino acid sequence SEQ ID NO:127, assuming the first codon spans from nucleotide 1 through nucleotide 3 of SEQ ID NO:126 and the last codon spans from nucleotide 181 through nucleotide 183 of SEQ ID NO:126. The nucleic acid sequence encoding PfspL3$_{611}$ is represented by nucleic acid molecule nfspL3$_{183}$, having a coding strand with the nucleic acid sequence represented by SEQ ID NO:129 and a complementary strand with nucleic acid sequence SEQ ID NO:130. The amino acid sequence of PfspL36$_1$ predicts that PfspL3$_{61}$ has an estimated molecular weight of about 6.6 kD and an estimated pI of about 8.28.

A GenBank homology search revealed no significant homology between amino acid sequence SEQ ID NO:127 and nucleic acid sequence SEQ ID NO:129 and known amino acid sequences or nucleic acid sequences, respectively.

Using standard techniques, nucleic acid molecule nfspL$_{500}$ can be used as a probe to isolate a nucleic acid molecule that encodes a protein corresponding to a full-length, or larger partial, fspL protein.

EXAMPLE 15

This example describes the collection of flea saliva proteins using a saliva collection apparatus of the present invention.

Figure 4A:
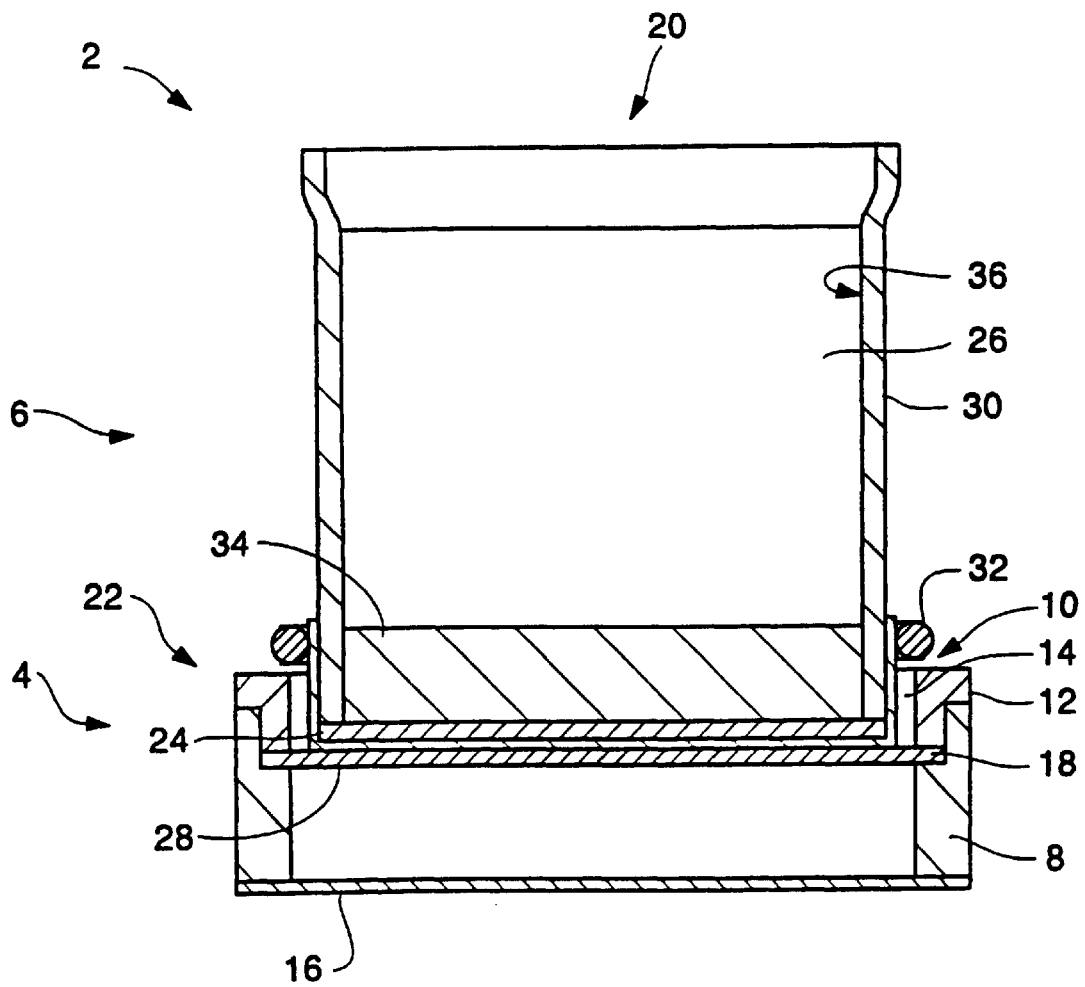
FIG. 4A illustrates a cross-section of a flea saliva collection apparatus of the present invention.
Figure 4B:
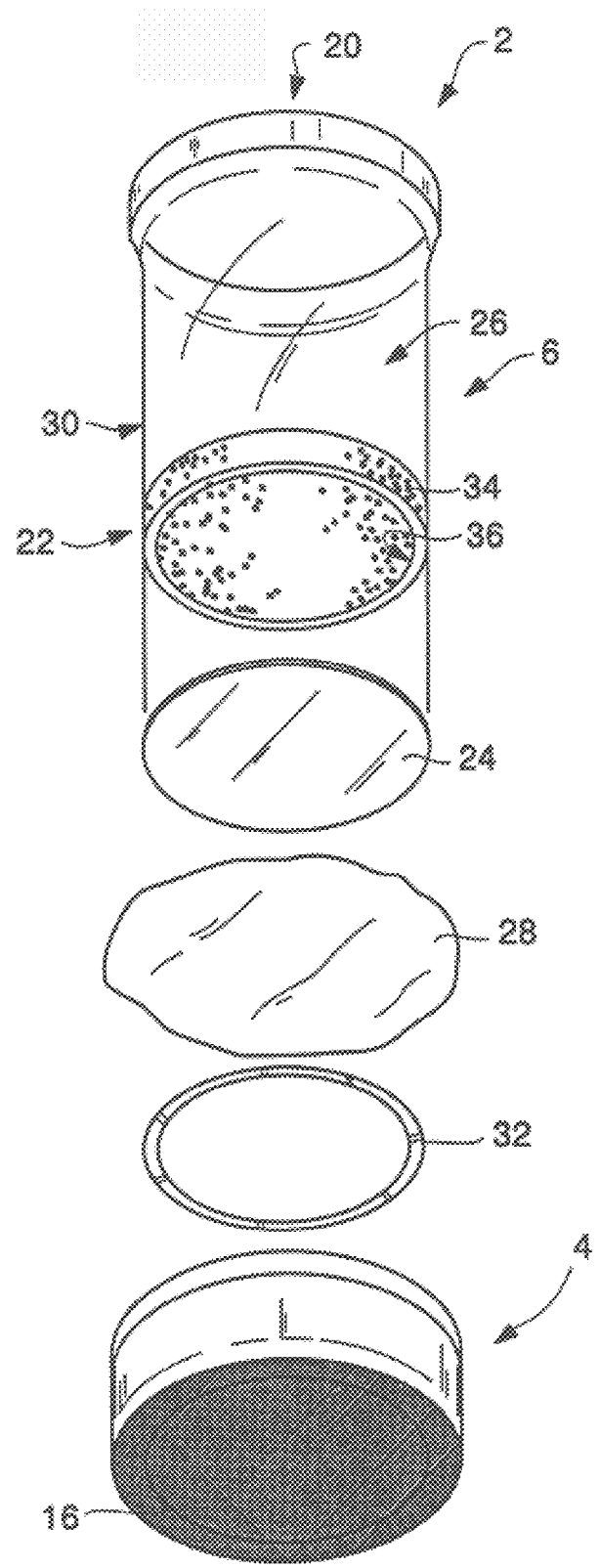
FIG. 4B illustrates a blow-out of a flea saliva collection apparatus of the present invention.

A saliva collection apparatus was prepared as follows. Referring to FIG. 4A and 4B, a humidifying means (34) comprising about 4 pieces of VWR blotting pads #320 (VWR, Denver, Colo.) was prepared that fit the inner diameter (about 47 mm in diameter) of a chamber (6) of a saliva collection apparatus (2). The blotting pads were pre-wetted using a sufficient amount of pre-wetting solution (sterile water containing 50 units/ml penicillin and 50 μg/ml streptomycin, available from Sigma, St. Louis, Mo.) such that the blotting pads were damp but not dripping wet. The pre-wetted filters (34) were placed inside the bottom end (22) of the chamber (6) of the saliva collection apparatus (2) such that the filter paper sat immediately inside the bottom end (22) of the chamber (6).

A collection means (24) comprising a Durapore™ membrane (available from Millipore, Bedford, Mass.) was cut to fit the outer diameter (about 48 mm in diameter) of the chamber (6) of the saliva collection apparatus (2). The Durapore™ membrane was pre-wetted using the pre-wetting solution described above. The Durapore™ membrane (24) was placed immediately outside the bottom end (22) of the chamber (6) such that the Durapore™ membrane (24) contacted the outer rim of the bottom end (22) of the chamber (6) and also contacted the damp filter paper. A barrier means comprising a piece of stretched Parafilm™ (28) (available from American National Can™, Greenwich, Conn.) was stretched over the collection means (24) and bottom end (22) of the chamber (6) and up the outer wall (30) of the chamber (6). A rubber seal (32) (i.e., an O-ring) was placed over the Parafilm™ (28) thereby further securing the Parafilm™ (28) across the collection means (24) and to the outer wall (30) and to seal in the chamber (6) environment.

The collection apparatus (2) was preassembled and then the top end (20) of the chamber (6) was attached to an artificial feeding system capable of acting as a source of heat and humidity such as that described by Wade et al., (ibid.). The artificial feeding system comprised a large plexiglass box (40 cm×40 cm×40 cm) divided horizontally into an upper compartment and a lower compartment by a plexiglass shelf having holes drilled through. A collection apparatus (2) was inserted into a hole such that the chamber (6) of the apparatus (2) was located above the shelf in the upper compartment and the housing (4) was located below the shelf in the lower compartment. The apparatus (2) was secured to the shelf by attaching a rubber band attached to metal hooks placed in the shelf Any open holes in the shelf were closed off using rubber stoppers to isolate the environment within the upper compartment from the environment within the lower compartment. The upper compartment contained two trays of water, a fan and a heating block. The trays of water were placed such that the fan faced the trays. While the apparatus (2) was maintained in the artificial feeding system, the fan was blown continuously thereby circulating heat and humidity throughout the upper compartment and the chamber (6) of the collection apparatus (2). As such, the relative humidity within the chamber (6) was maintained at about 94% humidity and the temperature was maintained at about 37° C.

About 3,000 to 5,000 newly emerged unfed *Ctenocephalides felis* fleas were added to the housing (4) of the collection apparatus (2). The fleas were first collected in a 20 gallon glass aquarium. The fleas were then transferred to the housing (4) of a collection apparatus (2) by placing the end of the housing (4) having the nylon mesh of the exchange means (16) on top of a vacuum chamber and aspirating the fleas from the aquarium into the housing (4) through a tygon tubing. The housing (4) was then covered with the nylon mesh of the retaining means (18) to secure the fleas within the housing (4). The bottom end (22) of the chamber (6) was then placed on the housing (4) such that the Parafilm™ (28) and the nylon mesh of the retaining means (18) were juxtaposed. When the collection apparatus (2) was attached to the artificial feeding system, the ambient temperature within the housing (4) was maintained at about 27° C. while the ambient temperature of the chamber (6) was maintained at about 37° C. The relative humidity of the housing (4) was maintained at about 50% by closing the lower compartment with the plexiglass shelving.

In one experiment, flea saliva products were collected on a Durapore™ membrane (24) and visualized by immersing the membrane in 0.1 % Coomassie blue stain for 20 minutes, destaining the membrane in 50% methanol and air drying the membrane. Proteins deposited on the membrane were detected by their blue color.

In another experiment, flea saliva products were collected for 0 through 24 hours, 24 through 72 hours, and 72 through 120 hours after loading fleas into the collection apparatus. At 24 hours, 72 hours and 120 hours, the Durapore™ membrane (24) attached to the collection apparatus (2) was removed and a new pre-wetted Durapore™ membrane (24) was attached to the same apparatus. The blotting pads were re-wetted using the pre-wetting solution described above when the new Durapore™ membrane (24) was replaced. Flea saliva products were extracted from the Durapore™ membrane (24) by soaking each membrane from each time point separately in a solvent comprising 50% acetonitrile with 1% TFA overnight at room temperature with stirring to obtain a flea saliva product mixture comprising flea saliva products that had eluted into the solvent. The mixture containing the flea saliva products was recovered and lyophilized until dry to form a pellet. The amount and characteristics of flea saliva proteins eluted from each Durapore™ membrane from each time point was determined by reducing 14% Tris-glycine SDS-PAGE using techniques similar to those described by Sambrook et al., ibid. The resultant protein pattern was visualized by staining the gel with Coomassie blue stain using techniques as described above. The amount of saliva proteins collected on the membranes decreased when the fleas had been in the collection apparatus for more than 72 hours.

EXAMPLE 16

Standard procedures to collect FS-1, FS-2 and FS-3 flea saliva extracts of the present invention were performed as follows. Flea saliva products were collected for 72 hours on collection membranes using the method described in Example 15, except that for flea saliva extract FS-3, the collection membrane was DE-81 chromatography paper, available from Whatman, Inc., Clifton, N.J.

A. Flea Saliva Extracts FS-1 and FS-2

Flea saliva products were extracted from the Durapore™ membrane (24) by soaking each membrane from each time point separately in a first solvent comprising 50% acetonitrile with 0.1% TFA for 8 hours. The first mixture containing the eluted flea saliva products was recovered and lyophilized until dry, thereby forming a first pellet. The same membranes were then soaked in a second solvent comprising 50% acetonitrile with 1% TFA overnight at room temperature with stirring to obtain a flea saliva product mixture comprising flea saliva products that had eluted into the second solvent. The second mixture was recovered from this second extraction and lyophilized until dry to form a second pellet.

The two pellets recovered from the two lyophilization steps were mixed with a third solvent comprising 12.8% acetonitrile and flea saliva products solubilized in the solvent were recovered. The non-solubilized material was mixed again with 12.8% acetonitrile and additional flea saliva products solubilized in the solvent were recovered. The two mixtures were combined to obtain the extract FS-1.

The non-solubilized material remaining after the second solubilization step was then mixed with 50% acetonitrile which solubilized the remaining material to obtain the extract FS-2.

The amount and characteristics of flea saliva proteins contained in the FS-1 and FS-2 flea saliva extracts obtained in at least one experiment were determined according to the following method. Each extract was concentrated by evaporation under vacuum and evaluated by reducing 16% Trisglycine SDS-PAGE using techniques similar to those described by Sambrook et al., ibid. Using such standard procedures, about 10 $\mu$g of FS-1 or FS-2 eluted from the Durapore™ membrane was loaded onto a 16% Tris-glycine polyacrylamide gel and subjected to electrophoresis under reducing conditions. The gel was stained with Coomassie blue and dried.

Figure 1B:
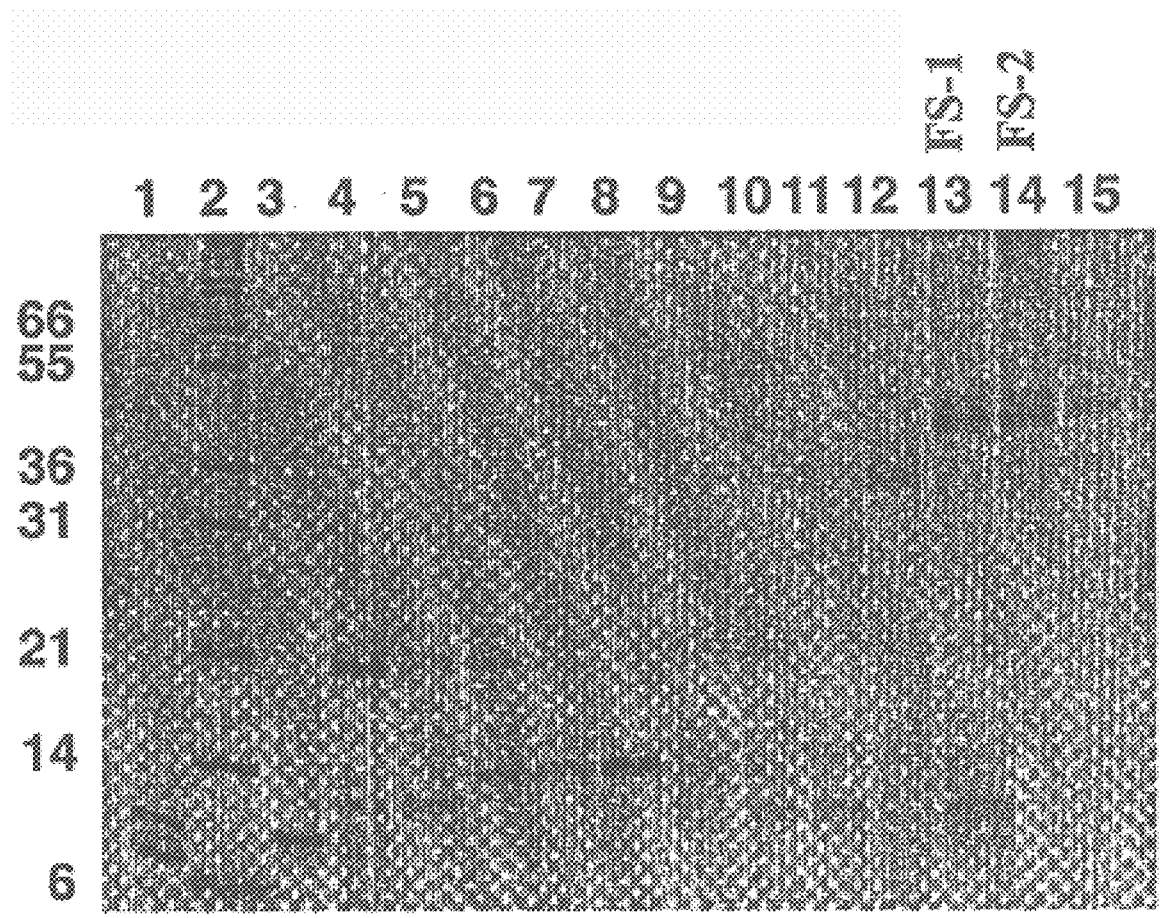
FIG. 1B illustrates the resolution of flea saliva proteins, FS-1 and FS-2 by reducing 16% Tris glycine SDS-PAGE.

The results are shown in FIG. 1B. FS-1 is shown in lane 13 of FIG. 1B and FS-2 is shown in lanes 14 and 15 of FIG. 1B. FS-1 was found to contain proteins estimated to have the following molecular weights: 9 kD, 11 kD, 12 kD, 15 kD, 22 kD, 48 kD, 50 kD, 53 kD, 80 kD, 124 kD, 130 kD, 189 kD and 201 kD. Those proteins of 80 kD and above were much fainter than the lower molecular weight bands. FS-2 was found to contain proteins having the following molecular weights: 47 kD, 49 kD, 52 kD, 57 kD, 64 kD, 71 kD, 88 kD, 96 kD, 97 kD, 130 kD, 161 kD, 175 kD, 189 kD, 222 kD, 235 kD and 302 kD. The bands at 47 kD, 49 kD and 52 kD were more prominent than the bands having higher molecular weights. The results suggest that a substantial portion of the protein contained in FS-2 is fspN1, fspN2 and/or fspN3.

Protein concentrations were measured using a Bio-Rad Bradford assay (available from Bio-Rad, Hercules, Calif.). The results indicate that about 750 $\mu$g of protein can be collected in about $3.66 \times 10^7$ flea hours ($5.08 \times 10^5$ fleas for 72 hours) in an FS-1 extract and about 2.35 mg of protein can be collected in about $3.66 \times 10^7$ flea hours in an FS-2 extract.

B. Flea Saliva Extract FS-3

Flea saliva products to produce FS-3 flea saliva extract were collected in a manner similar to the method by which FS-1 and FS-2 were collected, except that the collection membrane (24) was DE-81 chromatography paper. Flea saliva products were extracted from the DE-81 membrane by soaking each membrane from each time point separately in a solvent comprising 1M NaCl in phosphate buffered saline for about 8 hours. The products were recovered from the solvent using standard techniques, such as disclosed for FS-1 and FS-2.

Analysis of an FS-3 flea saliva extract indicated that FS-3 appeared to contain proteins such as those found in FS-1 and FS-2, at least based on 1-dimensional gel electrophoresis. The SDS-PAGE pattern of FS-3, for example, was very similar to that of FS-1 except that there appeared to be increased quantities of the higher molecular weight proteins in the FS-3 extract. FS-3 flea saliva extract was also shown to have anti-coagulation activity, using techniques standard in the art; see, for example, Dunwiddle et al., 1991, *Thrombosis Research* 64,787–794; Ribeiro et al., 1990, *Comp. Biochem. Physiol.* 95,215–218; Ribeiro et al., 1990, *Br. J. Pharmacol.* 101, 932–936; Ribeiro et al., 1987, *Exper. Parasitol.* 64,347–353; Cupp et al., 1994, *Am. J. Trop. Med. Hyg.* 50,241–246; Garcia et al., 1994, *Exper. Parasitol.* 78, 287–293. The FS-3 extract was also shown to exhibit acid phosphatase activity, using techniques standard in the art, such as those supplied by Sigma, St. Louis, Mo., with the Sigma acid phosphtase assay kit.

EXAMPLE 17

This example describes the characterization by HPLC of flea saliva proteins collected using a saliva collection apparatus of the present invention.

An FS-1 flea saliva extract was collected as described in Example 16 from about 140,000 fleas for 72 hours. Proteins contained in FS-1 were resolved using standard procedures of high pressure liquid chromatography (HPLC). Specifically, the proteins were passed over a 15 cm×0.46 cm C4 column using a gradient from 0.1% TFA in water (Solvent A) to 0.085% TFA in 90% CH$_3$CN (Solvent B) at a flow rate of 0.8 ml per minute. Thus, the gradient was about 5.6% Solvent B at 15 minutes and about 100% Solvent B at 75 minutes.

Figure 2:
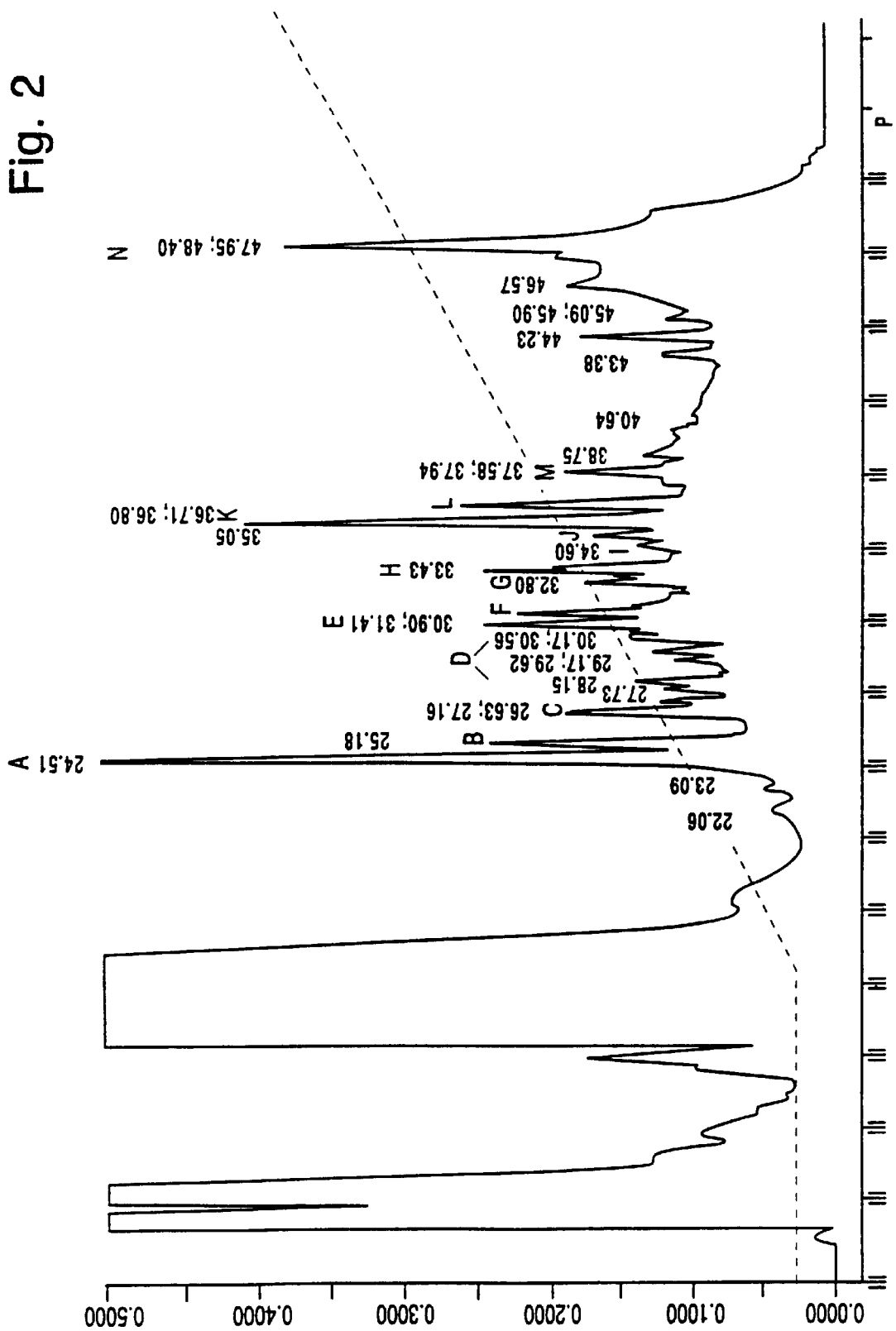
FIG. 2 illustrates the resolution of flea saliva proteins using high pressure liquid chromatography.

The results are shown in FIG. 2. About 14 major protein fractions were resolved. The recovery for each peak was about 5 $\mu$g to 10 $\mu$g of protein per peak. The peaks were labelled peak A, peak B, peak C, peak D, peak E, peak F, peak G, peak H, peak I, peak J, peak K, peak L, peak M and peak N, as shown in FIG. 2, and represent, respectively, protein formulations fspA, fspB, fspC1 and fspC2, fspD1 and fspD2, fspE, fspF, fspG1, fspG2, fspG3, fspH, fsp1, fspJ1 and fspJ2, fspK, fspL1 and fspL2, fspM1 and fspM2, and fspN1, fspN2 and fspN3.

Figure 1C:
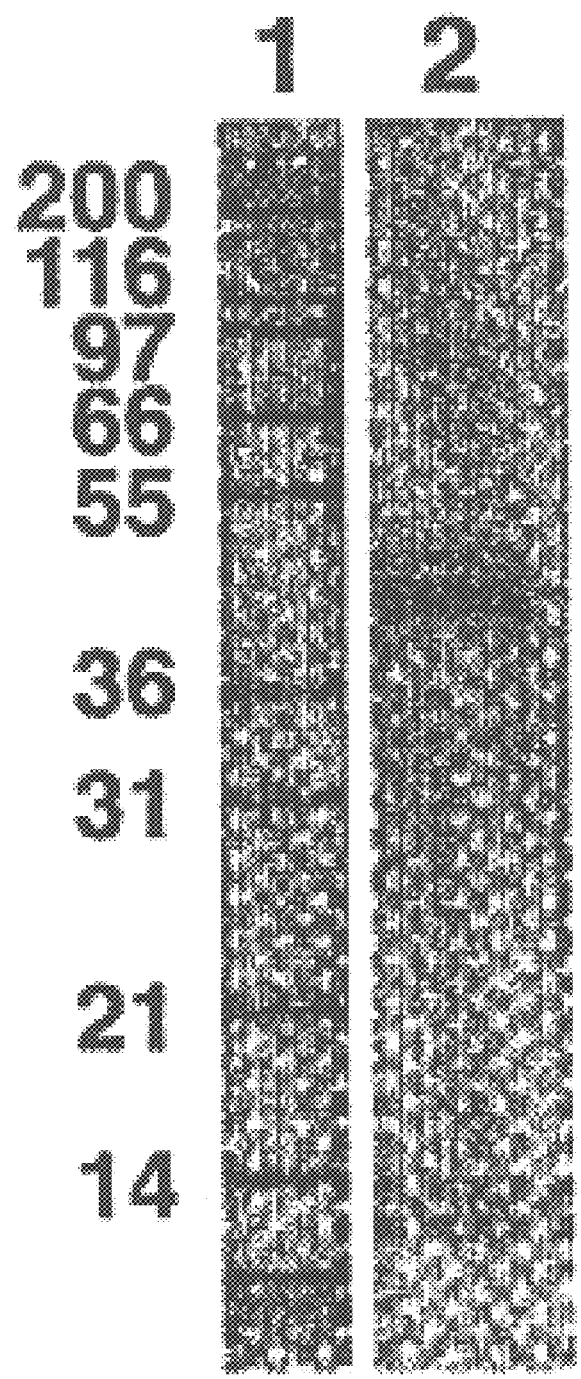
FIG. 1C illustrates the resolution of fspN by reducing 16% Tris glycine SDS-PAGE.

Samples from each HPLC peak were resolved by Tris Glycine SDS-PAGE gels using the method described in Example 15. The results are shown in FIGS. 1A, 1B and 1C. The proteins shown in FIGS. 1A and 1B were resolved on 16% Tris Glycine SDS-PAGE gels and the proteins shown in FIG. 1C were resolved on a 14% Tris Glycine SDS-PAGE gel. Protein markers are shown in lane 1 of FIG. 1A, lane 2 of FIG. 1B and lane 1 of FIG. 1C. The additional lanes show saliva formulation samples as follows:

| Lane | Fraction(s) | Fs-() |
|---|---|---|
| FIG. 1A | | |
| 1) | — | Mol. Wt. Std. |
| 2) | 10 | — |
| 3) | 11–13 | A |
| 4) | 14 | B |
| 5) | 15 | B |
| 6) | 16 | C1 |
| 7) | 17 | C2 |
| 8) | 18 | D1 |
| 9) | 19 | D1 |
| 10) | 20 | D2 |
| 11) | 21 | D2 |
| 12) | 22 | E |
| 13) | 23 | F |
| 14) | 24 | G |
| 15) | 25 | G |
| FIG. 1B | | |
| 1) | 26–27 | G |
| 2) | — | Mol. Wt. Std. |
| 3) | 28 | H |
| 4) | 29–30 | I |
| 5) | 31 | J |
| 6) | 32 | K |
| 7) | 33 | K |
| 8) | 34 | L |
| 9) | 35 | M1 |
| 10) | 36–37 | M1 |
| 11) | 38 | M1 |
| 12) | 39–50 | M2 |
| 13) | — | FS-1 |
| 14) | — | FS-2 |
| 15) | — | FS-2 |
| FIG. 1C | | |
| 1) | — | Mol. Wt. Std. |
| 2) | 56–68 | N |

Referring to FIG. 1A, the following flea saliva proteins (referred to as bands) were observed: a prominent band of about 10 kD in peak A and peak B samples; a prominent band of about 6 kD and a less prominent band of 9 kD in a peak C sample referred to as C1; a prominent band of about 7 kD in a peak C sample referred to as C2; a prominent band of about 7 kD and a less prominent band of 8 kD in a peak D sample referred to as D1; a prominent band of about 8 kD and a less prominent band of 9 kD in a peak D sample referred to as D2; a prominent band of 8 kD and a less prominent band of about 7 kD in peaks E and F samples; and a prominent band of about 9 kD, and less prominent bands of about 7 kD and 10 kD in a peak G sample. Referring to FIG. 1B, the following flea saliva proteins were observed: a prominent band of about 9 kD and a less prominent band of about 12 kD in a peak H sample; a prominent band of about 21 kD, and less prominent bands of about 7 kD, 9 kD, 12 kD, 14 kD, and 70 kD in a peak I sample; prominent bands of about 14 kD and 21 kD, and less prominent bands of about 11 kD and 17 kD in a peak J sample; prominent bands of about 14 kD and 15 kD and less prominent bands of about 12 kD, 18 kD and 21 kD in a peak K sample; a prominent band of about 15 kD in a peak L sample; prominent bands of about 11 kD, 12 kD and 21 kD and less prominent bands of about 15 kD, 17 kD, 22 kD and 37 kD in a peak M sample referred to as M1; and a prominent band of about 36 kD and less prominent bands of about 11 kD, 21 kD and 22 kD in a peak M sample referred to as M2. Referring to FIG. 1C, prominent bands of about 42 kD, 43 kD and 44 kD and a less prominent band of about 32 kD were detected in a peak N sample.

EXAMPLE 18

This example describes the amino acid sequence analysis of the isolated and HPLC purified flea saliva proteins.

Amino (N-) terminal amino acid sequencing analysis was performed on several of the HPLC-separated flea saliva proteins described in Example 17 using standard procedures known to those in the art (see, for example, Geisow et al., 1989, in *Protein Sequencing: A Practical Approach*, J B C Findlay and M J Geisow (eds.), IRL Press, Oxford, England, pp.85–98; Hewick et al., 1981, *J. Biol. Chem.*, Vol. 256, pp. 7990–7997).

The N-terminal partial amino acid sequence of flea saliva protein fspA, which migrated as Peak A in FIG. 2, was determined to be

```
Y G K Q Y S E K G G R G Q R H Q I L K K G K
    Q Y S         S K       I   L D L
    S
    R
``` as represented in standard single letter code. This N-terminal partial amino acid sequence of fspA is denoted SEQ ID NO:132. It should be noted that there was heterogeneity in several positions which may represent sequence errors (i.e., misidentification of amino acids) or allelic variations in the flea population from which the saliva proteins were collected. There was an apparently equal likelihood of finding any one of the alternative amino acids at the indicated positions.

The N-terminal partial amino acid sequence of flea saliva protein fspB, which migrated as Peak B in FIG. 2, was determined to be S/QGKQYSEXG/SK, denoted SEQ ID NO:133. This amino acid sequence was essentially the same, or at least a subset of, the N-terminal amino acid sequence obtained from flea saliva protein fspA.

Sequence analysis of Peak G proteins indicated the presence of three proteins in that peak, referred to herein as fspG1, fspG2 and fspG3. Flea saliva protein fspG1, having a molecular weight of about 9 kD, had an N-terminal partial amino acid sequence of DRRVSK, denoted SEQ ID NO:134. This N-terminal amino acid sequence is the same as that for fspH, as shown in SEQ ID NO:135, SEQ ID NO:136, SEQ ID NO:137, SEQ ID NO:138 and SEQ ID NO:139. Flea saliva protein fspG2, having a molecular weight of about 7 kD, had an N-terminal partial amino acid sequence of SKMVTEKXKSGGNNPSTKEVSIP, denoted SEQ ID NO:140. Flea saliva protein fspG3, having a molecular weight of about 6 kD, had an N-terminal partial amino acid sequence of EVSIPSGKLTIEDFXIGNHQ, denoted SEQ ID NO:141. A comparison of SEQ ID NO:141 with SEQ ID NO:140 indicates that fspG3 may be a proteolytic degradation product of fspG2, as the last five amino acids of fspG2 are identical with those at the N-terminus of fspG3.

The N-terminal partial amino acid sequence of flea saliva protein fspH, which migrated as Peak H in FIG. 2, was determined to be DRRVSKTXQSGGKIQSEXQVVIKS GQH/YILENYXSDGR, denoted herein as SEQ ID NO:139. Histidine and tyrosine were equally likely at amino acid position 27.

Figure 3:
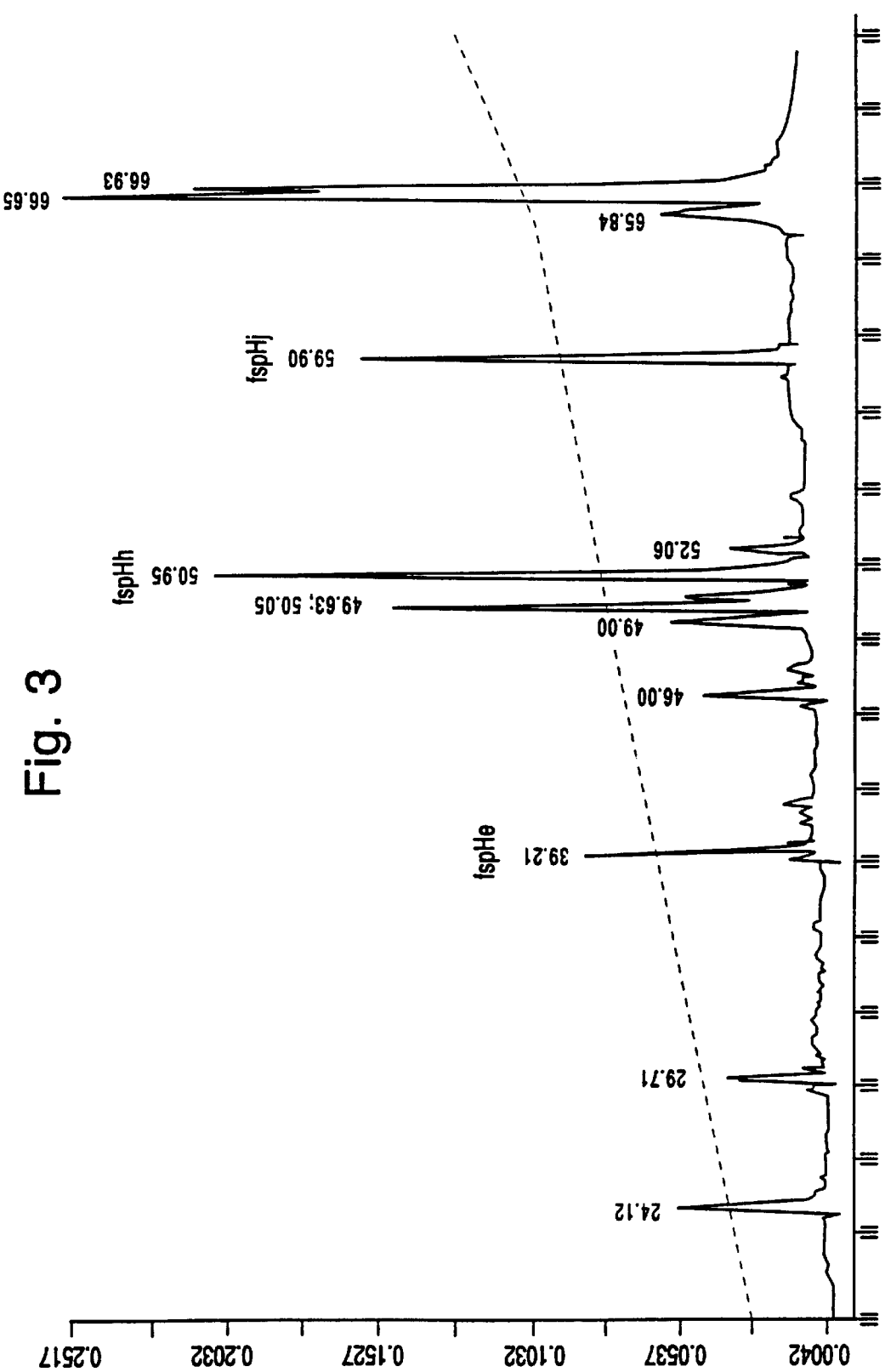
FIG. 3 illustrates the peaks obtained from reverse phase HPLC resolution of proteolytic fragments of fspH protein digested with Endoproteinase Asp-N.

Flea saliva protein fspH was also subjected to proteolytic cleavage in order to obtain internal amino acid sequence data. Specifically, fspH was cleaved with Endoproteinase Asp-N (available from Boehringer Mannheim Biochemica, Indianapolis, Ind.) using methods standard in the art. The digested protein was then resolved by HPLC using the method described by Stone et al. (ibid.). The resultant HPLC profile is shown in FIG. 3. Three proteolytic fragments were isolated, that are referred to herein as fspHe, fspHh and fspHj.

The N-terminal partial amino acid sequence of fspHe was determined to be DSKHCYCEAPYS, also denoted SEQ ID NO:136. The N-terminal partial amino acid sequence of fspHh was determined to be DGRNNNNPCHLFCMR ECRSGNGGCGNGGRTRPDSKHC, also denoted SEQ ID NO:137. The N-terminal partial amino acid sequence of fspHj was determined to be DRRVSKTCQSG, also denoted SEQ ID NO:138. Comparison of SEQ ID NO:138 to SEQ ID NO:139 indicated that fspHj was the N-terminal fragment of fspH.

By aligning SEQ ID NO:139, SEQ ID NO:136, SEQ ID NO:137 and SEQ ID NO:138, the following amino acid sequence was deduced, starting at the N-terminus of fspH: DRRVSKTCQSGGKIQSEXQVVIKSGQHIYILENYXS DGRNNNNPCHLFCMRECRSGNGGCGNGGRTRPD SKHCYCEAPYS. This amino acid sequence is denoted SEQ ID NO:135 and is believed to represent most of fspH since the molecular weight of a protein having this sequence is about 8600 kD.

The N-terminal partial amino acid sequence of flea saliva protein fspI, which migrated as Peak I in FIG. 2, was determined to be EDIWKVNKKXTSGGKNQDRKLDQI IQKGQQVXXQNXXK, denoted herein as SEQ ID NO:142.

Sequence analysis of Peak J proteins indicated the presence of two proteins in that peak, referred to herein as fspj1 and fspJ2. The N-terminal partial amino acid sequence of flea saliva protein fspJ1 was determined to be NSHEPGNTRKIREVMDKLRKQHP, denoted herein as SEQ ID NO:143. The N-terminal partial amino acid sequence of flea saliva protein fspJ2 was determined to be EIKRNSHEPGNTRKIREVMDKLRKQHP, denoted herein as SEQ ID NO:144. The proteins represented by SEQ ID NO:143 and SEQ ID NO:144 were not separately resolved by SDS-PAGE as described in Example 15. Comparison of SEQ ID NO:143 and SEQ ID NO:144 suggest that fspj1 may be a truncated version of fspJ2, in that the N-terminal partial amino acid sequence of fspJ1 appears to be very similar to that of fspJ2 except that fspj1 lacks the first 4 amino acids found at the N-terminus of fspJ2.

Sequence analysis of Peak L proteins indicated the presence of two proteins in that peak, referred to herein as fspL1 and fspL2. That there were two proteins, namely fspL1 and fspL2, was shown by subjecting peak L to C4 reverse phase chromatography using 0.13% heptafluorobutyric acid (Solvent A) and 0.1 % heptafluorobutyric acid in 90% acetonitrile (Solvent B) in the following gradient format: an 80 minute gradient from 30% Solvent B to 70% Solvent B. The N-terminal partial amino acid sequence of the HPLC-separated fspL1 was determined to be NDKEPGNTRKIREVMDKLRKQAQPRTDGQRPKTXIM, also denoted SEQ ID NO:145. The N-terminal partial amino acid sequence for fspL2 was determined to be XLXRNDKEPGNTRKIREVMDK, also denoted SEQ ID NO:146. A comparison of SEQ ID NO:145 and SEQ ID NO:146 indicates that fspL1 and fspL2 are similar proteins, except that fspL1 is 4 amino acids shorter than fspL2 at the N-terminus.

Resolution of proteins contained in Peak N by SDS-PAGE as described in Example 17 revealed 3 distinct bands. The bands were denoted flea saliva proteins fspN 1, fspN2 and fspN3. The N-terminal partial amino acid sequence of fspN1 was determined to be NDELKFVFVMAK, also denoted SEQ ID NO:147. The N-terminal partial amino acid sequence of fspN2 was determined to be XDELKFVFVMAKGPSXQAXDYPC, also denoted SEQ ID NO:148. The N-terminal partial amino acid sequence of fspN3 was determined to be ELKFVFATARGMSH TPCDYP, also denoted SEQ ID NO:149. Comparison of SEQ ID NO:147 and SEQ ID NO:148 suggests that fspN1 and fspN2 share the same N-terminal sequence. Since fspN1 and fspN2 migrate differently when subjected to SDS-PAGE, however, the two proteins are likely to be different homologues, possibly due to one protein having a longer C-terminal domain and/or due to post-translational modification(s). Comparison of SEQ ID NO:149 to SEQ ID NO:147 and SEQ ID NO:148 suggests that fspN3 may be a homologue of fspN1 and fspN2 with internal sequence variations.

Flea saliva proteins in Peak N were also subjected to proteolytic cleavage in order to obtain internal amino acid sequence data. Specifically, the proteins in Peak N were cleaved with Endoproteinase Asp-N (available from Boehringer Mannheim Biochemica, Indianapolis, Ind.) using methods standard in the art. The digested protein was then resolved by HPLC using the method described by Stone et al. (ibid.) and sequenced as previously described. A partial amino acid sequence of flea saliva proteins in Peak N, named fragment pfspN(100–101), was determined to be DIENIKKGEGQPGAPGGKENNLS/LVL, denoted herein as SEQ ID NO:150.

EXAMPLE 19

This example demonstrates the ability of a formulation of the present invention to induce flea allergy dermatitis in an animal susceptible to flea allergy dermatitis.

To determine whether the isolated flea saliva proteins described in Examples 2 and 3 were capable of inducing an allergic response in animals susceptible to flea allergy dermatitis, skin tests were performed on sensitized dogs. Six dogs were sensitized to fleas using the method of Gross, et al., 1985, *Veterinary Pathology*, Vol. 22, pp. 78–71. Briefly, each dog was exposed to about 25 *C. felis* fleas contained in chambers by allowing the contained fleas to feed on the experimental dogs for about 15-minute periods at weekly intervals. The six dogs were sensitized over the following periods: Dog 2080109 was exposed to fleas 38 times over a period spanning Aug. 31, 1993 through Jun. 7,1994. Dog 2082101 was exposed to fleas 22 times over a period spanning Dec. 14, 1993 through Jun. 7, 1994. Dog 2082128 was exposed to fleas 20 times over a period spanning Aug. 31, 1993 through May 24, 1994. Dog BFQ2 was exposed to fleas 17 times over a period spanning Mar. 15, 1994 through Jul. 12, 1994. Dog CPO2 was exposed to fleas 12 times over a period spanning Mar. 15, 1994 through Jun. 7, 1994. Dog CQQ2 was exposed to fleas 1 time on Mar. 15, 1994.

Skin testing was performed the morning of Jul. 21, 1994. The dogs were shaved in the lateral thorax/abdominal area and intradermally injected in that area with a variety of formulations of the present invention as well as with control solutions. The total volume per injection was 50 microliters ($\mu$l), with the formulations and controls being diluted in phenolated saline. Each dog received the injections listed in Table 1.

TABLE 1

Samples administered to dogs.

| SAMPLE | REPLICATES | μg/inj | FLEA-HOUR |
|---|---|---|---|
| DILUENT | 2 | N/A* | N/A |
| HISTAMINE | 2 | 1.38 | N/A |
| GREER | 3 | 50 (w/v) | N/A |
| FS-1 | 3 | 1.88 | 4,660 |
| A | 3 | 0.23 | 23,000 |
| B | 3 | 0.32 | 23,000 |
| C1 | 3 | 1.10** | 23,000 |
| C2 | 3 | 0.42 | 23,000 |
| D1 | 3 | 0.24 | 23,000 |
| D2 | 3 | 0.29 | 23,000 |
| E | 3 | 0.16 | 23,000 |
| F | 3 | 0.10 | 23,000 |
| G | 3 | 0.21 | 23,000 |
| H | 3 | 0.20 | 23,000 |
| I | 3 | 0.12 | 23,000 |
| J | 3 | 0.08 | 23,000 |
| K | 3 | 0.12 | 23,000 |
| L | 3 | 0.08 | 23,000 |
| M1 | 3 | 0.16 | 23,000 |
| M2 | 3 | 0.27 | 23,000 |
| N | 3 | 0.20 | 23,000 |
| FS-2 | 3 | 0.71 | 4,660 |

*N/A is not applicable
**Apparent amount, probably artificially high due to assay interference Note that in these studies, fspJ1 and fspJ2 were administered together as fspj; fspL1 and fspL2 were administered together as fspL; fspN1, fspN2 and fspN3 were administered together as fspN. It is also to be noted that A, B, C1, C2, D1, D2, E, F, G, H, I, J, K, L, M1, M2 and N refer to flea saliva proteins fspA, fspB, fspC1, fspC2, fspD1, fspD2, fspE, fspF, fspG, fspH, fspI, fspJ, fspK, fspL, fspM1, fspM2 and fspN. The negative control comprised diluent (NC) and the positive controls comprised Greer antigen (GR) and histamine (HIS). The amount of Greer antigen used was determined by weight per volume (w/v) according to the information provided by the manufacturers (Greer Laboratories, Inc., Lenoir, N.C.). The amount of histamine used was determined by information provided on the supplier's label (available from Greer Laboratories, Inc., Lenoir, N.C.).

A. Comparison of Wheal Sizes at Sites of Injection

All injection sites were objectively (Obj) measured in millimeters (mm) at 15 min and subjectively (Sub) scored on a scale of 0 to 4. The subjective scoring was performed by Kenneth W. Kwochka, D. V. M., Diplomat ACVD, (American College of Veterinary Dermatologists) at Ohio State University, Columbus, Ohio. Tables 2 through 7 indicate the results obtained for each dog. # refers to the number designation given to each sample; antigen refers to the sample. Inj 1, Inj 2 and Inj 3 refer to triplicate injections and NA refers to "not applicable."

TABLE 2

DOG ID: 2082101

| # | Antigen | Inj 1 Sub | Inj 1 Obj | Inj 2 Sub | Inj 2 Obj | Inj 3 Sub | Inj 3 Obj |
|---|---|---|---|---|---|---|---|
| 1 | Neg Cntl | 0 | 6 | NA | NA | NA | NA |
| 2 | Histamine | 4 | 12 | NA | NA | NA | NA |
| 3 | Greer | 3 | 10 | 3 | 10 | 3 | 10 |
| 4 | FS-1 | 3 | 10 | 4 | 12 | 4 | 12 |
| 5 | A | 1 | 8 | 0 | 8 | 0 | 8 |
| 6 | B | 0 | 6 | 0 | 6 | 0 | 6 |
| 7 | C1 | 0 | 6 | 0 | 6 | 0 | 6 |
| 8 | C2 | 0 | 6 | 0 | 6 | 0 | 6 |
| 9 | D1 | 0 | 8 | 0 | 8 | 0 | 6 |
| 10 | D2 | 0 | 6 | 0 | 6 | 0 | 8 |
| 11 | E | 3 | 12 | 3 | 12 | 3 | 12 |
| 12 | F | 3 | 14 | 3 | 12 | 3 | 12 |
| 13 | G | 3 | 12 | 3 | 12 | 3 | 12 |
| 14 | H | 3 | 11 | 2 | 12 | 3 | 12 |
| 15 | I | 3 | 12 | 2 | 12 | 3 | 11 |
| 16 | J | 2 | 10 | 2 | 11 | 2 | 10 |
| 17 | K | 2 | 11 | 2 | 10 | 2 | 9 |
| 18 | L | 2 | 9 | 1 | 10 | 1 | 10 |
| 19 | M1 | 2 | 12 | 2 | 11 | 2 | 11 |
| 20 | M2 | 3 | 12 | 3 | 11 | 3 | 12 |
| 21 | N | 3 | 11 | 3 | 10 | 2 | 11 |
| 22 | FS-2 | 2 | 11 | 3 | 12 | 2 | 10 |
| 23 | Neg Cntl | 0 | 8 | NA | NA | NA | NA |
| 24 | Histamine | 4 | 14 | NA | NA | NA | NA |

TABLE 3

DOG ID: 2080109

| # | Antigen | Inj 1 Sub | Inj 1 Obj | Inj 2 Sub | Inj 2 Obj | Inj 3 Sub | Inj 3 Obj |
|---|---|---|---|---|---|---|---|
| 1 | Neg Cntl | 0 | 7 | NA | NA | NA | NA |
| 2 | Histamine | 4 | 14 | NA | NA | NA | NA |
| 3 | Greer | 0 | 8 | 0 | 8 | 0 | 8 |
| 4 | FS-1 | 4 | 13 | 4 | 13 | 4 | 13 |
| 5 | A | 0 | 9 | 0 | 8 | 0 | 8 |
| 6 | B | 0 | 7 | 0 | 7 | 0 | 7 |
| 7 | C1 | 0 | 8 | 0 | 7 | 0 | 7 |
| 8 | C2 | 0 | 8 | 0 | 7 | 0 | 8 |
| 9 | D1 | 1 | 9 | 1 | 9 | 1 | 9 |
| 10 | D2 | 1 | 9 | 1 | 8 | 1 | 8 |
| 11 | E | 3 | 11 | 3 | 11 | 2 | 10 |
| 12 | F | 3 | 11 | 3 | 13 | 4 | 13 |
| 13 | G | 3 | 14 | 3 | 13 | 3 | 13 |
| 14 | H | 2 | 12 | 2 | 11 | 2 | 10 |
| 15 | I | 2 | 10 | 3 | 10 | 3 | 10 |
| 16 | J | 2 | 10 | 3 | 10 | 3 | 10 |
| 17 | K | 2 | 9 | 2 | 9 | 2 | 9 |
| 18 | L | 1 | 9 | 1 | 6 | 1 | 7 |
| 19 | M1 | 3 | 11 | 3 | 13 | 3 | 13 |
| 20 | M2 | 3 | 14 | 3 | 13 | 3 | 14 |
| 21 | N | 3 | 13 | 3 | 14 | 2 | 10 |
| 22 | FS-2 | 2 | 9 | 1 | 7 | 1 | 8 |
| 23 | Neg Cntl | 0 | 6 | NA | NA | NA | NA |
| 24 | Histamine | 4 | 16 | NA | NA | NA | NA |

TABLE 4

DOG ID: 2082128

| # | Antigen | Inj 1 Sub | Inj 1 Obj | Inj 2 Sub | Inj 2 Obj | Inj 3 Sub | Inj 3 Obj |
|---|---|---|---|---|---|---|---|
| 1 | Neg Cntl | 0 | 6 | NA | NA | NA | NA |
| 2 | Histamine | 4 | 12 | NA | NA | NA | NA |
| 3 | Greer | 0 | 6 | 0 | 6 | 0 | 6 |
| 4 | FS-1 | 3 | 12 | 3 | 12 | 3 | 12 |
| 5 | A | 0 | 7 | 0 | 7 | 0 | 6 |
| 6 | B | 0 | 7 | 0 | 7 | 0 | 6 |
| 7 | C1 | 0 | 7 | 0 | 6 | 0 | 7 |
| 8 | C2 | 0 | 6 | 0 | 7 | 0 | 7 |
| 9 | D1 | 0 | 7 | 0 | 7 | 0 | 7 |
| 10 | D2 | 0 | 7 | 0 | 7 | 0 | 7 |

TABLE 4-continued

DOG ID: 2082128

| # | Antigen | Inj 1 Sub | Inj 1 Obj | Inj 2 Sub | Inj 2 Obj | Inj 3 Sub | Inj 3 Obj |
|---|---|---|---|---|---|---|---|
| 11 | E | 0 | 7 | 0 | 6 | 0 | 7 |
| 12 | F | 0 | 6 | 0 | 6 | 0 | 6 |
| 13 | G | 1 | 10 | 1 | 9 | 1 | 9 |
| 14 | H | 2 | 10 | 2 | 10 | 2 | 11 |
| 15 | I | 3 | 12 | 3 | 12 | 3 | 11 |
| 16 | J | 3 | 12 | 3 | 11 | 3 | 11 |
| 17 | K | 3 | 11 | 3 | 12 | 3 | 12 |
| 18 | L | 3 | 11 | 3 | 10 | 3 | 11 |
| 19 | M1 | 3 | 11 | 3 | 11 | 3 | 12 |
| 20 | M2 | 3 | 12 | 3 | 12 | 3 | 12 |
| 21 | N | 3 | 12 | 3 | 12 | 3 | 12 |
| 22 | FS-2 | 3 | 12 | 3 | 11 | 3 | 12 |
| 23 | Neg Cntl | 0 | 6 | NA | NA | NA | NA |
| 24 | Histamine | 4 | 14 | NA | NA | NA | NA |

TABLE 5

DOG ID: BFQ2

| # | Antigen | Inj 1 Sub | Inj 1 Obj | Inj 2 Sub | Inj 2 Obj | Inj 3 Sub | Inj 3 Obj |
|---|---|---|---|---|---|---|---|
| 1 | Neg Cntl | 0 | 6 | NA | NA | NA | NA |
| 2 | Histamine | 4 | 12 | NA | NA | NA | NA |
| 3 | Greer | 0 | 6 | 0 | 6 | 0 | 6 |
| 4 | FS-1 | 1 | 9 | 1 | 9 | 1 | 9 |
| 5 | A | 0 | 7 | 0 | 7 | 0 | 7 |
| 6 | B | 0 | 7 | 0 | 7 | 0 | 7 |
| 7 | C1 | 0 | 7 | 1 | 7 | 1 | 7 |
| 8 | C2 | 0 | 7 | 0 | 7 | 0 | 6 |
| 9 | D1 | 0 | 8 | 1 | 7 | 1 | 8 |
| 10 | D2 | 0 | 7 | 0 | 6 | 1 | 7 |
| 11 | E | 1 | 7 | 0 | 6 | 0 | 6 |
| 12 | F | 1 | 6 | 1 | 7 | 0 | 7 |
| 13 | G | 0 | 8 | 1 | 8 | 1 | 8 |
| 14 | H | 0 | 8 | 0 | 7 | 0 | 7 |
| 15 | I | 1 | 7 | 0 | 7 | 0 | 8 |
| 16 | J | 0 | 7 | 0 | 7 | 0 | 7 |
| 17 | K | 0 | 7 | 0 | 7 | 0 | 6 |
| 18 | L | 0 | 8 | 0 | 7 | 0 | 7 |
| 19 | M1 | 0 | 7 | 0 | 7 | 0 | 7 |
| 20 | M2 | 0 | 7 | 0 | 7 | 1 | 8 |
| 21 | N | 3 | 12 | 3 | 11 | 3 | 11 |
| 22 | FS-2 | 3 | 11 | 3 | 11 | 3 | 11 |
| 23 | Neg Cntl | 0 | 7 | NA | NA | NA | NA |
| 24 | Histamine | 4 | 15 | NA | NA | NA | NA |

TABLE 6

DOG ID: CPO2

| # | Antigen | Inj 1 Sub | Inj 1 Obj | Inj 2 Sub | Inj 2 Obj | Inj 3 Sub | Inj 3 Obj |
|---|---|---|---|---|---|---|---|
| 1 | Neg Cntl | 0 | 3 | NA | NA | NA | NA |
| 2 | Histamine | 4 | 13 | NA | NA | NA | NA |
| 3 | Greer | 0 | 7 | 0 | 7 | 0 | 6 |
| 4 | FS-1 | 4 | 12 | 4 | 12 | 4 | 12 |
| 5 | A | 0 | 7 | 0 | 6 | 0 | 6 |
| 6 | B | 0 | 6 | 0 | 7 | 0 | 7 |
| 7 | C1 | 0 | 7 | 0 | 6 | 0 | 7 |
| 8 | C2 | 0 | 6 | 0 | 6 | 0 | 6 |
| 9 | D1 | 0 | 7 | 1 | 7 | 0 | 7 |
| 10 | D2 | 1 | 6 | 0 | 6 | 0 | 5 |
| 11 | E | 0 | 6 | 0 | 6 | 0 | 6 |
| 12 | F | 0 | 6 | 0 | 6 | 2 | 7 |
| 13 | G | 2 | 9 | 2 | 8 | 2 | 8 |
| 14 | H | 4 | 11 | 4 | 12 | 4 | 11 |
| 15 | I | 3 | 12 | 3 | 11 | 3 | 10 |

TABLE 6-continued

DOG ID: CPO2

| # | Antigen | Inj 1 Sub | Inj 1 Obj | Inj 2 Sub | Inj 2 Obj | Inj 3 Sub | Inj 3 Obj |
|---|---|---|---|---|---|---|---|
| 16 | J | 3 | 10 | 3 | 11 | 3 | 10 |
| 17 | K | 2 | 8 | 2 | 8 | 2 | 8 |
| 18 | L | 1 | 8 | 1 | 7 | 1 | 7 |
| 19 | M1 | 3 | 11 | 3 | 11 | 3 | 11 |
| 20 | M2 | 3 | 11 | 4 | 12 | 4 | 12 |
| 21 | N | 4 | 12 | 3 | 10 | 3 | 11 |
| 22 | FS-2 | 3 | 11 | 3 | 12 | 3 | 12 |
| 23 | Neg Cntl | 0 | 6 | NA | NA | NA | NA |
| 24 | Histamine | 4 | 13 | NA | NA | NA | NA |

TABLE 7

DOG ID: CQQ2

| # | Antigen | Inj 1 Sub | Inj 1 Obj | Inj 2 Sub | Inj 2 Obj | Inj 3 Sub | Inj 3 Obj |
|---|---|---|---|---|---|---|---|
| 1 | Neg Cntl | 0 | 6 | NA | NA | NA | NA |
| 2 | Histamine | 4 | 13 | NA | NA | NA | NA |
| 3 | Greer | 0 | 7 | 0 | 7 | 0 | 7 |
| 4 | FS-1 | 2 | 8 | 2 | 8 | 2 | 8 |
| 5 | A | 0 | 6 | 0 | 6 | 0 | 7 |
| 6 | B | 0 | 7 | 0 | 7 | 0 | 6 |
| 7 | C1 | 0 | 7 | 0 | 6 | 0 | 6 |
| 8 | C2 | 0 | 7 | 0 | 7 | 0 | 6 |
| 9 | D1 | 0 | 6 | 0 | 6 | 0 | 6 |
| 10 | D2 | 0 | 6 | 0 | 6 | 0 | 7 |
| 11 | E | 0 | 6 | 0 | 6 | 0 | 6 |
| 12 | F | 0 | 6 | 0 | 7 | 0 | 7 |
| 13 | G | 0 | 7 | 0 | 7 | 0 | 6 |
| 14 | H | 1 | 7 | 1 | 7 | 1 | 7 |
| 15 | I | 2 | 8 | 2 | 9 | 2 | 8 |
| 16 | J | 2 | 8 | 2 | 8 | 2 | 8 |
| 17 | K | 1 | 7 | 1 | 7 | 1 | 7 |
| 18 | L | 1 | 6 | 0 | 6 | 0 | 6 |
| 19 | M1 | 2 | 7 | 2 | 8 | 2 | 8 |
| 20 | M2 | 2 | 8 | 2 | 8 | 2 | 9 |
| 21 | N | 3 | 11 | 3 | 12 | 3 | 11 |
| 22 | FS-2 | 3 | 11 | 3 | 11 | 3 | 10 |
| 23 | Neg Cntl | 0 | 7 | NA | NA | NA | NA |
| 24 | Histamine | 4 | 14 | NA | NA | NA | NA |

As a control, 2 flea naive dogs (i.e., dogs that had never been exposed to fleas) were also tested with single replicates of the same samples that were injected into the sensitized dogs. These dogs are referred to as WANU and WBCE. Objective and subjective wheal size measurements 15 minutes after injection of the samples are shown in Tables 8 and 9.

TABLE 8

DOG ID: WANU

| # | Antigen | Inj 1 Sub | Inj 1 Obj |
|---|---|---|---|
| 1 | Neg Cntl | 0 | 7 |
| 2 | Histamine | 4 | 10 |
| 3 | Greer | 0 | 6 |
| 4 | FS-1 | 0 | 6 |
| 5 | A | 0 | 7 |
| 6 | B | 0 | 6 |
| 7 | C1 | 0 | 6 |
| 8 | C2 | 0 | 6 |
| 9 | D1 | 0 | 7 |
| 10 | D2 | 0 | 6 |
| 11 | E | 0 | 6 |

TABLE 8-continued

DOG ID: WANU

| # | Antigen | Inj 1 Sub | Inj 1 Obj |
|---|---|---|---|
| 12 | F | 0 | 6 |
| 13 | G | 0 | 7 |
| 14 | H | 0 | 7 |
| 15 | I | 0 | 7 |
| 16 | J | 0 | 7 |
| 17 | K | 0 | 6 |
| 18 | L | 0 | 7 |
| 19 | M1 | 0 | 6 |
| 20 | M2 | 0 | 6 |
| 21 | N | 1 | 8 |
| 22 | FS-2 | 1 | 8 |
| 23 | Neg Cntl | NA | NA |
| 24 | Histamine | NA | NA |

TABLE 9

DOG ID: WBCE

| # | Antigen | Inj 1 Sub | Inj 1 Obj |
|---|---|---|---|
| 1 | Neg Cntl | 0 | 6 |
| 2 | Histamine | 4 | 12 |
| 3 | Greer | 0 | 7 |
| 4 | FS-1 | 0 | 7 |
| 5 | A | 0 | 7 |
| 6 | B | 0 | 7 |
| 7 | C1 | 0 | 7 |
| 8 | C2 | 0 | 7 |
| 9 | D1 | 0 | 7 |
| 10 | D2 | 0 | 6 |
| 11 | E | 0 | 7 |
| 12 | F | 0 | 7 |
| 13 | G | 0 | 8 |
| 14 | H | 0 | 7 |
| 15 | I | 0 | 7 |
| 16 | J | 0 | 7 |
| 17 | K | 0 | 7 |
| 18 | L | 0 | 6 |
| 19 | M1 | 0 | 7 |
| 20 | M2 | 0 | 7 |
| 21 | N | 0 | 7 |
| 22 | FS-2 | 0 | 7 |
| 23 | Neg Cntl | NA | NA |
| 24 | Histamine | NA | NA |

Figure 5:
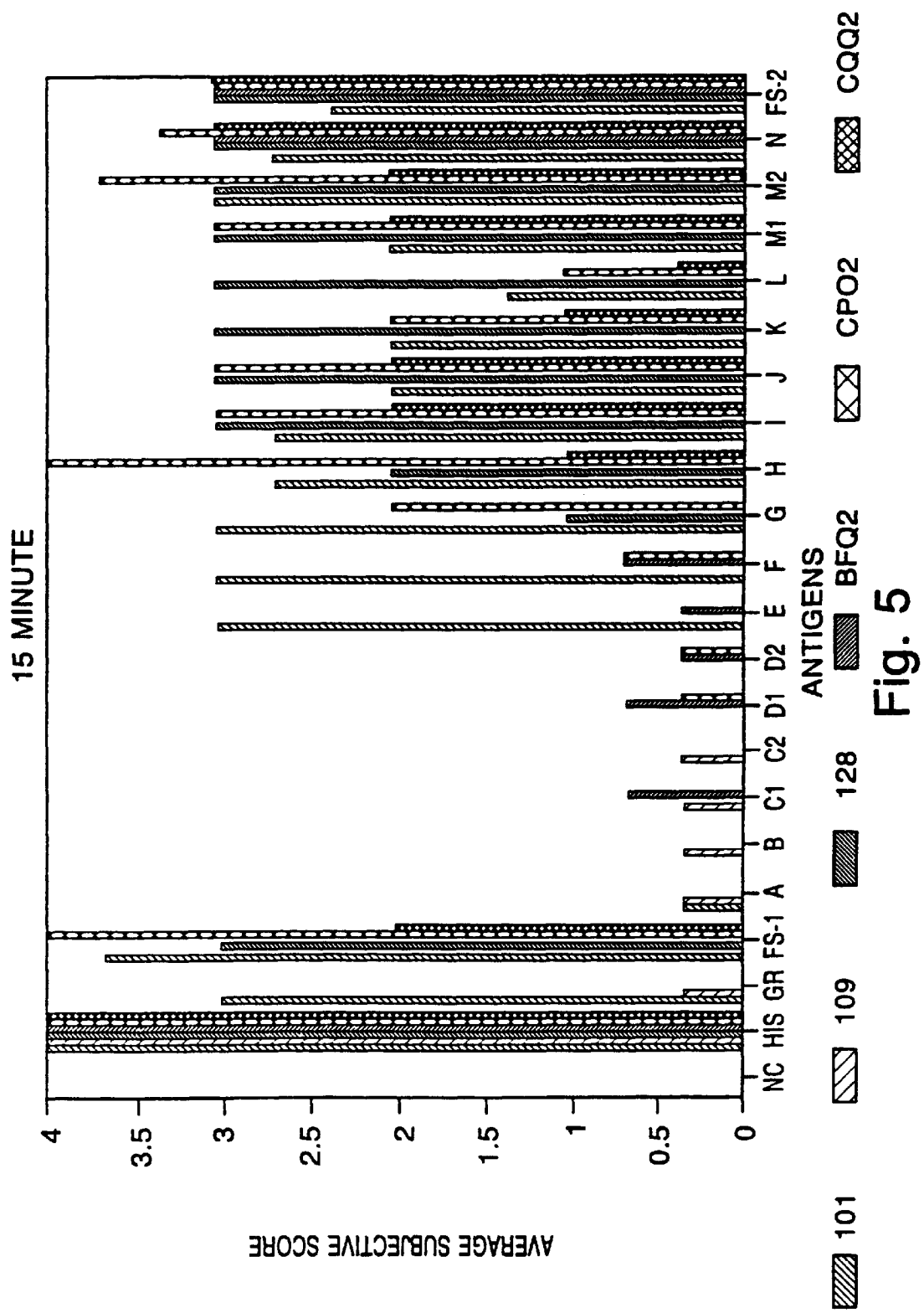
FIG. 5 illustrates the relative size of wheals produced 15 minutes after injection of various flea saliva protein formulations into flea-sensitized dogs.

The average subjective score obtained for each flea saliva antigen from the 6 sensitized dogs tested was calculated and is summarized in FIG. 5. The results indicate that the flea saliva products produced as described in Examples 2 and 3 include at least one allergenic protein capable of inducing an immediate hypersensitive response in a sensitized dog. In particular, injection of the mixtures of flea saliva antigens referred to as FS-1 and FS-2 resulted in substantial wheal formation. Flea saliva proteins fspE, fspF, fspG, fspH, fspI, fspJ, fspK, fspL, fspM1, fspM2 and fspN also resulted in substantial wheal formation. Flea saliva proteins fspA, fspB, fspC1, fspC2, fspD1 and fspD2 produced minimal, if any, allergic response, depending on the dog being tested. The sample containing fspH produced the largest wheal formation when compared with the other flea saliva proteins.

*B. Comparison of Levels of Induration and Erythema at the Injection Sites

In addition to wheal size, the amount of induration and erythema were also measured at each site of injection. Induration produced by the injection of the flea saliva antigens was measured at 6 hours and 24 hours by subjective scoring. Such subjective induration measurements were performed by Kenneth W. Kwochka, D. V. M. In addition, the amount of erythema at each site of injection were subjectively scored by Kenneth W. Kwochka, D. V. M.

The amounts of induration and erythema measured by subjective scoring at 6 hours were negative for each of the sensitized and control dogs except for the following formulations in the following sensitized dogs. Administration of FS-1 to Dog 2082101 produced an average induration score of 1 at 2 sites of injection but no erythema score. Administration of fspL to Dog 2082101 produced no induration but an erythema score of 1 at 1 site of injection. Administration of fspM1 to Dog 2082101 produced no induration but an erythema score of 3 at 1 site of injection. Administration of FS-2 to Dog 2082101 produced no induration but an average erythema score of 1.33 at 3 sites of injection. Administration of fspH to Dog 2082128 produced no induration but an average erythema score of 2 at 3 sites of injection. Administration of fspI to Dog 2082128 produced an average induration score of 1 and an average erythema score of 1 at 2 sites of injection. Administration of fspj to Dog 2082128 produced an average induration score of 1 and an average erythema score of 1 at 3 sites of injection. Administration of FS-2 to Dog 2082128 produced no induration but an average erythema score of 2 at 3 sites of injection.

Administration of FS-1 to Dog BFQ2 produced an average induration score of 2 and an average erythema score of 2 at 3 sites of injection. Administration of fspN to Dog BFQ2 produced an average induration score of 1 and an average erythema score of 2 at 2 sites of injection. Administration of FS-2 to Dog BFQ2 produced an average induration score of 1 and an average erythema score of 2 at 2 sites of injection.

Administration of FS-1 to Dog CPO2 produced an average induration score of 2.5 but no erythema at 2 sites of injection. Administration of fspG to Dog CPO2 produced no induration but an average erythema score of 2 at 3 sites of injection. Administration of fspH to Dog CPO2 produced no induration but an average erythema score of 1 at 2 sites of injection. Administration of FS-2 to Dog CPO2 produced no induration but an average erythema score of 2 at 3 sites of injection.

Figure 6:
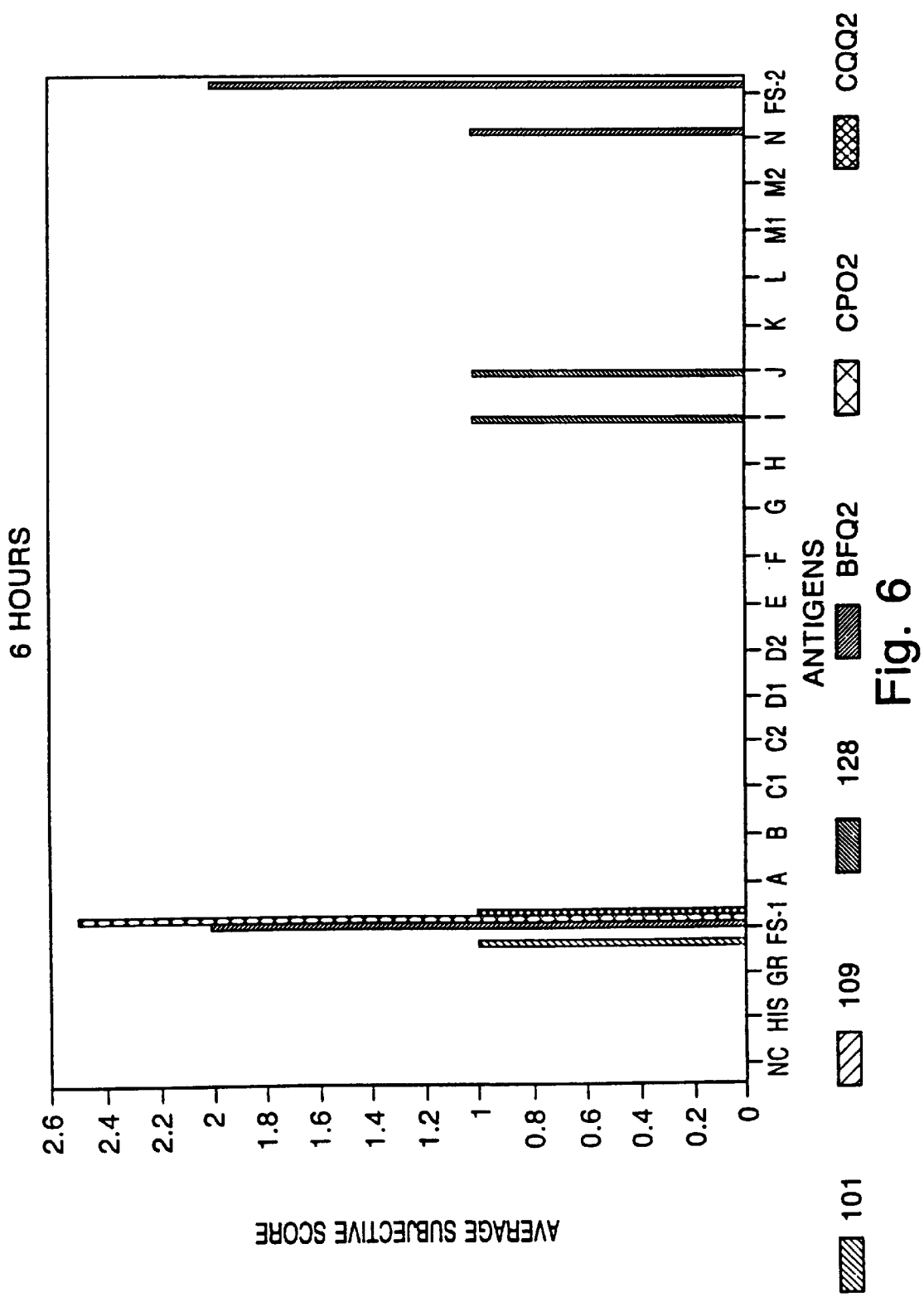
FIG. 6 illustrates the relative induration of wheals 6 hours after injection of various flea saliva protein formulations into flea-sensitized dogs.
Figure 7:
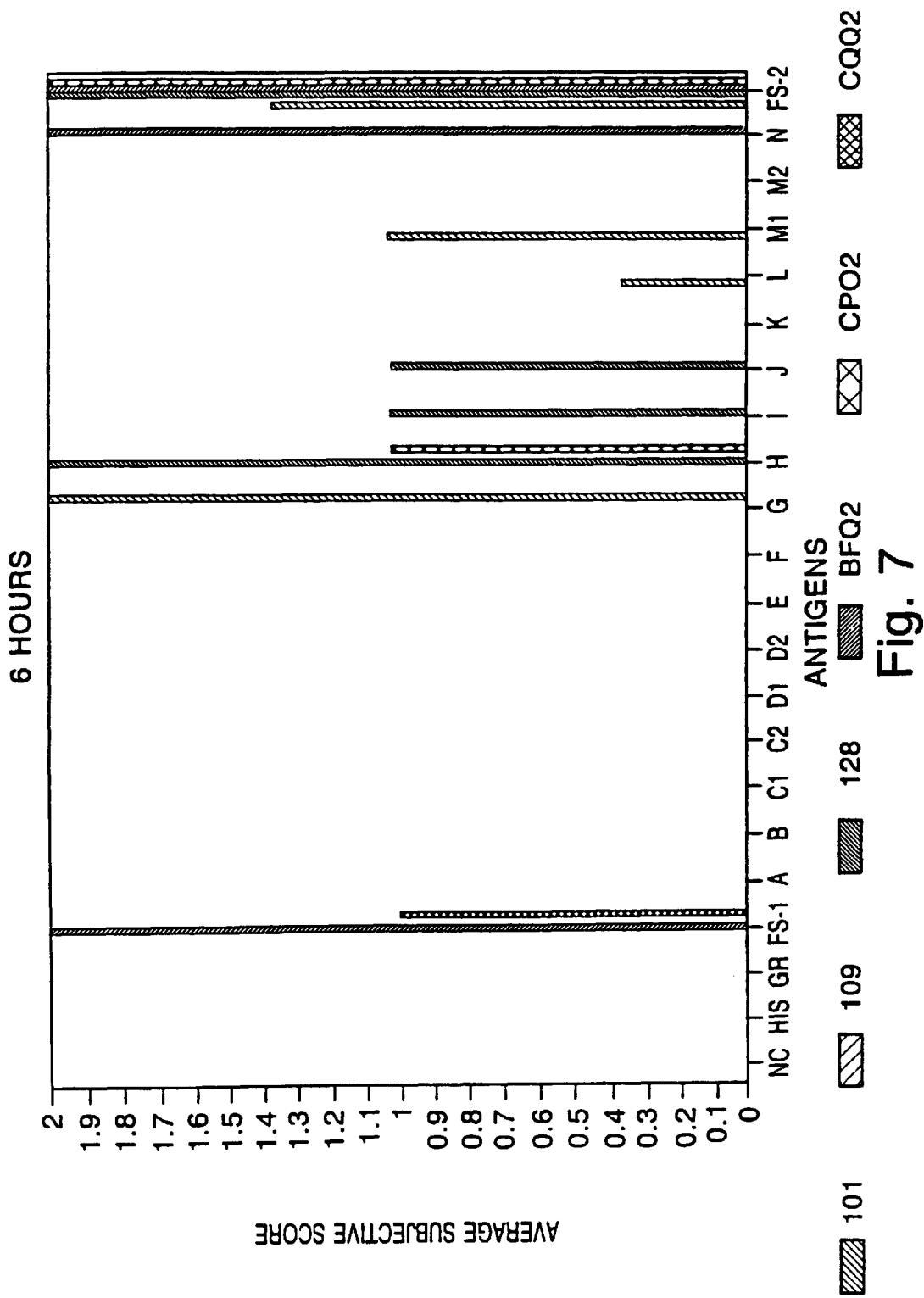
FIG. 7 illustrates the relative erythema of wheals 6 hours after injection of various flea saliva protein formulations into flea-sensitized dogs.

The average subjective score for induration obtained for each flea saliva antigen from the 6 sensitized dogs tested was calculated and is summarized in FIG. 6. The average subjective score for erythema obtained for each flea saliva antigen from the 6 sensitized dogs tested was calculated and is summarized in FIG. 7.

The amounts of induration and erythema measured by subjective scoring at 24 hours results for five of the flea-sensitized dogs and the two control dogs were negative except for the following formulations in the following sensitized dogs.

Administration of fspI to Dog 2082101 produced an average induration score of 1 and an average erythema score of 1 at 3 sites of injection. Administration of fspj to Dog 2082101 produced an average induration score of 1 and an average erythema score of 1 at 3 sites of injection. Administration of fspM 1 to Dog 2082101 produced an average induration score of 1 and an average erythema score of 3 at 3 sites of injection. Administration of fspN to Dog 2082101 produced an average induration score of 1 and an average erythema score of 2 at 3 sites of injection. Administration of FS-2 to Dog 2082101 produced an average induration score of 3 and an average erythema score of 4 at 3 sites of injection.

Administration of FS-1 to Dog BFQ2 produced an average induration score of 1 and an average erythema score of 1 at 3 sites of injection. Administration of FS-2 to Dog BFQ2 produced an induration score of 1 and an erythema score of 1 at 1 site of injection.

Administration of FS1 to Dog CPO2 produced an induration score of 2 and an erythema score of 1 at 1 site of injection. Administration of fspI to Dog CPO2 produced an average induration score of 1 and an average erythema score of 1 at 3 sites of injection. Administration of FS-2 to Dog CPO2 produced an average induration score of 1 and an average erythema score of 2 at 3 sites of injection.

Administration of Greer antigen to Dog CQQ2 produced no induration but an average erythema score of 1 at 3 sites of injection. Administration of FS-1 to Dog CQQ2 produced an induration score of 1 and an erythema score of 1 at 1 site of injection. Administration of fspI, fspJ, fspM 1 or fspM2 to Dog CQQ2 produced no induration but an average erythema score of 1 at 3 sites of injection. Administration of fspN to Dog CQQ2 produced an induration score of 1 and an erythema score of 1 at 1 site of injection. Administration of FS-2 to Dog CQQ2 produced an average induration score of 1 and an average erythema score of 2 at 3 sites of injection.

Figure 8:
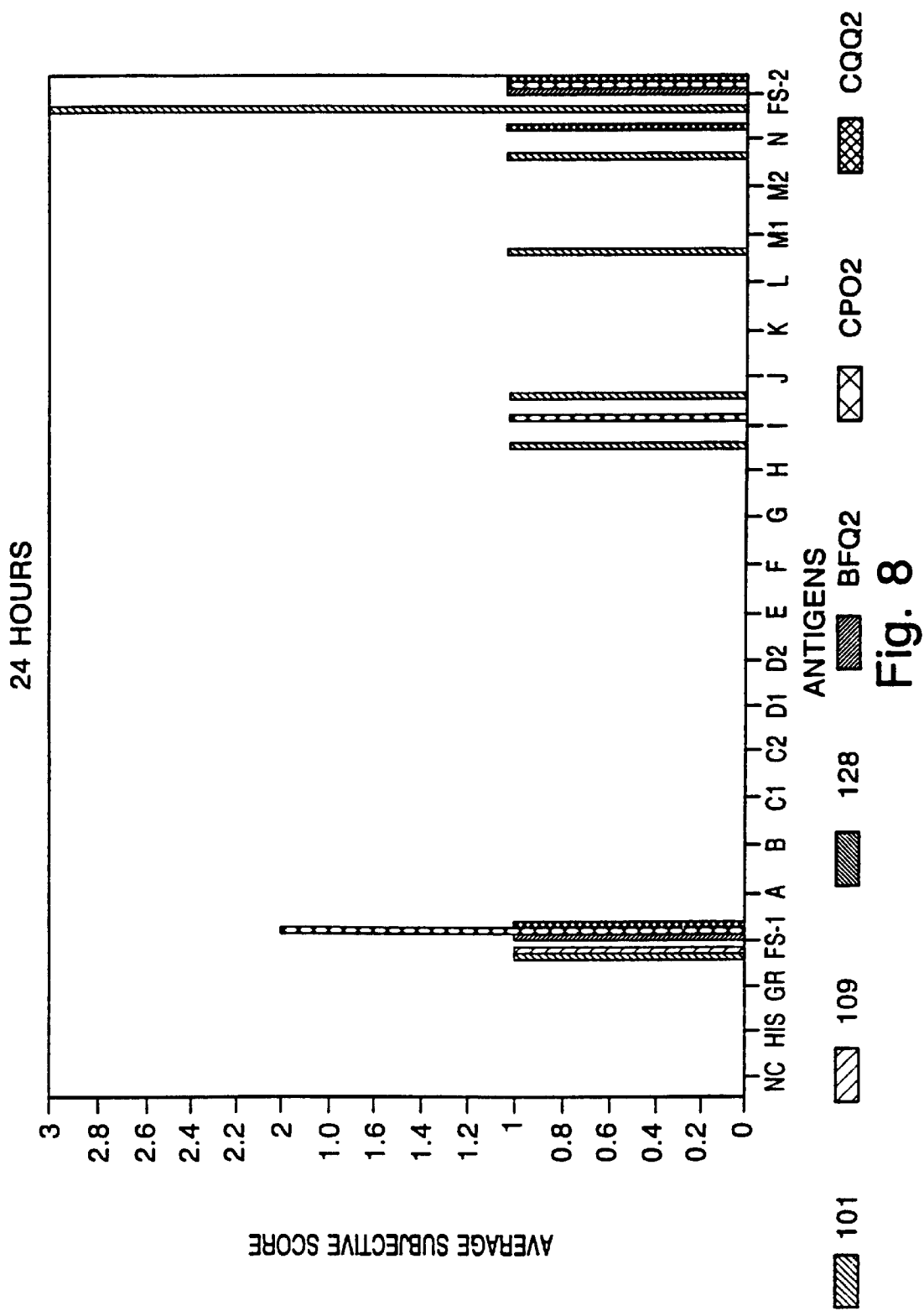
FIG. 8 illustrates the relative induration of wheals 24 hours after injection of various flea saliva protein formulations into flea-sensitized dogs.
Figure 9:
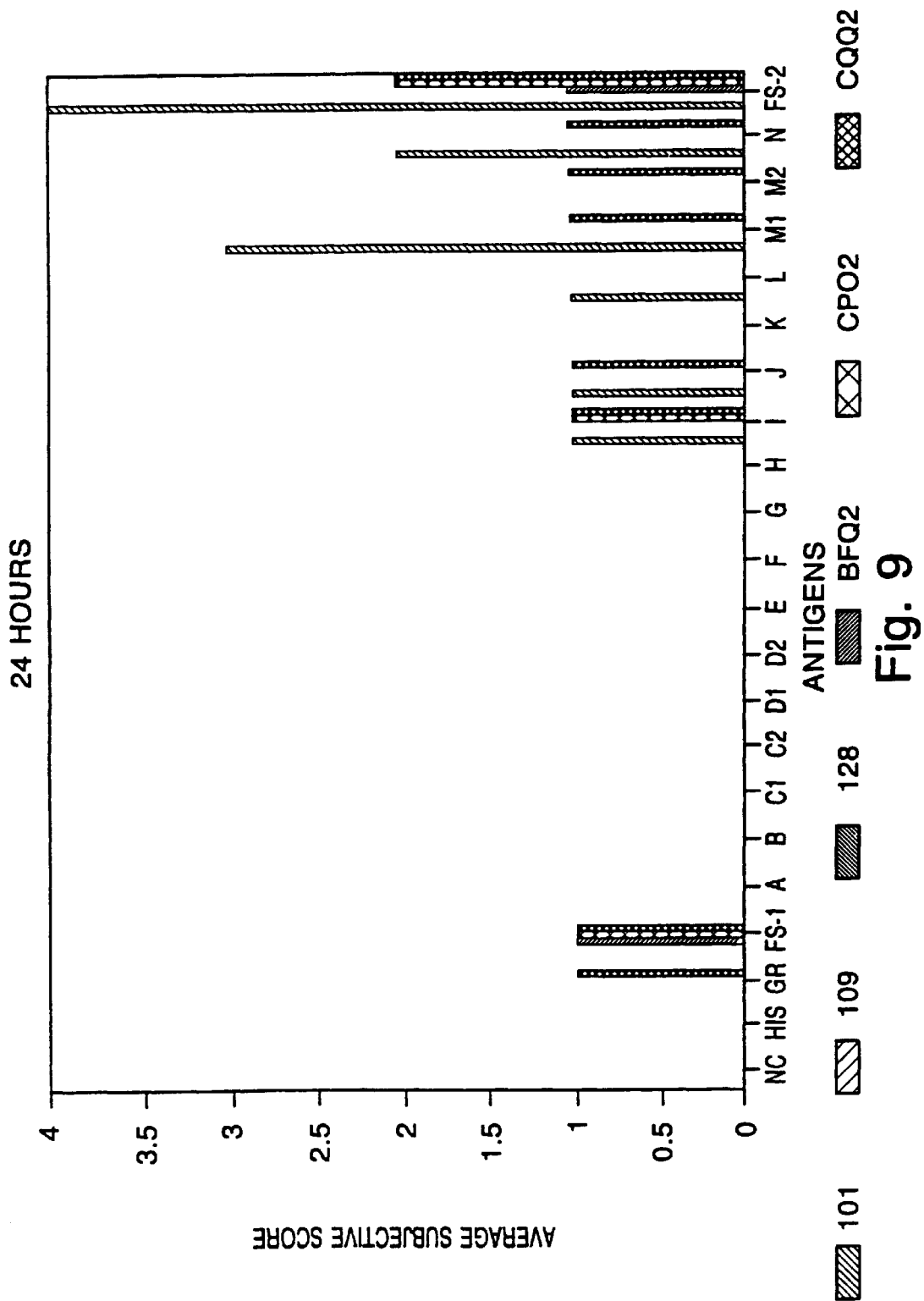
FIG. 9 illustrates the relative erythema of wheals 24 hours after injection of various flea saliva protein formulations into flea-sensitized dogs.

The average subjective score for induration obtained for each flea saliva antigen from the 6 sensitized dogs tested was calculated and is summarized in FIG. 8. The average subjective score for erythema obtained for each flea saliva antigen from the 6 sensitized dogs tested was calculated and is summarized in FIG. 9.

The results indicate that at least some of the flea saliva protein formulations produced as described in Examples 2 and 3 include at least one allergenic protein capable of inducing a delayed hypersensitive response in a sensitized dog. Injection of the mixtures of flea saliva proteins referred to as FS-1 and FS-2 induced substantial induration and erythema for at least 24 hours. In addition, the flea saliva protein samples fspI, fspj, M1 and fspN were sufficiently allergenic to induce induration and erythema for at least 24 hours. The flea saliva protein sample fspL and fspM2 induced substantial levels of induration but not substantial levels of erythema at 24 hours.

Taken together, the results shown indicated above and shown in FIGS. 5 through 9, indicate that saliva protein formulations of the present invention are sufficiently allergenic to induce a hypersensitive response in a sensitized dog. Numerous samples induced both an immediate hypersensitive response and a delayed hypersensitive response.

EXAMPLE 20

This example demonstrates the ability of numerous flea saliva protein samples isolated in Examples 2 and 3 to induce a hypersensitive response by histopathology of tissue removed from selected lesions on the dogs described in Example 19.

Two tissue samples per dog were removed from each sensitized dog described in Example 19. No biopsies were taken from the two naive dogs. The selected sites from which the tissue samples were removed are indicated in Table 10 below. Biopsies were taken with a 4 mm biopsy punch after subcutaneous injections of Lidocaine. Biopsies were processed and read by Dr. David M. Getzy, D V M, Diplomat ACVP (American College of Veterinary Pathologists) at the Colorado Veterinary Diagnostic Laboratory (College of Veterinary Medicine and Biomedical Sciences, Colorado State University, Fort Collins, Colo.).

TABLE 10

Histopathology

| Dog | Antigen | Time | No. | Slide | Lesion Type | Grade |
|-----|---------|---------|-----|-------|-------------|-------|
| 101 | FS-1 | 15 min. | 1 | A | A | 1 |
|     |      | 6 hr.   | 2 | B | A | 2.5 |
|     |      | 24 hr.  | 3 | C | A | 3 |
| 109 | FS-1 | 15 min. | 4 | D | A | 1 |
|     |      | 6 hr.   | 5 | E | C | 2 |
|     |      | 24 hr.  | 6 | F | C | 3 |
| 128 | FS-1 | 15 min. | 7 | G | A | 1.5 |
|     |      | 6 hr.   | 8 | H | C | 1.5 |
|     |      | 24 hr.  | 9 | I | C | 3 |
| CPO2 | FS-1 | 15 min. | 10 | J | A | 1.5 |
|     |      | 6 hr.   | 11 | K | C | 3 |
|     |      | 24 hr.  | 12 | L | C | 4 |
| CQQ2 | FS-1 | 15 min. | 13 | M | A | 1.5 |
|     |      | 6 hr.   | 14 | N | C | 2.5 |
|     |      | 24 hr.  | 15 | O | C | 2.5 |
| 101 | fspE | 15 min. | 16 | P | A | 1 |
|     |      | 6 hr.   | 17 | Q | C | 1.5 |
|     |      | 24 hr.  | 18 | R | A | 1.5 |
| 109 | fspF | 15 min. | 19 | S | A | 1 |
|     |      | 6 hr.   | 20 | T | A | 1.5 |
|     |      | 24 hr.  | 21 | U | A | 1.5 |
| 128 | fspI | 15 min. | 22 | V | A | 1 |
|     |      | 6 hr.   | 23 | W | C | 2.5 |
|     |      | 24 hr.  | 24 | X | C | 2.5 |
| BFQ2 | fspN | 15 min. | 25 | Y | A | 1.5 |
|     |      | 6 hr.   | 26 | Z | C | 2 |
|     |      | 24 hr.  | 27 | AA | C | 3.5 |
| BFQ2 | fspO | 15 min. | 28 | BB | A | 1 |
|     |      | 6 hr.   | 29 | CC | C | 3 |
|     |      | 24 hr.  | 30 | DD | C | 2.5 |
| CPO2 | fspH | 15 min. | 31 | EE | A | 1.5 |
|     |      | 6 hr.   | 32 | FF | C | 1.5 |
|     |      | 24 hr.  | 33 | GG | A | 1.5 |
| CQQ2 | fspN | 15 min. | 34 | HH | A | 1 |
|     |      | 6 hr.   | 35 | II | C | 2.5 |
|     |      | 24 hr.  | 36 | JJ | C | 2.5 |

Two types of lesions were found in the tissue samples tested. Lesion Type A refers to a moderate superficial dermal edema having mild numbers of mast cells in a perivascular orientation within the superficial dermis. Vascular endothelium exhibited mild reactive hypertrophy. Minimal numbers of neutrophils were noted in this region as well. Lesion Type C refers to lesions that were similar to those described in Lesion Type A except that the eosinophils were mild to moderate in severity, while neutrophils and mast cells were mild in severity.

On a scale of 0 to 5, lesions ranged from grade 1 to grade 4 in severity. Some of the specimens had predominantly mastocytic inflammatory perivascular infiltrates, edema, and minimal numbers of other cellular components. Other sections showed a predominance of eosinophilic inflammatory infiltrates, with lesser numbers of mast cells and neutrophils. The severity of these lesions was variable, however, in some areas, it progressed to intraepidermal eosinophilic pustulation and collagen necrobiosis within the superficial dermis.

Taken together, the tissue samples indicated the presence of superficial perivascular/periadnexal, mastocytic and eosinophilic, subacute dermatitis. Lesions noted in all the slide specimens examined are consistent with an allergic Type I hypersensitivity reaction.

EXAMPLE 21

This example further demonstrates the ability of proteins described in Examples 2 and 3 to induce an allergic response in animals naturally susceptible to flea allergy dermatitis through skin tests performed on dogs. These reactions were compared to those obtained using the current standard for diagnosis of flea allergy dermatitis, Greer Whole Flea Extract (Greer Laboratories, Inc., Lenoir, N.C.). In addition, in order to determine specificity of the reactions, test results were compared to those obtained from a population of control dogs with normal skin and a population of dogs with pruritic skin disorders other than flea allergy dermatitis.

Three groups of dogs were used in the study: (1) 10 dogs with naturally occurring flea allergy dermatitis as determined by clinical signs, presence of fleas at the time of diagnosis, and a positive immediate or delayed reaction to Greer Whole Flea Extract; (2) 10 dogs with non-flea-related pruritic dermatoses including, but not limited to, atopy, food allergy dermatitis, pyoderma, seborrhea, and other parasitic hypersensitivity reactions; and (3) 10 dogs with normal skin and no history of chronic skin diseases. The dogs were of any breed, age or sex. They were recruited from the hospital population of the Ohio State University Veterinary Teaching Hospital, Columbus, Ohio. All dogs had written owner consent to participate in the study.

All tests and subjective scoring were performed by Kenneth W. Kwochka, D. V. M., Diplomat ACVD, (American College of Veterinary Dermatologists), in the Dermatology Examination Room at the Veterinary Teaching Hospital, College of Veterinary Medicine, The Ohio State University, Columbus, Ohio. All dogs were tested on the anterior-ventral-lateral aspect of the chest on the left side. Dogs were sedated for testing using standard dosages of xylazine and atropine administered intravenously immediately before the skin test. No glucocorticoids, antihistamines, or other non-steroidal antiinflamatory medications were allowed for at least 3 weeks prior to testing. The area for testing was gently clipped with a #40 electric clipper blade and the injection sites marked with an indelible black felt-tipped marking pen. Twenty-two sites were marked: two rows of ten dots and one row of two dots. Intradermal injections were placed both above and below each mark for a total of forty-four injections that were administered in the following order:

Row 1: Neg. cont.-Histamine-Greer-Greer-Flea saliva-Flea saliva-A-A-B-B
Row 2: C1-C1-C2-C2-D1-D1-D2-D2-E-E
Row 3: F-F-G-G-H-H-I-I-J-J-
Row 4: K-K-L-L-MI-MI-M2-M2-N-N
Row 5: FS2-FS2
Row 6: Neg. cont.-Histamine Each site was injected intradermally with 50 μl of sterile diluent (Neg. cont.), 1/100,000 w/v histamine phosphate (Histamine), Greer Whole Flea Extract (Greer), whole flea saliva (Flea saliva), or individual salivary protein fractions (fspA, (A); fspB, (B); fspC1, (C1); fspC2, (C2); fspD1, (D1); fspD2, (D2); fspE, (E); fspF, (F); fspG, (G); fspH, (H); fspI, (I); fspJ, (J); fspK, (K); fspL, (L); fspM1, (M1); fspM2, (M2); fspN, (N); and FS-2 (FS2). All injections were diluted in the same sterile diluent as the Neg. cont.

Skin reactions were read subjectively and objectively at 15 minutes and 24 hours after injections. Owners were required to return their dogs to the Veterinary Teaching Hospital for the 24 hour readings. Subjective assessments were basted on a scale of 0, 1+, 2+, 3+ and 4+ based on wheal size, amount of erythema and amount of induration. Objective assessment was based on wheal diameter measured in millimeters.

Comparison of Skin Reactions

A. FAD Dogs:

Of the 10 dogs positive to Greer, 7 (70%) were positive the Flea Saliva (FS). None of the 3 FS-negative dogs reacted to any of the salivary protein fractions. Additionally, the 3 dogs negative to FS at 15 minutes were negative to everything at 24 hours. The 7 FS-positive dogs were used to summarize the 15 minute reactions, shown below in Table 11.

TABLE 11

Immediate (15 min) subjective scores of 7 FS-positive dogs to test antigens

| % Positive | Scores ≥ 2+ | Scores ≥ 3+ |
|---|---|---|
| 0 | | I |
| 14 | B, I, J, L | B, D1, J, L |
| 29 | A, C1, C2, D1 | A, C1, C2, K |
| 43 | E, F, K | D2, E, F, H, M2 |
| 57 | D2, H, M2 | G, N, FS2 |
| 71 | G, M1 | M1 |
| 86 | N, FS2 | Greer |
| 100 | Greer, FS | FS |

Four of the 7 FS-positive dogs could not be evaluated at 24 hours because the severity of the immediate reactions warranted antiinflammatory therapy. The remaining 3 FS-positive dogs were used to summarize the 24 hour reactions, shown below in Table 12.

TABLE 12

Delayed (24 hr) subjective scores of 3 FS-positive dogs to test antigens

| % Positive | Scores ≥ 2+ | Scores ≥ 3+ |
|---|---|---|
| 0 | | |
| 33 | M2 | |
| 67 | Greer, FS, N, FS2 | FS, N, FS2 |
| 100 | | |

B. Normal Dogs:

Three dogs had an immediate reaction to the skin test antigens to some extent. None had a positive delayed reaction at 24 hours. A summary of the immediate (15 min) subjective results is shown below in Table 13.

TABLE 13

Immediate (15 min) subjective scores of 10 normal dogs to test antigens

| % Positive | Scores ≥ 2+ | Scores ≥ 3+ |
|---|---|---|
| 0 | | |
| 10 | N, FS2 | FS2 |
| 20 | Greer, FS | Greer, FS |
| 30 | | |
| 40 | | |
| 50 | | |
| 60 | | |
| 70 | | |
| 80 | | |
| 90 | | |
| 100 | | |

Individual dog comments:

Dog #1: Greer 3+, FS 3+, N 2+, FS2 4+

Dog #2: Greer 3+

Dog #3: FS 3+

C. Non-FAD Pruritis Dogs:

Six dogs had an immediate reaction to the skin test antigens to some extent. A summary of the immediate (15 min) subjective results is shown below in Table 14.

TABLE 14

Immediate (15 min) subjective scores of 10 Non-FAD pruritis dogs to test antigens

| % Positive | Scores ≥ 2+ | Scores ≥ 3+ |
|---|---|---|
| 0 | | |
| 10 | G, O | G, O |
| 20 | Greer, M1 | Greer, FS, M1, M2 |
| 30 | FS, M2, N | N |
| 40 | | |
| 50 | | |
| 60 | | |
| 70 | | |
| 80 | | |
| 90 | | |
| 100 | | |

Individual dog comments:

Dog #1: FS 2+, M1 3+, M2 3+, N 3+, FS2 3+
    Atopic dog under chronic flea exposure Dog #2: FS 4+, G 4+, M1 4+, M2 3+, N 3+
    Atopic dog under chronic flea exposure Dog #3: FS 4+, M2 2+
    Atopic dog under chronic flea exposure Dog#4: N3+
    Atopic dog under chronic flea exposure Dog #5: Greer 4+
    Chronic otitis externa Dog #6: Greer 4+
    Generalized Demodicosis (Mange)

Dogs #1, #2 and #3 all came back to the clinic subsequently and were diagnosed with FAD and were Greer positive.

Three dogs had a delayed reaction to the skin test antigens to some extent. A summary of the delayed (24 hr) subjective results is shown below in Table 15.

TABLE 15

Delayed (24 hr) subjective scores of 10 Non-FAD pruritis dogs to test antigens

| % Positive | Scores ≥ 2+ | Scores ≥ 3+ |
|---|---|---|
| 0 | | |
| 10 | FS, N, FS2 | Greer, FS, N, FS2 |
| 20 | | |
| 30 | Greer | |
| 40 | | |
| 50 | | |
| 60 | | |
| 70 | | |
| 80 | | |
| 90 | | |
| 100 | | |

Individual dog comments:

Dog #3: Greer 2+
    Atopic dog under chronic flea exposure

Dog #4: Greer 2+
    Atopic dog under chronic flea exposure

Dog #6: Greer 3+, FS 3+, N 3+, FS2 3+
    Generalized demodicosis (mange)

As an aid in determining the fraction(s) of flea saliva that correlate best with a positive skin test result, all the data for the artificially sensitized and clinically diagnosed FAD dogs that were 2+or greater to FS (12 dogs total; 5 artificially sensitized and 7 clinically diagnosed as FAD positive) were tabulated according to the responses to the test antigens. The immediate (15 min) subjective results are shown below in Table 16, and the delayed (24 h) subjective results are shown below in Table 17.

TABLE 16

PERCENT RESPONDING
(15 min subjective score)

| Antigen | Artificially Sensitized (5) | | Clinical Diagnosis (7) | | Combined (12) | |
|---|---|---|---|---|---|---|
| | Score ≥ 2+ | Score ≥ 3+ | Score ≥ 2+ | Score ≥ 3+ | Score ≥ 2+ | Score ≥ 3+ |
| Greer | 20 | 20 | 100 | 86 | 67 | 58 |
| FS | 100 | 80 | 100 | 100 | 100 | 92 |
| A | 0 | 0 | 29 | 29 | 17 | 17 |
| B | 0 | 0 | 14 | 14 | 8 | 8 |
| C | 0 | 0 | 29 | 29 | 17 | 17 |
| D1 | 0 | 0 | 29 | 14 | 17 | 8 |
| D2 | 0 | 0 | 57 | 43 | 33 | 25 |
| E | 40 | 20 | 43 | 43 | 42 | 33 |
| F | 40 | 40 | 43 | 43 | 42 | 42 |
| G | 60 | 40 | 71 | 57 | 67 | 50 |
| H | 80 | 20 | 57 | 43 | 67 | 33 |
| I | 100 | 40 | 14 | 0 | 50 | 17 |
| J | 100 | 40 | 14 | 14 | 50 | 25 |
| K | 80 | 20 | 43 | 29 | 58 | 25 |
| L | 20 | 20 | 14 | 14 | 17 | 17 |
| M1 | 100 | 60 | 71 | 71 | 83 | 67 |
| M2 | 100 | 80 | 57 | 43 | 75 | 58 |
| N | 100 | 60 | 86 | 57 | 92 | 58 |
| FS2 | 80 | 60 | 86 | 57 | 83 | 58 |

TABLE 17

PERCENT RESPONDING
(24 hr subjective score)

| Antigen | Artificially Sensitized (5) | | Clinical Diagnosis (7) | | Combined (12) | |
|---|---|---|---|---|---|---|
| | Score ≥ 2+ | Score ≥ 3+ | Score ≥ 2+ | Score ≥ 3+ | Score ≥ 2+ | Score ≥ 3+ |
| Greer | 0 | 0 | 67 | 0 | 25 | 0 |
| FS | 0 | 0 | 67 | 67 | 25 | 25 |
| A | 0 | 0 | 0 | 0 | 0 | 0 |
| B | 0 | 0 | 0 | 0 | 0 | 0 |
| C | 0 | 0 | 0 | 0 | 0 | 0 |
| D1 | 0 | 0 | 0 | 0 | 0 | 0 |
| D2 | 0 | 0 | 0 | 0 | 0 | 0 |
| E | 0 | 0 | 0 | 0 | 0 | 0 |
| F | 0 | 0 | 0 | 0 | 0 | 0 |
| G | 0 | 0 | 0 | 0 | 0 | 0 |
| H | 0 | 0 | 0 | 0 | 0 | 0 |
| I | 0 | 0 | 0 | 0 | 0 | 0 |
| J | 0 | 0 | 0 | 0 | 0 | 0 |
| K | 0 | 0 | 0 | 0 | 0 | 0 |
| L | 0 | 0 | 0 | 0 | 0 | 0 |
| M1 | 20 | 0 | 0 | 0 | 13 | 0 |
| M2 | 0 | 0 | 33 | 0 | 13 | 0 |
| N | 20 | 0 | 67 | 67 | 38 | 25 |
| FS2 | 60 | 20 | 67 | 67 | 63 | 38 |

The results of these studies indicate that the most substantial responses were obtained for fractions fspG, fspH, fspM 1, fspM2 and fspN.

EXAMPLE 22

This Example demonstrates that use of ELISAs to detect anti-flea saliva IgE antibodies in the sera of dogs sensitized to fleas or flea saliva.

A. In a first study, sera collected from three dogs that had been artificially sensitized to flea bites were pooled and pretreated by contacting the pooled sera with Protein G to remove at least some of the non-IgE immunoglobulins present in the sera. IgE antibodies were then affinity-purified from the pretreated sera using Con-A chromatography.

The affinity-purified IgE antibodies were exposed to the following flea saliva products and proteins: FS-1 saliva extract at 2 mg/ml (23,300 flea-hours per µl); fspA, fspB, fspC1, fspC2, fspD1, fspD2, fspE, fspF, fspG, fspH, fspI, fspJ, fspK, fspL, fspM1, fspM2, and fspN (from a 233,000 flea-hours per µl sample applied to HPLC chromatography as described in Example 17). The flea saliva products and proteins were suspended in 0.1 M sodium carbonate, pH 9.6, and 100 µl samples of each were placed in microtiter dish wells. The samples were incubated overnight at room temperature, washed 5 times with PBS/Tween, blocked with a solution of PBS, 2% BSA, 0.02% NaN$_3$, for 1 hour at 37° C., and washed 5 times with PBS/Tween. The washed wells were each exposed to 100 µl aliquots of the affinity-purified dog IgE antibodies for 1 hour at 37° C. The wells were washed 5 times with PBS/Tween and exposed for 1 hour, at 37° C., to 100 µl of a monoclonal mouse anti-canine IgE antibody preparation diluted 1:000 in PBS, 2% BSA, 0.05% Triton X-100. The wells were washed 5 times with PBS/Tween, exposed for 1 hour, at 37° C., to 100 µl donkey anti-mouse IgG (H+L)-HRP, and washed 5 times with PBS/Tween. The wells were developed with 100 µl KPL TMB:H$_2$O$_2$, 1:1, for 10 minutes, the reaction being stopped with 50 µl 2.5 N hydrogen sulfate. The wells were read at 450 nm.

Figure 10:
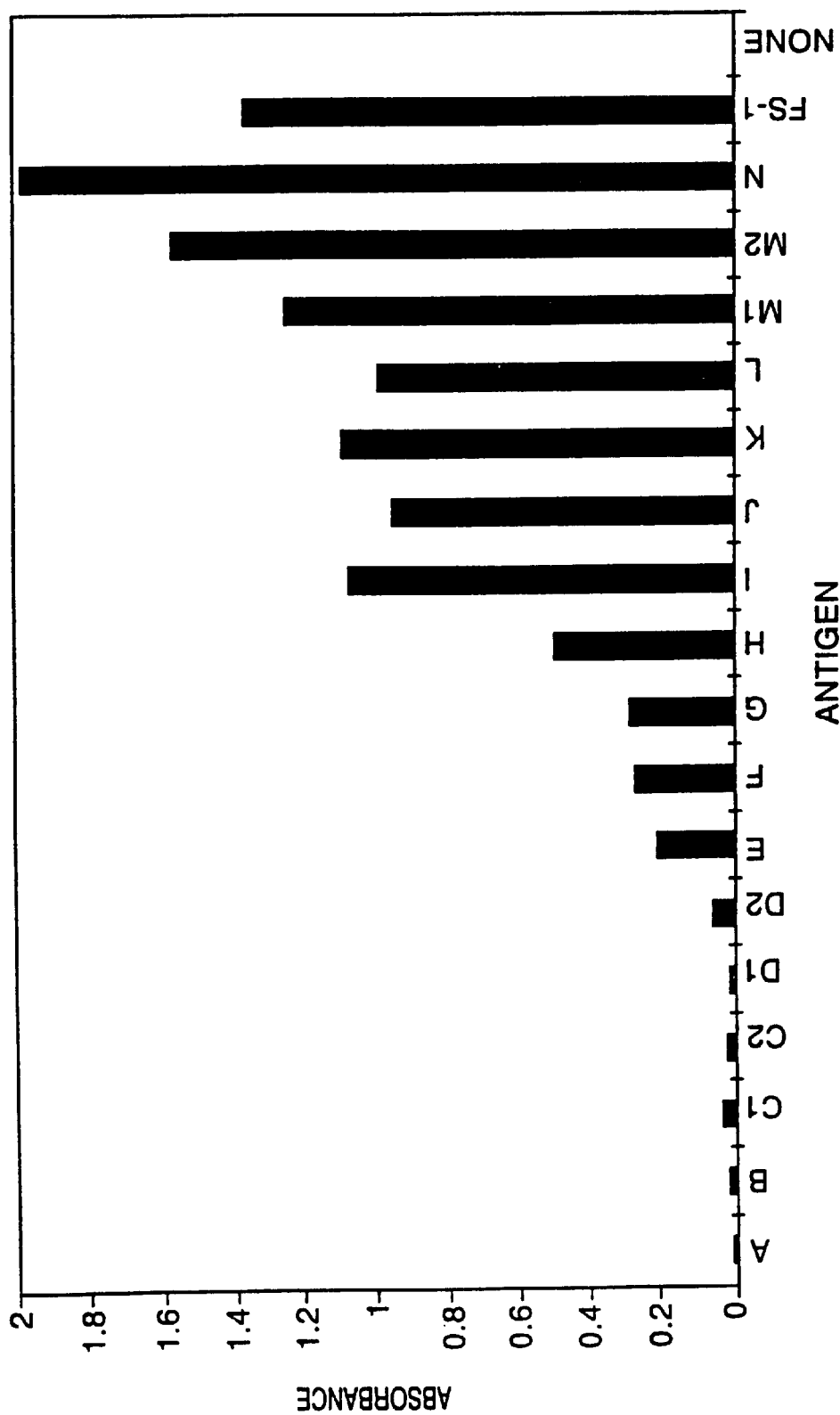
FIG. 10 depicts ELISA results measuring anti-flea saliva IgE antibodies in the sera of flea sensitized dogs.

The results, shown in Table 18 and FIG. 10, indicate that FAD+dogs have in their sera IgE antibodies that react in a sensitive and specific manner with FS-1 flea saliva extract as well as with flea saliva proteins fspE, fspF, fspG, fspH, fspI, fspj, fspK, fspL, fspM 1, fspM2 and fspN. The IgE antibody preparation reacted minimally, if at all, with flea saliva proteins fspA, fspB, fspC1, fspC2, fspD1 and fspD2. Thus, the IgE reactivity closely followed the skin test results of Example 19 in the artificially sensitized dogs with the same flea saliva products and proteins.

TABLE 18

| Fraction | Volume of Antigen | | | |
|---|---|---|---|---|
| | 0.5 µl | 0.25 µl | 0.125 µl | 0.063 µl |
| A | 0.007 | 0.008 | 0.012 | 0.018 |
| B | 0.016 | 0.010 | 0.013 | 0.052 |
| C1 | 0.035 | 0.008 | 0.035 | 0.020 |
| C2 | 0.022 | 0.009 | 0.002 | 0.005 |
| D1 | 0.013 | 0.025 | 0.004 | 0.005 |
| D2 | 0.059 | 0.018 | 0.017 | 0.012 |
| E | 0.214 | 0.263 | 0.206 | 0.092 |
| F | 0.276 | 0.393 | 0.217 | 0.114 |
| G | 0.288 | 0.217 | −0.010 | −0.010 |
| H | 0.503 | 0.336 | 0.203 | 0.062 |
| I | 1.076 | 0.997 | 0.917 | 0.637 |

TABLE 18-continued

| Fraction | Volume of Antigen | | | |
|---|---|---|---|---|
| | 0.5 µl | 0.25 µl | 0.125 µl | 0.063 µl |
| J | 0.955 | 0.816 | 0.673 | 0.456 |
| K | 1.095 | 0.898 | 0.815 | 0.690 |
| L | 0.991 | 0.721 | 0.485 | 0.162 |
| M1 | 1.251 | 1.190 | 0.840 | 0.454 |
| M2 | 1.561 | 1.105 | 0.902 | 0.558 |
| N | 1.989 | 1.887 | 1.819 | 1.435 |
| FS-1 | 1.367 | 1.246 | 0.982 | 0.604 |
| none | 0.002 | 0.005 | 0.008 | 0.121 |

B. In a second study, serum collected from a dog that had been artificially sensitized to flea bites was pretreated by contacting the serum with Protein G to remove at least some of the non-IgE immunoglobulins present in the serum. The reactivity of the pretreated serum to FS1 flea saliva extract was determined as described in Example 22A. Also tested was the reactivity to FS-1 flea saliva extract of sera collected from dogs infected with heartworm, pooled and pretreated by contacting the serum with Protein G. The results, shown in Table 19 and FIGS. 11A and 11B, demonstrate a dose dependent reactivity of IgE from the FAD+ dog while IgE from heartworm infected dogs had no reactivity against FS1 flea saliva extract.

TABLE 19

| | Sera dil. | | | | | | | |
|---|---|---|---|---|---|---|---|---|
| | 1:2 | 1:4 | 1:8 | 1:16 | 1:32 | 1:64 | 1:128 | none |
| DOG 2082128 | | | | | | | | |
| 2 µg | 1.67 | 1.20 | 0.85 | 0.57 | 0.34 | 0.19 | 0.11 | 0.01 |
| 1 µg | 1.43 | 1.16 | 0.80 | 0.49 | 0.30 | 0.17 | 0.10 | 0.00 |
| 0.5 µg | 1.32 | 1.02 | 0.71 | 0.46 | 0.28 | 0.14 | 0.08 | 0.00 |
| 0.25 µg | 1.18 | 0.92 | 0.59 | 0.38 | 0.22 | 0.12 | 0.06 | 0.00 |
| 0.13 µg | 0.95 | 0.80 | 0.52 | 0.30 | 0.19 | 0.11 | 0.06 | 0.00 |
| none | 0.00 | 0.01 | 0.00 | 0.00 | 0.00 | 0.00 | 0.00 | 0.01 |
| HEART-WORM POOL | | | | | | | | |
| 2 µg | 0.00 | 0.00 | 0.00 | 0.00 | 0.00 | 0.00 | 0.00 | 0.00 |
| 1 µg | 0.00 | 0.00 | 0.00 | 0.00 | 0.00 | 0.00 | 0.00 | 0.00 |
| 0.5 µg | 0.00 | 0.00 | 0.00 | 0.00 | 0.00 | 0.00 | 0.00 | 0.00 |
| 0.25 µg | 0.00 | 0.01 | 0.01 | 0.00 | 0.00 | 0.00 | 0.00 | 0.00 |
| 0.13 µg | 0.01 | 0.00 | 0.00 | 0.00 | 0.00 | 0.00 | 0.00 | 0.00 |
| none | 0.01 | 0.01 | 0.01 | 0.00 | 0.00 | 0.00 | 0.01 | 0.00 |

What is claimed is:

1. An isolated protein selected from the group consisting of:
   (a) a protein comprising an amino acid sequence selected from the group consisting of SEQ ID NO:90, SEQ ID NO:94, SEQ ID NO:101, SEQ ID NO:105, SEQ ID NO:112, SEQ ID NO:115, and SEQ ID NO:119; and
   (b) a protein comprising a homologue of a flea protein of (a), wherein said homologue comprises at least a 6 contiguous amino acid portion of an amino acid sequence selected from the group consisting of SEQ ID NO:112, SEQ ID NO:115 and SEQ ID NO:119, wherein said protein elicits an antibody response against a protein of (a).

2. The protein of claim 1, wherein said protein comprises an amino acid sequence selected from the group consisting of SEQ ID NO:90, SEQ ID NO:94, SEQ ID NO:101, SEQ ID NO:105, SEQ ID NO:112, SEQ ID NO:115, and SEQ ID NO:119.

3. A composition comprising at least one isolated protein selected from the group consisting of:
   (a) a protein comprising an amino acid sequence selected from the group consisting of SEQ ID NO:90, SEQ ID NO:94, SEQ ID NO:101, SEQ ID NO:105, SEQ ID NO:112, SEQ ID NO:115, and SEQ ID NO:119; and
   (b) a protein comprising a homologue of a flea protein of (a), wherein said homologue comprises at least a 6 contiguous amino acid portion of an amino acid sequence selected from the group consisting of SEQ ID NO:112, SEQ ID NO:115 and SEQ ID NO:119, wherein said protein elicits an antibody response against a protein of (a).

4. The composition of claim 3, wherein said composition further comprises at least one component selected from the group consisting of an excipient, an adjuvant and a carrier.

5. The composition of claim 3, wherein said composition comprises a controlled release composition.

6. A method to desensitize a host animal to flea allergic dermatitis, wherein the animal is susceptible to or has flea allergic dematitis, the method comprising administering to said animal a therapeutic composition comprising a formulation comprising at least one isolated protein selected from the group consisting of:
   (a) a protein comprising an amino acid sequence selected from the group consisting of SEQ ID NO:90, SEQ ID NO:94, SEQ ID NO:101, SEQ ID NO:105, SEQ ID NO:112, SEQ ID NO:115, and SEQ ID NO:119; and
   (b) a protein comprising a homologue of a flea protein of (a), wherein said homologue comprises at least a 6 contiguous amino acid portion of an amino acid sequence selected from the group consisting of SEQ ID NO:112, SEQ ID NO:115 and SEQ ID NO:119, wherein said protein elicits an antibody se against a protein of (a), wherein said protein is administered in an amount and manner effective to desensitize a host animal to allergic dermatitis.

7. The method of claim 6, wherein said composition further comprises at least one component selected from the group consisting of an excipient, an adjuvant and a carrier.

8. The method of claim 6, wherein said composition comprises a controlled release composition.

9. A method to desensitize a host animal selected from the group consisting of a dog, a and a horse, to allergic dermatitis, comprising administering to said animal a therapeutic composition comprising a formulation comprising at least one isolated protein selected from the group consisting of:
   (a) a protein comprising an amino acid sequence selected from the group consisting of SEQ ID NO:90, SEQ ID NO:94, SEQ ID NO:101, SEQ ID NO:105, SEQ ID NO:112, SEQ ID NO:115, and SEQ ID NO:119; and,
   (b) a protein comprising a homologue of a flea protein of (a), wherein said homologue comprises at least a 6 contiguous amino acid portion of an amino acid sequence selected from the group consisting of SEQ ID NO:112, SEQ ID NO:115 and SEQ ID NO:119, wherein said protein elicits an antibody response against a protein of (a), wherein said protein is administered in an amount and manner effective to desensitize a host animal to allergic dermatitis.

10. The method of claim 9, wherein said composition further comprises at least one component selected from the group consisting of an excipient, an adjuvant and a carrier.

11. The method of claim 9, wherein said composition further comprises a controlled release composition.

* * * * *

UNITED STATES PATENT AND TRADEMARK OFFICE
CERTIFICATE OF CORRECTION

PATENT NO. : 6,576,238 B1
DATED : June 10, 2003
INVENTOR(S) : Weber et al.

It is certified that error appears in the above-identified patent and that said Letters Patent is hereby corrected as shown below:

Column 206,
Line 43, please delete "se" and replace with -- response --;
Line 53, delete "dog, a and" and replace with -- dog, a cat and --;

Signed and Sealed this

Twenty-ninth Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,576,238 B1
DATED : June 10, 2003
INVENTOR(S) : Weber et al.

It is certified that error appears in the above-identified patent and that said Letters Patent is hereby corrected as shown below:

Title page,
Item [75], Inventors, after "Eric R. Weber, Ft. Collins, CO (US);" please insert
-- Gek-Kee Sim, Denver, CO (US); --

Column 206,
Line 52, delete "composition comprises" and replace with -- composition further comprises --

Signed and Sealed this

Eighth Day of February, 2005

JON W. DUDAS
*Director of the United States Patent and Trademark Office*